US012806197B2

(12) United States Patent
Foster et al.

(10) Patent No.: US 12,806,197 B2
(45) Date of Patent: Nov. 24, 2026

(54) OTIC FORMULATIONS FOR DRUG-INDUCED OTOTOXICITY

(71) Applicant: Spiral Therapeutics Inc., South San Francisco, CA (US)

(72) Inventors: Alan Foster, San Diego, CA (US); Fabrice Piu, San Diego, CA (US); Bonnie Elizabeth Jacques, San Diego, CA (US); Phillip Michael Uribe, San Diego, CA (US); Stephanie Szobota, San Diego, CA (US); Pranav Dinesh Mathur, San Diego, CA (US)

(73) Assignee: Spiral Therapeutics Inc., South San Francisco, CA (US)

( * ) Notice: Subject to any disclaimer, the term of this patent is extended or adjusted under 35 U.S.C. 154(b) by 631 days.

(21) Appl. No.: 17/772,727

(22) PCT Filed: Oct. 30, 2020

(86) PCT No.: PCT/US2020/058423
§ 371 (c)(1),
(2) Date: Apr. 28, 2022

(87) PCT Pub. No.: WO2021/087408
PCT Pub. Date: May 6, 2021

(65) Prior Publication Data

US 2023/0293524 A1 Sep. 21, 2023

Related U.S. Application Data

(60) Provisional application No. 62/928,196, filed on Oct. 30, 2019.

(51) Int. Cl.
*A61K 31/513* (2006.01)
*A61P 27/16* (2006.01)

(52) U.S. Cl.
CPC ............ *A61K 31/513* (2013.01); *A61P 27/16* (2018.01)

(58) Field of Classification Search
CPC .................................................... A61K 31/513
See application file for complete search history.

(56) References Cited

U.S. PATENT DOCUMENTS

| | | | | |
|---|---|---|---|---|
| 7,700,134 | B2 * | 4/2010 | Laurell | A61P 27/16 514/580 |
| 8,048,888 | B2 * | 11/2011 | Wosikowski-Buters | A61P 1/00 514/266.4 |
| 8,455,477 | B2 * | 6/2013 | Katz | A61P 43/00 514/233.2 |
| 11,065,360 | B2 | 7/2021 | Lin et al. | |
| 11,154,624 | B2 | 10/2021 | Campbell et al. | |
| 11,324,828 | B2 | 5/2022 | Sawhney et al. | |
| 12,251,466 | B2 | 3/2025 | Bassett et al. | |
| 2003/0180388 | A1 * | 9/2003 | Laurell | A61K 31/17 514/580 |
| 2005/0101534 | A1 * | 5/2005 | Zepp | A61P 27/16 514/19.2 |
| 2013/0045957 | A1 | 2/2013 | Piu et al. | |
| 2019/0298799 | A1 | 10/2019 | Lichter et al. | |

FOREIGN PATENT DOCUMENTS

| | | |
|---|---|---|
| WO | WO 2003/061574 | 7/2003 |
| WO | WO 2004/043447 | 5/2004 |
| WO | 2016020408 A3 | 11/2016 |
| WO | 2019157370 A1 | 8/2019 |

OTHER PUBLICATIONS

Principles of Pharmacology: Basic Concepts & Clinical Applications, Thiourylenes:, 1995, Chapman & Hall, pp. 802-805.*
Videhult, Experimental Biology and Medicine (Maywood, NJ, United States) (2006), 231(10), 1638-1645.*
Andersson, J. Fagerberg, R. Lewensohn and H. Ehrsson, Pharmacokinetics of cisplatin and its monohydrated complex in man, J. Pharm. Sci. 85 (1996) 824-827.*
Yachnina, The kinetics and cytotoxicity of cisplatin and its monohydrated Complex, Cancer Letters 132 (1998) 175-180.*
Wolff, Burger's medicinal Chemistry and Drug Discovery, vol. 1, Principles and Practice, John Wiley & sons, New York, 1997.*
West, Solid State Chemistry and Its Applications, john Wiley & Sons, 1984; Chapter 10.*
The Merck Manual, "Hearing LossandDeafness", 2007 http:/Avww.merck.com/mmhe/sec19/ch218/ch218a.htmi?qt=hearing%20loss&alt=sh,pp. 1-9of9.*
International Search Report and Written Opinion for PCT/US20/58423 dated Jan. 28, 2021, 9 pages.
Pubchem CID 4170383 Created Date: Sep. 13, 2005, Date Accessed: Dec. 28, 2020, p. 2.
Axelstad et al., "Developmental Neurotoxicity of Propylthiouracil (PTU) in rats: Relationship between between transient hypothyroxinemia during development and long-lasting behavioral and functional changes," Toxicology and Applied Pharamacology, Oct. 1, 2008, 232(1): 1-13.
Ekborn et al., "Intracochlear Administration of Thiourea Protects Against Cisplatin-Induced Outer Hair Cell Loss in the Guinea Pig, " Hearing Research, Elsevier Science Publishers, Jul. 1, 2003, 181(1/2): 109-115.
International Preliminary Report on Patentability in International Appln. No. PCT/US2020/058423, mailed on May 3, 2022, 8 pages.
Supplementary European Search Report in European Appln No. 20882822, dated Nov. 13, 2023, 18 pages.
Supplementary Partial European Search Report in European Appln No. 20882822, dated Jul. 7, 2023, 16 pages.

(Continued)

*Primary Examiner* — Nizal S Chandrakumar
(74) *Attorney, Agent, or Firm* — Fish & Richardson P.C.

(57) ABSTRACT

Provided herein are methods for preventing and/or reducing the severity of drug induced ototoxicity. Provided herein are methods for recovery from hearing loss due to drug-induced ototoxicity.

10 Claims, 21 Drawing Sheets

(56) References Cited

OTHER PUBLICATIONS

Tanabe et al., "A patient with sudden hearing loss induced by propylthiouracil," Feb. 1, 2021, 7(2): e06196.

Videhult et al., "Kinetics of Cisplatin and Its Monohydrated Complex with Sulfur-Containing Compounds Designed for Local Otoprotective Administration," Experimental Biology and Medicine, Nov. 1, 2006, 231(10), 8 pages.

Leeuwenkamp et al., "Reaction kinetics of cisplatin and its monoaquated species with the (potential) renal protecting agents (di)mesna and thiosulfate," Cancer Chemotherapy and Pharmacology, Mar. 1990, 27(2):111-114.

* cited by examiner

FIG. 8

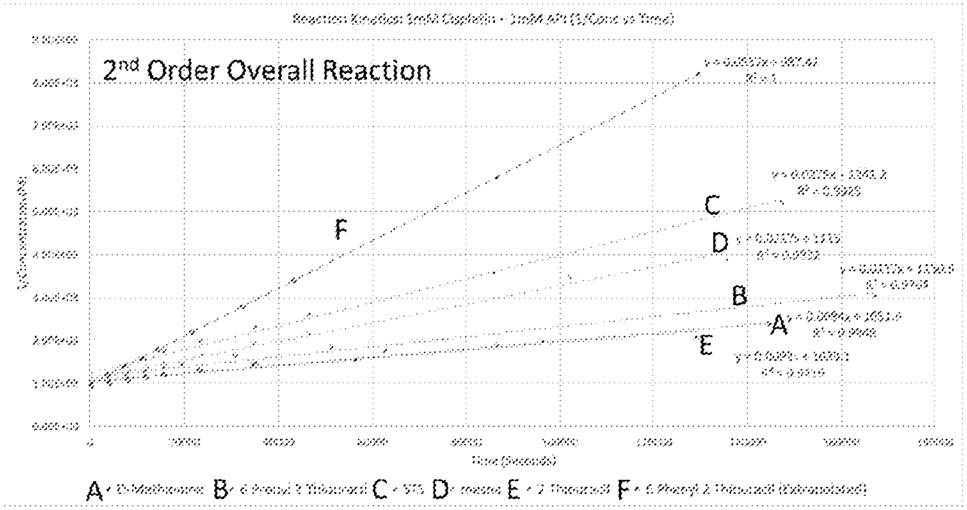

| Second-Order Reactions |
|---|
| Rate Law = $k[A]^2$ |
| Integrated Rate Law = $1/[A]_t = -kt + 1/[A]_0$ |
| k = slope ($L \cdot mol^{-1} S^{-1}$) |
| Half-Life = $1/(k[A]_0)$ |

| Sample | Initial pH | Final pH | k ($M^{-1}s^{-1}$) | Rate (M/s) | Half-Life (s) | Half-Life (hrs) |
|---|---|---|---|---|---|---|
| 1 mM Cis + 1 mM 6 Phenyl (Extrapolated) | 5.39 | 5.46 | 0.0536 | 5.50E-08 | 18422.0 | 5.1 |
| 1 mM Cisplatin + 1 mM STS (20C) | 5.17 | 8.51 | 0.0275 | 2.64E-08 | 37102.5 | 10.3 |
| 1 mM Cisplatin + 1 mM Mesna | 5.57 | NA | 0.0217 | 2.10E-08 | 46807.2 | 13.0 |
| 1 mM Cisplatin + 1 mM 6 Propyl Thiouracil | 5.02 | 3.62 | 0.0117 | 1.15E-08 | 86259.3 | 24.0 |
| 1 mM Cisplatin + 1 mM 2 Thiouracil | 5.67 | 5.36 | 0.0092 | 1.05E-08 | 101557.9 | 28.2 |
| 1 mM Cisplatin + 1 mM D-Methionine | 4.42 | 4.76 | 0.0094 | 9.30E-09 | 106932.4 | 29.7 |
| | | | | | | |
| 1 mM Cis + 1 mM STS (37C) | 7.05 | NA | 0.3212 | 3.06E-07 | 3.19E+03 | 0.89 |

*Autosampler was set at 20C, except for the last experiment which was at 37C

Perilymph

Cochlear Epithelium

Plasma
OMY-141 in Perilymph [ng/mL]
OMY-141 in Cochlear Epithelium [ng/g]
OMY-141 in Plasma [ng/mL]
1,000
100
10
1
0 1 2 3 4 5 6 7 8
Days post IT injection
Days Post IT injection
16 mg/mL in P407
50 mg/mL in P407
16 mg/mL in MCT
50 mg/mL in MCT
Background from naïve samples 6-Phenyl-2-thiouracil FIG. 13A
- Carboxythiouracil protects strial cells with similar affinity compared to phenyl and propyl.
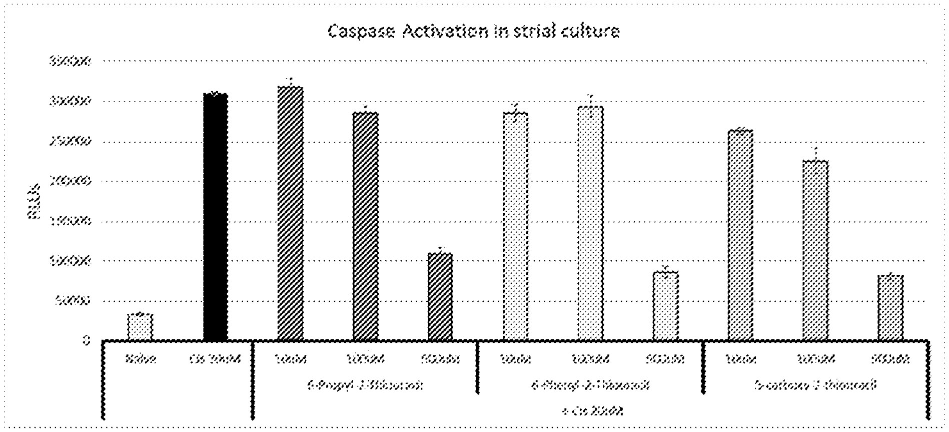
- HPLC study showed similar CIS binding affinity for Carboxythiouracil.
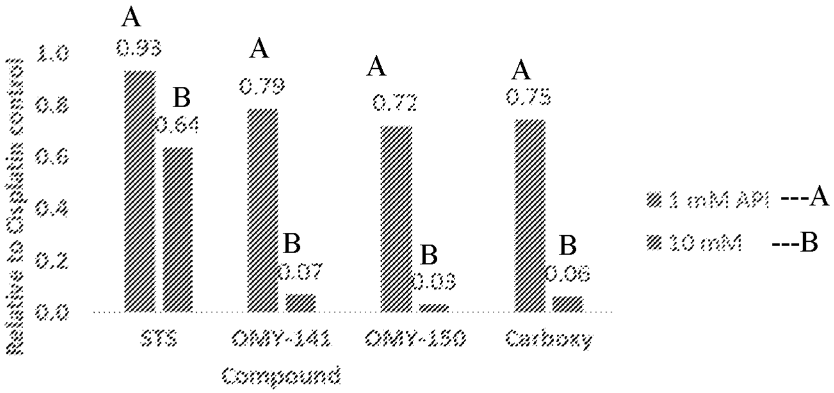
FIG. 13B

- Pooled data from 3 experiments (each dot represents a cochlea)
- Standard cisplatin explant protocol: p3 rat, 1.5hr API pretreat, 72hr cotreat API+ cisplatin
  - Cisplatin was from a new supplier (less potent) and adjusted from the historical 10uM to 12uM

- Significant, dose-dependent protection with OMY-150 in P407 (better than STS)
- No evidence of protection when OMY-150 formulated in MCT FIG. 20A
- Measured total platinum (Pt) using ICP-MS
Platinum Average mass (Da): 195.084
Analyte Mass Ranges (Da): 194-196
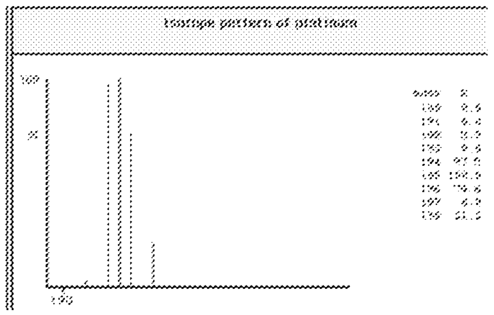
- Internal standard using Rhenium (Re)
Ru Average mass (Da): 187.95
Analyte Mass Ranges (Da): 185.00 -185.0
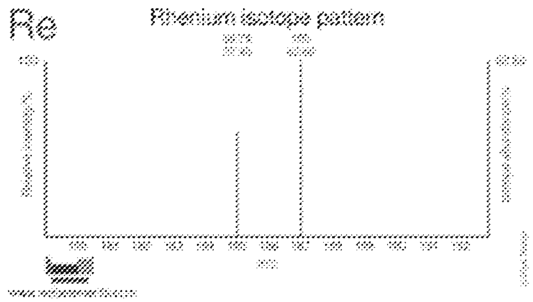
FIG. 20B

| CIS. 10 mg/kg | Plasma | Perilymph | Cochlear Epithelium |
|---|---|---|---|
| Cmax (ng/mL) | 16,478 | 744 | 699 |
| AUC$_{0-24h}$ (ng*hr/mL) | 116,660 | 2,020 | 14,454 |
| Tmax (hr) | 0.5 | 0.5 | 6.0 |
| AUC (ng*hr/mL) | 241,486 | 3,689 | 35,611 |
| T ½ (hr) | 22.2 | 16.1 | 89.9 |
| MRT (hr) | 25.3 | 24.4 | 31.6 |

| CIS. 12 mg/kg | Plasma | Perilymph | Cochlear Epithelium |
|---|---|---|---|
| Cmax (ng/mL) | 18,275 | 694 | 909 |
| Tmax (hr) | 0.5 | 0.5 | 6.0 |
| AUC$_{0-24h}$ (ng*hr/mL) | 154,809 | 3,156 | 18,121 |

OTIC FORMULATIONS FOR DRUG-INDUCED OTOTOXICITY

CROSS-REFERENCE

This application is a U.S. National Stage entry of PCT Application No. PCT/US2020/058423, filed Oct. 30, 2020, which claims the benefit of U.S. Provisional Application No. 62/928,196, filed Oct. 30, 2019, the contents of each of which are considered part of, and is incorporated by reference in their entirety.

BACKGROUND OF THE DISCLOSURE

The ear is generally divided into three portions: *Auris externa* (outer ear), *Auris media* (middle ear), and *Auris interna* (inner ear). Ototoxicity is a pharmacological adverse reaction affecting the inner ear or auditory nerve, characterized by cochlear and/or vestibular dysfunction. The effects of ototoxicity, which can be reversible or irreversible, include sensorineural hearing loss, dysequilibrium, or both.

There are over 600 categories of drugs that have the potential to cause ototoxicity, including certain antibiotics, loop diuretics, and platinum-based chemotherapy agents.

SUMMARY OF THE DISCLOSURE

Provided herein are compositions and methods for treating and/or preventing drug-induced ototoxicity and/or reversing hearing loss due to drug-induced ototoxicity. Ototoxicity is often a side effect of certain treatment regimens (e.g., chemotherapy, use of aminoglycoside antibiotics, salicylates or the like). In some embodiments, the methods provided herein allow for continued use of agents that would otherwise cause the side-effect of hearing loss and/or would be discontinued due to ototoxicity. Where ototoxicity is dose-limiting for a drug (e.g., a chemotherapeutic agent, an aminoglycoside antibiotic, or the like), the methods provided herein prevent onset of drug induced ototoxic side-effects, thereby allowing for use of higher doses of the drug and/or a better treatment outcome for a patient undergoing therapy with the ototoxic drug. In other embodiments, the methods provided herein allow for recovery of hearing in a patient who has already undergone treatment with an ototoxicity-inducing drug with the intent of recovering and/or reversing the hearing loss associated with previous regimen(s) of the ototoxic drug.

In an aspect, provided herein is a method of treating and/or preventing drug-induced ototoxicity, comprising administering to a subject in need thereof a pharmaceutical composition, comprising:

(i) an otoprotectant; and (ii) at least one pharmaceutically acceptable excipient or carrier, wherein the otoprotectant comprises at least one of: a thiopyrimidine, a thiopurine, a thiouracil, a thiouracil derivative, a thiourea, a thioamide, or a tautomer, prodrug, pharmaceutically acceptable salt, solvate, or hydrate thereof, and wherein the otoprotectant has a second order reaction rate of greater than 9.30E-09 M/s when reacting with cisplatin at about 20° C. In some embodiments, the reaction is measured at a concentration of about 1 mM cisplatin and 1 mM of the compounds disclosed herein.

In another aspect, provided herein is a method of treating and/or preventing drug-induced ototoxicity, comprising administering to a subject in need thereof a pharmaceutical composition, comprising:

(i) an otoprotectant; and (ii) at least one pharmaceutically acceptable excipient or carrier, wherein the otoprotectant comprises at least one of: a thiopyrimidine, a thiopurine, a thiouracil, a thiouracil derivative, a thiourea, a thioamide, or a tautomer, prodrug, pharmaceutically acceptable salt, solvate, or hydrate thereof, and wherein the otoprotectant has a rate constant (k) of at least about 0.001 when reacting with cisplatin.

In another aspect, provided herein is a method of treating and/or preventing drug-induced ototoxicity, comprising administering to a subject in need thereof a pharmaceutical composition, comprising:

(i) an otoprotectant; and (ii) at least one pharmaceutically acceptable excipient or carrier, wherein the otoprotectant comprises at least one of: a thiopyrimidine, a thiopurine, a thiouracil, a thiouracil derivative, a thiourea, a thioamide, or a tautomer, prodrug, pharmaceutically acceptable salt, solvate, or hydrate thereof, and wherein the otoprotectant has a rate constant (k) of at least about 0.07 when reacting with cisplatin.

In some embodiments, the rate constant is from about 0.01 to about 1.0. In some embodiments, the rate constant is about 0.01, about 0.02, about 0.03, about 0.04, about 0.05, about 0.06, about 0.07, about 0.08, about 0.09, about 0.1, about 0.2, about 0.3, about 0.5, about 0.6, about 0.7, about 0.9, or about 1.0.

In some embodiments, the rate constant of the otoprotectant is calculated with cisplatin comprises a stock solution of about 0.9% cisplatin in aqueous NaCl. In some embodiments, the rate constant of the otoprotectant is calculated with cisplatin comprises a stock solution of about 0.9% cisplatin in aqueous NaCl at pH of from about 4.0 to about 5.0. In some embodiments, the rate constant of the otoprotectant is calculated with cisplatin comprises a stock solution of about 0.9% cisplatin in aqueous NaCl at pH of from about 4.0 to about 5.0 and a temperature of from about 20° C. to about 30° C. In some embodiments, the rate constant of the otoprotectant is calculated with cisplatin comprises a stock solution of about 0.9% cisplatin in aqueous NaCl at pH of from about 4.0 to about 5.0 and a temperature of about 25° C.

In some embodiments, the rate constant of the otoprotectant is calculated with cisplatin comprises a stock solution of about 50 μM cisplatin in PBS. In some embodiments, the rate constant of the otoprotectant is calculated with cisplatin comprises a stock solution of about 50 μM cisplatin in PBS at a pH of from about 7.0 to about 8.0. In some embodiments, the rate constant of the otoprotectant is calculated with cisplatin comprises a stock solution of about 50 μM cisplatin in PBS at a pH of from about 7.0 to about 8.0 and a temperature of from about 30° C. to about 40° C. In some embodiments, the rate constant of the otoprotectant is calculated with cisplatin comprises a stock solution of about 50 μM cisplatin in PBS at a pH of from about 7.0 to about 8.0 and a temperature of about 37° C.

In an aspect there is provided, A method of treating and/or preventing drug-induced ototoxicity, comprising administering to a subject in need thereof a pharmaceutical composition, comprising:

(i) an otoprotectant; and (ii) at least one pharmaceutically acceptable excipient or carrier, wherein the otoprotectant comprises a thiouracil or a thiouracil derivative of structural Formula (III):

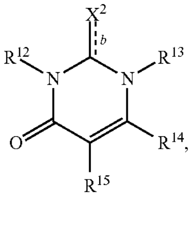

(III)

or a tautomer, prodrug, pharmaceutically acceptable salt, solvate, or hydrate thereof, wherein:

$X^2$ is S or $SR^{11}$;

$\underline{\overset{b}{- -}}$ is a single bond or double bond, wherein if $\underline{\overset{b}{- -}}$ is a single bond, then $X^2$ is $SR^{11}$, and if $\underline{\overset{b}{- -}}$ is a double bond, then $X^2$ is S; and $R^{11}$, $R^{12}$, $R^{13}$, $R^{14}$, and $R^{15}$ are each independently hydrogen, substituted or unsubstituted alkyl, substituted or unsubstituted alkenyl, substituted or unsubstituted alkynyl, substituted or unsubstituted alkylthio, imine, substituted or unsubstituted amine, hydroxyl, amide, cyano, isocyano, carbonyl, carboxyl, carboxamide, substituted or unsubstituted alkylsulfonyl, substituted or unsubstituted arylsulfonyl, ketone, aldehyde, substituted or unsubstituted ester, heteroalkyl, nitrile, amidine, acetal, ketal, substituted or unsubstituted cycloalkyl, substituted or unsubstituted heterocycloalkyl, substituted or unsubstituted aryl, substituted or unsubstituted heteroaryl, aziridine, carbamate, imide, urea, or thiourea.

In some embodiments, $\underline{\overset{b}{- -}}$ is a double bond and $X^2$ is S.

In some embodiments, $R^{12}$ is hydrogen, substituted or unsubstituted alkyl, or substituted or unsubstituted aryl.

In some embodiments, $R^{13}$ is hydrogen.

In some embodiments, $R^{14}$ is hydrogen, substituted or unsubstituted alkyl, substituted or unsubstituted aryl, or a carboxyl.

In some embodiments, $R^{15}$ is hydrogen or a $C_1$-$C_6$ ketone.

In some embodiments, the thiouracil is:

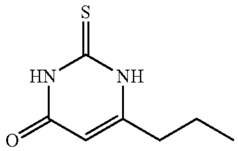,

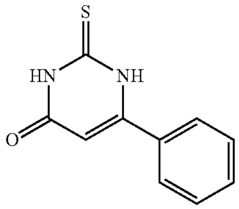, 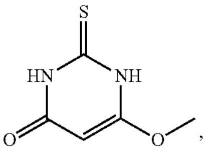,

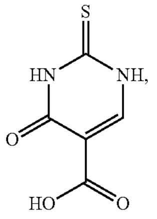 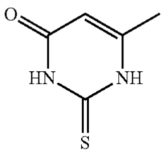, 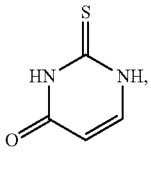

-continued

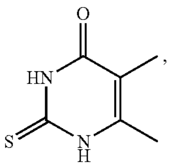, 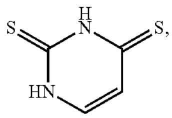

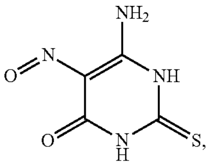 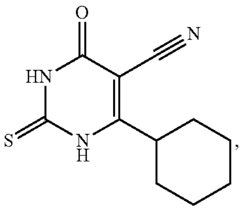,

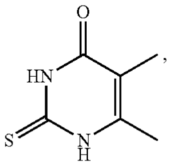, 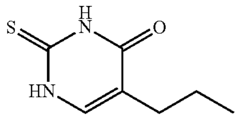,

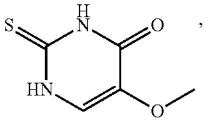, 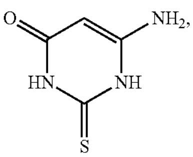

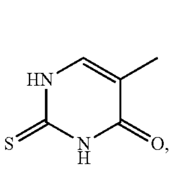 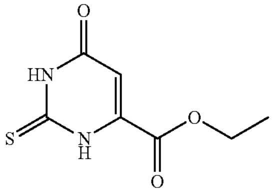,

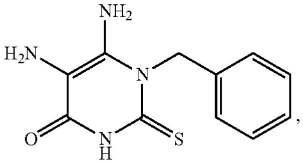,

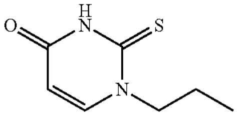, 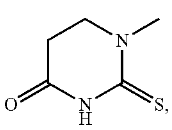

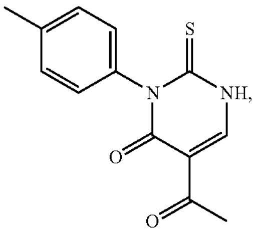 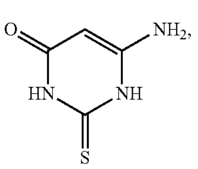 or

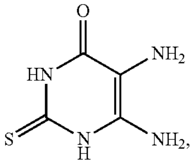

or a tautomer, prodrug, pharmaceutically acceptable salt, solvate, or hydrate thereof.

In some embodiments, the thiouracil is:

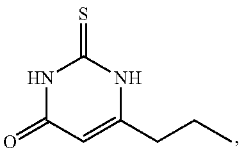

or a tautomer, prodrug, pharmaceutically acceptable salt, solvate, or hydrate thereof.

In some embodiments, the thiouracil is:

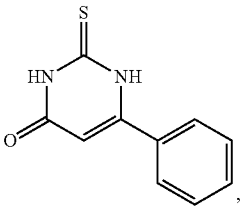 [SMILES: O=c1cc(-c2ccccc2)[nH]c(=S)[nH]1]

or a tautomer, prodrug, pharmaceutically acceptable salt, solvate, or hydrate thereof.

In some embodiments, the thiouracil is:

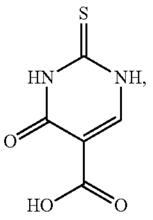 [SMILES: O=C(O)c1c[nH]c(=S)[nH]c1=O]

or a tautomer, prodrug, pharmaceutically acceptable salt, solvate, or hydrate thereof.

In some embodiments, the thiouracil is:

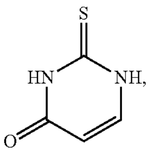

or a tautomer, prodrug, pharmaceutically acceptable salt, solvate, or hydrate thereof.

In some embodiments, the thiouracil is:

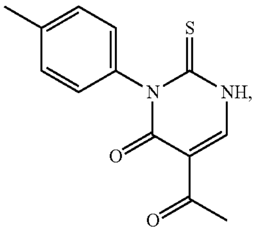 [SMILES: CC(=O)c1c[nH]c(=S)n(-c2ccc(C)cc2)c1=O]

or a tautomer, prodrug, pharmaceutically acceptable salt, solvate, or hydrate thereof.

In some embodiments, the thiouracil derivative is:

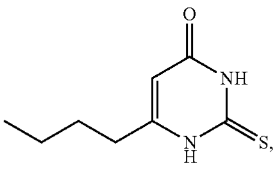
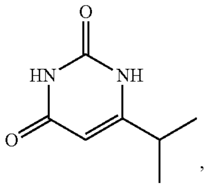
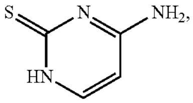
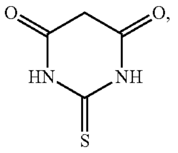
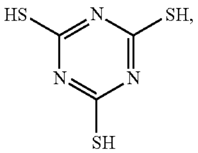
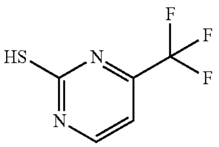
or
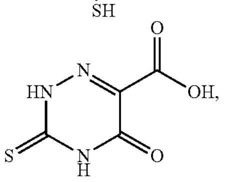

or a tautomer, prodrug, pharmaceutically acceptable salt, solvate, or hydrate thereof.

In some embodiments, the composition provides sustained release of the otoprotectant for a period of at least one (1) day after a single administration.

In some embodiments, the composition provides sustained release of the otoprotectant for a period of at least five (5) days after a single administration.

In some embodiments, the drug-induced ototoxicity comprises hearing loss.

In some embodiments, the drug-induced ototoxicity is chemotherapy-induced ototoxicity.

In some embodiments, the composition comprises a gel or a viscous preparation.

In some embodiments, the gel is a thermoreversible gel.

In some embodiments, the gel comprises a copolymer of polyoxyethylene and polyoxypropylene.

In some embodiments, the composition comprises from about 14 wt % to about 18 wt % of the copolymer of polyoxytheylene and polyoxypropylene.

In some embodiments, the gel has a gelation viscosity of from about 15,000 cP to about 3,000,000 cP.

In some embodiments, the composition further comprises at least one viscosity modulating agent.

In some embodiments, the at least one viscosity modulating agent is silicon dioxide, povidone, carbomer, poloxamer, or a combination thereof.

In some embodiments, the composition has a gelation temperature of from about 19° C. to about 42° C.

In some embodiments, the composition has an osmolarity from about 100 mOsm/L to about 1000 mOsm/L.

In some embodiments, the composition comprises triglycerides comprising medium chain fatty acids.

In some embodiments, the medium chain fatty acids are saturated medium chain fatty acids, unsaturated medium chain fatty acids, or any combinations thereof.

In some embodiments, the composition comprises at least about 50% by weight of the triglycerides.

In some embodiments, the otoprotectant is multiparticulate.

In some embodiments, the otoprotectant is essentially in the form of micronized particles.

In some embodiments, the otoprotectant is essentially dissolved in the composition.

In some embodiments, the composition further comprises an antioxidant, a mucoadhesive, a penetration enhancer, a preservative, a thickening agent, a viscosity modulator agent, a chelator, an antimicrobial agent, a dye, cholesterol, an excipient that increases the release rate of the otoprotectant, or an excipient that increases the release rate of the otoprotectant, or any combination thereof.

In some embodiments, the otoprotectant is not:

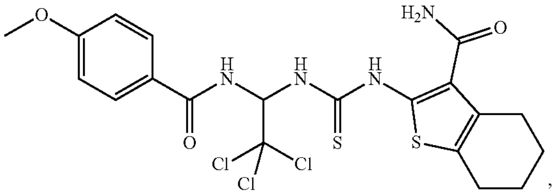
,

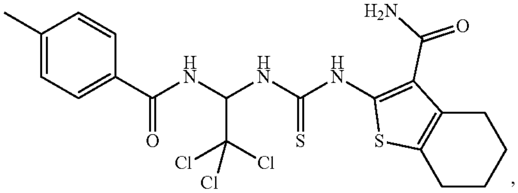
, or

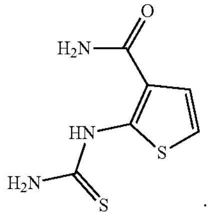
.

In some embodiments, the otoprotectant is not a compound of Formula (V):

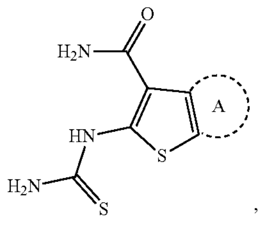
, wherein A is a 5-7 membered aryl, heteroaryl, or heterocycloalkyl optionally containing one more heteroatoms N, O, or S.

In some embodiments, the pharmaceutical composition and the ototoxic drug are administered simultaneously, approximately simultaneously, or sequentially, in any order.

In some embodiments, the pharmaceutical composition is administered at least one day after the ototoxic drug.

In some embodiments, the pharmaceutical composition is administered at least seven days after the ototoxic drug.

In some embodiments, the otoprotectant is formulated for intratympanic administration.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

FIG. 8 shows the reaction kinetics at 20° C. for various compounds of the present disclosure.

FIGS. 13A-13B show protection in strial cells and CIS-API binding affinity experiments. A: carboxythiouracil compared to phenyl and propyl; and B: HPLC study for CIS binding affinity for carboxythiouracil.

FIGS. 20A-20B show an analytical method for cisplatin. A: measured by ICP-MS; and B: internal standard using rhenium (Re).

DETAILED DESCRIPTION

Figure 1A:
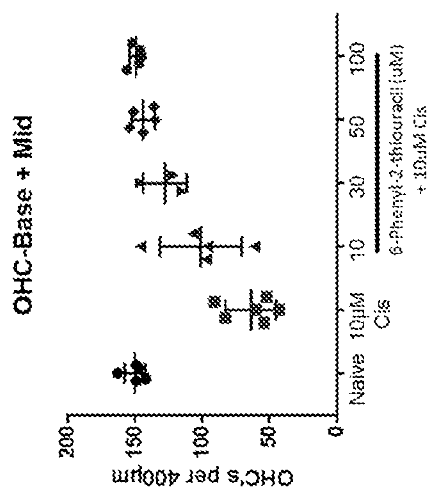
FIGS. 1A-1B show quantified graphs for outer hair cells (OHCs) (FIG. 1A) and spiral ganglion neurons (SGNs) (FIG. 1B), combined from base and mid region, showing complete protection of hair cells and spiral ganglion neurons against cisplatin in a cochlear explant model with 1.5 hour pretreatment followed by co-treatment of a thiopyrimidine compound (6-Phenyl-2-thiouracil) at different concentrations with 10 μM cisplatin.

A wide variety of drugs are ototoxic. Factors affecting ototoxicity include dose, duration of therapy, concurrent renal failure, infusion rate, lifetime dose, co-administration with other drugs having ototoxic potential, and/or genetic susceptibility. In cases where hearing loss is inevitable due to cumulative ototoxic exposures, patients need to be cognizant of the tradeoffs of potentially curative therapy versus permanent hearing loss. There is a need for treatment regimens that minimize this complication. Accordingly, provided herein are prophylactic methods and/or treatment regimens that prevent or delay onset of drug-induced ototoxicity and exert an otoprotective effect. Advantageously, the methods described herein comprise localized administration to the ear thereby avoiding interference with the therapeutic efficacy of the systemically administered ototoxicity-inducing drugs (e.g., chemotherapeutic drugs, aminoglycoside antibiotics and the like).

Ototoxicity and Inner Ear Damage

The inner ear comprises two parts: the osseous labyrinth and the membranous labyrinth. The vestibule, the semicircular canals and the cochlea form the osseous labyrinth. The osseous labyrinth is filled with the perilymph which also surrounds the soft tissue of the membranous labyrinth. The membranous labyrinth contains a series of closed sacs containing the endolymph.

The vestibule connects the cochlea in front with the semicircular canals at the back. The cochlea is a conical and spiraled structure located in the rostral part of the labyrinth. The cochlear duct is a single bony tube approximately 34 mm long in humans and spirals around a middle core that contains the spiral ganglion of the auditory nerve. The cochlear duct is divided into three chambers called *scalae*: the scala vestibule, the scala media and the scala tympani. The oval window touches the scala vestibule and the round window touches the scala tympani. The organ of *Corti* is the sensory epithelium of the cochlea and comprises rod-shaped cells, supporting cells, and hair cells.

Human ears contain about 17,000 hair cells: a single row of inner hair cells long the length of the cochlea and three rows of outer hair cells extending from the base to the apex of the cochlea. The distribution of receptor cells in the ear is sparse when compared to other sensory organs such as the retina or nasal epithelium; hence the loss of even a few thousand hair cells results in severe hearing loss. Any cochleo-vestibular ototoxicity affects hair cells profoundly; humans cannot regenerate hair cells and once a cochlear hair cell is damaged, the reduction in hearing is permanent. Accordingly, provided herein are methods that protect hair cells and/or prevent ototoxic damage to hair cells. Further provided herein are methods that allow for recovery of hearing following hearing loss and/or inner ear damage.

Ototoxicity Inducing Drugs

Platinum Based Chemotherapeutic Agents

Platinum based compounds are commonly used as antineoplastic agents. Examples of platinum based chemotherapeutic agents include cisplatin, carboplatin or oxiplatin. Other platinum based chemotherapeutic agents include the bis-platinates. Examples of bis-platinates include and are not limited to CT-47613 and CT-47609.

Platinum-based drugs induce ototoxicity which manifests as sensorineural hearing loss with or without tinnitus. For example, children with neuroblastoma receive high-dose carboplatin as part of their conditioning regimen for autologous marrow transplantation and have a high incidence of speech frequency hearing loss. Ototoxicity is dose-related and cumulative. When ototoxicity develops, treatment of cancer with platinum-based drugs is stopped, or a less potent antineoplastic agent is used. This affects treatment outcome for cancer patients. There is currently no treatment available for platinum-based chemotherapeutic-induced ototoxicity. Attempts to co-administer systemic antioxidants with cisplatin treatment have not been successful because the antioxidants inhibit the antineoplastic effect of cisplatin or exhibit toxicities of their own. See for example, Rybak et Al., Drug Disc. Today 2005, 10:1313-21.

Accordingly provided herein are methods for pretreatment of cancer patients in need of carboplatin and/or cisplatin and/or oxiplatin therapy comprising administration of an intratympanic injection of a composition comprising a thermoreversible gel and an otoprotectant such that the composition exerts an otoprotective effect and prevents ototoxicity induced by platinum-containing chemotherapeutic agents. In some of such embodiments, the composition provides sustained release of the otoprotectant into the cochlea for at least 5 days after a single administration.

Other Anticancer Agents

Other anticancer drugs that cause ototoxicity at high doses include, for example, vincristine. Accordingly, also contemplated within the scope of embodiments presented herein are methods for preventing ototoxicity in individuals in need of chemotherapy (e.g., vincristine treatment) comprising administration of an intratympanic injection of a composition comprising a thermoreversible gel and an otoprotectant such that the composition exerts an otoprotective effect and prevents ototoxicity.

Aminoglycoside Antibiotics

Certain aminoglycoside antibiotics are associated with ototoxic side effects. Streptomycin causes damage to the vestibular portion of the inner ear. Although vertigo and difficulty maintaining balance tend to be temporary, severe loss of vestibular sensitivity persists, sometimes permanently. Loss of vestibular sensitivity causes difficulty walking, especially in the dark, and oscillopsia (a sensation of bouncing of the environment with each step). About 4 to 15% of patients who receive 1 g/day for >1 wk develop measurable hearing loss, which usually occurs after a short latent period (7 to 10 days) and slowly worsens if treatment is continued. Complete, permanent deafness may follow.

Neomycin, kanamycin and amikacin are cochleotoxic and cause profound, permanent hearing loss while sparing balance. Viomycin has both cochlear and vestibular toxicity. Gentamicin and tobramycin cause vestibular and cochlear toxicity, causing impairment in balance and hearing. The aminoglycoside Vancomycin causes hearing loss, often in the presence of renal insufficiency.

Aminoglycoside ototoxicity causes irreversible damage to the outer hair cells at the basal turn of the cochlea. There is currently no treatment available for aminoglycoside ototoxicity. Accordingly provided herein are methods for preventing ototoxicity in individuals in need of treatment with aminoglycoside antibiotics comprising administration of an intratympanic injection of a composition comprising a thermoreversible gel and an otoprotectant such that the composition exerts an otoprotective effect and prevents ototoxicity induced by an aminoglycoside antibiotic. In some of such embodiments, the composition provides sustained release of the otoprotectant into the cochlea for at least 5 days after a single administration.

Other Antibiotics

Erythromycin, azithromycin and clindamycin are macrolide antibiotics that cause hearing loss in some individuals. Accordingly, also contemplated within the scope of embodiments presented herein are methods for preventing ototoxicity in individuals in need of treatment with antibiotics that induce ototoxicity comprising administration of an intratympanic injection of a composition comprising a thermoreversible gel and an otoprotectant such that the composition exerts an otoprotective effect and prevents ototoxicity induced by the drug.

Diuretics and Salicylates

Certain diuretics such as ethacrynic acid and furosemide cause profound and permanent hearing loss. Salicylates in high doses and the antimalarial drug quinine are also associated with temporary hearing loss. Accordingly, also contemplated within the scope of embodiments presented herein are methods for preventing ototoxicity in individuals in need of treatment with diuretics (including loop diuretics), salicylates and/or any other ototoxic agent comprising administration of an intratympanic injection of a composition comprising a thermoreversible gel and an otoprotectant such that the composition exerts an otoprotective effect and prevents ototoxicity induced by the drug.

Radiation-Induced Ototoxicity

Also provided herein are prophylactic methods and/or treatment regimens that prevent or delay onset of radiation-induced ototoxicity and exert an otoprotective effect. Also provided herein are methods for preventing hearing loss due to radiation-induced ototoxicity.

Radiation therapy is a type of cancer treatment that uses high-energy radiation, such as X-rays, gamma rays and charged particles, to shrink tumors and kill cancer cells. External-beam radiation therapy is when radiation is delivered by a machine outside the body. External-beam radiation therapy is most often delivered in the form of photon beams (either x-rays or gamma rays). Examples of external-beam radiation therapy include, but are not limited to, three-dimensional conformal radiation therapy (3D-CRT), which delivers radiation beams from different directions designed to match the shape of the tumor; image guided radiation therapy (IGRT), which is a form of 3D-CRT where imaging scans (like a CT scan) are done before each treatment; intensity modulated radiation therapy (IMRT), which is similar to 3D-CRT, but it also changes the strength of some of the beams in certain areas; and helical-tomotherapy; which is a form of IMRT delivers radiation inside a large “donut”. Photon beam radiation therapy is another name for what is traditionally known as external beam radiation therapy and refers to the use of photon beams to get to the tumor. Photons are generated by a linear accelerator. Proton beam radiation therapy uses proton beams instead of photons or electrons. Protons are parts of atoms that cause little damage to the tissues they pass through but are very good at killing cells at the end of their path. Protons are generated by a cyclotron or synchrotron. Stereotactic radiosurgery is a type of radiation treatment that gives a large dose of radiation to a small tumor area and is usually used for brain tumors. Once the exact location of the tumor is known from brain scans, radiation is sent to the area from many different angles. The radiation is very precisely aimed to affect nearby tissues as little as possible. Stereotactic body radiation therapy (SBRT) refers to treatment areas outside of the brain, such as lung, spine, and liver. Intraoperative radiation therapy (IORT) is external radiation given directly to the tumor or tumors during surgery.

In other instances, radiation is delivered internally by placing radioactive material in the body near cancer cells (internal radiation therapy, also called brachytherapy). Interstitial brachytherapy uses a radiation source placed within tumor tissue while intracavitary brachytherapy uses a source placed within a surgical cavity or a body cavity. Episcleral brachytherapy is a specific type of therapy used to treat melanoma inside the eye and requires a source that is attached to the eye. Brachytherapy uses radioactive isotopes that are sealed in tiny pellets and are placed in patients using suitable delivery devices, such as needles, catheters, or some other type of carrier. As the isotopes decay naturally, radiation is emitted and causes damage to nearby cancer cells. In addition, brachytherapy is administered at a low-dose-rate or a high-dose-rate treatment. In low-dose-rate treatment, cancer cells receive continuous low-dose radiation from the source over a period of several days. In high-dose-rate treatment, one or more radioactive sources are placed inside of the body and into or near a tumor and are removed at the end of each treatment session. High-dose-rate treatment is administered in one or more treatment sessions. The placement of brachytherapy sources is either temporary or permanent. For permanent brachytherapy, the sources are surgically sealed within the body and are not removed, even after all of the radiation has been given off Permanent brachytherapy is a type of low-dose-rate brachytherapy. For temporary brachytherapy, tubes (catheters) or other carriers are used to deliver the radiation sources, and both the carriers and the radiation sources are removed after treatment. Temporary brachytherapy can be either low-dose-rate or high-dose-rate treatment.

Another type of radiation therapy is systemic radiation therapy, where radioactive drugs given by mouth or put into a vein are used to treat certain types of cancer. These drugs then travel throughout the body.

About half of all cancer patients receive some type of radiation therapy sometime during the course of their treatment. In some instances, radiation therapy causes hair cell damage resulting in permanent hearing loss.

In some embodiments, the radiation-induced ototoxicity is from external-beam radiation therapy. In some embodiments, the radiation-induced ototoxicity is from three-dimensional conformal radiation therapy (3D-CRT). In some embodiments, the radiation-induced ototoxicity is from image guided radiation therapy (IGRT). In some embodiments, the radiation-induced ototoxicity is from intensity modulated radiation therapy (IMRT). In some embodiments, the radiation-induced ototoxicity is from helical-tomotherapy. In some embodiments, the radiation-induced ototoxicity is from photon beam radiation therapy. In some embodiments, the radiation-induced ototoxicity is from proton beam radiation therapy. In some embodiments, the radiation-induced ototoxicity is from stereotactic radiosurgery. In some embodiments, the radiation-induced ototoxicity is from stereotactic body radiation therapy (SBRT). In some embodiments, the radiation-induced ototoxicity is from intraoperative radiation therapy (IORT).

In some embodiments, the radiation-induced ototoxicity is from internal radiation therapy. In some embodiments, the internal radiation therapy is intracavitary radiation. In some embodiments, the internal radiation therapy is interstitial radiation. In some embodiments, the radiation-induced ototoxicity is from low dose rate internal radiation therapy. In some embodiments, the radiation-induced ototoxicity is from high dose rate internal radiation therapy. In some embodiments, the radiation-induced ototoxicity is from permanent internal radiation therapy. In some embodiments, the radiation-induced ototoxicity is from temporary internal radiation therapy.

In some embodiments, the radiation-induced ototoxicity is from systemic radiation therapy.

Certain Definitions

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, (cyclohexyl) methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, $—CH_2CH_2CH_2CH_2—$. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., N, S, Si, or P) may be placed at any interior position of the heteroalkyl group or at the position at which the alkyl group is attached to the remainder of the molecule. Heteroalkyl is an uncyclized chain. Examples include, but are not limited to: $—CH_2—CH_2—O—CH_3$, $—CH_2—CH_2—NH—CH_3$, $—CH_2—CH_2—N(CH_3)—CH_3$, $—CH_2—S—CH_2—CH_3$, $—CH_2—CH_2$, $—S(O)—CH_3$, $—CH_2—CH_2—S(O)_2—CH_3$, $—CH{=}CH—O—CH_3$, $—Si(CH_3)_3$, $—CH_2—CH{=}N—OCH_3$, $—CH{=}CH—N(CH_3)—CH_3$, $—O—CH_3$, $—O—CH_2—CH_3$, and —CN. Up to two or three heteroatoms may be consecutive, such as, for example, $—CH_2—NH—OCH_3$ and $—CH_2—O—Si(CH_3)_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P).

Similarly, the term "heteroalkylene," by itself or as part of another substituent, means, unless otherwise stated, a divalent radical derived from heteroalkyl, as exemplified, but not limited by, $—CH_2—CH_2—S—CH_2—CH_2—$ and $—CH_2—S—CH_2—CH_2—NH—CH_2—$. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula $—C(O)_2R'—$ represents both $—C(O)_2R'—$ and $—R'C(O)_2—$. As described above, heteroalkyl groups, as used herein, include those groups that are attached to the remainder of the molecule through a heteroatom, such as —C(O)R', —C(O)NR', —NR'R", —OR', —SR', and/or $—SO_2R'$. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. "Cycloalkyl" is also meant to refer to bicyclic and polycyclic hydrocarbon rings such as, for example, bicyclo[2.2.1]heptane, bicyclo[2.2.2]octane, etc.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "" denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

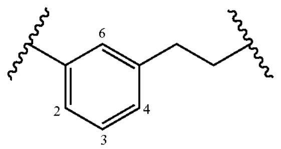

or

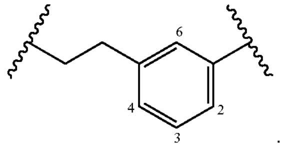

.

An alkylarylene moiety may be substituted (e.g. with a substituent group) on the alkylene moiety or the arylene linker (e.g. at carbons 2, 3, 4, or 6) with halogen, oxo, $—N_3$, $—CF_3$, $—CCl_3$, $—CBr_3$, $—CI_3$, —CN, —CHO, —OH, $—NH_2$, —COOH, $—CONH_2$, $—NO_2$, —SH, $—SO_2CH_3$ $—SO_3H$, $—OSO_3H$, $—SO_2NH_2$, $—NHNH_2$, $—ONH_2$, $—NHC(O)NHNH_2$, substituted or unsubstituted $C_1$-$C_5$ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R"', —OC(O)R', —C(O)R', $—CO_2R'$, —CONR'R", —OC(O)NR'R", —NR"C(O)R', —NR'—C(O)NR"R"', $—NR"C(O)_2R'$, —NR—C(NR'R"R"')=NR"", —NR—C(NR'R")=NR"', —S(O)R', $—S(O)_2R'$, $—S(O)_2NR'R"$, $—NRSO_2R'$, —NR'NR"R"', —ONR'R", —NR'C(O)NR"NR"'R"", —CN, $—NO_2$, $—NR'SO_2R"$, —NR'C(O)R", —NR'C(O)—OR", —NR'OR", in a number ranging from zero to (2m'+1), where m' is the total number of carbon atoms in such radical. R, R', R", R"', and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R'', R''', and R'''' group when more than one of these groups is present. When R' and R'' are attached to the same nitrogen atom, they can be combined with the nitrogen atom to form a 4-, 5-, 6-, or 7-membered ring. For example, —NR'R'' includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., $—CF_3$ and $—CH_2CF_3$) and acyl (e.g., $—C(O)CH_3$, $—C(O)CF_3$, $—C(O)CH_2OCH_3$, and the like).

Similar to the substituents described for the alkyl radical, substituents for the aryl and heteroaryl groups are varied and are selected from, for example: —OR', —NR'R'', —SR', -halogen, —SiR'R''R''', —OC(O)R', —C(O)R', $—CO_2R'$, —CONR'R'', —OC(O)NR'R'', —NR''C(O)R', —NR'—C(O)NR''R''', $—NR''C(O)_2R'$, —NR—C(NR'R''R''')═NR'''', —NR—C(NR'R'')═NR''', —S(O)R', $—S(O)_2R'$, $—S(O)_2NR'R''$, $—NRSO_2R'$, —NR'NR''R''', —ONR'R'', —NR'C(O)NR''NR'''R'''', —CN, $—NO_2$, —R', $—N_3$, $—CH(Ph)_2$, fluoro($C_1$-$C_4$)alkoxy, and fluoro($C_1$-$C_4$)alkyl, $—NR'SO_2R''$, —NR'C(O)R'', —NR'C(O)—OR'', —NR'OR'', in a number ranging from zero to the total number of open valences on the aromatic ring system; and where R', R', R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R'', R''', and R'''' groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula $-T-C(O)—(CRR')_q—U—$, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula $-A-(CH_2)_r—B—$, wherein A and B are independently —CRR'—, —O—, —NR—, —S—, —S(O)—, $—S(O)_2—$, $—S(O)_2NR'—$, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula $—(CRR')_s—X'—(C''R''R''')_d—$, where s and d are independently integers of from 0 to 3, and X' is —O—, —NR'—, —S—, —S(O)—, $—S(O)_2—$, or $—S(O)_2NR'—$. The substituents R, R', R'', and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, $—CF_3$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC═(O)NHNH_2$, $—NHC═(O) NH_2$, $—NHSO_2H$, —NHC═(O)H, —NHC(O)—OH, —NHOH, $—OCF_3$, $—OCHF_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:

(i) oxo, halogen, $—CF_3$, —CN, —OH, $—NH_2$, —COOH, $—CONH_2$, $—NO_2$, —SH, $—SO_3H$, $—SO_4H$, $—SO_2NH_2$, $—NHNH_2$, $—ONH_2$, $—NHC═(O)NHNH_2$, $—NHC═(O) NH_2$, $—NHSO_2H$, —NHC═(O)H, —NHC(O)—OH, —NHOH, $—OCF_3$, $—OCHF_2$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, heteroaryl, substituted with at least one substituent selected from:

(a) oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O) $NH_2$, —$NHSO_2H$, —NHC═(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, heteroaryl, substituted with at least one substituent selected from: oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O) $NH_2$, —$NHSO_2H$, —NHC═(O)H, —NHC(O)—OH, —NHOH, —$OCF_3$, —$OCHF_2$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those that are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^{3}H$), iodine-125 ($^{125}I$), or carbon-14 ($^{14}C$). All isotopic variations of the compounds of the present invention, whether radioactive or not, are encompassed within the scope of the present invention.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

A "detectable moiety" as used herein refers to a moiety that can be covalently or noncovalently attached to a compound or biomolecule that can be detected for instance, using techniques known in the art. In embodiments, the detectable moiety is covalently attached. The detectable moiety may provide for imaging of the attached compound or biomolecule. The detectable moiety may indicate the contacting between two compounds. Exemplary detectable moieties are fluorophores, antibodies, reactive dies, radiolabeled moieties, magnetic contrast agents, and quantum dots. Exemplary fluorophores include fluorescein, rhodamine, GFP, coumarin, FITC, Alexa fluor, Cy3, Cy5, BODIPY, and cyanine dyes. Exemplary radionuclides include Fluorine-18, Gallium-68, and Copper-64. Exemplary magnetic contrast agents include gadolinium, iron oxide and iron platinum, and manganese.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "*auris*-acceptable" with respect to a formulation, composition or ingredient, as used herein, includes having no persistent detrimental effect on the *Auris externa* (or external ear or outer ear), *Auris media* (or middle ear) and/or the *Auris interna* (or inner ear) of the subject being treated. By "*auris*-pharmaceutically acceptable," as used herein, refers to a material, such as a carrier or diluent, which does not abrogate the biological activity or properties of the compound in reference to the *Auris externa* (or external ear or outer ear), *Auris media* (or middle ear) and/or the *Auris interna* (or inner ear), and is relatively or is reduced in toxicity to the *Auris externa* (or external ear or outer ear), *Auris media* (or middle ear) and the *Auris interna* (or inner ear), i.e., the material is administered to an individual without causing undesirable biological effects or interacting in a deleterious manner with any of the components of the composition in which it is contained.

As used herein, amelioration or lessening of the symptoms of a particular otic disease, disorder or condition by administration of a particular compound or pharmaceutical composition refers to any decrease of severity, delay in onset, slowing of progression, or shortening of duration, whether permanent or temporary, lasting or transient that is attributed to or associated with administration of the compound or composition.

As used herein, the term "antimicrobial agent" refers to compounds that inhibit the growth, proliferation, or multiplication of microbes, or that kill microbes. Suitable "antimicrobial agents" are antibacterial agents (effective against bacteria), antiviral agents (effective against viruses), antifungal agents (effective against fungi), antiprotozoal (effective against protozoa), and/or antiparasitic to any class of microbial parasites. "Antimicrobial agents" work by any suitable mechanism against the microbes, including by being toxic or cytostatic.

"Antioxidants" are *auris*-pharmaceutically acceptable antioxidants, and include, for example, butylated hydroxytoluene (BHT), sodium ascorbate, ascorbic acid, sodium metabisulfite and tocopherol. In certain embodiments, antioxidants enhance chemical stability where required. Antioxidants are also used to counteract the ototoxic effects of certain therapeutic agents.

The term "*auris*-acceptable penetration enhancer" with respect to a formulation, composition or ingredient, as used herein, refers to the property of reducing barrier resistance.

"*Auris externa*" refers to the external (or outer) ear and includes the pinna and the external auditory canal (EAC).

"*Auris interna*" refers to the inner ear, including the cochlea and the vestibular labyrinth, and the round window that connects the cochlea with the middle ear.

"*Auris*-interna bioavailability" or "*Auris media* bioavailability" refers to the percentage of the administered dose of compounds disclosed herein that becomes available in the inner or middle ear, respectively, of the animal or human being studied.

"*Auris media*" refers to the middle ear, including the tympanic cavity, auditory ossicles and oval window, which connects the middle ear with the inner ear.

"*Auris*-interna bioavailability" refers to the percentage of the administered dose of compounds disclosed herein that becomes available in the inner ear of the animal or human being studied.

As used herein, the term "administering" means parenteral or enteral administration. Accordingly, as used herein, "administering" refers to administration including, but not limited to, oral administration, administration as a suppository, topical contact, intravenous, intraperitoneal, intramuscular, inhalation, nebulization, intralesional, intrathecal, intracranial, intranasal, subcutaneous administration, or the implantation of a slow-release device, e.g., a mini-osmotic pump, to a subject. Administration is by any route, including transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, by ocular route, by otic route, etc. By "co-administer" it is meant that a composition described herein is administered at the same time, just prior to, or just after the administration of one or more additional therapies (e.g., otoprotectant and/or chemotherapeutic agent). The compound of the invention can be administered alone or can be co-administered to the patient. Co-administration is meant to include simultaneous, approximately simultaneous, or sequential administration of the compound individually or in combination (more than one compound or agent). Thus, the preparations can also be combined, when desired, with other active substances (e.g., to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., *Gao Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered using liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J Microencapsul.* 13:293-306, 1996*; Chonn, Curr. Opin. Biotechnol.* 6:698-708, 1995*; Ostro, Am. J Hosp. Pharm.* 46:1576-1587, 1989). The compositions of the present invention can also be delivered as nanoparticles.

"Blood plasma concentration" refers to the concentration of compounds provided herein in the plasma component of blood of a subject.

"Carrier materials" are excipients that are compatible with the otic agent, the *Auris media*, the *Auris interna* and the release profile properties of the *auris*-acceptable pharmaceutical formulations. Such carrier materials include, e.g., binders, suspending agents, disintegration agents, filling agents, surfactants, solubilizers, stabilizers, lubricants, wetting agents, diluents, and the like. "*Auris*-pharmaceutically compatible carrier materials" include, but are not limited to, acacia, gelatin, colloidal silicon dioxide, calcium glycerophosphate, calcium lactate, maltodextrin, glycerine, magnesium silicate, polyvinylpyrrolidone (PVP), cholesterol, cholesterol esters, sodium caseinate, soy lecithin, taurocholic acid, phosphatidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, alginate, carbomer, hyaluronic acid (HA), poloxamer, dextran, and the like.

The term "diluent" are chemical compounds that are used to dilute the otic agent prior to delivery and which are compatible with the *Auris media* and/or *Auris interna.*

"Dispersing agents," "viscosity modulating agents," and/or "thickening agents" are materials that control the diffusion and homogeneity of the otic agent through liquid media. Examples of diffusion facilitators/dispersing agents include but are not limited to hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, HPMC E10M, and HPMC K100M), carboxymethylcellulose, carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), noncrystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, F108®, and F127®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol has a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans, silicon dioxide, and combinations thereof. Plasticizers such as cellulose or triethyl cellulose are also be used as dispersing agents. Optional dispersing agents useful in liposomal dispersions and self-emulsifying dispersions of the otic agents disclosed herein are dimyristoyl phosphatidyl choline, natural phosphatidyl choline from eggs, natural phosphatidyl glycerol from eggs, cholesterol, and isopropyl myristate. In some embodiments, the "dispersing agent," and/or "viscosity modulating agent" and/or "thickening agent" is not a poloxamer.

"Drug absorption" or "absorption" refers to the process of movement of the otic agent from the localized site of administration, by way of example only, the round window membrane of the inner ear, and across a barrier (the round window membranes, as described below) into the *Auris interna* or inner ear structures. The terms "co-administration" or the like, as used herein, are meant to encompass administration of the otic agent to a single patient and are intended to include treatment regimens in which the otic agents are administered by the same or different route of administration or at the same or different time.

The terms "effective amount" or "therapeutically effective amount," as used herein, refer to a sufficient amount of the otic agent being administered that would be expected to relieve to some extent one or more of the symptoms of the disease or condition being treated. For example, the result of administration of the otic agents disclosed herein is reduction and/or alleviation of the signs, symptoms, or causes of any one of the diseases or conditions disclosed herein. For example, an "effective amount" for therapeutic uses is the amount of the otic agent, including a formulation as disclosed herein required to provide a decrease or amelioration in disease symptoms without undue adverse side effects. The term "therapeutically effective amount" includes, for example, a prophylactically effective amount. An "effective amount" of an otic agent composition disclosed herein is an amount effective to achieve a desired pharmacologic effect or therapeutic improvement without undue adverse side effects. It is understood that "an effective amount" or "a therapeutically effective amount" varies, in some embodiments, from subject to subject, due to variation in metabolism of the compound administered, age, weight, general condition of the subject, the condition being treated, the severity of the condition being treated, and the judgment of the prescribing physician. In some instances, it is also understood that "an effective amount" in an extended-release dosing format differs from "an effective amount" in an immediate-release dosing format based upon pharmacokinetic and pharmacodynamic considerations.

The terms "enhance" or "enhancing" refers to an increase or prolongation of either the potency or duration of a desired effect of the otic agent, or a diminution of any adverse symptomatology. For example, in reference to enhancing the effect of the otic agents disclosed herein, the term "enhancing" refers to the ability to increase or prolong, either in potency or duration, the effect of other therapeutic agents that are used in combination with the otic agents disclosed herein. An "enhancing-effective amount," as used herein, refers to an amount of an otic agent or other therapeutic agent that is adequate to enhance the effect of another therapeutic agent or otic agent in a desired system. When used in a patient, amounts effective for this use will depend on the severity and course of the disease, disorder or condition, previous therapy, the patient's health status and response to the drugs, and the judgment of the treating physician.

The term "inhibiting" includes preventing, slowing, or reversing the development of a condition, including any of one of the conditions described herein, or advancement of a condition in a patient necessitating treatment.

The terms "kit" and "article of manufacture" are used as synonyms.

As used herein, the term "otic agent" or "otic structure modulating agent" or "otic therapeutic agent" or "otic active agent" or "active agent" or "therapeutic agent" refers to compounds that are effective for the treatment of otic disorders disclosed herein and are suitable for use in the formulations disclosed herein. An "otic agent" or "otic structure modulating agent" or "otic therapeutic agent" or "otic active agent" or "active agent" includes, but is not limited to, compounds that act as an agonist, a partial agonist, an antagonist, a partial antagonist, an inverse agonist, a competitive antagonist, a neutral antagonist, an orthosteric antagonist, an allosteric antagonist, a positive allosteric modulator of an otic structure modulating target, a negative allosteric modulator of an otic structure modulating target, or combinations thereof.

The term "otic intervention" means an external insult or trauma to one or more *auris* structures and includes implants, otic surgery, injections, cannulations, or the like. Implants include *auris*-interna or *auris*-media medical devices, examples of which include cochlear implants, hearing sparing devices, hearing-improvement devices, short electrodes, micro-prostheses or piston-like prostheses; needles; stem cell transplants; drug delivery devices; any cell-based therapeutic; or the like. Otic surgery includes middle ear surgery, inner ear surgery, tympanostomy, cochleostomy, labyrinthotomy, mastoidectomy, stapedectomy, stapedotomy, endolymphatic sacculotomy, or the like. Injections include intratympanic injections, intracochlear injections, injections across the round window membrane or the like. Cannulations include intratympanic, intracochlear, endolymphatic, perilymphatic or vestibular cannulations, or the like.

The term "penetration enhancer" refers to an agent that reduces barrier resistance (e.g., barrier resistance of the round window membrane, BLB or the like).

"Pharmacodynamics" refers to the factors which determine the biologic response observed relative to the concentration of drug at the desired site within the *Auris media* and/or *Auris interna.*

"Pharmacokinetics" refers to the factors which determine the attainment and maintenance of the appropriate concentration of drug at the desired site within the *Auris media* and/or *Auris interna.*

In prophylactic applications, compositions containing the otic agents described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like.

A "prodrug" refers to the otic agent that is converted into the parent drug in vivo. In certain embodiments, a prodrug is enzymatically metabolized by one or more steps or processes to the biologically, pharmaceutically or therapeutic form of the compound. To produce a prodrug, a pharmaceutically active compound is modified such that the active compound will be regenerated upon in vivo administration. In one embodiment, the prodrug is designed to alter the metabolic stability or the transport characteristics of a drug, to mask side effects or toxicity, or to alter other characteristics or properties of a drug. Compounds provided herein, in some embodiments, are derivatized into suitable prodrugs.

"Solubilizers" refers to *auris*-acceptable compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, Transcutol®, propylene glycol, and dimethyl isosorbide and the like.

"Stabilizers" refers to compounds such as any antioxidation agents, buffers, acids, preservatives and the like that are compatible with the environment of the *Auris media* and/or *Auris interna*. Stabilizers include but are not limited to agents that will do any of (1) improve the compatibility of excipients with a container, or a delivery system, including a syringe or a glass bottle, (2) improve the stability of a component of the composition, or (3) improve formulation stability.

"Steady state," as used herein, is when the amount of drug administered to the *Auris media* and/or *Auris interna* is equal to the amount of drug eliminated within one dosing interval resulting in a plateau or constant levels of drug exposure within the targeted structure.

As used herein, the term "subject" is used to mean an animal, preferably a mammal, including a human or non-human. The terms patient and subject are used interchangeably.

"Surfactants" refers to compounds that are *auris*-acceptable, such as sodium lauryl sulfate, sodium docusate, Tween 60 or 80, triacetin, vitamin E TPGS, phospholipids, lecithins, phosphatidyl cholines (c8-c18), phosphatidylethanolamines (c8-c18), phosphatidylglycerols (c8-c18), sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants are included to enhance physical stability or for other purposes.

The terms "treat," "treating," or "treatment," as used herein, include alleviating, abating or ameliorating a disease or condition or the associated symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or controlling or stopping the symptoms of the disease or condition either prophylactically and/or therapeutically.

The term "substantially low degradation products" means about 10% by weight of the active agent are degradation products of the active agent. In further embodiments, the term means less than 10% by weight of the active agent are degradation products of the active agent. In further embodiments, the term means less than 9% by weight of the active agent are degradation products of the active agent. In further embodiments, the term means less than 8% by weight of the active agent are degradation products of the active agent. In further embodiments, the term means less than 7% by weight of the active agent are degradation products of the active agent. In further embodiments, the term means less than 6% by weight of the active agent are degradation products of the active agent. In further embodiments, the term means less than 5% by weight of the active agent are degradation products of the active agent. In further embodiments, the term means less than 4% by weight of the active agent are degradation products of the active agent. In further embodiments, the term means less than 3% by weight of the active agent are degradation products of the active agent. In yet further embodiments, the term means less than 2% by weight of the active agent are degradation products of the active agent. In further embodiments, the term means less than 1% by weight of the active agent are degradation products of the active agent. In some embodiments, any individual impurity (e.g., metal impurity, degradation products of active agent and/or excipients, or the like) present in a formulation described herein is less than 5%, less than 2%, or less than 1% by weight of the active agent. In some embodiments the formulation does not contain precipitate during storage or change in color after manufacturing and storage.

"Amino" as used herein refers to the $=NH_2$ radical.

"Cyano" as used herein refers to the —CN radical.

"Nitro" as used herein refers to the $-NO_2$ radical.

"Oxa" as used herein refers to the —O— radical.

"Oxo" as used herein refers to the =O radical.

"Thioxo" as used herein refers to the =S radical.

"Amino" as used herein refers to the =N—H radical.

"Oximao" as used herein refers to the =N—OH radical.

"Hydrazino" as used herein refers to the $=N-NH_2$ radical.

"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl), In certain embodiments, an alkyl comprises one to eight carbon atoms (e.g., $C_1$-$C_8$ alkyl). In other embodiments, an alkyl comprises one to six carbon atoms (e.g., $C_1$-$C_6$ alkyl). In other embodiments, an alkyl comprises one to five carbon atoms (e.g. $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$alkyl). In other embodiments, an alkyl comprises two to six carbon atoms (e.g., $C_2$-$C_6$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). Unless stated otherwise specifically in the specification, an alkyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)$OR^a$, —C(O)$N(R^a)_2$, —$N(R^a)$C(O) $OR^a$, —OC (O)—$N(R^a)_2$, —$N(R^a)$C(O)$R^a$, —$N(R^a)S(O)_tR^a$ (where t is 1 or 2), —$S(O)_tOR^a$ (where t is 1 or 2), —$S(O)_tR^a$ (where t is 1 or 2) and —S(O)$N(R^a)_2$ (where t is 1 or 2) where each R is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl. Depending on the structure, an alkyl group is optionally a monoradical or a diradical (i.e. an alkylene group).

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to six carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)$OR^a$, —C(O)$N(R^a)_2$, —$N(R^a)$C(O)$OR^a$, OC(O)—$N(R^a)_2$, —$N(R^a)$C(O)$R^a$, —$N(R^a)S(O)_tR^a$ (where t is 1 or 2), —$S(O)_tR^a$ (where t is 1 or 2), —$S(O)_tR^a$ (where t is 1 or 2) and —S(O)—$N(R^a)_2$ (where t is 1 or 2) where each $R^a$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl.

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —$OR^a$, —SR, —OC(O)—$R^a$, —$N(R^a)_2$, —C(O)$R^a$, —C(O)$OR^a$, —C(O)$N(R^a)_2$, —$N(R^a)$C(O)$OR^a$, —OC(O)—$N(R^a)_2$, —$N(R^a)$C(O)$R^a$, —$N(R^a)S(O)_1R^a$ (where t is 1 or 2), —$S(O)_tOR^a$ (where t is 1 or 2), —$S(O)_tR^a$ (where t is 1 or 2) and —$S(O)_tN(R^a)_2$ (where t is 1 or 2) where each $R^a$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group are optionally through one carbon in the alkylene chain or through any two carbons within the chain. In certain embodiments, an alkylene comprises one to eight carbon atoms (e.g., $C_1$-$C_8$alkylene). In other embodiments, an alkylene comprises one to five carbon atoms (e.g., $C_1$-$C_5$alkylene). In other embodiments, an alkylene comprises one to four carbon atoms (e.g., $C_1$-$C_4$alkylene). In other embodiments, an alkylene comprises one to three carbon atoms (e.g. $C_1$-$C_3$alkylene). In other embodiments, an alkylene comprises one to two carbon atoms (e.g., $C_1$-$C_2$alkylene). In other embodiments, an alkylene comprises one carbon atom (e.g., $C_1$ alkylene). In other embodiments, an alkylene comprises five to eight carbon atoms (e.g., $C_5$-$C_8$alkylene). In other embodiments, an alkylene comprises two to five carbon atoms (e.g., $C_2$-$C_5$ alkylene), In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —$OR^a$, —$SR^a$, —OC(O)—R, —$N(R^a)_2$, —C(O)$R^a$, —C(O)$OR^a$, —C(O)$N(R^a)_2$, —$N(R^a)$C(O)$OR^a$, —OC (O)—$N(R^a)_2$, —N(R)C(O)$R^a$, —$N(R^a)$S(O)$R^a$ (where t is 1 or 2), —$S(O)_tOR^a$ (where t is 1 or 2), —$S(O)_tR^a$ (where t is 1 or 2) and —$S(O)_tN(R^a)_2$ (where t is 1 or 2) where each $R^a$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted heterocycloalkyl, optionally substituted heterocycloalkylalkyl, optionally substituted heteroaryl, optionally substituted heteroarylalkyl, $—R^b—OR^a$, $—R^b—OC(O)—R^a$, $—R^b—OC(O)—OR^a$, $—R^b—OC(O)—N(R^a)_2$, $—R^b—N(R^a)_2$, $—R^b—C(O)R^a$, $—R^b—C(O)OR^a$, $—R^b—C(O)N(R^a)_2$, $—R^b—O—R^c—C(O)N(R^a)_2$, $—R^b—N(R^a)C(O)OR^a$, $—R^b—N(R^a)C(O)R^a$, $—R^b—N(R^a)S(O)—R^a$ (where t is 1 or 2), $—R^b—S(O)_tOR^a$ (where t is 1 or 2), $—R^b—S(O)_tOR^a$ (where t is 1 or 2) and $—R^b—S(O)_tN(R^a)_2$ (where t is 1 or 2), where each $R^a$ is independently hydrogen, alkyl, fluoroalkyl, cycloalkyl, cycloalkylalkyl, aryl (optionally substituted with one or more halo groups), aralkyl, heterocycloalkyl, heterocycloalkylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Aralkyl" refers to a radical of the formula $—R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula $—R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula $—R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a radical bonded through an oxygen atom of the formula $—O—R^c$-aryl where R is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms. In certain embodiments, a cycloalkyl comprises three to ten carbon atoms. In other embodiments, a cycloalkyl comprises five to seven carbon atoms. The cycloalkyl is attached to the rest of the molecule by a single bond. Cycloalkyl may be saturated, (i.e., containing single C—C bonds only) or partially unsaturated. Examples of monocyclic cycloalkyls include, e.g., cyclopropyl, cyclobutyl, cyclopentyl, cyclohexyl, cycloheptyl, and cyclooctyl. An unsaturated cycloalkyl is also referred to as "cycloalkenyl." Examples of monocyclic cycloalkenyls include, e.g., cyclopentenyl, cyclohexenyl, cycloheptenyl, and cyclooctenyl. Polycyclic cycloalkyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "cycloalkyl" is meant to include cycloalkyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted heterocycloalkyl, optionally substituted heterocycloalkylalkyl, optionally substituted heteroaryl, optionally substituted heteroarylalkyl, $—R^b—OR^a$, $—R^b—OC(O)—R^a$, $—R^b—OC(O)—OR^a$, $—R^b—OC(O)—N(R^a)_2$, $—R^b—N(R^a)_2$, $—R^b—C(O)R^a$, $—R^b—C(O)OR^a$, $—R^b—C(O)N(R)_2$, $—R^b—O—R—C(O)N(R^a)_2$, $—R^b—N(R^a)C(O)OR^a$, $—R^b—N(R^a)C(O)R^a$, $—R^b—N(R^a)S(O)_tR^a$ (where t is 1 or 2), $—R^b—S(O)_tOR^a$ (where t is 1 or 2), $—R^b—S(O)_tOR^a$ (where t is 1 or 2) and $—R^b—S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Cycloalkylalkyl" refers to a radical of the formula $—R^c$-cycloalkyl where $R^c$ is an alkylene chain as defined above. The alkylene chain and the cycloalkyl radical is optionally substituted as defined above.

"Cycloalkylalkoxy" refers to a radical bonded through an oxygen atom of the formula $—O—R^c$-cycloalkyl where $R^c$ is an alkylene chain as defined above. The alkylene chain and the cycloalkyl radical is optionally substituted as defined above.

"Halo" or "halogen" refers to bromo, chloro, fluoro, or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. The alkyl part of the fluoroalkyl radical may be optionally substituted as defined above for an alkyl group.

"Heterocycloalkyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocycloalkyl radical is a monocyclic, bicyclic, tricyclic or tetracyclic ring system, which may include fused or bridged ring systems. The heteroatoms in the heterocycloalkyl radical may be optionally oxidized. One or more nitrogen atoms, if present, are optionally quaternized. The heterocycloalkyl radical is partially or fully saturated. The heterocycloalkyl may be attached to the rest of the molecule through any atom of the ring(s), Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocycloalkyl" is meant to include heterocycloalkyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted heterocycloalkyl, optionally substituted heterocycloalkylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—C(O)$R^a$, —$R^b$—C(O)$OR^a$, —$R^b$—C(O)$N(R^a)_2$, —$R^b$—O—$R^c$—C(O)$N(R^a)_2$, —$R^b$—$N(R^a)$C(O)$OR^a$, —$R^b$—$N(R^a)$C(O)$R^a$, —$R^b$—$N(R^a)S(O)_tR^a$ (where t is 1 or 2), —$R^b$—$S(O)_tOR^a$ (where t is 1 or 2), —$R^b$—S(O)$OR^a$ (where t is 1 or 2) and —$R^b$—$S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocycloalkyl" or "N-attached heterocycloalkyl" refers to a heterocycloalkyl radical as defined above containing at least one nitrogen and where the point of attachment of the heterocycloalkyl radical to the rest of the molecule is through a nitrogen atom in the heterocycloalkyl radical. An N-heterocycloalkyl radical is optionally substituted as described above for heterocycloalkyl radicals. Examples of such N-heterocycloalkyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocycloalkyl" or "C-attached heterocycloalkyl" refers to a heterocycloalkyl radical as defined above containing at least one heteroatom and where the point of attachment of the heterocycloalkyl radical to the rest of the molecule is through a carbon atom in the heterocycloalkyl radical A C-heterocycloalkyl radical is optionally substituted as described above for heterocycloalkyl radicals. Examples of such C-heterocycloalkyl radicals include, but are not limited to, 2-morpholinyl, 2- or 3- or 4-piperidinyl, 2-piperazinyl, 2- or 3-pyrrolidinyl, and the like.

"Heterocycloalkylalkyl" refers to a radical of the formula —$R^c$-heterocycloalkyl where $R^c$ is an alkylene chain as defined above. If the heterocycloalkyl is a nitrogen-containing heterocycloalkyl, the heterocycloalkyl is optionally attached to the alkyl radical at the nitrogen atom. The alkylene chain of the heterocycloalkylalkyl radical is optionally substituted as defined above for an alkylene chain. The heterocycloalkyl part of the heterocycloalkylalkyl radical is optionally substituted as defined above for a heterocycloalkyl group.

"Heterocycloalkylalkoxy" refers to a radical bonded through an oxygen atom of the formula —O—$R^c$-heterocycloalkyl where $R^c$ is an alkylene chain as defined above. If the heterocycloalkyl is a nitrogen-containing heterocycloalkyl, the heterocycloalkyl is optionally attached to the alkyl radical at the nitrogen atom. The alkylene chain of the heterocycloalkylalkoxy radical is optionally substituted as defined above for an alkylene chain. The heterocycloalkyl part of the heterocycloalkylalkoxy radical is optionally substituted as defined above for a heterocycloalkyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical may be a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazol, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl. 5,6-dihydrobenrzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted heterocycloalkyl, optionally substituted heterocycloalkylalkyl, optionally substituted heteroaryl, optionally substituted heteroarylalkyl, -$^b$-$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—C(O)$R^a$, —$R^b$—C(O)$OR^a$, —$R^b$—C(O)$N(R^a)_2$, —$R^b$—O—$R^c$—C(O)$N(R^a)_2$, —$R^b$—$N(R^a)$C(O)$OR^a$, —$R^b$—$N(R^a)$C(O)$R^a$, —$R^b$—$N(R^a)S(O)_tR^a$ (where t is 1 or 2), —$R^b$—$S(O)_tOR^a$ (where t is 1 or 2), —$R^b$—$S(O)_tOR^a$ (where t is 1 or 2) and —$R^b$—$S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical A C-heteroaryl radical is optionally substituted as described above for heteroaryl radicals.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

The compounds disclosed herein may contain one or more asymmetric centers and may thus give rise to enantiomers, diastereomers, and other stereoisomeric forms that may be defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g. cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. The compounds presented herein may, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

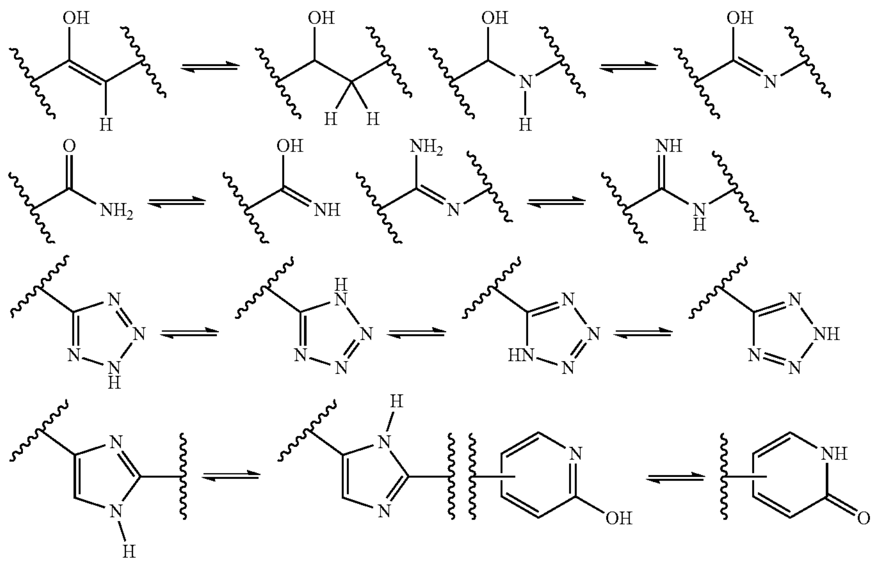

"Optional" or "optionally" means that a subsequently described event or circumstance may or may not occur and that the description includes instances when the event or circumstance occurs and instances in which it does not.

"Optionally substituted" or "substituted" means that the referenced group may be substituted with one or more additional group(s) individually and independently selected from alkyl, cycloalkyl, aryl, heteroaryl, heterocycloalkyl, —OH, alkoxy, aryloxy, alkylthio, arylthio, alkylsulfoxide, arylsulfoxide, alkylsulfone, arylsulfone, —CN, alkyne, $C_1$-$C_6$alkylalkyne, halo, acyl, acyloxy, —$CO_2H$, —$CO_2$-alkyl, nitro, haloalkyl, fluoroalkyl, and amino, including mono- and di-substituted amino groups (e.g. —$NH_2$, —NHR, —$N(R)_2$), and the protected derivatives thereof. By way of example, an optional substituents may be $L^sR^s$, wherein each $L^s$ is independently selected from a bond, —O—, —C(═O)—, —S—, —S(═O)—, —$S(═O)_2$—, —NH—, —NHC(O)—, —C(O)NH—, $S(═O)_2NH$—, —NHS(═O), —OC(O)NH—, —NHC(O)O—, —($C_1$-$C_6$alkyl)-, or —($C_2$-$C_6$alkenyl)-; and each $R^s$ is independently selected from among H, ($C_1$-$C_6$alkyl), ($C_3$-$C_8$cycloalkyl), aryl, heteroaryl, heterocycloalkyl, and $C_1$-$C_6$heteroalkyl. The protecting groups that may form the protective derivatives of the above substituents are found in sources such as Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

"Pharmaceutically acceptable salt" includes both acid and base addition salts. A pharmaceutically acceptable salt of any one of the compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid hydrobromic acid, sulfuric acid, nitric acid, phosphoric acid, hydroiodic acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphate, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66.1-19 (1997), which is hereby incorporated by reference in its entirety). Acid addition salts of basic compounds may be prepared by contacting the free base forms with a sufficient amount of the desired acid to produce the salt according to known methods and techniques.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

"Pharmaceutically acceptable counterion" refers to an ion that accompanies an ionic species in order to maintain electric neutrality that is not biologically or otherwise undesirable.

As used herein, "treatment" or "treating," or "palliating" or "ameliorating" are used interchangeably herein. These terms refers to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

"Prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like.

Other objects, features, and advantages of the methods and compositions described herein will become apparent from the following detailed description. It should be understood, however, that the detailed description and the specific examples, while indicating specific embodiments, are given by way of illustration only.

Anatomy of the Ear

The ear serves as both the sense organ that detects sound and the organ that maintains balance and body position. The ear is generally divided into three portions: the outer ear, middle ear and the inner ear (or *Auris interna*). The outer ear is the external portion of the organ and is composed of the pinna (auricle), the auditory canal (external auditory meatus) and the outward facing portion of the tympanic membrane, also known as the ear drum. The pinna, which is the fleshy part of the externa ear that is visible on the side of the head, collects sound waves and directs them toward the auditory canal. Thus, the function of the outer ear, in part, is to collect and direct sound waves towards the tympanic membrane and the middle ear.

The middle ear is an air-filled cavity, called the tympanic cavity, behind the tympanic membrane. The tympanic membrane, also known as the ear drum, is a thin membrane that separates the external ear from the middle ear. The middle ear lies within the temporal bone, and includes within this space the three ear bones (auditory ossicles): the malleus, the incus and the stapes. The auditory ossicles are linked together via tiny ligaments, which form a bridge across the space of the tympanic cavity. The malleus, which is attached to the tympanic membrane at one end, is linked to the incus at its anterior end, which in turn is linked to the stapes. The stapes is attached to the oval window, one of two windows located within the tympanic cavity. A fibrous tissue layer, known as the annular ligament connects the stapes to the oval window. Sound waves from the outer ear first cause the tympanic membrane to vibrate. The vibration is transmitted across to the cochlea through the auditory ossicles and oval window, which transfers the motion to the fluids in the *Auris interna*. Thus, the auditory ossicles are arranged to provide a mechanical linkage between the tympanic membrane and the oval window of the fluid-filled *Auris interna*, where sound is transformed and transduced to the *Auris interna* for further processing. Stiffness, rigidity or loss of movement of the auditory ossicles, tympanic membrane or oval window leads to hearing loss, e.g. otosclerosis, or rigidity of the stapes bone.

The tympanic cavity also connects to the throat via the eustachian tube. The eustachian tube provides the ability to equalize the pressure between the outside air and the middle ear cavity. The round window, a component of the *Auris interna* but which is also accessible within the tympanic cavity, opens into the cochlea of the *Auris interna*. The round window is covered by a membrane, which consists of three layers: an external or mucous layer, an intermediate or fibrous layer, and an internal membrane, which communicates directly with the cochlear fluid. The round window, therefore, has direct communication with the *Auris interna* via the internal membrane.

Movements in the oval and round window are interconnected, i.e. as the stapes bone transmits movement from the tympanic membrane to the oval window to move inward against the *Auris interna* fluid, the round window is correspondingly pushed out and away from the cochlear fluid. This movement of the round window allows movement of fluid within the cochlea, which eventually leads in turn to movement of the cochlear inner hair cells, allowing hearing signals to be transduced. Stiffness and rigidity in the round window leads to hearing loss because of the lack of ability of movement in the cochlear fluid. Recent studies have focused on implanting mechanical transducers onto the round window, which bypasses the normal conductive pathway through the oval window and provides amplified input into the cochlear chamber.

Auditory signal transduction takes place in the *Auris interna*. The fluid-filled inner ear, or *Auris interna*, consists of two major components: the cochlear and the vestibular apparatus.

The cochlea is the portion of the *Auris interna* related to hearing. The cochlea is a tapered tube-like structure which is coiled into a shape resembling a snail. The inside of the cochlea is divided into three regions, which is further defined by the position of the vestibular membrane and the basilar membrane. The portion above the vestibular membrane is the *scala* vestibuli, which extends from the oval window to the apex of the cochlea and contains perilymph fluid, an aqueous liquid low in potassium and high in sodium content. The basilar membrane defines the *scala* tympani region, which extends from the apex of the cochlea to the round window and also contains perilymph. The basilar membrane contains thousands of stiff fibers, which gradually increase in length from the round window to the apex of the cochlea. The fibers of the basement membrane vibrate when activated by sound. In between the *scala* vestibuli and the *scala* tympani is the cochlear duct, which ends as a closed sac at the apex of the cochlea. The cochlear duct contains endolymph fluid, which is similar to cerebrospinal fluid and is high in potassium.

The Organ of *Corti*, the sensory organ for hearing, is located on the basilar membrane and extends upward into the cochlear duct. The Organ of *Corti* contains hair cells, which have hairlike projections that extend from their free surface, and contacts a gelatinous surface called the tectorial membrane. Although hair cells have no axons, they are surrounded by sensory nerve fibers that form the cochlear branch of the vestibulocochlear nerve (cranial nerve VIII).

As discussed, the oval window, also known as the elliptical window communicates with the stapes to relay sound waves that vibrate from the tympanic membrane. Vibrations transferred to the oval window increases pressure inside the fluid-filled cochlea via the perilymph and *scala* vestibuli/*scala* tympani, which in turn causes the membrane on the round window to expand in response. The concerted inward pressing of the oval window/outward expansion of the round window allows for the movement of fluid within the cochlea without a change of intra-cochlear pressure. However, as vibrations travel through the perilymph in the *scala* vestibuli, they create corresponding oscillations in the vestibular membrane. These corresponding oscillations travel through the endolymph of the cochlear duct, and transfer to the basilar membrane. When the basilar membrane oscillates, or moves up and down, the Organ of *Corti* moves along with it. The hair cell receptors in the Organ of *Corti* then move against the tectorial membrane, causing a mechanical deformation in the tectorial membrane. This mechanical deformation initiates the nerve impulse which travels via the vestibulocochlear nerve to the central nervous system, mechanically transmitting the sound wave received into signals that are subsequently processed by the central nervous system.

The *Auris interna* is located in part within the osseous or bony labyrinth, an intricate series of passages in the temporal bone of the skull. The vestibular apparatus is the organ of balance and consists of the three semi-circular canals and the vestibule. The three semi-circular canals are arranged relative to each other such that movement of the head along the three orthogonal planes in space is detected by the movement of the fluid and subsequent signal processing by the sensory organs of the semi-circular canals, called the *crista ampullaris*. The *crista ampullaris* contains hair cells and supporting cells and is covered by a dome-shaped gelatinous mass called the cupula. The hairs of the hair cells are embedded in the cupula. The semi-circular canals detect dynamic equilibrium, the equilibrium of rotational or angular movements.

When the head turns rapidly, the semicircular canals move with the head, but endolymph fluid located in the membranous semi-circular canals tends to remain stationary. The endolymph fluid pushes against the cupula, which tilts to one side. As the cupula tilts, it bends some of the hairs on the hair cells of the *crista ampullaris*, which triggers a sensory impulse. Because each semicircular canal is located in a different plane, the corresponding *crista ampullaris* of each semi-circular canal responds differently to the same movement of the head. This creates a mosaic of impulses that are transmitted to the central nervous system on the vestibular branch of the vestibulocochlear nerve. The central nervous system interprets this information and initiates the appropriate responses to maintain balance. Of importance in the central nervous system is the cerebellum, which mediates the sense of balance and equilibrium.

The vestibule is the central portion of the *Auris interna* and contains mechanoreceptors bearing hair cells that ascertain static equilibrium, or the position of the head relative to gravity. Static equilibrium plays a role when the head is motionless or moving in a straight line. The membranous labyrinth in the vestibule is divided into two sac-like structures, the utricle and the saccule. Each structure in turn contains a small structure called a macula, which is responsible for maintenance of static equilibrium. The macula consists of sensory hair cells, which are embedded in a gelatinous mass (similar to the cupula) that covers the macula. Grains of calcium carbonate, called otoliths, are embedded on the surface of the gelatinous layer.

When the head is in an upright position, the hairs are straight along the macula. When the head tilts, the gelatinous mass and otoliths tilts correspondingly, bending some of the hairs on the hair cells of the macula. This bending action initiates a signal impulse to the central nervous system, which travels via the vestibular branch of the vestibulocochlear nerve, which in turn relays motor impulses to the appropriate muscles to maintain balance.

In some instances, the otic formulations described herein are placed in the outer ear. In some instances, the otic formulations described herein are placed in the middle or inner ear, including the cochlea and vestibular labyrinth: one option is to use a syringe/needle or pump and inject the formulation across the tympanic membrane (the eardrum). In some instances, for cochlear and vestibular labyrinth delivery, one option is to deliver the active ingredient across the round window membrane or even by microinjection directly into the *Auris interna* also known as cochlear microperfusion.

Local Otic Administration

Also provided herein are methods, formulations, and compositions for local delivery of therapeutic agents (otic agents) to *Auris externa, Auris media*, and/or *Auris interna* structures. In some embodiments, local delivery of the therapeutic agent (otic agent) overcomes the toxic and attendant side effects of systemic delivery. In some embodiments, access to the vestibular and cochlear apparatus is through the *Auris media* and includes the round window membrane, the oval window/stapes footplate, the annular ligament and through the otic capsule/temporal bone.

Provided herein, in certain embodiments, are otic formulations and compositions that remain in contact with the target auditory surfaces (e.g., the round window) for extended periods of time. In some embodiments, the otic formulations and compositions further comprise mucoadhesives that allow the otic formulations to adhere to otic mucosal surfaces. In some instances, the formulations and compositions described herein avoid attenuation of therapeutic benefit due to drainage or leakage of active agents via the eustachian tube.

In some embodiments, the localized treatment of the *Auris externa, Auris media* and/or *Auris interna* affords the use of previously undesired therapeutic agents, including agents with poor PK profiles, poor uptake, low systemic release and/or toxicity issues. In some embodiments, localized targeting of the otic agent formulations and compositions reduces the risk of adverse effects with previously characterized toxic or ineffective therapeutic agents (otic active agents).

In some embodiments, specifically targeting the *Auris externa, Auris media* and/or *Auris interna* structures avoids the adverse side effects usually associated with systemic treatment. In some embodiments, the otic formulations and compositions described herein are controlled release therapeutic agent formulations and compositions that treat otic disorders by providing a constant, variable and/or extended source of a therapeutic agent (otic agent) to the individual or patient suffering from an otic disorder, thereby reducing or eliminating the variability of treatment. Accordingly, one embodiment disclosed herein is to provide a formulation or composition that enables at least one therapeutic agent (otic agent) to be released in therapeutically effective doses either at variable or constant rates such as to ensure a continuous release of the at least one therapeutic agent (otic agent). In some embodiments, the therapeutic agents (otic agents) disclosed herein are administered as an immediate release formulation or composition. In other embodiments, the therapeutic agents (otic agents) are administered as a controlled release formulation, released either continuously or in a pulsatile manner, or variants of both. In still other embodiments, the therapeutic agent (otic agent) formulation or composition is administered as both an immediate release and controlled release formulation or composition, released either continuously or in a pulsatile manner, or variants of both. The release is optionally dependent on environmental or physiological conditions, for example, the external ionic environment (see, e.g. Oros® release system, Johnson & Johnson).

In addition, the otic compositions or formulations included herein also optionally include carriers, adjuvants, such as preserving, stabilizing, wetting or emulsifying agents, solution promoters, salts for regulating the osmotic pressure, and/or buffers. Such carriers, adjuvants, and other excipients are compatible with the environment in the *Auris externa, Auris media* and/or *Auris interna*. Accordingly, specifically contemplated are carriers, adjuvants and excipients that lack ototoxicity or are minimally ototoxic in order to allow effective treatment of the otic disorders contemplated herein with minimal side effects in the targeted regions or areas. To prevent ototoxicity, otic compositions or formulations disclosed herein are optionally targeted to distinct regions of the *Auris externa, Auris media* and/or *Auris interna*, including but not limited to the tympanic cavity, vestibular bony and membranous labyrinths, cochlear bony and membranous labyrinths and other anatomical or physiological structures located within the *Auris interna*.

Sustained Release

In some embodiments, the otic formulations and compositions described herein provide a steady sustained release of a therapeutic agent (otic agent) after a single administration. In some embodiments, the otic formulations and compositions described herein provide a steady sustained release of a therapeutic agent (otic agent) into the cochlea. In some embodiments, the otic formulations and compositions described herein provide a steady sustained release of a therapeutic agent (otic agent) for a period of at least one day, three days, five days, one week, two weeks, three weeks, a month, two months, three months, four months, five months, six months, or a year. In some embodiments, the otic formulations and compositions described herein provide a steady sustained release of a therapeutic agent (otic agent) for a period of at least a day. In some embodiments, the otic formulations and compositions described herein provide a steady sustained release of a therapeutic agent (otic agent) for a period of at least two days. In some embodiments, the otic formulations and compositions described herein provide a steady sustained release of a therapeutic agent (otic agent) for a period of at least three days. In some embodiments, the otic formulations and compositions described herein provide a steady sustained release of a therapeutic agent (otic agent) for a period of at least four days. In some embodiments, the otic formulations and compositions described herein provide a steady sustained release of a therapeutic agent (otic agent) for a period of at least five days. In some embodiments, the otic formulations and compositions described herein provide a steady sustained release of a therapeutic agent (otic agent) for a period of at least six days. In some embodiments, the otic formulations and compositions described herein provide a steady sustained release of a therapeutic agent (otic agent) for a period of at least one week. In some embodiments, the otic formulations and compositions described herein provide a steady sustained release of a therapeutic agent (otic agent) for a period of at least two weeks. In some embodiments, the otic formulations and compositions described herein provide a steady sustained release of a therapeutic agent (otic agent) for a period of at least three weeks. In some embodiments, the otic formulations and compositions described herein provide a steady sustained release of a therapeutic agent (otic agent) for a period of at least a month. In some embodiments, the otic formulations and compositions described herein provide a steady sustained release of a therapeutic agent (otic agent) for a period of at least two months. In some embodiments, the otic formulations and compositions described herein provide a steady sustained release of a therapeutic agent (otic agent) for a period of at least three months. In some embodiments, the otic formulations and compositions described herein provide a steady sustained release of a therapeutic agent (otic agent) for a period of at least four months. In some embodiments, the otic formulations and compositions described herein provide a steady sustained release of a therapeutic agent (otic agent) for a period of at least five months. In some embodiments, the otic formulations and compositions described herein provide a steady sustained release of a therapeutic agent (otic agent) for a period of at least six months. In some embodiments, the otic formulations and compositions described herein provide a steady sustained release of a therapeutic agent (otic agent) for a period of at least a year.

In some embodiments, the otic formulations and compositions described herein provide a steady sustained release of a therapeutic agent (otic agent) after a single administration. In some embodiments, the otic formulations and compositions described herein provide a steady sustained release of a therapeutic agent (otic agent) into the cochlea. In some embodiments, the otic formulations and compositions described herein provide a steady sustained release of a therapeutic agent (otic agent) for a period of about a day, three days, five days, one week, two weeks, three weeks, a month, two months, three months, four months, five months, six months, or a year. In some embodiments, the otic formulations and compositions described herein provide a steady sustained release of a therapeutic agent (otic agent) for a period of about a day. In some embodiments, the otic formulations and compositions described herein provide a steady sustained release of a therapeutic agent (otic agent) for a period of about two days. In some embodiments, the otic formulations and compositions described herein provide a steady sustained release of a therapeutic agent (otic agent) for a period of about three days. In some embodiments, the otic formulations and compositions described herein provide a steady sustained release of a therapeutic agent (otic agent) for a period of about four days. In some embodiments, the otic formulations and compositions described herein provide a steady sustained release of a therapeutic agent (otic agent) for a period of about five days. In some embodiments, the otic formulations and compositions described herein provide a steady sustained release of a therapeutic agent (otic agent) for a period of about six days. In some embodiments, the otic formulations and compositions described herein provide a steady sustained release of a therapeutic agent (otic agent) for a period of about one week. In some embodiments, the otic formulations and compositions described herein provide a steady sustained release of a therapeutic agent for a period of about two weeks. In some embodiments, the otic formulations and compositions described herein provide a steady sustained release of a therapeutic agent (otic agent) for a period of about three weeks. In some embodiments, the otic formulations and compositions described herein provide a steady sustained release of a therapeutic agent (otic agent) for a period of about a month. In some embodiments, the otic formulations and compositions described herein provide a steady sustained release of a therapeutic agent (otic agent) for a period of about two months. In some embodiments, the otic formulations and compositions described herein provide a steady sustained release of a therapeutic agent (otic agent) for a period of about three months. In some embodiments, the otic formulations and compositions described herein provide a steady sustained release of a therapeutic agent (otic agent) for a period of about four months. In some embodiments, the otic formulations and compositions described herein provide a steady sustained release of a therapeutic agent (otic agent) for a period of about five months. In some embodiments, the otic formulations and compositions described herein provide a steady sustained release of a therapeutic agent (otic agent) for a period of about six months. In some embodiments, the otic formulations and compositions described herein provide a steady sustained release of a therapeutic agent (otic agent) for a period of about a year.

Otoprotectants

Contemplated for use with any otic formulation described herein are otoprotectants, which reduce, inhibit or ameliorate the ototoxicity of agents such as chemotherapeutic agents and/or antibiotics as described herein, and/or reduce, inhibit or ameliorate the effects of other environmental factors, including excessive noise and the like.

In some embodiments, the otic formulations and compositions described herein have pH and osmolarity that are *auris*-acceptable. In some embodiments, the otic formulations and compositions described herein meet the stringent sterility requirements described herein and are compatible with the endolymph and/or the perilymph. Pharmaceutical agents that are used in conjunction with the formulations and compositions disclosed herein include the following therapeutic agents disclosed herein. In some embodiments, pharmaceutically active metabolites, salts, polymorphs, prodrugs, analogues, and derivatives of the therapeutic agents disclosed herein are used in the formulations.

In some embodiments, the formulations and compositions disclosed herein are contemplated to be targeted directly to otic structures where treatment is needed; for example, one embodiment contemplated is the direct application of the otic formulations disclosed herein onto the round window membrane or the *crista* fenestrae cochlea of the *Auris interna*, allowing direct access and treatment of the *Auris interna*, or inner ear components. In other embodiments, the otic formulations and compositions disclosed herein are applied directly to the oval window. In yet other embodiments, direct access is obtained through microinjection directly into the *Auris interna*, for example, through cochlear microperfusion. Such embodiments also optionally comprise a drug delivery device, wherein the drug delivery device delivers the otic formulations through use of a needle and syringe, a pump, a microinjection device, a spongy material or any combination thereof.

In still other embodiments, application of any otic formulation or composition described herein is targeted to the *Auris media* through piercing of the intratympanic membrane and applying the otic agent formulation directly to the *Auris media* structures affected, including the walls of the tympanic cavity or auditory ossicles. In some embodiments, the *auris* active agent formulations and compositions disclosed herein are confined to the targeted *Auris media* structure, and will not be lost, for example, through diffusion or leakage through the eustachian tube or pierced tympanic membrane. In some embodiments, the otic formulations and compositions disclosed herein are delivered to the *Auris externa* in any suitable manner, including by cotton swab, injection or ear drops. Also, in other embodiments, the otic formulations and compositions described herein are targeted to specific regions of the *Auris externa* by application with a needle and syringe, a pump, a microinjection device, a spongy material, or any combination thereof. For example, in the case of treatment of otitis externa, antimicrobial agent formulations disclosed herein are delivered directly to the ear canal, where they are retained, thereby reducing loss of the active agents from the target ear structure by drainage or leakage.

Also contemplated for use with the formulations disclosed herein are agents that modulate the degeneration of neurons, hair cells, support cells, and cells of the stria vascularis, and agents for treating or ameliorating hearing loss or reduction resulting from destroyed, stunted, malfunctioning, damaged, fragile or missing hairs in the inner ear.

In an aspect, provided herein is a method of treating and/or preventing drug-induced ototoxicity, comprising administering to a subject in need thereof a pharmaceutical composition, comprising:

(i) an otoprotectant;

(ii) and at least one pharmaceutically acceptable excipient or carrier, wherein the otoprotectant comprises at least one of: a thiopyrimidine, a thiopurine, a thiopurine derivative, a thiouracil, a thiouracil derivative, a thiourea, a thioamide, or a sulfur-containing compound selected from tiopronin, penicillamine, dimercaprol, captodiame, fursultiamine, famotidine, cysteamine, thiabendazole, succimer, glutathione, or mercaptopyruvate.

In some embodiments, the otoprotectant comprises at least one of: tiopronin, penicillamine, dimercaprol, captodiame, fursultiamine, famotidine, cysteamine, thiabendazole, succimer, glutathione, mercaptopyruvate, a thiopyrimidine, a thiopurine, a thiouracil, a thiouracil derivative, a thiourea, a thioamide, or a tautomer, prodrug, pharmaceutically acceptable salt, solvate, or hydrate thereof.

In an aspect, provided herein is a method of treating and/or preventing drug-induced ototoxicity, comprising administering to a subject in need thereof a pharmaceutical composition, comprising:

(i) an otoprotectant;

(ii) and at least one pharmaceutically acceptable excipient or carrier, wherein the otoprotectant comprises a thiopurine or thiopurine derivative of structural Formula (I):

(I)

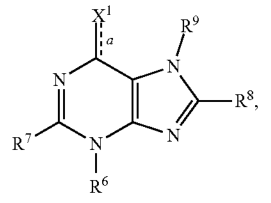

or a tautomer, prodrug, pharmaceutically acceptable salt, solvate, or hydrate thereof, wherein:

$X^1$ is S or $SR^{10}$;

$\overset{a}{---}$ is a single bond or double bond, wherein if $\overset{a}{---}$ is a single bond, then $X^1$ is $SR^{10}$, and if $\overset{a}{---}$ is a double bond, then $X^1$ is S; and $R^6$, $R^7$, $R^8$, $R^9$, and $R^{10}$ are each independently hydrogen, substituted or unsubstituted alkyl, substituted or unsubstituted alkenyl, substituted or unsubstituted alkynyl, substituted or unsubstituted alkylthio, substituted or unsubstituted amine, hydroxyl, imine, amide, cyano, isocyano, carbonyl, carboxyl, carboxamide, substituted or unsubstituted amine alkylsulfonyl, substituted or unsubstituted amine arylsulfonyl, ketone, aldehyde, ester, heteroalkyl, nitrile, amidine, acetal, ketal, substituted or unsubstituted cycloalkyl, substituted or unsubstituted heterocycloalkyl, substituted or unsubstituted aryl, substituted or unsubstituted heteroaryl, aziridine, carbamate, imide, urea, or thiourea.

In some embodiments, $R^7$ is $-NH_2$.

In some embodiments, $\overset{a}{---}$ is a double bond and $X^1$ is S.

In some embodiments, $R^8$ is hydrogen.

In some embodiments, $R^9$ is hydrogen, substituted or unsubstituted cycloalkyl, or substituted or unsubstituted heterocycloalkyl.

In some embodiments, the thiopurine or thiopurine derivative is:

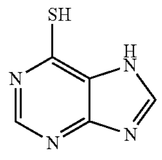

,

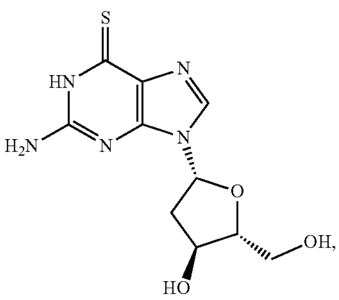

,

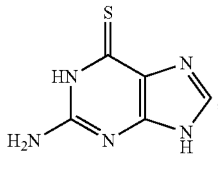

,

-continued

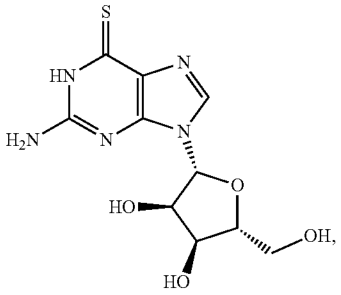

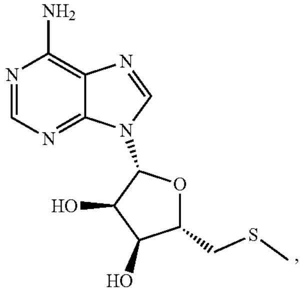

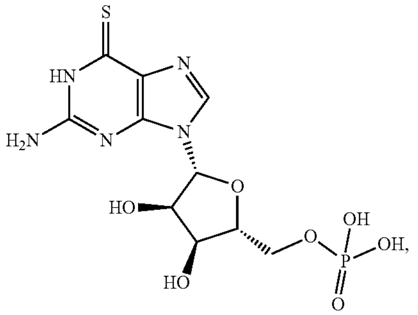

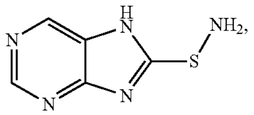

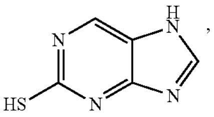

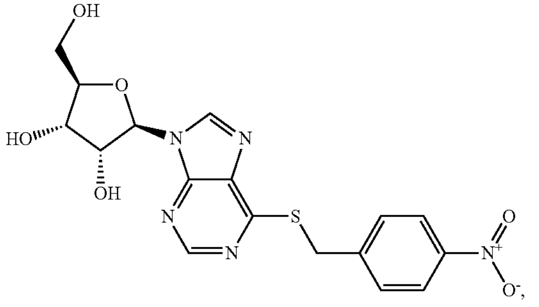

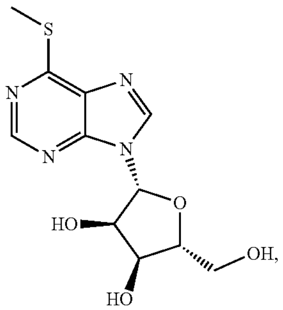 or

-continued

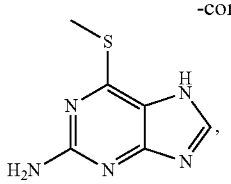

or a tautomer, prodrug, pharmaceutically acceptable salt, solvate, or hydrate thereof.

In an aspect, provided herein is a method of treating and/or preventing drug-induced ototoxicity, comprising administering to a subject in need thereof a pharmaceutical composition, comprising:

(i) an otoprotectant;

(ii) and at least one pharmaceutically acceptable excipient or carrier, wherein the otoprotectant comprises a thiourea of structural Formula (II-A) or (II-B):

(II-A)

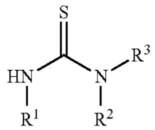

or (II-B)

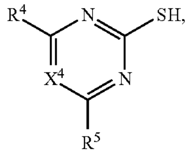

or a tautomer, prodrug, pharmaceutically acceptable salt, solvate, or hydrate thereof, wherein:

$X^4$ is a bond, —O—, —S—, or —C—$R^{21}$; and $R^1$, $R^2$, $R^3$ are each independently hydrogen, substituted or unsubstituted alkyl, substituted or unsubstituted alkenyl, substituted or unsubstituted alkynyl, substituted or unsubstituted alkylthio, substituted or unsubstituted amine, hydroxyl, imine, amide, cyano, isocyano, carbonyl, carboxyl, carboxamide, substituted or unsubstituted amine alkylsulfonyl, substituted or unsubstituted amine arylsulfonyl, ketone, aldehyde, ester, heteroalkyl, nitrile, amidine, acetal, ketal, substituted or unsubstituted cycloalkyl, substituted or unsubstituted heterocycloalkyl, substituted or unsubstituted aryl, substituted or unsubstituted heteroaryl, aziridine, carbamate, imide, urea, or thiourea, or $R^1$ and $R^2$; or $R^2$ and $R^3$ taken together form a substituted or unsubstituted aryl, substituted or unsubstituted heteroaryl, substituted or unsubstituted cycloalkyl, or substituted or unsubstituted heterocycloalkyl having 4 to 8 members;

$R^4$, $R^5$, and $R^{21}$ are each independently hydrogen, substituted or unsubstituted alkyl, substituted or unsubstituted alkenyl, substituted or unsubstituted alkynyl, substituted or unsubstituted alkylthio, imine, substituted or unsubstituted amine, amide, cyano, isocyano, carbonyl, carboxyl, carboxamide, substituted or unsubstituted alkylsulfonyl, substituted or unsubstituted arylsulfonyl, ketone, aldehyde, ester, heteroalkyl, nitrile, amidine, acetal, ketal, substituted or unsubstituted cycloalkyl, substituted or unsubstituted heterocycloalkyl, substituted or unsubstituted aryl, substituted or unsubstituted heteroaryl, aziridine, carbamate, imide, urea, or thiourea, or $R^4$ and $R^{21}$ joined together form a substituted or unsubstituted aryl, substituted or unsubstituted heteroaryl, substituted or unsubstituted cycloalkyl, or substituted or unsubstituted heterocycloalkyl ring having 4 to 8 members.

In some embodiments, the thiourea has structural Formula (II-A), or a tautomer, prodrug, pharmaceutically acceptable salt, solvate, or hydrate thereof.

In some embodiments, $R^1$ and $R^2$ are each independently hydrogen, substituted or unsubstituted alkyl or substituted or unsubstituted aryl.

In some embodiments, $R^3$ is hydrogen.

In some embodiments, the thiourea has structural Formula (II-B), or a tautomer, prodrug, pharmaceutically acceptable salt, solvate, or hydrate thereof.

In some embodiments, $X^4$ is —C—$R^{21}$ and $R^{21}$ is hydrogen.

In some embodiments, $R^4$ is —$NH_2$ or hydrogen and $R^5$ is hydrogen.

In some embodiments, the thiourea is:

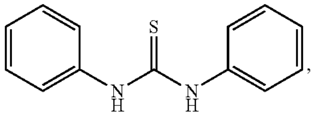

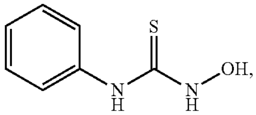

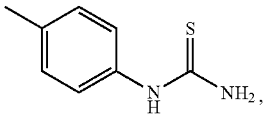

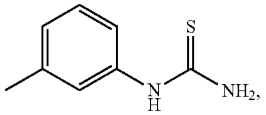

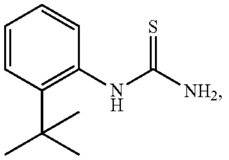

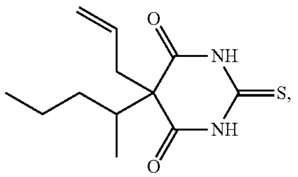

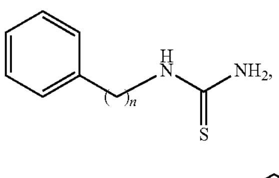

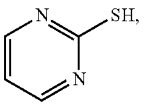

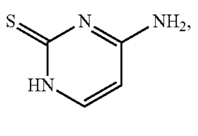

or

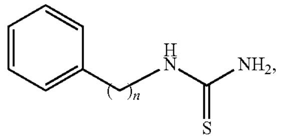

or a tautomer, prodrug, pharmaceutically acceptable salt, solvate, or hydrate thereof, wherein n is an integer from 0 to 6.

In some embodiments, the thiourea is:

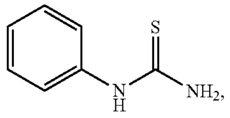

or a tautomer, prodrug, pharmaceutically acceptable salt, solvate, or hydrate thereof.

In an aspect, provided herein is a method of treating and/or preventing drug-induced ototoxicity, comprising administering to a subject in need thereof a pharmaceutical composition, comprising:

(i) an otoprotectant;

(ii) and at least one pharmaceutically acceptable excipient or carrier, wherein the otoprotectant comprises a thiouracil or thiouracil derivative of structural Formula (III):

(III)

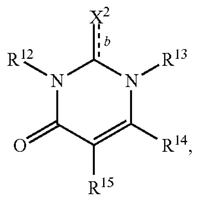

or a tautomer, prodrug, pharmaceutically acceptable salt, solvate, or hydrate thereof, wherein:

$X^2$ is S or $SR^{11}$;

$\stackrel{b}{- -}$ is a single bond or double bond, wherein if $\stackrel{b}{- -}$ is a single bond, then $X^2$ is $SR^{11}$, and if $\stackrel{b}{- -}$ is a double bond, then $X^2$ is S; and $R^{11}$, $R^{12}$, $R^{13}$, $R^{14}$, and $R^{15}$ are each independently hydrogen, substituted or unsubstituted alkyl, substituted or unsubstituted alkenyl, substituted or unsubstituted alkynyl, substituted or unsubstituted alkylthio, imine, substituted or unsubstituted amine, hydroxyl, amide, cyano, isocyano, carbonyl, carboxyl, carboxamide, substituted or unsubstituted alkylsulfonyl, substituted or unsubstituted arylsulfonyl, ketone, aldehyde, substituted or unsubstituted ester, heteroalkyl, nitrile, amidine, acetal, ketal, substituted or unsubstituted cycloalkyl, substituted or unsubstituted heterocycloalkyl, substituted or unsubstituted aryl, substituted or unsubstituted heteroaryl, aziridine, carbamate, imide, urea, or thiourea.

In some embodiments, $\stackrel{b}{- -}$ is a double bond and $X^2$ is S.

In some embodiments, the thiouracil is:

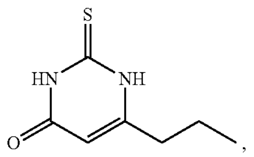

-continued
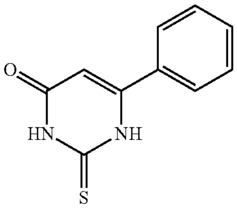, 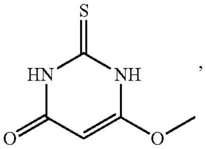,
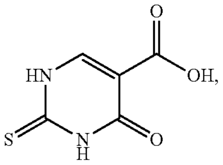 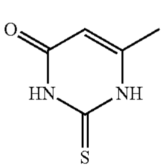,
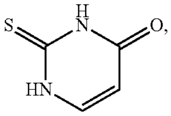 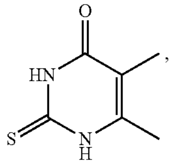, 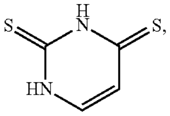
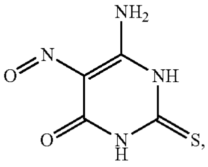 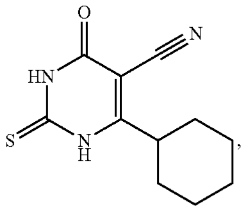,
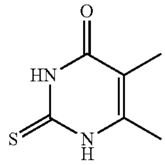, 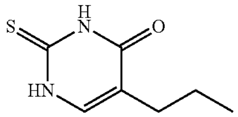,
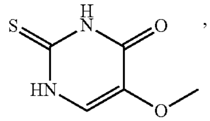, 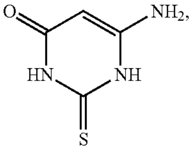
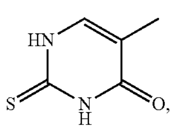 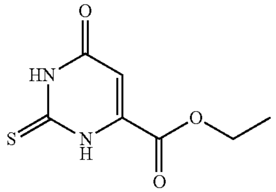,
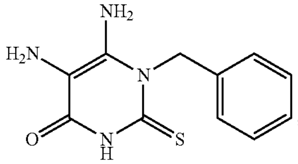,
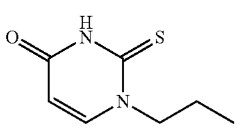, 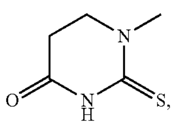
-continued
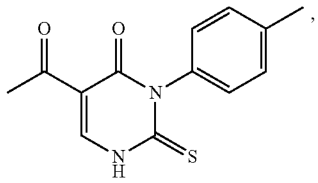,
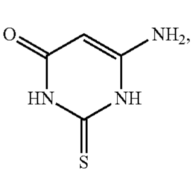 or 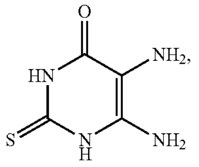
or a tautomer, prodrug, pharmaceutically acceptable salt, solvate, or hydrate thereof.
In some embodiments, the thiouracil derivative is:
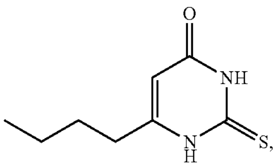 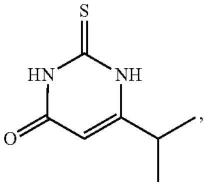,
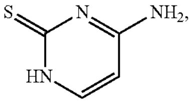 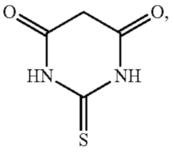 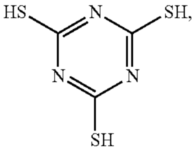
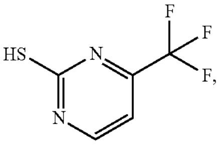 or 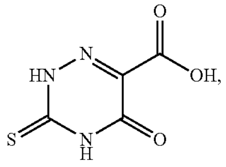
or a tautomer, prodrug, pharmaceutically acceptable salt, solvate, or hydrate thereof.
In some embodiments, the thioamide is:
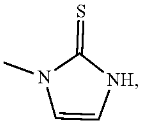 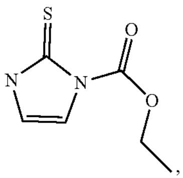, 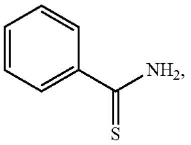
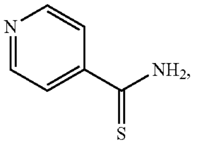 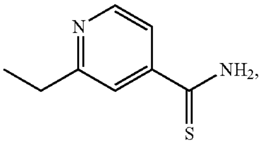

-continued

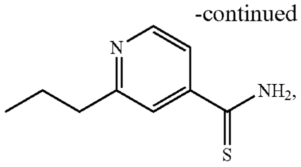

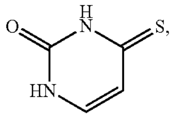

or

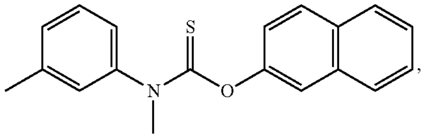

or a tautomer, prodrug pharmaceutically acceptable salt, solvate, or hydrate thereof.

In an aspect, provided herein is a method of treating and/or preventing drug-induced ototoxicity, comprising administering to a subject in need thereof a pharmaceutical composition, comprising:

(i) an otoprotectant;

(ii) and at least one pharmaceutically acceptable excipient or carrier, wherein the otoprotectant comprises a thiopyrimidine of structural Formula (IV):

(IV)

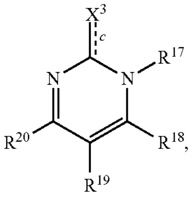

or a tautomer, prodrug, pharmaceutically acceptable salt, solvate, or hydrate thereof, wherein:

$X^3$ is S or $SR^{16}$.

$\overset{c}{---}$ is a single bond or double bond, wherein if $\overset{c}{---}$ is a single bond, then $X^3$ is $SR^{16}$, and if $\overset{c}{---}$ is a double bond, then $X^3$ is S; and $R^{16}$, $R^{17}$, $R^{18}$, $R^{19}$, and $R^{20}$ are each independently hydrogen, substituted or unsubstituted alkyl, substituted or unsubstituted alkenyl, substituted or unsubstituted alkynyl, substituted or unsubstituted alkylthio, imine, substituted or unsubstituted amine, hydroxyl, amide, cyano, isocyano, carbonyl, carboxyl, carboxamide, substituted or unsubstituted alkylsulfonyl, substituted or unsubstituted arylsulfonyl, ketone, aldehyde, substituted or unsubstituted ester, heteroalkyl, nitrile, amidine, acetal, ketal, substituted or unsubstituted cycloalkyl, substituted or unsubstituted heterocycloalkyl, substituted or unsubstituted aryl, substituted or unsubstituted heteroaryl, aziridine, carbamate, imide, urea, or thiourea.

In some embodiments, $R^{20}$ is $-NH_2$.

In some embodiments, $\overset{c}{---}$ is a double bond and $X^3$ is S.

In some embodiments, $R^{16}$, $R^{17}$, $R^{18}$, $R^{19}$, and $R^{20}$ are each independently hydrogen, $-NH_2$, hydroxyl, or substituted or unsubstituted heterocycloalkyl.

In some embodiments, the thiopyrimidine is:

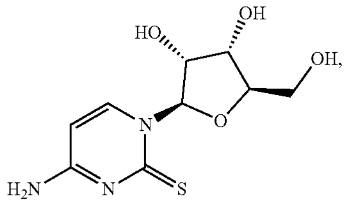

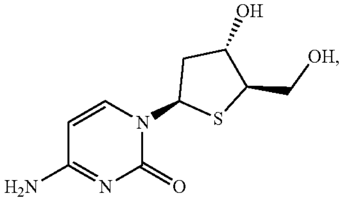

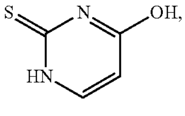

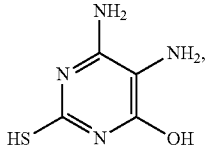

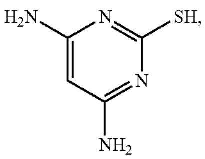

or

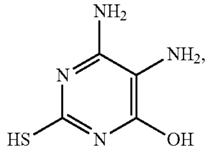

or a tautomer, prodrug pharmaceutically acceptable salt, solvate, or hydrate thereof.

In some embodiments, the otoprotectant comprises 6-phenyl-2-thiouracil, 6-propyl-2-thiouracil, 6-thio-2-deoxyguanosine, 6-thioguanine, 6-mercaptopurine, 6-thioguanosine, or 6-methoxymethyl-2-thiouracil, or 5-carboxy-2-thiouracil, or a combination thereof.

In some embodiments, the composition provides sustained release of the otoprotectant for a period of at least one (1) day after a single administration.

In some embodiments, the composition provides sustained release of the otoprotectant for a period of at least five (5) days after a single administration.

In some embodiments, the drug-induced ototoxicity comprises hearing loss.

In some embodiments, the drug-induced ototoxicity is chemotherapy-induced ototoxicity.

In some embodiments, the chemotherapy-induced ototoxicity is caused by a platinum-based chemotherapeutic agent, a bis-platinate, vincristine, an aminoglycoside antibiotic, a macrolide antibiotic, a diuretic, or a salicylate, or a combination thereof.

In some embodiments, the platinum based chemotherapeutic agent is cisplatin, carboplatin, or oxiplatin, or a combination thereof.

In some embodiments, the chemotherapeutic agent is first-line treatment, primary treatment, or adjuvant treatment.

In some embodiments, the method further comprising surgery, radiation therapy, bone marrow transplantation, or a combination thereof.

In some embodiments, the composition comprises a gel or a viscous preparation.

In some embodiments, the gel is a thermoreversible gel.

In some embodiments, the gel comprises a copolymer of polyoxyethylene and polyoxypropylene.

In some embodiments, the composition comprises from about 14 wt % to about 18 wt % of the copolymer of polyoxytheylene and polyoxypropylene.

In some embodiments, the gel has a gelation viscosity of from about 15,000 cP to about 3,000,000 cP.

In some embodiments, the composition further comprises at least one viscosity modulating agent.

In some embodiments, the at least one viscosity modulating agent is silicon dioxide, povidone, carbomer, poloxamer, or a combination thereof.

In some embodiments, the composition has a gelation temperature of from about 19° C. to about 42° C.

In some embodiments, the composition has an osmolarity from about 100 mOsm/L to about 1000 mOsm/L.

In some embodiments, the composition has a pH of from about 7.0 to about 8.0.

In some embodiments, the composition comprises triglycerides comprising medium chain fatty acids.

In some embodiments, the medium chain fatty acids are saturated medium chain fatty acids, unsaturated medium chain fatty acids, or any combinations thereof.

In some embodiments, the composition comprises at least about 50% by weight of the triglycerides.

In some embodiments, the otoprotectant is multiparticulate. In some embodiments, the otoprotectant is essentially in the form of micronized particles.

In some embodiments, the otoprotectant is essentially dissolved in the composition.

In some embodiments, the composition further comprises an antioxidant, a mucoadhesive, a penetration enhancer, a preservative, a thickening agent, a viscosity modulator agent, a chelator, an antimicrobial agent, a dye, cholesterol, an excipient that increases the release rate of the otoprotectant, or an excipient that increases the release rate of the otoprotectant, or any combination thereof.

In some embodiments, the otoprotectant is not:

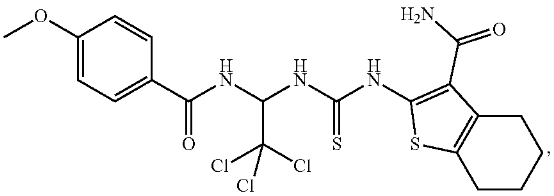
,

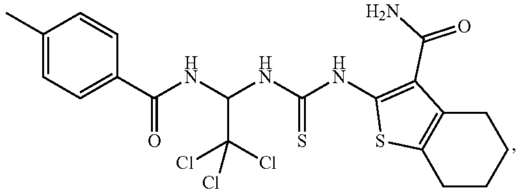
, or

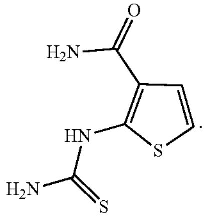
.

In some embodiments, the otoprotectant is not a compound of Formula (V):

(V)

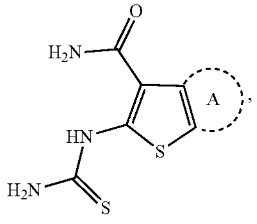

wherein A is a 5-7 membered aryl, heteroaryl, or heterocycle optionally containing one more heteroatoms N, O, or S.

In some embodiments, the pharmaceutical composition and the ototoxic drug are administered simultaneously, approximately simultaneously, or sequentially, in any order. In some embodiments, the pharmaceutical composition and the ototoxic drug are administered sequentially. In some embodiments, the pharmaceutical composition is administered before the ototoxic drug. In some embodiments, the pharmaceutical composition is administered after the ototoxic drug. In some embodiments, the pharmaceutical composition is administered at least one day after the ototoxic drug. In some embodiments, the pharmaceutical composition is administered at least seven days after the ototoxic drug. In some embodiments, the pharmaceutical composition is administered by enteral route or by parenteral route.

In some embodiments, the otoprotectant is formulated for oral administration, injection, topical administration, sublingual administration, buccal administration, transdermal administration, or transmucosal administration. In some embodiments, the composition is formulated for administration by injection. In some embodiments, the injection is a depot injection. In some embodiments, the otoprotectant is formulated for intratympanic administration.

In some embodiments, a concentration of the otoprotectant is in a range of about 0.1 μM to about 100 μM, about 1 μM to about 100 μM, about 10 μM to about 100 μM, or about 50 μM to about 100 μM. In some embodiments, a concentration of the otoprotectant is at least or about 0.001 μM, 0.005 μM, 0.01 μM, 0.05 μM, 0.10 μM, 0.5 μM, 1 μM, 5 μM, 10 μM, 20 μM, 30 μM, 40 μM, 50 μM, 60 μM, 70 μM, 80 μM, 90 μM, 100 μM, 120 μM, 140 μM, 160 μM, 180 μM, 200 μM, or more than 200 μM. In some embodiments, a concentration of the otoprotectant is in a range of about 0.1 mM to about 100 mM, about 1 mM to about 100 mM, about 10 mM to about 100 mM, or about 50 mM to about 100 mM. In some embodiments, a concentration of the otoprotectant is at least or about 0.001 mM, 0.005 mM, 0.01 mM, 0.05 mM, 0.10 mM, 0.5 mM, 1 mM, 5 mM, 10 mM, 20 mM, 30 mM, 40 mM, 50 mM, 60 mM, 70 mM, 80 mM, 90 mM, 100 mM, 120 mM, 140 mM, 160 mM, 180 mM, 200 mM, or more than 200 mM.

In an aspect, provided herein is a method of treating and/or preventing drug-induced ototoxicity, comprising administering to a subject in need thereof a pharmaceutical composition, comprising:

1. an otoprotectant; and
2. at least one pharmaceutically acceptable excipient or carrier, wherein the otoprotectant comprises at least one of: a thiopyrimidine, a thiopurine, a thiouracil, a thiouracil derivative, a thiourea, a thioamide, or a tautomer, prodrug, pharmaceutically acceptable salt, solvate, or hydrate thereof, and wherein the otoprotectant has a second order reaction rate of greater than 9.30E-09 M/s when reacting with cisplatin at about 20° C. In some embodiments, the reaction is measured at a concentration of about 1 mM cisplatin and 1 mM of the compounds disclosed herein.

In another aspect, provided herein is a method of treating and/or preventing drug-induced ototoxicity, comprising administering to a subject in need thereof a pharmaceutical composition, comprising:

(iii) an otoprotectant; and (iv) at least one pharmaceutically acceptable excipient or carrier, wherein the otoprotectant comprises at least one of: a thiopyrimidine, a thiopurine, a thiouracil, a thiouracil derivative, a thiourea, a thioamide, or a tautomer, prodrug, pharmaceutically acceptable salt, solvate, or hydrate thereof, and wherein the otoprotectant has a rate constant (k) of at least about 0.001 when reacting with cisplatin.

In another aspect, provided herein is a method of treating and/or preventing drug-induced ototoxicity, comprising administering to a subject in need thereof a pharmaceutical composition, comprising:

(i) an otoprotectant; and (ii) at least one pharmaceutically acceptable excipient or carrier, wherein the otoprotectant comprises at least one of: a thiopyrimidine, a thiopurine, a thiouracil, a thiouracil derivative, a thiourea, a thioamide, or a tautomer, prodrug, pharmaceutically acceptable salt, solvate, or hydrate thereof, and wherein the otoprotectant has a rate constant (k) of at least about 0.07 when reacting with cisplatin.

In some embodiments, the rate constant is from about 0.01 to about 1.0. In some embodiments, the rate constant is about 0.01, about 0.02, about 0.03, about 0.04, about 0.05, about 0.06, about 0.07, about 0.08, about 0.09, about 0.1, about 0.2, about 0.3, about 0.5, about 0.6, about 0.7, about 0.9, or about 1.0.

In some embodiments, the rate constant of the otoprotectant is calculated with cisplatin comprises a stock solution of about 0.9% cisplatin in aqueous NaCl. In some embodiments, the rate constant of the otoprotectant is calculated with cisplatin comprises a stock solution of about 0.9% cisplatin in aqueous NaCl at pH of from about 4.0 to about 5.0. In some embodiments, the rate constant of the otoprotectant is calculated with cisplatin comprises a stock solution of about 0.9% cisplatin in aqueous NaCl at pH of from about 4.0 to about 5.0 and a temperature of from about 20° C. to about 30° C. In some embodiments, the rate constant of the otoprotectant is calculated with cisplatin comprises a stock solution of about 0.9% cisplatin in aqueous NaCl at pH of from about 4.0 to about 5.0 and a temperature of about 25° C.

In some embodiments, the rate constant of the otoprotectant is calculated with cisplatin comprises a stock solution of about 50 μM cisplatin in PBS. In some embodiments, the rate constant of the otoprotectant is calculated with cisplatin comprises a stock solution of about 50 μM cisplatin in PBS at a pH of from about 7.0 to about 8.0. In some embodiments, the rate constant of the otoprotectant is calculated with cisplatin comprises a stock solution of about 50 μM cisplatin in PBS at a pH of from about 7.0 to about 8.0 and a temperature of from about 30° C. to about 40° C. In some embodiments, the rate constant of the otoprotectant is calculated with cisplatin comprises a stock solution of about 50 μM cisplatin in PBS at a pH of from about 7.0 to about 8.0 and a temperature of about 37° C.

In an aspect there is provided, a method of treating and/or preventing drug-induced ototoxicity, comprising administering to a subject in need thereof a pharmaceutical composition, comprising:

(iii) an otoprotectant; and (iv) at least one pharmaceutically acceptable excipient or carrier, wherein the otoprotectant comprises a thiouracil or a thiouracil derivative of structural Formula (III):

(III)

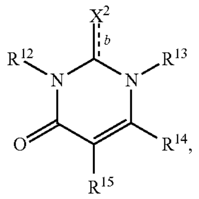

or a tautomer, prodrug, pharmaceutically acceptable salt, solvate, or hydrate thereof, wherein:

$X^2$ is S or $SR^{11}$;

$\overset{b}{\text{---}}$ is a single bond or double bond, wherein if $\overset{b}{\text{---}}$ is a single bond, then $X^2$ is $SR^{11}$, and if $\overset{b}{\text{---}}$ is a double bond, then $X^2$ is S; and $R^{11}$, $R^{12}$, $R^{13}$, $R^{14}$, and $R^{15}$ are each independently hydrogen, substituted or unsubstituted alkyl, substituted or unsubstituted alkenyl, substituted or unsubstituted alkynyl, substituted or unsubstituted alkylthio, imine, substituted or unsubstituted amine, hydroxyl, amide, cyano, isocyano, carbonyl, carboxyl, carboxamide, substituted or unsubstituted alkylsulfonyl, substituted or unsubstituted arylsulfonyl, ketone, aldehyde, substituted or unsubstituted ester, heteroalkyl, nitrile, amidine, acetal, ketal, substituted or unsubstituted cycloalkyl, substituted or unsubstituted heterocycloalkyl, substituted or unsubstituted aryl, substituted or unsubstituted heteroaryl, aziridine, carbamate, imide, urea, or thiourea.

In some embodiments, $\overset{b}{\text{---}}$ is a double bond and $X^2$ is S.

In some embodiments, $R^{12}$ is hydrogen, substituted or unsubstituted alkyl, or substituted or unsubstituted aryl.

In some embodiments, $R^{13}$ is hydrogen.

In some embodiments, $R^{14}$ is hydrogen, substituted or unsubstituted alkyl, substituted or unsubstituted aryl, or a carboxyl.

In some embodiments, $R^{15}$ is hydrogen or a $C_1$-$C_6$ ketone.

In some embodiments, the thiouracil is:

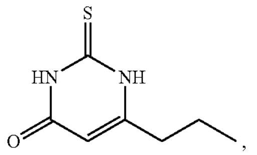

-continued

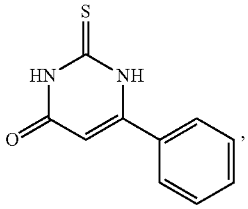, 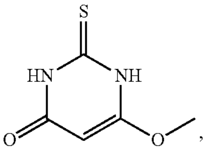,

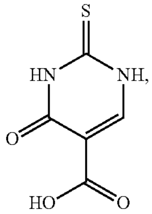 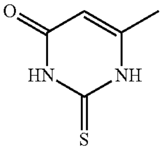, 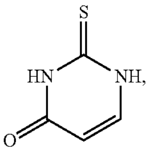

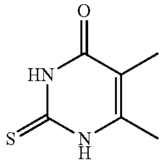, 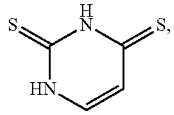

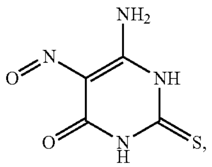 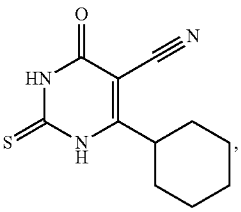,

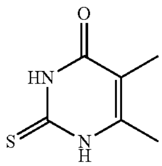, 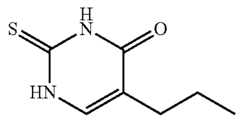,

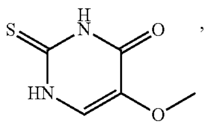, 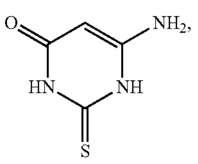

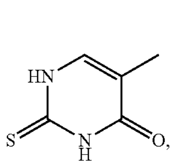 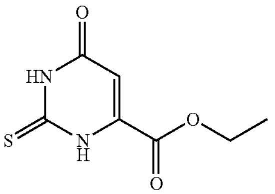,

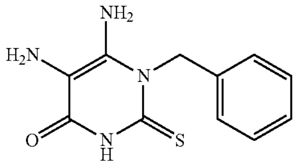,

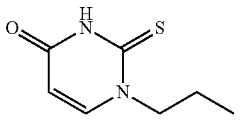, 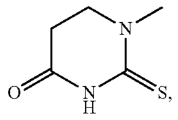

-continued

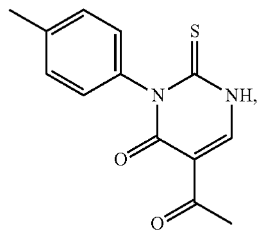 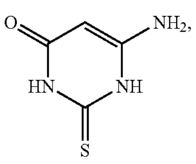 or

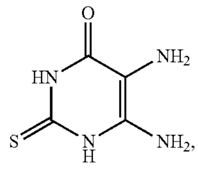

or a tautomer, prodrug, pharmaceutically acceptable salt, solvate, or hydrate thereof.

In some embodiments, the thiouracil is:

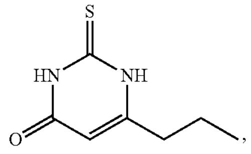, or a tautomer, prodrug, pharmaceutically acceptable salt, solvate, or hydrate thereof.

In some embodiments, the thiouracil is:

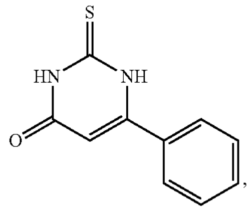 [SMILES: O=c1cc(-c2ccccc2)[nH]c(=S)[nH]1], or a tautomer, prodrug, pharmaceutically acceptable salt, solvate, or hydrate thereof.

In some embodiments, the thiouracil is:

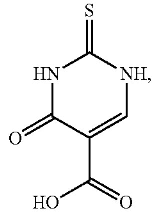 [SMILES: O=C(O)c1c[nH]c(=S)[nH]c1=O]

or a tautomer, prodrug, pharmaceutically acceptable salt, solvate, or hydrate thereof.

In some embodiments, the thiouracil is:

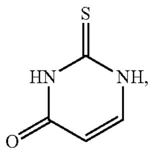

or a tautomer, prodrug, pharmaceutically acceptable salt, solvate, or hydrate thereof.

In some embodiments, the thiouracil is:

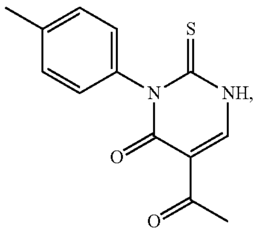 [SMILES: CC(=O)c1c[nH]c(=S)n(-c2ccc(C)cc2)c1=O]

or a tautomer, prodrug, pharmaceutically acceptable salt, solvate, or hydrate thereof.

In some embodiments, the thiouracil derivative is:

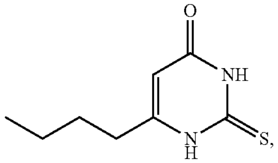
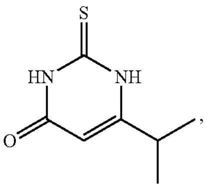
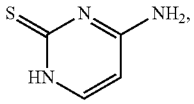
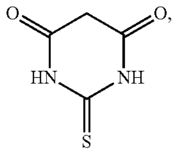
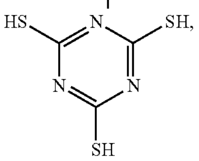
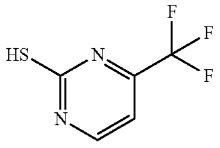
or
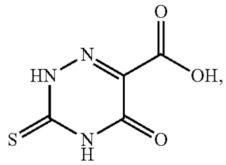

or a tautomer, prodrug, pharmaceutically acceptable salt, solvate, or hydrate thereof.

In some embodiments, the composition provides sustained release of the otoprotectant for a period of at least one (1) day after a single administration.

In some embodiments, the composition provides sustained release of the otoprotectant for a period of at least five (5) days after a single administration.

In some embodiments, the drug-induced ototoxicity comprises hearing loss.

In some embodiments, the drug-induced ototoxicity is chemotherapy-induced ototoxicity.

In some embodiments, the composition comprises a gel or a viscous preparation.

In some embodiments, the gel is a thermoreversible gel.

In some embodiments, the gel comprises a copolymer of polyoxyethylene and polyoxypropylene.

In some embodiments, the composition comprises from about 14 wt % to about 18 wt % of the copolymer of polyoxytheylene and polyoxypropylene.

In some embodiments, the gel has a gelation viscosity of from about 15,000 cP to about 3,000,000 cP.

In some embodiments, the composition further comprises at least one viscosity modulating agent.

In some embodiments, the at least one viscosity modulating agent is silicon dioxide, povidone, carbomer, poloxamer, or a combination thereof.

In some embodiments, the composition has a gelation temperature of from about 19° C. to about 42° C.

In some embodiments, the composition has an osmolarity from about 100 mOsm/L to about 1000 mOsm/L.

In some embodiments, the composition comprises triglycerides comprising medium chain fatty acids.

In some embodiments, the medium chain fatty acids are saturated medium chain fatty acids, unsaturated medium chain fatty acids, or any combinations thereof.

In some embodiments, the composition comprises at least about 50% by weight of the triglycerides.

In some embodiments, the otoprotectant is multiparticulate.

In some embodiments, the otoprotectant is essentially in the form of micronized particles.

In some embodiments, the otoprotectant is essentially dissolved in the composition.

In some embodiments, the composition further comprises an antioxidant, a mucoadhesive, a penetration enhancer, a preservative, a thickening agent, a viscosity modulator agent, a chelator, an antimicrobial agent, a dye, cholesterol, an excipient that increases the release rate of the otoprotectant, or an excipient that increases the release rate of the otoprotectant, or any combination thereof.

In some embodiments, the otoprotectant is not:

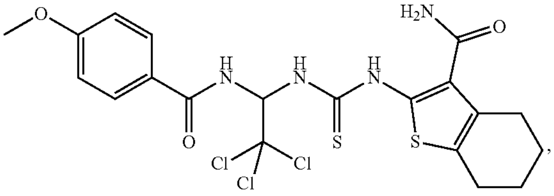
,
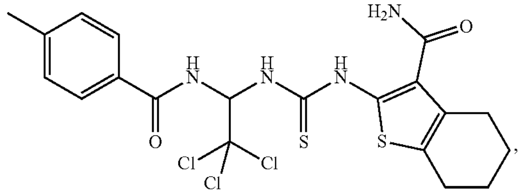
, or
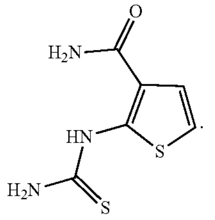
.

In some embodiments, the otoprotectant is not a compound of Formula (V):

(V)

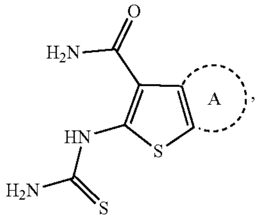

wherein A is a 5-7 membered aryl, heteroaryl, or heterocycloalkyl optionally containing one more heteroatoms N, O, or S.

In some embodiments, the pharmaceutical composition and the ototoxic drug are administered simultaneously, approximately simultaneously, or sequentially, in any order.

In some embodiments, the pharmaceutical composition is administered at least one day after the ototoxic drug.

In some embodiments, the pharmaceutical composition is administered at least seven days after the ototoxic drug.

In some embodiments, the otoprotectant is formulated for intratympanic administration.

In some embodiments, the otoprotectants described herein protect against drug-induced ototoxicity. In some embodiments, the otoprotectants protect against chemotherapy-induced ototoxicity. In some embodiments, the chemotherapy-induced ototoxicity is caused by a platinum based chemotherapeutic agent, a bis-platinate, vincristine, an aminoglycoside antibiotic, a macrolide antibiotic, a diuretic or a salicylate. In some embodiments, the platinum based chemotherapeutic agent is cisplatin.

In some embodiments, the otoprotectants protect hair cells from chemotherapy-induced damage. In some embodiments, chemotherapy-induced damage affects hair cell survival, function, viability, health, growth, or a combination thereof. In some embodiments, the otoprotectants improve hair cell survival, function, viability, health, growth, or a combination thereof following chemotherapy-induced ototoxicity by at least or about 5%, 10%, 15%, 20%, 25%, 30%, 35%, 40%, 45%, 50%, 55%, 60%, 65%, 70%, 75%, 80%, 85%, 90%, 95%, or more than 95%. In some embodiments, the hair cell survival is of the outer hair cells. In some embodiments, the hair cell survival is of the inner hair cells.

In some embodiments, the otoprotectants protect support cells from chemotherapy-induced damage. In some embodiments, chemotherapy-induced damage affects support cell survival, function, viability, health, growth, or a combination thereof. In some embodiments, the otoprotectants improve support cell survival, function, viability, health, growth, or a combination thereof following chemotherapy-induced ototoxicity by at least or about 5%, 10%, 15%, 20%, 25%, 30%, 35%, 40%, 45%, 50%, 55%, 60%, 65%, 70%, 75%, 80%, 85%, 90%, 95%, or more than 95%. In some embodiments, the support cell survival is of the outer support cells. In some embodiments, the support cell survival is of the inner support cells.

In some embodiments, the otoprotectants described herein protect spiral ganglion neurons from chemotherapy-induced damage. In some embodiments, chemotherapy-induced damage affects spiral ganglion neuron survival, function, viability, health, growth, or a combination thereof. In some embodiments, the otoprotectants improve spiral ganglion neuron survival, function, viability, health, growth, or a combination thereof following chemotherapy-induced ototoxicity by at least or about 5%, 10%, 15%, 20%, 25%, 30%, 35%, 40%, 45%, 50%, 55%, 60%, 65%, 70%, 75%, 80%, 85%, 90%, 95%, or more than 95%. In some embodiments, the otoprotectants described herein protect spiral ganglion neurons from stress.

In some embodiments, the otoprotectants described herein protect strial cells from chemotherapy-induced damage. In some embodiments, chemotherapy-induced damage affects strial cell survival, function, viability, health, growth, or a combination thereof. In some embodiments, the otoprotectants described herein improve strial cell survival, function, viability, health, growth, or a combination thereof following chemotherapy-induced ototoxicity by at least or about 5%, 10%, 15%, 20%, 25%, 30%, 35%, 40%, 45%, 50%, 55%, 60%, 65%, 70%, 75%, 80%, 85%, 90%, 95%, or more than 95%.

An otoprotectant may have anti-oxidant and/or anti-inflammatory properties. An otoprotectant may be capable of directly binding a chemotherapeutic agent such as cisplatin.

Amount of Therapeutic Agent

In some embodiments, the otic formulation comprises between about 0.0001% to about 99.9999% by weight of the weight of the therapeutic agent, or pharmaceutically acceptable prodrug or salt thereof. In some embodiments, the otic formulation comprises between about 0.0001% to about 20% by weight of the weight of the therapeutic agent, or pharmaceutically acceptable prodrug or salt thereof. In some embodiments, the otic formulation comprises between about 0.0001% to about 15% by weight of the weight of the therapeutic agent, or pharmaceutically acceptable prodrug or salt thereof. In some embodiments, the otic formulation comprises between about 0.0001% to about 10% by weight of the weight of the therapeutic agent, or pharmaceutically acceptable prodrug or salt thereof. In some embodiments, the otic formulation comprises between about 0.0001% to about 5% by weight of the weight of the therapeutic agent, or pharmaceutically acceptable prodrug or salt thereof. In some embodiments, the otic formulation comprises between about 0.0001% to about 10% by weight of the weight of the therapeutic agent, or pharmaceutically acceptable prodrug or salt thereof.

In some embodiments, the otic formulation or composition comprises between about 0.001% to about 99.99% by weight of the therapeutic agent, or pharmaceutically acceptable prodrug or salt thereof. In some embodiments, the otic formulation or composition comprises between about 0.001% to about 99.9% by weight of the therapeutic agent, or pharmaceutically acceptable prodrug or salt thereof. In some embodiments, the otic formulation or composition comprises between about 0.001% to about 99% by weight of the therapeutic agent, or pharmaceutically acceptable prodrug or salt thereof. In some embodiments, the otic formulation or composition comprises between about 0.001% to about 90% by weight of the therapeutic agent, or pharmaceutically acceptable prodrug or salt thereof. In some embodiments, the otic formulation or composition comprises between about 0.001% to about 80% by weight of the therapeutic agent, or pharmaceutically acceptable prodrug or salt thereof. In some embodiments, the otic formulation or composition comprises between about 0.001% to about 70% by weight of the therapeutic agent, or pharmaceutically acceptable prodrug or salt thereof. In some embodiments, the otic formulation or composition comprises between about 0.001% to about 60% by weight of the therapeutic agent, or pharmaceutically acceptable prodrug or salt thereof. In some embodiments, the otic formulation or composition comprises between about 0.001% to about 50% by weight of the therapeutic agent, or pharmaceutically acceptable prodrug or salt thereof. In some embodiments, the otic formulation or composition comprises between about 0.001% to about 40% by weight of the therapeutic agent, or pharmaceutically acceptable prodrug or salt thereof. In some embodiments, the otic formulation or composition comprises between about 0.001% to about 30% by weight of the therapeutic agent, or pharmaceutically acceptable prodrug or salt thereof. In some embodiments, the otic formulation or composition comprises between about 0.001% to about 20% by weight of the therapeutic agent, or pharmaceutically acceptable prodrug or salt thereof. In some embodiments, the otic formulation or composition comprises between about 0.001% to about 15% by weight of the therapeutic agent, or pharmaceutically acceptable prodrug or salt thereof. In some embodiments, the otic formulation or composition comprises between about 0.001% to about 10% by weight of the therapeutic agent, or pharmaceutically acceptable prodrug or salt thereof. In some embodiments, the otic formulation or composition comprises between about 0.001% to about 7% by weight of the therapeutic agent, or pharmaceutically acceptable prodrug or salt thereof. In some embodiments, the otic formulation or composition comprises between about 0.001% to about 5% by weight of the therapeutic agent, or pharmaceutically acceptable prodrug or salt thereof. In some embodiments, the otic formulation or composition comprises between about 0.001% to about 3% by weight of the therapeutic agent, or pharmaceutically acceptable prodrug or salt thereof. In some embodiments, the otic formulation or composition comprises between about 0.001% to about 2% by weight of the therapeutic agent, or pharmaceutically acceptable prodrug or salt thereof. In some embodiments, the otic formulation or composition comprises between about 0.001% to about 10% by weight of the therapeutic agent, or pharmaceutically acceptable prodrug or salt thereof.

In some embodiments, the otic formulation or composition comprises between about 0.01% to about 99.99% by weight of the therapeutic agent, or pharmaceutically acceptable prodrug or salt thereof. In some embodiments, the otic formulation or composition comprises between about 0.01% to about 99.9% by weight of the therapeutic agent, or pharmaceutically acceptable prodrug or salt thereof. In some embodiments, the otic formulation or composition comprises between about 0.01% to about 99% by weight of the therapeutic agent, or pharmaceutically acceptable prodrug or salt thereof. In some embodiments, the otic formulation or composition comprises between about 0.01% to about 90% by weight of the therapeutic agent, or pharmaceutically acceptable prodrug or salt thereof. In some embodiments, the otic formulation or composition comprises between about 0.01% to about 80% by weight of the therapeutic agent, or pharmaceutically acceptable prodrug or salt thereof. In some embodiments, the otic formulation or composition comprises between about 0.01% to about 70% by weight of the therapeutic agent, or pharmaceutically acceptable prodrug or salt thereof. In some embodiments, the otic formulation or composition comprises between about 0.01% to about 60% by weight of the therapeutic agent, or pharmaceutically acceptable prodrug or salt thereof. In some embodiments, the otic formulation or composition comprises between about 0.01% to about 50% by weight of the therapeutic agent, or pharmaceutically acceptable prodrug or salt thereof. In some embodiments, the otic formulation or composition comprises between about 0.01% to about 40% by weight of the therapeutic agent, or pharmaceutically acceptable prodrug or salt thereof. In some embodiments, the otic formulation or composition comprises between about 0.01% to about 30% by weight of the therapeutic agent, or pharmaceutically acceptable prodrug or salt thereof. In some embodiments, the otic formulation or composition comprises between about 0.01% to about 20% by weight of the therapeutic agent, or pharmaceutically acceptable prodrug or salt thereof. In some embodiments, the otic formulation or composition comprises between about 0.01% to about 15% by weight of the therapeutic agent, or pharmaceutically acceptable prodrug or salt thereof. In some embodiments, the otic formulation or composition comprises between about 0.01% to about 10% by weight of the therapeutic agent, or pharmaceutically acceptable prodrug or salt thereof. In some embodiments, the otic formulation or composition comprises between about 0.01% to about 7% by weight of the therapeutic agent, or pharmaceutically acceptable prodrug or salt thereof. In some embodiments, the otic formulation or composition comprises between about 0.01% to about 5% by weight of the therapeutic agent, or pharmaceutically acceptable prodrug or salt thereof. In some embodiments, the otic formulation or composition comprises between about 0.01% to about 3% by weight of the therapeutic agent, or pharmaceutically acceptable prodrug or salt thereof. In some embodiments, the otic formulation or composition comprises between about 0.01% to about 2% by weight of the therapeutic agent, or pharmaceutically acceptable prodrug or salt thereof. In some embodiments, the otic formulation or composition comprises between about 0.01% to about 1% by weight of the therapeutic agent, or pharmaceutically acceptable prodrug or salt thereof.

In some embodiments, the otic formulation or composition comprises between about 0.1% to about 40% by weight of the therapeutic agent, or pharmaceutically acceptable prodrug or salt thereof. In some embodiments, the otic formulation or composition comprises between about 0.1% to about 30% by weight of the therapeutic agent, or pharmaceutically acceptable prodrug or salt thereof. In some embodiments, the otic formulation or composition comprises between about 0.10% to about 20% by weight of the therapeutic agent, or pharmaceutically acceptable prodrug or salt thereof. In some embodiments, the otic formulation or composition comprises between about 0.10% to about 15% by weight of the therapeutic agent, or pharmaceutically acceptable prodrug or salt thereof. In some embodiments, the otic formulation or composition comprises between about 0.10% to about 10% by weight of the therapeutic agent, or pharmaceutically acceptable prodrug or salt thereof. In some embodiments, the otic formulation or composition comprises between about 0.10% to about 7% by weight of the therapeutic agent, or pharmaceutically acceptable prodrug or salt thereof. In some embodiments, the otic formulation or composition comprises between about 0.10% to about 5% by weight of the therapeutic agent, or pharmaceutically acceptable prodrug or salt thereof. In some embodiments, the otic formulation or composition comprises between about 0.10% to about 3% by weight of the therapeutic agent, or pharmaceutically acceptable prodrug or salt thereof. In some embodiments, the otic formulation or composition comprises between about 0.10% to about 2% by weight of the therapeutic agent, or pharmaceutically acceptable prodrug or salt thereof. In some embodiments, the otic formulation or composition comprises between about 0.10% to about 1% by weight of the therapeutic agent, or pharmaceutically acceptable prodrug or salt thereof.

In some embodiments, the otic formulation or composition comprises between about 1% to about 40% by weight of the therapeutic agent, or pharmaceutically acceptable prodrug or salt thereof. In some embodiments, the otic formulation or composition comprises between about 1% to about 30% by weight of the therapeutic agent, or pharmaceutically acceptable prodrug or salt thereof. In some embodiments, the otic formulation or composition comprises between about 1% to about 20% by weight of the therapeutic agent, or pharmaceutically acceptable prodrug or salt thereof. In some embodiments, the otic formulation or composition comprises between about 1% to about 150% by weight of the therapeutic agent, or pharmaceutically acceptable prodrug or salt thereof. In some embodiments, the otic formulation or composition comprises between about 1% to about 10% by weight of the therapeutic agent, or pharmaceutically acceptable prodrug or salt thereof. In some embodiments, the otic formulation or composition comprises between about 1% to about 7% by weight of the therapeutic agent, or pharmaceutically acceptable prodrug or salt thereof. In some embodiments, the otic formulation or composition comprises between about 1% to about 5% by weight of the therapeutic agent, or pharmaceutically acceptable prodrug or salt thereof. In some embodiments, the otic formulation or composition comprises between about 1% to about 3% by weight of the therapeutic agent, or pharmaceutically acceptable prodrug or salt thereof. In some embodiments, the otic formulation or composition comprises between about 1% to about 2% by weight of the therapeutic agent, or pharmaceutically acceptable prodrug or salt thereof.

In some embodiments, the otic formulation or composition comprises about 0.0001%, about 0.0002%, about 0.0003%, about 0.0004%, about 0.0005%, about 0.0006%, about 0.0007%, about 0.0008%, about 0.0009%, about 0.001%, about 0.002%, about 0.003%, about 0.004%, about 0.005%, about 0.006%, about 0.007%, about 0.008%, about 0.009%, about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7% m about 8%, about 9%, about 10%, about 11%, about 12%, about 13%, about 14%, about 15%, about 16%, about 17%, about 18%, about 19%, about 20%, about 25%, about 30%, about 35%, or about 40% by weight of the therapeutic agent, or pharmaceutically acceptable prodrug or salt thereof.

In some embodiments, the otic formulation or composition comprises about 0.001%, about 0.002%, about 0.003%, about 0.004%, about 0.005%, about 0.006%, about 0.007%, about 0.008%, about 0.009%, about 0.01%, about 0.02%, about 0.03%, about 0.04%, about 0.05%, about 0.06%, about 0.07%, about 0.08%, about 0.09%, about 0.1%, about 0.2% about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 35%, or about 40% by weight of the therapeutic agent, or pharmaceutically acceptable prodrug or salt thereof. In some embodiments, the otic formulation or composition comprises about 0.01% by weight of the therapeutic agent, or pharmaceutically acceptable prodrug or salt thereof. In some embodiments, the otic formulation or composition comprises about 0.02% by weight of the therapeutic agent, or pharmaceutically acceptable prodrug or salt thereof. In some embodiments, the otic formulation or composition comprises about 0.03% by weight of the therapeutic agent, or pharmaceutically acceptable prodrug or salt thereof. In some embodiments, the otic formulation or composition comprises about 0.04% by weight of the therapeutic agent, or pharmaceutically acceptable prodrug or salt thereof. In some embodiments, the otic formulation or composition comprises about 0.05% by weight of the therapeutic agent, or pharmaceutically acceptable prodrug or salt thereof. In some embodiments, the otic formulation or composition comprises about 0.06% by weight of the therapeutic agent, or pharmaceutically acceptable prodrug or salt thereof. In some embodiments, the otic formulation or composition comprises about 0.07% by weight of the therapeutic agent, or pharmaceutically acceptable prodrug or salt thereof. In some embodiments, the otic formulation or composition comprises about 0.08% by weight of the therapeutic agent, or pharmaceutically acceptable prodrug or salt thereof. In some embodiments, the otic formulation or composition comprises about 0.09% by weight of the therapeutic agent, or pharmaceutically acceptable prodrug or salt thereof. In some embodiments, the otic formulation or composition comprises about 0.1% by weight of the therapeutic agent, or pharmaceutically acceptable prodrug or salt thereof. In some embodiments, the otic formulation or composition comprises about 0.2% by weight of the therapeutic agent, or pharmaceutically acceptable prodrug or salt thereof. In some embodiments, the otic formulation or composition comprises about 0.3% by weight of the therapeutic agent, or pharmaceutically acceptable prodrug or salt thereof. In some embodiments, the otic formulation or composition comprises about 0.4% by weight of the therapeutic agent, or pharmaceutically acceptable prodrug or salt thereof. In some embodiments, the otic formulation or composition comprises about 0.5% by weight of the therapeutic agent, or pharmaceutically acceptable prodrug or salt thereof. In some embodiments, the otic formulation or composition comprises about 0.6% by weight of the therapeutic agent, or pharmaceutically acceptable prodrug or salt thereof. In some embodiments, the otic formulation or composition comprises about 0.7% by weight of the therapeutic agent, or pharmaceutically acceptable prodrug or salt thereof. In some embodiments, the otic formulation or composition comprises about 0.8% by weight of the therapeutic agent, or pharmaceutically acceptable prodrug or salt thereof. In some embodiments, the otic formulation or composition comprises about 0.9% by weight of the therapeutic agent, or pharmaceutically acceptable prodrug or salt thereof. In some embodiments, the otic formulation or composition comprises about 1% by weight of the therapeutic agent, or pharmaceutically acceptable prodrug or salt thereof. In some embodiments, the otic formulation or composition comprises about 2% by weight of the therapeutic agent, or pharmaceutically acceptable prodrug or salt thereof. In some embodiments, the otic formulation or composition comprises about 3% by weight of the therapeutic agent, or pharmaceutically acceptable prodrug or salt thereof. In some embodiments, the otic formulation or composition comprises about 4% by weight of the therapeutic agent, or pharmaceutically acceptable prodrug or salt thereof. In some embodiments, the otic formulation or composition comprises about 5% by weight of the therapeutic agent, or pharmaceutically acceptable prodrug or salt thereof. In some embodiments, the otic formulation or composition comprises about 6% by weight of the therapeutic agent, or pharmaceutically acceptable prodrug or salt thereof. In some embodiments, the otic formulation or composition comprises about 7% by weight of the therapeutic agent, or pharmaceutically acceptable prodrug or salt thereof. In some embodiments, the otic formulation or composition comprises about 8% by weight of the therapeutic agent, or pharmaceutically acceptable prodrug or salt thereof. In some embodiments, the otic formulation or composition comprises about 9% by weight of the therapeutic agent, or pharmaceutically acceptable prodrug or salt thereof. In some embodiments, the otic formulation or composition comprises about 10% by weight of the therapeutic agent, or pharmaceutically acceptable prodrug or salt thereof. In some embodiments, the otic formulation or composition comprises about 11% by weight of the therapeutic agent, or pharmaceutically acceptable prodrug or salt thereof. In some embodiments, the otic formulation or composition comprises about 12% by weight of the therapeutic agent, or pharmaceutically acceptable prodrug or salt thereof. In some embodiments, the otic formulation or composition comprises about 13% by weight of the therapeutic agent, or pharmaceutically acceptable prodrug or salt thereof. In some embodiments, the otic formulation or composition comprises about 14% by weight of the therapeutic agent, or pharmaceutically acceptable prodrug or salt thereof. In some embodiments, the otic formulation or composition comprises about 15% by weight of the therapeutic agent, or pharmaceutically acceptable prodrug or salt thereof. In some embodiments, the otic formulation or composition comprises about 16% by weight of the therapeutic agent, or pharmaceutically acceptable prodrug or salt thereof. In some embodiments, the otic formulation or composition comprises about 17% by weight of the therapeutic agent, or pharmaceutically acceptable prodrug or salt thereof. In some embodiments, the otic formulation or composition comprises about 18% by weight of the therapeutic agent, or pharmaceutically acceptable prodrug or salt thereof. In some embodiments, the otic formulation or composition comprises about 19% by weight of the therapeutic agent, or pharmaceutically acceptable prodrug or salt thereof. In some embodiments, the otic formulation or composition comprises about 20% by weight of the therapeutic agent, or pharmaceutically acceptable prodrug or salt thereof.

Devices

Also contemplated herein are the use of devices for the delivery of the pharmaceutical formulations and compositions disclosed herein, or alternatively for the measurement or surveillance of the function of the *auris* formulations disclosed herein. For example, in one embodiment pumps, osmotic devices or other means of mechanically delivering pharmaceutical formulations and compositions are used for the delivery of the pharmaceutical formulations disclosed herein. Reservoir devices are optionally used with the pharmaceutical drug delivery units and reside either internally along with the drug delivery unit, or externally of the *auris* structures.

Other embodiments contemplate the use of mechanical or imaging devices to monitor or survey the hearing, balance or other *auris* disorder. For example, magnetic resonance imaging (MRI) devices are specifically contemplated within the scope of the embodiments, wherein the MRI devices (for example, 3 Tesla MRI devices) are capable of evaluating Meniere Disease progression and subsequent treatment with the pharmaceutical formulations disclosed herein. See, Carfrae et al. Laryngoscope 118:501-505 (March 2008). Whole body scanners, or alternatively cranial scanners, are contemplated, as well as higher resolution (7 Tesla, 8 Tesla, 9.5 Tesla or 11 Tesla for humans) are optionally used in MRI scanning.

Visualization of Otic Formulations

Also provided herein in some embodiments are otic formulations and compositions that comprise a dye (e.g., a Trypan blue dye, Evans blue dye) or other tracer compound. In some instances, addition of an *auris*-compatible dye to an otic formulation or composition described herein aids visualization of any administered formulation or composition in an ear (e.g., a rodent ear and/or a human ear). In certain embodiments, an otic formulation or composition comprising a dye or other tracer compound eliminates the need for invasive procedures that are currently used in animal models to monitor the concentrations of drugs in the endolymph and/or perilymph.

In some instances, intratympanic injections require the need of a specialist and the formulation or composition needs to be delivered to a specific site of the ear to maximize efficiency of the medication delivered. In certain instances, a visualization technique for any formulation or composition described herein allows for visualization of a dosing site (e.g., the round window) so that the medication is applied in the proper place. In some instances, a formulation or composition comprising a dye allows visualization of the formulation or composition during administration of the formulation to an ear (e.g., a human ear), ensures that the medication will be delivered at the intended site, and avoids any complications due to incorrect placement of a formulation or composition. The inclusion of a dye to help enhance the visualization of the formulation or composition when applied, and the ability to visually inspect the location of the formulation or composition after administration without further intervention, represents an advance over currently available methods for testing intratympanic therapeutics in animal models and/or human trials. In some embodiments, dyes that are compatible with the otic compositions described herein include Evans blue (e.g., 0.5% of the total weight of an otic formulation), Methylene blue (e.g., 1% of the total weight of an otic formulation), Isosulfan blue (e.g., 1% of the total weight of an otic formulation), Trypan blue (e.g., 0.15% of the total weight of an otic formulation), and/or indocyanine green (e.g., 25 mg/vial). Other common dyes, e.g., FD&C red 40, FD&C red 3, FD&C yellow 5, FD&C yellow 6, FD&C blue 1, FD&C blue2, FD&C green 3, fluorescence dyes (e.g., Fluorescein isothiocyanate, rhodamine, Alexa Fluors, DyLight Fluors) and/or dyes that are visualizable in conjunction with non-invasive imaging techniques such as MRI, CAT scans, PET scans or the like (e.g., Gadolinium-based MRI dyes, iodine-base dyes, barium-based dyes or the like) are also contemplated for use with any otic formulation or composition described herein. Other dyes that are compatible with any formulation or composition described herein are listed in the Sigma-Aldrich catalog under dyes (which is included herein by reference for such disclosure). In some embodiments, concentration of a dye in any otic formulation described herein is less than 2%, less than 1.5%, less than 1%, less than 0.5%, less than 0.25%, less than 0.1%, or less than 100 ppm of the total weight and/or volume of any formulation or composition described herein.

In certain embodiments of such *auris*-compatible formulations or compositions that comprise a dye, the ability to visualize a controlled release otic formulation or composition comprising a dye in an ear meets a long-standing need for suitable testing methods that are applicable to the development of intratympanic otic formulations or compositions suitable for human use. In certain embodiments of such *auris*-compatible formulations or compositions that comprise a dye, the ability to visualize a controlled release otic formulation or composition comprising a dye allows for testing of any otic formulation described herein in human clinical trials.

General Methods of Sterilization

The environment of the inner ear is an isolated environment. The endolymph and the perilymph are static fluids and are not in contiguous contact with the circulatory system. The blood-labyrinth-barrier (BLB), which includes a blood-endolymph barrier and a blood-perilymph barrier, consists of tight junctions between specialized epithelial cells in the labyrinth spaces (i.e., the vestibular and cochlear spaces). The presence of the BLB limits delivery of active agents to the isolated microenvironment of the inner ear. *Auris* hair cells are bathed in endolymphatic or perilymphatic fluids and cochlear recycling of potassium ions is important for hair cell function. When the inner ear is infected, there is an influx of leukocytes and/or immunoglobins (e.g. in response to a microbial infection) into the endolymph and/or the perilymph and the delicate ionic composition of inner ear fluids is upset by the influx of leukocytes and/or immunoglobins. In certain instances, a change in the ionic composition of inner ear fluids results in hearing loss, loss of balance and/or ossification of auditory structures. In certain instances, even trace amounts of pyrogens and/or microbes trigger infections and related physiological changes in the isolated microenvironment of the inner ear.

In one aspect, provided herein are otic formulations or compositions that are sterilized with stringent sterility requirements and are suitable for administration to the middle and/or inner ear. In some embodiments, the otic formulations or compositions described herein are *auris* compatible compositions. In some embodiment, the otic formulations or compositions are substantially free of pyrogens and/or microbes.

Provided herein are otic formulations or compositions that ameliorate or lessen otic disorders described herein. Further provided herein are methods comprising the administration of said otic formulations or compositions. In some embodiments, the formulations or compositions are sterilized. Included within the embodiments disclosed herein are means and processes for sterilization of a pharmaceutical composition disclosed herein for use in humans. The goal is to provide a safe pharmaceutical product, relatively free of infection causing microorganisms. The U. S. Food and Drug Administration has provided regulatory guidance in the publication "Guidance for Industry: Sterile Drug Products Produced by Aseptic Processing" available at: http://www.fda.gov/cder/guidance/5882fnl.htm, which is incorporated herein by reference in its entirety. No specific guidelines are available for safe pharmaceutical products for treatment of the inner ear.

As used herein, sterilization means a process used to destroy or remove microorganisms that are present in a product or packaging. Any suitable method available for sterilization of objects and formulations or compositions is used. Available methods for the inactivation of microorganisms include, but are not limited to, the application of extreme heat, lethal chemicals, or gamma radiation. In some embodiments is a process for the preparation of an otic therapeutic formulation comprising subjecting the formulation to a sterilization method selected from heat sterilization, chemical sterilization, radiation sterilization or filtration sterilization. The method used depends largely upon the nature of the device or composition to be sterilized. Detailed descriptions of many methods of sterilization are given in Chapter 40 of Remington: The Science and Practice of Pharmacy published by Lippincott, Williams & Wilkins, and is incorporated by reference with respect to this subject matter.

Sterilization by Heat

Many methods are available for sterilization by the application of extreme heat. One method is through the use of a saturated steam autoclave. In this method, saturated steam at a temperature of at least 121° C. is allowed to contact the object to be sterilized. The transfer of heat is either directly to the microorganism, in the case of an object to be sterilized, or indirectly to the microorganism by heating the bulk of an aqueous solution to be sterilized. This method is widely practiced as it allows flexibility, safety and economy in the sterilization process.

Dry heat sterilization is a method which is used to kill microorganisms and perform depyrogenation at elevated temperatures. This process takes place in an apparatus suitable for heating HEPA-filtered microorganism-free air to temperatures of at least 130-180° C. for the sterilization process and to temperatures of at least 230-250° C. for the depyrogenation process. Water to reconstitute concentrated or powdered formulations is also sterilized by autoclave.

Chemical Sterilization

Chemical sterilization methods are an alternative for products that do not withstand the extremes of heat sterilization. In this method, a variety of gases and vapors with germicidal properties, such as ethylene oxide, chlorine dioxide, formaldehyde or ozone are used as the anti-apoptotic agents. The germicidal activity of ethylene oxide, for example, arises from its ability to serve as a reactive alkylating agent. Thus, the sterilization process requires the ethylene oxide vapors to make direct contact with the product to be sterilized.

Radiation Sterilization

One advantage of radiation sterilization is the ability to sterilize many types of products without heat degradation or other damage. The radiation commonly employed is beta radiation or alternatively, gamma radiation from a $^{60}Co$ source. The penetrating ability of gamma radiation allows its use in the sterilization of many product types, including solutions, compositions and heterogeneous mixtures. The germicidal effects of irradiation arise from the interaction of gamma radiation with biological macromolecules. This interaction generates charged species and free radicals. Subsequent chemical reactions, such as rearrangements and cross-linking processes, result in the loss of normal function for these biological macromolecules. The formulations described herein are also optionally sterilized using beta irradiation.

Filtration

Filtration sterilization is a method used to remove but not destroy microorganisms from solutions. Membrane filters are used to filter heat-sensitive solutions. Such filters are thin, strong, homogenous polymers of mixed cellulosic esters (MCE), polyvinylidene fluoride (PVF; also known as PVDF), or polytetrafluoroethylene (PTFE) and have pore sizes ranging from 0.1 to 0.22 μm. Solutions of various characteristics are optionally filtered using different filter membranes. For example, PVF and PTFE membranes are well suited to filtering organic solvents while aqueous solutions are filtered through PVF or MCE membranes. Filter apparatus are available for use on many scales ranging from the single point-of-use disposable filter attached to a syringe up to commercial scale filters for use in manufacturing plants. The membrane filters are sterilized by autoclave or chemical sterilization. Validation of membrane filtration systems is performed following standardized protocols (Microbiological Evaluation of Filters for Sterilizing Liquids, Vol 4, No. 3. Washington, D.C: Health Industry Manufacturers Association, 1981) and involve challenging the membrane filter with a known quantity (ca. $10^7/cm^2$) of unusually small microorganisms, such as *Brevundimonas diminuta* (ATCC 19146).

Pharmaceutical formulations or compositions are optionally sterilized by passing through membrane filters. In some embodiments, formulations or compositions comprising nanoparticles (U.S. Pat. No. 6,139,870) or multilamellar vesicles (Richard et al., International Journal of Pharmaceutics (2006), 312(1-2):144-50) are amenable to sterilization by filtration through 0.22 m filters without destroying their organized structure.

In some embodiments, the methods disclosed herein comprise sterilizing the formulation or compositions (or components thereof) by means of filtration sterilization. In another embodiment the otic formulation or composition comprises a particle wherein the particle formulation or composition is suitable for filtration sterilization. In a further embodiment said particle formulation or composition comprises particles of less than 300 nm in size, of less than 200 nm in size, of less than 100 nm in size. In another embodiment the otic formulation or composition comprises a particle formulation or composition wherein the sterility of the particle is ensured by sterile filtration of the precursor component solutions. In another embodiment the otic formulation or composition comprises a particle formulation or composition wherein the sterility of the particle formulation or composition is ensured by low temperature sterile filtration. In a further embodiment, said low temperature sterile filtration occurs at a temperature between 0 and 30° C., or between 0 and 20° C., or between 0 and 10° C., or between 10 and 20° C., or between 20 and 30° C. In another embodiment is a process for the preparation of an *auris*-acceptable particle formulation or composition comprising: filtering the aqueous solution containing the particle formulation or composition at low temperature through a sterilization filter; lyophilizing the sterile solution; and reconstituting the particle formulation or composition with sterile water prior to administration. In some embodiments, a formulation described herein is manufactured as a suspension in a single vial formulation containing the micronized active pharmaceutical ingredient. A single vial formulation is prepared by aseptically mixing a sterile poloxamer solution with sterile micronized active ingredient (e.g., ketamine) and transferring the formulation to sterile pharmaceutical containers. In some embodiments, a single vial containing a formulation described herein as a suspension is resuspended before dispensing and/or administration.

In specific embodiments, filtration and/or filling procedures are carried out at about 5° C. below the gel temperature (Tgel) of a formulation described herein and with viscosity below a theoretical value of 100 cP to allow for filtration in a reasonable time using a peristaltic pump.

In another embodiment the otic formulation or composition comprises a nanoparticle formulation or composition wherein the nanoparticle formulation or composition is suitable for filtration sterilization. In a further embodiment the nanoparticle formulation or composition comprises nanoparticles of less than 300 nm in size, of less than 200 nm in size, or of less than 100 nm in size. In another embodiment the otic formulation or composition comprises a microsphere formulation or composition wherein the sterility of the microsphere is ensured by sterile filtration of the precursor organic solution and aqueous solutions. In another embodiment, the sterility of the otic formulation or composition is ensured by low temperature sterile filtration. In a further embodiment, the low temperature sterile filtration occurs at a temperature between 0 and 30° C., or between 0 and 20° C., or between 0 and 10° C., or between 10 and 20° C., or between 20 and 30° C. In another embodiment is a process for the preparation of an *auris*-acceptable thermoreversible gel formulation comprising: filtering the aqueous solution containing the thermoreversible gel components at low temperature through a sterilization filter; lyophilizing the sterile solution; and reconstituting the thermoreversible gel formulation with sterile water prior to administration.

In certain embodiments, the active ingredients are dissolved in a suitable vehicle (e.g. a buffer) and sterilized separately (e.g. by heat treatment, filtration, gamma radiation); the remaining excipients are sterilized in a separate step by a suitable method (e.g. filtration and/or irradiation of a cooled mixture of excipients); the two solutions that were separately sterilized are then mixed aseptically to provide a final otic formulation or composition.

In some instances, conventionally used methods of sterilization (e.g., heat treatment (e.g., in an autoclave), gamma irradiation, filtration) lead to irreversible degradation of the therapeutic agent in the formulation or composition.

In some instances, conventionally used methods of sterilization (e.g., heat treatment (e.g., in an autoclave), gamma irradiation, filtration) lead to irreversible degradation of polymeric components (e.g., thermosetting, gelling or mucoadhesive polymer components) and/or the active agent in the formulation. In some instances, sterilization of an *auris* formulation by filtration through membranes (e.g., 0.2 μM membranes) is not possible if the formulation comprises thixotropic polymers that gel during the process of filtration.

Accordingly, provided herein are methods for sterilization of *auris* formulations that prevent degradation of polymeric components (e.g., thermosetting and/or gelling and/or mucoadhesive polymer components) and/or the therapeutic agent during the process of sterilization. In some embodiments, degradation of the therapeutic agent is reduced or eliminated through the use of specific pH ranges for buffer components and specific proportions of gelling agents in the formulations. In some embodiments, the choice of an appropriate gelling agent and/or thermosetting polymer allows for sterilization of formulations described herein by filtration. In some embodiments, the use of an appropriate thermosetting polymer and an appropriate copolymer (e.g., a gelling agent) in combination with a specific pH range for the formulation allows for high temperature sterilization of formulations described with substantially no degradation of the therapeutic agent or the polymeric excipients. An advantage of the methods of sterilization provided herein is that, in certain instances, the formulations are subjected to terminal sterilization via autoclaving without any loss of the active agent and/or excipients and/or polymeric components during the sterilization step and are rendered substantially free of microbes and/or pyrogens.

Microorganisms

Provided herein are otic formulations or compositions that ameliorate or lessen otic disorders described herein. Further provided herein are methods comprising the administration of said otic formulations or compositions. In some embodiments, the formulations or compositions are substantially free of microorganisms. Acceptable sterility levels are based on applicable standards that define therapeutically acceptable otic formulations or compositions, including but not limited to United States Pharmacopeia Chapters <1111> et seq. For example, acceptable sterility levels include 10 colony forming units (cfu) per gram of formulation or composition, 50 cfu per gram of formulation or composition, 100 cfu per gram of formulation or composition, 500 cfu per gram of formulation or composition or 1000 cfu per gram of formulation or composition. In addition, acceptable sterility levels include the exclusion of specified objectionable microbiological agents. By way of example, specified objectionable microbiological agents include but are not limited to *Escherichia coli* (*E. coli*), *Salmonella* sp., *Pseudomonas aeruginosa* (*P. aeruginosa*) and/or other specific microbial agents.

Sterility of the otic formulation is confirmed through a sterility assurance program in accordance with United States Pharmacopeia Chapters <61>, <62> and <71>. A key component of the sterility assurance quality control, quality assurance and validation process is the method of sterility testing. Sterility testing, by way of example only, is performed by two methods. The first is direct inoculation wherein a sample of the formulation to be tested is added to growth medium and incubated for a period of time up to 21 days. Turbidity of the growth medium indicates contamination. Drawbacks to this method include the small sampling size of bulk materials which reduces sensitivity, and detection of microorganism growth based on a visual observation. An alternative method is membrane filtration sterility testing. In this method, a volume of product is passed through a small membrane filter paper. The filter paper is then placed into media to promote the growth of microorganisms. This method has the advantage of greater sensitivity as the bulk product is sampled. The commercially available Millipore Steritest sterility testing system is optionally used for determinations by membrane filtration sterility testing. For the filtration testing of creams or ointments Steritest filter system No. TLHVSL210 are used. For the filtration testing of emulsions or viscous products Steritest filter system No. TLAREM210 or TDAREM210 are used. For the filtration testing of pre-filled syringes Steritest filter system No. TTHASY210 are used. For the filtration testing of material dispensed as an aerosol or foam Steritest filter system No. TTHVA210 are used. For the filtration testing of soluble powders in ampoules or vials Steritest filter system No. TTHADA210 or TTHADV210 are used.

Testing for *E. coli* and *Salmonella* includes the use of lactose broths incubated at 30-35° C. for 24-72 hours, incubation in MacConkey and/or EMB agars for 18-24 hours, and/or the use of Rappaport medium. Testing for the detection of *P. aeruginosa* includes the use of NAC agar. United States Pharmacopeia Chapter <62> further enumerates testing procedures for specified objectionable microorganisms.

In certain embodiments, any otic formulation or composition described herein has less than about 60 colony forming units (CFU), less than about 50 colony forming units, less than about 40 colony forming units, or less than about 30 colony forming units of microbial agents per gram of formulation. In certain embodiments, the otic formulations or compositions described herein are formulated to be isotonic with the endolymph and/or the perilymph.

Endotoxins

Provided herein are otic formulations or compositions that ameliorate or lessen otic disorders described herein. Further provided herein are methods comprising the administration of said otic formulations or compositions. In some embodiments, the otic formulations or compositions are substantially free of endotoxins. An additional aspect of the sterilization process is the removal of by-products from the killing of microorganisms (hereinafter, "Product"). The process of depyrogenation removes pyrogens from the sample. Pyrogens are endotoxins or exotoxins which induce an immune response. An example of an endotoxin is the lipopolysaccharide (LPS) molecule found in the cell wall of gram-negative bacteria. While sterilization procedures such as autoclaving or treatment with ethylene oxide kill the bacteria, the LPS residue induces a proinflammatory immune response, such as septic shock. Because the molecular size of endotoxins varies widely, the presence of endotoxins is expressed in "endotoxin units" (EU). One EU is equivalent to 100 picograms of *E. coli* LPS. In some cases, humans develop a response to as little as 5 EU/kg of body weight. The sterility is expressed in any units as recognized in the art. In certain embodiments, otic formulations or compositions described herein contain lower endotoxin levels (e.g. <4 EU/kg of body weight of a subject) when compared to conventionally acceptable endotoxin levels (e.g., 5 EU/kg of body weight of a subject). In some embodiments, the otic formulation or composition has less than about 5 EU/kg of body weight of a subject. In other embodiments, the otic formulation or composition has less than about 4 EU/kg of body weight of a subject. In additional embodiments, the otic formulation or composition has less than about 3 EU/kg of body weight of a subject. In additional embodiments, the otic formulation or composition has less than about 2 EU/kg of body weight of a subject.

In some embodiments, the otic formulation or composition has less than about 5 EU/kg of formulation. In other embodiments, the otic therapeutic formulation or composition has less than about 4 EU/kg of formulation. In additional embodiments, the otic formulation or composition has less than about 3 EU/kg of formulation. In some embodiments, the otic formulation or composition has less than about 5 EU/kg Product. In other embodiments, the otic formulation or composition has less than about 1 EU/kg Product. In additional embodiments, the otic formulation or composition has less than about 0.2 EU/kg Product. In some embodiments, the otic formulation or composition has less than about 5 EU/g of unit or Product. In other embodiments, the otic formulation or composition has less than about 4 EU/g of unit or Product. In additional embodiments, the otic formulation or composition has less than about 3 EU/g of unit or Product. In some embodiments, the otic formulation or composition has less than about 5 EU/mg of unit or Product. In other embodiments, the otic formulation or composition has less than about 4 EU/mg of unit or Product. In additional embodiments, the otic formulation or composition has less than about 3 EU/mg of unit or Product. In certain embodiments, otic formulations or compositions described herein contain from about 1 to about 5 EU/mL of formulation or composition. In certain embodiments, otic formulations or compositions described herein contain from about 2 to about 5 EU/mL of formulation or composition, from about 3 to about 5 EU/mL of formulation or composition, or from about 4 to about 5 EU/mL of formulation or composition.

In certain embodiments, otic formulations or compositions described herein contain lower endotoxin levels (e.g. <0.5 EU/mL of formulation or composition) when compared to conventionally acceptable endotoxin levels (e.g., 0.5 EU/mL of formulation or composition). In some embodiments, the otic formulation or composition has less than about 0.5 EU/mL of formulation or composition. In other embodiments, the otic formulation or composition has less than about 0.4 EU/mL of formulation or composition. In additional embodiments, the otic formulation or composition has less than about 0.2 EU/mL of formulation or composition.

Pyrogen detection, by way of example only, is performed by several methods. Suitable tests for sterility include tests described in United States Pharmacopoeia (USP)<71> Sterility Tests (23rd edition, 1995). The rabbit pyrogen test and the Limulus amebocyte lysate test are both specified in the United States Pharmacopeia Chapters <85> and <151> (USP23/NF 18, Biological Tests, The United States Pharmacopeial Convention, Rockville, M D, 1995). Alternative pyrogen assays have been developed based upon the monocyte activation-cytokine assay. Uniform cell lines suitable for quality control applications have been developed and have demonstrated the ability to detect pyrogenicity in samples that have passed the rabbit pyrogen test and the Limulus amebocyte lysate test (Taktak et al, J. Pharm. Pharmacol. (1990), 43:578-82). In an additional embodiment, the otic formulation or composition is subject to depyrogenation. In a further embodiment, the process for the manufacture of the otic formulation or composition comprises testing the formulation for pyrogenicity. In certain embodiments, the formulations or compositions described herein are substantially free of pyrogens.

pH and Osmolarity

Described herein are otic formulations or compositions with an ionic balance that is compatible with the perilymph and/or the endolymph and does not cause any change in cochlear potential. In specific embodiments, osmolarity/osmolality of the present formulations or compositions is adjusted, for example, by the use of appropriate salt concentrations (e.g., concentration of sodium salts) or the use of tonicity agents which renders the formulations or compositions endolymph-compatible and/or perilymph compatible (i.e. isotonic with the endolymph and/or perilymph). In some instances, the endolymph-compatible and/or perilymph-compatible formulations or compositions described herein cause minimal disturbance to the environment of the inner ear and cause minimum discomfort (e.g., vertigo) to a mammal (e.g., a human) upon administration. In some embodiments, the formulations or compositions described herein are free of preservatives and cause minimal disturbance (e.g., change in pH or osmolarity, irritation) in auditory structures. In some embodiments, the formulations or compositions described herein comprise antioxidants that are non-irritating and/or non-toxic to otic structures.

As used herein, "practical osmolarity" means the osmolarity of a formulation that is measured by including the active agent and all excipients except the gelling and/or the thickening agent (e.g., polyoxyethylene-polyoxypropylene copolymers, carboxymethylcellulose or the like). The practical osmolarity of a formulation described herein is measured by any suitable method, e.g., a freezing point depression method as described in Viegas et. al., *Int. J Pharm.*, 1998, 160, 157-162. In some instances, the practical osmolarity of a formulation described herein is measured by vapor pressure osmometry (e.g., vapor pressure depression method) that allows for determination of the osmolarity of a formulation at higher temperatures. In some instances, vapor pressure depression method allows for determination of the osmolarity of a formulation comprising a gelling agent (e.g., a thermoreversible polymer) at a higher temperature wherein the gelling agent is in the form of a gel. In some embodiments, the practical osmolality of an otic formulation described herein is from about 100 mOsm/kg to about 1000 mOsm/kg, from about 200 mOsm/kg to about 800 mOsm/kg, from about 250 mOsm/kg to about 500 mOsm/kg, or from about 250 mOsm/kg to about 320 mOsm/kg, or from about 250 mOsm/kg to about 350 mOsm/kg or from about 280 mOsm/kg to about 320 mOsm/kg. In some embodiments, the formulations described herein have a practical osmolarity of about 100 mOsm/L to about 1000 mOsm/L, about 200 mOsm/L to about 800 mOsm/L, about 250 mOsm/L to about 500 mOsm/L, about 250 mOsm/L to about 350 mOsm/L, about 250 mOsm/L to about 320 mOsm/L, or about 280 mOsm/L to about 320 mOsm/L.

In some embodiments, the osmolarity at a target site of action (e.g., the perilymph) is about the same as the delivered osmolarity (i.e., osmolarity of materials that cross or penetrate the round window membrane) of any formulation described herein. In some embodiments, the formulations described herein have a deliverable osmolarity of about 150 mOsm/L to about 500 mOsm/L, about 250 mOsm/L to about 500 mOsm/L, about 250 mOsm/L to about 350 mOsm/L, about 280 mOsm/L to about 370 mOsm/L or about 250 mOsm/L to about 320 mOsm/L.

The main cation present in the endolymph is potassium. In addition, the endolymph has a high concentration of positively charged amino acids. The main cation present in the perilymph is sodium. In certain instances, the ionic composition of the endolymph and perilymph regulate the electrochemical impulses of hair cells. In certain instances, any change in the ionic balance of the endolymph or perilymph results in a loss of hearing due to changes in the conduction of electrochemical impulses along otic hair cells. In some embodiments, a composition or formulation disclosed herein does not disrupt the ionic balance of the perilymph. In some embodiments, a composition or formulation disclosed herein has an ionic balance that is the same as or substantially the same as the perilymph. In some embodiments, a composition or formulation disclosed herein does not disrupt the ionic balance of the endolymph. In some embodiments, a composition or formulation disclosed herein has an ionic balance that is the same as or substantially the same as the endolymph. In some embodiments, a composition or formulation described herein is formulated to provide an ionic balance that is compatible with inner ear fluids (i.e., endolymph and/or perilymph).

The endolymph and the perilymph have a pH that is close to the physiological pH of blood. The endolymph has a pH range of about 7.2-7.9; the perilymph has a pH range of about 7.2-7.4. The in situ pH of the proximal endolymph is about 7.4 while the pH of distal endolymph is about 7.9.

In some embodiments, the pH of a formulation or composition described herein is adjusted (e.g., by use of a buffer) to an endolymph-compatible pH range of about 7.0 to 8.0, and a preferred pH range of about 7.2-7.9. In some embodiments, the pH of the formulations or compositions described herein is adjusted (e.g., by use of a buffer) to a perilymph-compatible pH of about 7.0-7.6, and a preferred pH range of about 7.2-7.4.

In some embodiments, useful formulations or compositions also include one or more pH adjusting agents or buffering agents. Suitable pH adjusting agents or buffers include, but are not limited to acetate, bicarbonate, ammonium chloride, citrate, phosphate, pharmaceutically acceptable salts thereof and combinations or mixtures thereof.

In one embodiment, when one or more buffers are utilized in the formulations or compositions of the present disclosure, they are combined, e.g., with a pharmaceutically acceptable vehicle and are present in the final formulation or composition, e.g., in an amount ranging from about 0.1% to about 20%, from about 0.5% to about 10%. In certain embodiments of the present disclosure, the amount of buffer included in the formulations or compositions are an amount such that the pH of the formulation or composition does not interfere with the body's natural buffering system. In some embodiments, from about 5 mM to about 200 mM concentration of a buffer is present in the formulation or composition. In certain embodiments, from about a 20 mM to about a 100 mM concentration of a buffer is present. In other embodiments, the concentration of buffer is such that a pH of the formulation or composition is between 3 and 9, between 5 and 8, or alternatively between 6 and 7. In other embodiments, the pH of the formulation or composition is about 7. In one embodiment is a buffer such as acetate or citrate at slightly acidic pH. In one embodiment the buffer is a sodium acetate buffer having a pH of about 4.5 to about 6.5. In another embodiment the buffer is a sodium acetate buffer having a pH of about 5.5 to about 6.0. In a further embodiment the buffer is a sodium acetate buffer having a pH of about 6.0 to about 6.5. In one embodiment the buffer is a sodium citrate buffer having a pH of about 5.0 to about 8.0. In another embodiment the buffer is a sodium citrate buffer having a pH of about 5.5 to about 7.0. In one embodiment the buffer is a sodium citrate buffer having a pH of about 6.0 to about 6.5.

In some embodiments, the concentration of buffer is such that a pH of the formulation or composition is between 6 and 9, between 6 and 8, between 6 and 7.6, between 7 and 8. In other embodiments, the pH of the formulation or composition is about 6.0, about 6.5, about 7 or about 7.5. In one embodiment is a buffer such as tris(hydroxymethyl)aminomethane, bicarbonate, carbonate or phosphate at slightly basic pH. In one embodiment, the buffer is a sodium bicarbonate buffer having a pH of about 7.5 to about 8.5. In another embodiment the buffer is a sodium bicarbonate buffer having a pH of about 7.0 to about 8.0. In a further embodiment the buffer is a sodium bicarbonate buffer having a pH of about 6.5 to about 7.0. In one embodiment the buffer is a sodium phosphate dibasic buffer having a pH of about 6.0 to about 9.0. In another embodiment the buffer is a sodium phosphate dibasic buffer having a pH of about 7.0 to about 8.5. In one embodiment the buffer is a sodium phosphate dibasic buffer having a pH of about 7.5 to about 8.0.

In one embodiment, diluents are also used to stabilize compounds because they provide a more stable environment. Salts dissolved in buffered solutions (which also provide pH control or maintenance) are utilized as diluents in the art, including, but not limited to a phosphate buffered saline solution.

In a specific embodiment the pH of a formulation or composition described herein is between about 6.0 and about 7.6, between 7 and about 7.8, between about 7.0 and about 7.6, between about 7.2 and about 7.6, or between about 7.2 and about 7.4. In certain embodiments the pH of a formulation or composition described herein is about 6.0, about 6.5, about 7.0, about 7.1, about 7.2, about 7.3, about 7.4, about 7.5, or about 7.6. In some embodiments, the pH of any formulation or composition described herein is designed to be compatible with the targeted otic structure (e.g., endolymph, perilymph or the like).

In some embodiments, any formulation or composition described herein has a pH that allows for sterilization (e.g., by filtration or aseptic mixing or heat treatment and/or autoclaving (e.g., terminal sterilization)) of a formulation or composition without degradation of the therapeutic agent. In order to reduce hydrolysis and/or degradation of the therapeutic agent during sterilization, the buffer pH is designed to maintain pH of the formulation or composition in the 7-8 range during the process of sterilization.

In specific embodiments, any formulation or composition described herein has a pH that allows for terminal sterilization (e.g., by heat treatment and/or autoclaving) of a formulation or composition without degradation of the therapeutic agent. For example, in order to reduce hydrolysis and/or degradation of the therapeutic agent during autoclaving, the buffer pH is designed to maintain pH of the formulation or composition in the 7-8 range at elevated temperatures. Any appropriate buffer is used depending on the therapeutic agent used in the formulation or composition. In some instances, since $pK_a$ of TRIS decreases as temperature increases at approximately −0.03/° C. and $pK_a$ of PBS increases as temperature increases at approximately 0.003/° C., autoclaving at 250° F. (121° C.) results in a significant downward pH shift (i.e. more acidic) in the TRIS buffer whereas a relatively much less upward pH shift in the PBS buffer and therefore much increased hydrolysis and/or degradation of an otic agent in TRIS than in PBS. In some embodiments, degradation of a therapeutic agent is reduced by the use of an appropriate of a buffer as described herein.

In some embodiments, a pH of between about 6.0 and about 7.6, between about 7 and about 7.8, between about 7.0 and about 7.6, between about 7.2 and 7.6, between about 7.2 and about 7.4 is suitable for sterilization (e.g., by filtration or aseptic mixing or heat treatment and/or autoclaving (e.g., terminal sterilization)) of formulations or compositions described herein. In specific embodiments a formulation or composition pH of about 6.0, about 6.5, about 7.0, about 7.1, about 7.2, about 7.3, about 7.4, about 7.5, or about 7.6 is suitable for sterilization (e.g., by filtration or aseptic mixing or heat treatment and/or autoclaving (e.g., terminal sterilization)) of any formulation or composition described herein.

In some embodiments, the formulations or compositions described herein have a pH between about 3 and about 9, or between about 4 and 8, or between about 5 and 8, or between about 6 and about 7, or between about 6.5 and about 7, or between about 5.5 and about 7.5, or between about 7.1 and about 7.7, and have a concentration of active pharmaceutical ingredient between about 0.1 mM and about 100 mM. In some embodiments, the formulations or compositions described herein have a pH between about 5 and about 8, or between about 6 and about 7, or between about 6.5 and about 7, or between about 5.5 and about 7.5, or between about 7.1 and about 7.7, and have a concentration of active pharmaceutical ingredient between about 1 and about 100 mM. In some embodiments, the formulations or compositions described herein have a pH between about 5 and about 8, or between about 6 and about 7, or between about 6.5 and about 7, or between about 5.5 and about 7.5, or between about 7.1 and about 7.7, and have a concentration of active pharmaceutical ingredient between about 50 and about 80 mM. In some embodiments, the concentration of active pharmaceutical ingredient between about 10 and about 100 mM. In other embodiments, the concentration of active pharmaceutical ingredient between about 20 and about 80 mM. In additional embodiments, the concentration of active pharmaceutical ingredient between about 10 and about 50 mM.

In some embodiments, the formulations or compositions have a pH as described herein, and include a thickening agent (i.e., a viscosity enhancing agent or viscosity modulating agent) such as, by way of non-limiting example, a cellulose based thickening agent described herein. In some instances, the addition of a thickening agent and a pH of formulation or compositions as described herein, allows for sterilization of a formulation described herein without any substantial degradation of the therapeutic agent in the otic formulation or composition. In some embodiments, the amount of thickening agent in any formulation or composition described herein is about 1%, 5%, about 10%, or about 15% of the total weight of the formulation or composition. In some embodiments, the amount of thickening agent in any formulation or composition described herein is about 0.5%, about 1%, about 1.5%, about 2%, about 2.5%, about 3%, about 3.5%, about 4.0%, about 4.5%, about 5.0%, about 5.5%, about 6.0%, about 6.5%, about 7.0%, about 7.5%, about 8.0%, about 8.5%, about 9.0%, about 9.5%, about 10%, or about 15%. In some instances, the addition of a secondary polymer (e.g., a thickening agent) and a pH of formulation as described herein, allows for sterilization of a formulation described herein without any substantial degradation of the otic agent and/or the polymer components in the otic formulation. In some embodiments, the ratio of a thermoreversible poloxamer to a thickening agent in a formulation that has a pH as described herein is about 40:1, about 35:1, about 30:1, about 25:1, about 20:1, about 15:1, about 10:1, or about 5:1. For example, in certain embodiments, a sustained and/or extended release formulation described herein comprises a combination of poloxamer 407 (pluronic F127) and carboxymethylcellulose (CMC) in a ratio of about 40:1, about 35:1, about 30:1, about 25:1, about 20:1, about 15:1, about 10:1, or about 5:1.4%, about 4.5%, or about 5% of the total weight of the formulation or composition.

In some embodiments, the amount of thermoreversible polymer in any formulation described herein is about 0.01%, about 0.05%, about 0.1%, about 0.5%, about 1%, about 5%, about 10%, about 15%, about 20%, about 25%, about 30%, about 35%, or about 40% of the total weight of the formulation. In some embodiments, the amount of thermoreversible polymer in any formulation described herein is about 0.01%, about 0.05%, about 0.1%, about 0.5%, about 1%, about 5%, about 10%, about 11%, about 12%, about 13%, about 14%, about 15%, about 16%, about 17%, about 18%, about 19%, about 20%, about 21%, about 22%, about 23%, about 24%, or about 25% of the total weight of the formulation. In some embodiments, the amount of thermoreversible polymer (e.g., pluronic F127) in any formulation described herein is about 7.5% of the total weight of the formulation. In some embodiments, the amount of thermoreversible polymer (e.g., pluronic F127) in any formulation described herein is about 10% of the total weight of the formulation. In some embodiments, the amount of thermoreversible polymer (e.g., pluronic F127) in any formulation described herein is about 11% of the total weight of the formulation. In some embodiments, the amount of thermoreversible polymer (e.g., pluronic F127) in any formulation described herein is about 12% of the total weight of the formulation. In some embodiments, the amount of thermoreversible polymer (e.g., pluronic F127) in any formulation described herein is about 13% of the total weight of the formulation. In some embodiments, the amount of thermoreversible polymer (e.g., pluronic F127) in any formulation described herein is about 14% of the total weight of the formulation. In some embodiments, the amount of thermoreversible polymer (e.g., pluronic F127) in any formulation described herein is about 15% of the total weight of the formulation. In some embodiments, the amount of thermoreversible polymer (e.g., pluronic F127) in any formulation described herein is about 16% of the total weight of the formulation. In some embodiments, the amount of thermoreversible polymer (e.g., pluronic F127) in any formulation described herein is about 17% of the total weight of the formulation. In some embodiments, the amount of thermoreversible polymer (e.g., pluronic F127) in any formulation described herein is about 18% of the total weight of the formulation. In some embodiments, the amount of thermoreversible polymer (e.g., pluronic F127) in any formulation described herein is about 19% of the total weight of the formulation. In some embodiments, the amount of thermoreversible polymer (e.g., pluronic F127) in any formulation described herein is about 20% of the total weight of the formulation. In some embodiments, the amount of thermoreversible polymer (e.g., pluronic F127) in any formulation described herein is about 21% of the total weight of the formulation. In some embodiments, the amount of thermoreversible polymer (e.g., pluronic F127) in any formulation described herein is about 23% of the total weight of the formulation. In some embodiments, the amount of thermoreversible polymer (e.g., pluronic F127) in any formulation described herein is about 25% of the total weight of the formulation.

In some embodiments, the amount of thickening agent (e.g., a gelling agent) in any formulation described herein is about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 5%, about 10%, or about 15% of the total weight of the formulation. In some embodiments, the amount of thickening agent (e.g., a gelling agent) in any formulation described herein is about 0.1%, 0.5%, about 1%, about 1.5%, about 2%, about 2.5%, about 3%, about 3.5%, about 4%, about 4.5%, or about 5% of the total weight of the formulation.

In some embodiments, the pharmaceutical formulations or compositions described herein are stable with respect to pH over a period of any of at least about 1 day, at least about 2 days, at least about 3 days, at least about 4 days, at least about 5 days, at least about 6 days, at least about 1 week, at least about 2 weeks, at least about 3 weeks, at least about 4 weeks, at least about 5 weeks, at least about 6 weeks, at least about 7 weeks, at least about 8 weeks, at least about 1 month, at least about 2 months, at least about 3 months, at least about 4 months, at least about 5 months, or at least about 6 months. In other embodiments, the formulations or compositions described herein are stable with respect to pH over a period of at least about 1 week. Also described herein are formulations or compositions that are stable with respect to pH over a period of at least about 1 month.

Tonicity Agents

In general, the endolymph has a higher osmolality than the perilymph. For example, the endolymph has an osmolality of about 304 mOsm/kg $H_2O$ while the perilymph has an osmolality of about 294 mOsm/kg $H_2O$. In some embodiments, formulations or compositions described herein are formulated to provide an osmolarity of about 250 to about 320 mM (osmolality of about 250 to about 320 mOsm/kg $H_2O$); and preferably about 270 to about 320 mM (osmolality of about 270 to about 320 mOsm/kg $H_2O$). In certain embodiments, tonicity agents are added to the formulations described herein in an amount as to provide a practical osmolality of an otic formulation of about 100 mOsm/kg to about 1000 mOsm/kg, from about 200 mOsm/kg to about 800 mOsm/kg, from about 250 mOsm/kg to about 500 mOsm/kg, from about 250 mOsm/kg to about 350 mOsm/kg, or from about 280 mOsm/kg to about 320 mOsm/kg. In some embodiments, the formulations described herein have a practical osmolarity of about 100 mOsm/L to about 1000 mOsm/L, about 200 mOsm/L to about 800 mOsm/L, about 250 mOsm/L to about 500 mOsm/L, about 250 mOsm/L to about 350 mOsm/L, about 280 mOsm/L to about 320 mOsm/L, or about 250 mOsm/L to about 320 mOsm/L.

In specific embodiments, osmolarity/osmolality of the present formulations or compositions is adjusted, for example, by the use of appropriate salt concentrations (e.g., concentration of potassium salts) or the use of tonicity agents which renders the formulations or compositions endolymph-compatible and/or perilymph-compatible (i.e. isotonic with the endolymph and/or perilymph. In some instances, the endolymph-compatible and/or perilymph-compatible formulations or compositions described herein cause minimal disturbance to the environment of the inner ear and cause minimum discomfort (e.g., vertigo and/or nausea) to a mammal upon administration.

In some embodiments, the deliverable osmolarity of any formulation described herein is designed to be isotonic with the targeted otic structure (e.g., endolymph, perilymph, or the like). In specific embodiments, *auris* formulations described herein are formulated to provide a delivered perilymph-suitable osmolarity at the target site of action of about 250 to about 320 mOsm/L and preferably about 270 to about 320 mOsm/L. In specific embodiments, *auris* formulations described herein are formulated to provide a delivered perilymph-suitable osmolality at the target site of action of about 250 to about 320 mOsm/kg $H_2O$ or an osmolality of about 270 to about 320 mOsm/kg $H_2O$. In specific embodiments, the deliverable osmolarity/osmolality of the formulations (i.e., the osmolarity/osmolality of the formulation in the absence of gelling or thickening agents (e.g., thermoreversible gel polymers) is adjusted, for example, by the use of appropriate salt concentrations (e.g., concentration of potassium or sodium salts) or the use of tonicity agents which renders the formulations endolymph-compatible and/or perilymph-compatible (i.e. isotonic with the endolymph and/or perilymph) upon delivery at the target site. The osmolarity of a formulation comprising a thermoreversible gel polymer is an unreliable measure due to the association of varying amounts of water with the monomeric units of the polymer. The practical osmolarity of a formulation (i.e., osmolarity in the absence of a gelling or thickening agent (e.g. a thermoreversible gel polymer) is a reliable measure and is measured by any suitable method (e.g., freezing point depression method, vapor depression method). In some instances, the formulations described herein provide a deliverable osmolarity (e.g., at a target site (e.g., perilymph) that causes minimal disturbance to the environment of the inner ear and causes minimum discomfort (e.g., vertigo and/or nausea) to a mammal upon administration.

In some embodiments, any formulation or composition described herein is isotonic with the perilymph. Isotonic formulations or compositions are provided by the addition of a tonicity agent. Suitable tonicity agents include, but are not limited to any pharmaceutically acceptable sugar, salt or any combinations or mixtures thereof, such as, but not limited to dextrose, glycerin, mannitol, sorbitol, sodium chloride, and other electrolytes.

Useful otic formulations or compositions include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, potassium thiosulfate, sodium bisulfite, and ammonium sulfate.

In further embodiments, the tonicity agents are present in an amount as to provide a final osmolality of an otic formulation or composition of about 100 mOsm/kg to about 500 mOsm/kg, from about 200 mOsm/kg to about 400 mOsm/kg, from about 250 mOsm/kg to about 350 mOsm/kg or from about 280 mOsm/kg to about 320 mOsm/kg. In some embodiments, the formulations or compositions described herein have a osmolarity of about 100 mOsm/L to about 500 mOsm/L, about 200 mOsm/L to about 400 mOsm/L, about 250 mOsm/L to about 350 mOsm/L, or about 280 mOsm/L to about 320 mOsm/L. In some embodiments, the osmolarity of any formulation or composition described herein is designed to be isotonic with the targeted otic structure (e.g., endolymph, perilymph or the like). In some embodiments, the formulations described herein have a pH and/or practical osmolarity as described herein, and have a concentration of active pharmaceutical ingredient from about 0.0001% to about 60%, from about 0.001% to about 40%, from about 0.01% to about 20%, from about 0.01% to about 10%, from about 0.01% to about 7.5%, from about 0.01% to about 6%, from about 0.01 to about 5%, from about 0.1 to about 10%, or from about 0.1 to about 6% of the active ingredient by weight of the formulation.

In some embodiments, the formulations or compositions described herein have a pH and osmolarity as described herein and have a concentration of active pharmaceutical ingredient between about 1 μM and about 10 μM, between about 1 mM and about 100 mM, between about 0.1 mM and about 100 mM, between about 0.1 mM and about 100 nM. In some embodiments, the formulations or compositions described herein have a pH and osmolarity as described herein, and have a concentration of active pharmaceutical ingredient from about 0.01-about 60%, from about 0.01-about 50%, from about 0.01-about 40%, from about 0.01-about 30%, from about 0.01-about 20%, from about 0.01-about 10%, from about 0.01-about 7%, from about 0.01-5%, from about 0.01-about 3%, from about 0.01-about 2% of the active ingredient by weight of the formulation or composition. In some embodiments, the formulations or composition described herein have a pH and osmolarity as described herein, and have a concentration of active pharmaceutical ingredient from about 0.1-about 70 mg/mL, from about 1 mg-about 70 mg/mL, from about 1 mg-about 50 mg/mL, from about 1 mg/mL and about 20 mg/mL, from about 1 mg/mL to about 10 mg/mL, from about 1 mg/mL to about 5 mg/mL, or from about 0.5 mg/mL to about 5 mg/mL of the active agent by volume of the formulation or composition.

Tunable Release Characteristics

The release of the therapeutic agent described herein from any formulation, or device described herein is optionally tunable to the desired release characteristics. In some embodiments, a formulation described herein is a solution that is substantially free of gelling components. In such instances, the formulation provides essentially immediate release of the therapeutic agent. In some of such embodiments, the formulation is useful in perfusion of otic structures, e.g., during surgery.

In some of such embodiments, the formulation provides release of the therapeutic agent from about 2 days to about 4 days.

In some embodiments, a formulation described herein, further comprises a gelling agent (e.g., poloxamer 407) and provides release of the therapeutic agent over a period of from about 1 day to about 3 days. In some embodiments, a formulation described herein, further comprises a gelling agent (e.g., poloxamer 407) and provides release of the therapeutic agent over a period of from about 1 day to about 5 days. In some embodiments, a formulation described herein, further comprises a gelling agent (e.g., poloxamer 407) and provides release of the therapeutic agent over a period of from about 2 days to about 7 days.

In some embodiments, a formulation described herein further comprises from about 14 to about 17% of a gelling agent (e.g., poloxamer 407), and provides extended sustained release over a period of from about 1 week to about 3 weeks. In some embodiments, a formulation described herein, further comprises from about 18 to about 21% of a gelling agent (e.g., poloxamer 407) and, provides extended sustained release over a period of from about 3 weeks to about 6 weeks.

In some embodiments, the viscosity of any formulation described herein, is designed to provide a suitable rate of release from an *auris* compatible gel. In some embodiments, the concentration of a thickening agent (e.g., gelling components such as polyoxyethylene-polyoxypropylene copolymers) allows for a tunable mean dissolution time (MDT). The MDT is inversely proportional to the release rate of an active agent from a formulation or device described herein. Experimentally, the released active agent is optionally fitted to the Korsmeyer-Peppas equation $$\frac{Q}{Q_\alpha} = kt^n + b$$

where Q is the amount of active agent released at time t, $Q_\alpha$ is the overall released amount of active agent, k is a release constant of the nth order, n is a dimensionless number related to the dissolution mechanism, and b is the axis intercept, characterizing the initial burst release mechanism wherein n=1 characterizes an erosion controlled mechanism. The mean dissolution time (MDT) is the sum of different periods of time the drug molecules stay in the matrix before release, divided by the total number of molecules, and is optionally calculated by:

$$MDT = \frac{nk^{-1/n}}{n+1}$$

For example, a linear relationship between the mean dissolution time (MDT) of a formulation or device and the concentration of the gelling agent (e.g., poloxamer) indicates that the active agent is released due to the erosion of the polymer gel (e.g., poloxamer) and not via diffusion. In another example, a non-linear relationship indicates release of otic agent via a combination of diffusion and/or polymer gel degradation. In another example, a faster gel elimination time course of a formulation or device (a faster release of active agent) indicates lower mean dissolution time (MDT). The concentration of gelling components and/or active agent in a formulation are tested to determine suitable parameters for MDT. In some embodiments, injection volumes are also tested to determine suitable parameters for preclinical and clinical studies. The gel strength and concentration of the active agent affects release kinetics of the active agent from the formulation. At low poloxamer concentration, elimination rate is accelerated (MDT is lower). An increase in the active agent concentration in the formulation or device prolongs residence time and/or MDT of the active agent in the ear.

In some embodiments, the MDT for poloxamer from a formulation or device described herein is at least 6 hours. In some embodiments, the MDT for poloxamer from a formulation or device described herein is at least 10 hours.

In some embodiments, the MDT for an active agent from a formulation or device described herein is from about 30 hours to about 48 hours. In some embodiments, the MDT for an active agent from a formulation or device described herein is from about 30 hours to about 96 hours. In some embodiments, the MDT for an active agent from a formulation or device described herein is from about 30 hours to about 1 week. In some embodiments, the MDT for an active agent from a formulation or device described herein is from about 1 week to about 6 weeks.

In certain embodiments, any controlled-release otic formulation described herein increases the exposure of an active agent and increases the Area Under the Curve (AUC) in otic fluids (e.g., endolymph and/or perilymph) by about 30%, about 40%, about 50%, about 60%, about 70%, about 80%, about 90%, about 100%, or higher than 100%, compared to an otic formulation that is not a controlled-release otic formulation. In certain embodiments, any controlled-release otic formulation described herein increases the exposure time of an active agent and decreases the $C_{max}$ in otic fluids (e.g., endolymph and/or perilymph) by about 40%, about 30%, about 20%, or about 10%, compared to a formulation that is not a controlled-release otic formulation. In certain embodiments, any controlled-release otic formulation described herein alters (e.g. reduces) the ratio of $C_{max}$ to $C_{min}$ compared to a formulation that is not a controlled-release otic formulation. In certain embodiments, any controlled-release otic formulation described herein increases the exposure of an active agent and increases the length of time that the concentration of the active agent is above $C_{min}$ by about 30%, about 40%, about 50%, about 60%, about 70%, about 80%, or about 90% compared to a formulation that is not a controlled-release otic formulation. In certain embodiments, the increase in exposure of an active agent and the increase in the length of time that the concentration of the active agent is above $C_{min}$ by a controlled-release otic formulation described herein is greater than 100% compared to a formulation that is not a controlled-release otic formulation. In certain instances, controlled-release otic formulations described herein delay the time to $C_{max}$. In certain instances, the controlled steady release of a drug prolongs the time the concentration of the active agent will stay above the $C_{min}$. In some embodiments, otic formulations described herein prolong the residence time of an active agent in the inner ear and provide a stable drug exposure profile. In some instances, an increase in concentration of an active agent in the otic formulation saturates the clearance process and allows for a more rapid and stable steady state to be reached.

In certain instances, once exposure to an active agent (e.g., concentration in the endolymph or perilymph) reaches steady state, the concentration of an active agent in the endolymph or perilymph stays at or about the therapeutic dose for an extended period of time (e.g., one day, 2 days, 3 days, 4 days, 5 days, 6 days, 1 week, 3 weeks, 6 weeks, or 2 months). In some embodiments, the steady state concentration of an active agent released from a controlled-release otic formulation described herein is from about 20 to about 50 times the steady state concentration of an active agent released from a formulation that is not a controlled-release otic formulation.

Particle Size

Size reduction is used to increase surface area and/or modulate formulation dissolution properties. It is also used to maintain a consistent average particle size distribution (PSD) (e.g., micrometer-sized particles, nanometer-sized particles or the like) for any formulation or composition described herein. In some embodiments, the formulation or composition comprises micrometer-sized particles. In some embodiments, the formulation or composition comprises nanometer-sized particles. In some instances, any formulation or composition described herein comprises multiparticulates, i.e., a plurality of particle sizes (e.g., micronized particles, nanosized particles, non-sized particles); i.e., the formulation or composition is a multiparticulate formulation or composition. In some embodiments, any formulation or composition described herein comprises one or more multiparticulate (e.g., micronized) therapeutic agents. Micronization is a process of reducing the average diameter of particles of a solid material. Micronized particles are from about micrometer-sized in diameter to about picometer-sized in diameter. In some embodiments, the use of multiparticulates (e.g., micronized particles) of a therapeutic agent, or an otic agent, allows for extended and/or sustained release of the therapeutic agent from any formulation described herein compared to a formulation or composition comprising non-multiparticulate (e.g., non-micronized) therapeutic agent. In some instances, formulations or compositions containing multiparticulate (e.g., micronized) therapeutic agents are ejected from a 1 mL syringe adapted with a 27G needle without any plugging or clogging. In some embodiments, the therapeutic agent is essentially in the form of micronized particles. In some embodiments, the therapeutic agent is essentially in the form of microsized particles. In some embodiments, the therapeutic agent is essentially in the form of nanosized particles.

In some embodiments, the particle size of the formulation or composition described herein increases the retention time of the formulation or composition described herein. In some embodiments, the particle size of the formulation or composition described herein provides slow release of the therapeutic agent. In some embodiments, the particle size of the formulation or composition described herein provides sustained release of the therapeutic agent. In some embodiments, the particle size is less than 450 nm, less than 400 nm, less than 350 nm, less than 300 nm, less than 275 nm, less than 250 nm, less than 225 nm, less than 200 nm in size, less than 175 nm, less than 150 nm, or less than 125 nm, or less than 100 nm. In some embodiments, the particle size is less than 300 nm. In some embodiments, the particle size is less than 250 nm. In some embodiments, the particle size is less than 200 nm.

In some instances, any particle in any formulation or composition described herein is a coated particle (e.g., a coated micronized particle) and/or a microsphere and/or a liposomal particle. Particle size reduction techniques include, by way of example, grinding, milling (e.g., air-attrition milling (jet milling), ball milling), coacervation, high pressure homogenization, spray drying and/or supercritical fluid crystallization. In some instances, particles are sized by mechanical impact (e.g., by hammer mills, ball mill and/or pin mills). In some instances, particles are sized via fluid energy (e.g., by spiral jet mills, loop jet mills, and/or fluidized bed jet mills). In some embodiments, formulations described herein comprise crystalline particles. In some embodiments, formulations or compositions described herein comprise amorphous particles. In some embodiments, formulations or compositions described herein comprise therapeutic agent particles wherein the therapeutic agent is a free base, or a salt, or a prodrug of a therapeutic agent, or any combination thereof.

In some instances, a combination of a therapeutic agent and a salt of the therapeutic agent is used to prepare pulsed release otic formulations or compositions using the procedures described herein. In some formulations, a combination of a micronized therapeutic agent (and/or salt or prodrug thereof) and coated particles (e.g., nanoparticles, liposomes, microspheres) is used to prepare pulsed release otic formulations or compositions using any procedure described herein.

In some embodiments, a pulsed release profile is achieved by solubilizing up to 40% of the delivered dose of the therapeutic agent (e.g., micronized therapeutic agent, or free base or salt or prodrug thereof, multiparticulate therapeutic agent, or free base or salt or prodrug thereof) with the aid of cyclodextrins, surfactants (e.g., poloxamers (407, 338, 188), tween (80, 60, 20,81), PEG-hydrogenated castor oil, cosolvents like N-methyl-2-Pyrrolidone or the like and preparing pulsed release formulations or compositions using any procedure described herein.

In some specific embodiments, any otic formulation or composition described herein comprises one or more micronized therapeutic agents. In some of such embodiments, a micronized therapeutic agent comprises micronized particles, coated (e.g., with an extended release coat) micronized particles, or a combination thereof. In some of such embodiments, a micronized therapeutic agent comprising micronized particles, coated micronized particles, or a combination thereof, comprises a therapeutic agent as a free base, a salt, a prodrug or any combination thereof.

Controlled Release Otic Formulations

In certain embodiments, any controlled release otic formulation or composition described herein increases the exposure of a therapeutic agent and increases the Area Under the Curve (AUC) in otic fluids (e.g., endolymph and/or perilymph) by about 30%, about 40%, about 50%, about 60%, about 70%, about 80%, or about 90% compared to a formulation or composition that is not a controlled release otic formulation or composition. In certain embodiments, any controlled release otic formulation or composition described herein increases the exposure of a therapeutic agent and decreases the $C_{max}$ in otic fluids (e.g., endolymph and/or perilymph) by about 40%, about 30%, about 20%, or about 10%, compared to a formulation or composition that is not a controlled release otic formulation or composition. In certain embodiments, any controlled release otic formulation or composition described herein alters (e.g. reduces) the ratio of $C_{max}$ to $C_{min}$ compared to a formulation or composition that is not a controlled release otic formulation. In certain embodiments, the ratio of $C_{max}$ to $C_{min}$ is 10:1, 9:1, 8:1, 7:1, 6:1, 5:1, 4:1, 3:1, 2:1 or 1:1. In certain embodiments, any controlled release otic formulation described herein increases the exposure of a therapeutic agent and increases the length of time that the concentration of a therapeutic agent is above $C_{min}$ by about 30%, about 40%, about 50%, about 60%, about 70%, about 80% or about 90% compared to a formulation or composition that is not a controlled release otic formulation or composition. In certain instances, controlled release formulations or compositions described herein delay the time to $C_{max}$. In certain instances, the controlled steady release of a drug prolongs the time the concentration of the drug will stay above the $C_{min}$. In some embodiments, *auris* formulations or compositions described herein prolong the residence time of a drug in the inner ear. In certain instances, once drug exposure (e.g., concentration in the endolymph or perilymph) of a drug reaches steady state, the concentration of the drug in the endolymph or perilymph stays at or about the therapeutic dose for an extended period of time (e.g., one day, 2 days, 3 days, 4 days, 5 days, 6 days, 1 week, 2 weeks, 3 weeks, a month, two months, three months, six months, or one year).

In some embodiments, the otic formulations or compositions described herein deliver an active agent to the external, middle and/or inner ear, including the cochlea and vestibular labyrinth. In some embodiments, local otic delivery of the *auris* formulations or compositions described herein allows for controlled release of active agents to *auris* structures and overcomes the drawbacks associated with systemic administration (e.g., low bioavailability of the drug in the endolymph or perilymph, variability in concentration of the drug in the external, middle and/or internal ear).

Controlled-release options include but are not limited to liposomes, cyclodextrins, biodegradable polymers, dispersible polymers, emulsions, microspheres or microparticles, other viscous media, paints, foams, in spongy materials, liposomes, nanocapsules or nanospheres, and combinations thereof, other options or components include mucoadhesives, penetration enhancers, bioadhesives, antioxidants, surfactants, buffering agents, diluents, salts and preservatives. To the extent viscosity considerations potentially limit the use of a syringe/needle delivery system, thermoreversible gels or post-administration viscosity-enhancing options are also envisioned, as well as alternative delivery systems, including pumps, microinjection devices and the like.

In one embodiment of the otic formulations or compositions described herein, the otic formulation or composition is provided as a thickened liquid formulation composition, also referred to herein as "*auris*-acceptable thickened liquid formulation or composition," "*auris* thickened liquid formulations or compositions" or variations thereof. All of the components of the thickened liquid formulation or composition must be compatible with the *Auris interna*. Further, the thickened liquid formulation or composition provides controlled release of the therapeutic agent to the desired site within the *Auris interna* for some embodiments. In some embodiments, the thickened liquid formulation or composition also has an immediate or rapid release component for delivery of the therapeutic agent to the desired target site.

In one embodiment of the otic formulations or compositions described herein, the otic formulation or composition is provided as a suspension formulation composition, also referred to herein as "*auris*-acceptable suspension formulation or composition," "*auris* suspension formulations or compositions" or variations thereof. All of the components of the suspension formulation or composition must be compatible with the *Auris interna*. Further, the suspension formulation or composition provides controlled release of the therapeutic agent to the desired site within the *Auris interna* for some embodiments. In some embodiments, the suspension formulation or composition also has an immediate or rapid release component for delivery of the therapeutic agent to the desired target site.

In one embodiment of the otic formulations or compositions described herein, the otic formulation or composition is provided as a solution formulation composition, also referred to herein as "*auris*-acceptable solution formulation or composition," "*auris* solution formulations or compositions" or variations thereof. All of the components of the solution formulation or composition must be compatible with the *Auris interna*. Further, the solution formulation or composition provides controlled release of the therapeutic agent to the desired site within the *Auris interna* for some embodiments. In some embodiments, the solution formulation or composition also has an immediate or rapid release component for delivery of the therapeutic agent to the desired target site.

In one embodiment of the otic formulations or compositions described herein, the otic formulation or composition is provided as a gel formulation composition, also referred to herein as "*auris*-acceptable gel formulation or composition," "*auris* gel formulations or compositions" or variations thereof. All of the components of the gel formulation or composition must be compatible with the *Auris interna*. Further, the gel formulation or composition provides controlled release of the therapeutic agent to the desired site within the *Auris interna* for some embodiments. In some embodiments, the gel formulation or composition also has an immediate or rapid release component for delivery of the therapeutic agent to the desired target site.

In some embodiments, the formulations or compositions described herein are bimodal formulations or compositions and comprise an immediate release component and an extended release component. In some instances, bimodal formulations allow for a constant rate of release of an immediate release component (multiparticulate agent (e.g., micronized active agent)) and a constant rate of release of an extended release component (e.g., an encapsulated active agent that serves as a depot for extending the release of an active agent). In other embodiments, the otic formulations or compositions described herein are administered as a controlled release formulation or compositions, released either continuously or in a pulsatile manner, or variants of both. In still other embodiments, the active agent formulation or composition is administered as both an immediate release and controlled release formulation or composition, released either continuously or in a pulsatile manner, or variants of both. In certain embodiments, the formulations or compositions comprise an excipient that increases the release rate of the therapeutic agent. In certain embodiments, the formulations or compositions comprise an excipient that decreases the release rate of the therapeutic agent. In certain embodiments, the formulations or compositions comprise penetration enhancers that allow for delivery of the active agents across the oval window or the round window of the ear.

In some embodiments, the otic formulations are biodegradable. In other embodiments, the otic formulations or compositions include a mucoadhesive excipient to allow adhesion to the external mucous membrane of the round window. In yet other embodiments, the otic formulations or compositions include a penetration enhancer excipient; in further embodiments, the otic formulation or composition contains a viscosity enhancing agent. In other embodiments, the otic pharmaceutical formulations or compositions provide an *auris*-acceptable microsphere or microparticle; in still other embodiments, the otic pharmaceutical formulations or compositions provide an *auris*-acceptable liposome, in yet other embodiments, the otic pharmaceutical formulations or compositions provide an *auris*-acceptable paint or foam. In other embodiments, the otic pharmaceutical formulations or compositions provide an *auris*-acceptable spongy material.

The formulations or compositions disclosed herein alternatively encompass an otoprotectant agent in addition to the at least one active agent and/or excipients, including but not limited to such as antioxidants, alpha lipoic acid, calcium, fosfomycin or iron chelators, to counteract potential ototoxic effects that arise from the use of specific therapeutic agents or excipients, diluents, or carriers.

One aspect of the embodiments disclosed herein is to provide a controlled release composition or formulation for the treatment of fluid homeostasis disorders. The controlled release aspect of the compositions and/or formulations disclosed herein is imparted through a variety of agents, including but not limited to excipients, agents or materials that are acceptable for use in the *Auris interna* or other otic structure. By way of example only, such excipients, agents or materials include an *auris*-acceptable polymer, an *auris*-acceptable viscosity enhancing agent, an *auris*-acceptable microsphere, an *auris*-acceptable liposome, an *auris*-acceptable nanocapsule or nanosphere, or combinations thereof.

Thus, provided herein are pharmaceutical formulations or compositions that include at least one *auris* therapeutic agent and *auris*-acceptable diluent(s), excipient(s), and/or carrier(s). In some embodiments, the pharmaceutical compositions include other medicinal or pharmaceutical agents, carriers, adjuvants, such as preserving, stabilizing, wetting or emulsifying agents, solution promoters, salts for regulating the osmotic pressure, and/or buffers. In other embodiments, the pharmaceutical formulations or compositions also contain other therapeutic substances.

*Auris*-Acceptable Gel Formulations/Compositions

In some embodiments, the *auris*-acceptable formulations or compositions described herein are gel formulations or gel compositions.

In some embodiments, the otic gel formulations or compositions that include at least therapeutic agent and a pharmaceutically acceptable diluent(s), excipient(s), or carrier(s). In some embodiments, the otic gel formulations or compositions include other medicinal or pharmaceutical agents; carriers; adjuvants; preserving, stabilizing, wetting or emulsifying agents; solution promoters; salts for regulating the osmotic pressure; and/or buffers. In some embodiments, the otic gel formulations or compositions comprises (i) a therapeutic agent, (ii) a gelling and viscosity enhancing agent, (iii) a pH adjusting agent, and (iv) sterile water.

Gels, sometimes referred to as jellies, have been defined in various ways. For example, the United States Pharmacopoeia defines gels as semisolid systems consisting of either suspensions made up of small inorganic particles or large organic molecules interpenetrated by a liquid. Gels include a single-phase or a two-phase system. A single-phase gel consists of organic macromolecules distributed uniformly throughout a liquid in such a manner that no apparent boundaries exist between the dispersed macromolecules and the liquid. Some single-phase gels are prepared from synthetic macromolecules (e.g., carbomer) or from natural gums (e.g., tragacanth). In some embodiments, single-phase gels are generally aqueous but will also be made using alcohols and oils. Two-phase gels consist of a network of small discrete particles.

Gels can also be classified as being hydrophobic or hydrophilic. In certain embodiments, the base of a hydrophobic gel consists of a liquid paraffin with polyethylene or fatty oils gelled with colloidal silica or aluminum or zinc soaps. In contrast, the base of hydrophilic gels usually consists of water, glycerol, or propylene glycol gelled with a suitable gelling agent (e.g., tragacanth, starch, cellulose derivatives, carboxyvinylpolymers, and magnesium-aluminum silicates). In certain embodiments, the rheology of the formulations or devices disclosed herein is pseudo plastic, plastic, thixotropic, or dilatant.

In one embodiment the enhanced viscosity *auris*-acceptable formulation described herein is not a liquid at room temperature. In certain embodiments, the enhanced viscosity formulation is characterized by a phase transition between room temperature and body temperature (including an individual with a serious fever, e.g., up to about 42° C.). In some embodiments, the phase transition occurs at about 1° C. below body temperature, at about 2° C. below body temperature, at about 3° C. below body temperature, at about 4° C. below body temperature, at about 6° C. below body temperature, at about 8° C. below body temperature, or at about 10° C. below body temperature. In some embodiments, the phase transition occurs at about 15° C. below body temperature, at about 20° C. below body temperature, or at about 25° C. below body temperature. In specific embodiments, the gelation temperature (Tgel) of a formulation described herein is about 20° C., about 25° C., or about 30° C. In certain embodiments, the gelation temperature (Tgel) of a formulation described herein is about 35° C. or about 40° C. In one embodiment, administration of any formulation described herein at about body temperature reduces or inhibits vertigo associated with intratympanic administration of otic formulations. Included within the definition of body temperature is the body temperature of a healthy individual or an unhealthy individual, including an individual with a fever (up to ~42° C.). In some embodiments, the pharmaceutical formulations or devices described herein are liquids at about room temperature and are administered at or about room temperature, reducing or ameliorating side effects such as, for example, vertigo.

Polymers composed of polyoxypropylene and polyoxyethylene form thermoreversible gels when incorporated into aqueous solutions. These polymers have the ability to change from the liquid state to the gel state at temperatures close to body temperature, therefore allowing useful formulations that are applied to the targeted *auris* structure(s). The liquid state-to-gel state phase transition is dependent on the polymer concentration and the ingredients in the solution.

Poloxamer 407 (PF-127) is a nonionic surfactant composed of polyoxyethylene-polyoxypropylene copolymers. Other poloxamers include 188 (F-68 grade), 237 (F-87 grade), and 338 (F-108 grade). Aqueous solutions of poloxamers are stable in the presence of acids, alkalis, and metal ions. PF-127 is a commercially available polyoxyethylene-polyoxypropylene triblock copolymer of general formula E106 P70 E106, with an average molar mass of 13,000. The polymer can be further purified by suitable methods that will enhance gelation properties of the polymer. It contains approximately 70% ethylene oxide, which accounts for its hydrophilicity. It is one of the series of poloxamer ABA block copolymers, whose members share the chemical formula shown below.

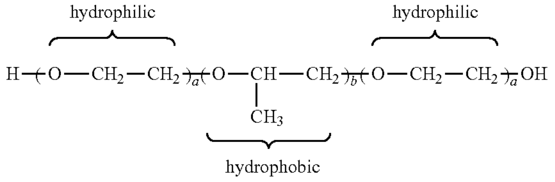

PF-127 is of particular interest since concentrated solutions (>20% w/w) of the copolymer are transformed from low viscosity transparent solutions to solid gels on heating to body temperature. This phenomenon, therefore, suggests that when placed in contact with the body, the gel preparation will form a semi-solid structure and a sustained release depot. Furthermore, PF-127 has good solubilizing capacity, low toxicity and is, therefore, considered a good medium for drug delivery systems.

In an alternative embodiment, the thermogel is a PEG-PLGA-PEG triblock copolymer (Jeong et al, Nature (1997), 388:860-2; Jeong et al, J. Control. Release (2000), 63:155-63; Jeong et al, Adv. Drug Delivery Rev. (2002), 54:37-51). The polymer exhibits sol-gel behavior over a concentration of about 5% w/w to about 40% w/w. Depending on the properties desired, the lactide/glycolide molar ratio in the PLGA copolymer ranges from about 1:1 to about 20:1. The resulting coploymers are soluble in water and form a free-flowing liquid at room temperature but form a hydrogel at body temperature. A commercially available PEG-PLGA-PEG triblock copolymer is RESOMER RGP t50106 manufactured by Boehringer Ingelheim. This material is composed of a PGLA copolymer of 50:50 poly(DL-lactide-co-glycolide), is 10% w/w of PEG, and has a molecular weight of about 6000.

ReGel® is a tradename of MacroMed Incorporated for a class of low molecular weight, biodegradable block copolymers having reverse thermal gelation properties as described in U.S. Pat. Nos. 6,004,573, 6,117,949, 6,201,072, and 6,287,588. It also includes biodegradable polymeric drug carriers disclosed in pending U.S. patent application Ser. Nos. 09/906,041, 09/559,799 and 10/919,603. The biodegradable drug carrier comprises ABA-type or BAB-type triblock copolymers, or mixtures thereof, wherein the A-blocks are relatively hydrophobic and comprise biodegradable polyesters or poly(orthoester)s, and the B-blocks are relatively hydrophilic and comprise polyethylene glycol (PEG), said copolymers having a hydrophobic content of between 50.1 to 83% by weight and a hydrophilic content of between 17 to 49.9% by weight, and an overall block copolymer molecular weight of between 2000 and 8000 Daltons. The drug carriers exhibit water solubility at temperatures below normal mammalian body temperatures and undergo reversible thermal gelation to then exist as a gel at temperatures equal to physiological mammalian body temperatures. The biodegradable, hydrophobic A polymer block comprises a polyester or poly(ortho ester), in which the polyester is synthesized from monomers selected from the group consisting of D,L-lactide, D-lactide, L-lactide, D,L-lactic acid, D-lactic acid, L-lactic acid, glycolide, glycolic acid, ε-caprolactone, ε-hydroxyhexanoic acid, γ-butyrolactone, γ-hydroxybutyric acid, δ-valerolactone, δ-hydroxyvaleric acid, hydroxybutyric acids, malic acid, and copolymers thereof and having an average molecular weight of between about 600 and 3000 Daltons. The hydrophilic B-block segment is preferably polyethylene glycol (PEG) having an average molecular weight of between about 500 and 2200 Daltons.

Additional biodegradable thermoplastic polyesters include AtriGel® (provided by Atrix Laboratories, Inc.) and/or those disclosed, e.g., in U.S. Pat. Nos. 5,324,519; 4,938,763; 5,702,716; 5,744,153; and 5,990,194; wherein the suitable biodegradable thermoplastic polyester is disclosed as a thermoplastic polymer. Examples of suitable biodegradable thermoplastic polyesters include polylactides, polyglycolides, polycaprolactones, copolymers thereof, terpolymers thereof, and any combinations thereof. In some such embodiments, the suitable biodegradable thermoplastic polyester is a polylactide, a polyglycolide, a copolymer thereof, a terpolymer thereof, or any combination thereof. In one embodiment, the biodegradable thermoplastic polyester is 50/50 poly(DL-lactide-co-glycolide) having a carboxy terminal group; is present in about 30 wt. % to about 40 wt. % of the formulation; and has an average molecular weight of about 23,000 to about 45,000. Alternatively, in another embodiment, the biodegradable thermoplastic polyester is 75/25 poly (DL-lactide-co-glycolide) without a carboxy terminal group; is present in about 40 wt. % to about 50 wt. % of the formulation; and has an average molecular weight of about 15,000 to about 24,000. In further or alternative embodiments, the terminal groups of the poly(DL-lactide-co-glycolide) are either hydroxyl, carboxyl, or ester depending upon the method of polymerization. Polycondensation of lactic or glycolic acid provides a polymer with terminal hydroxyl and carboxyl groups. Ring-opening polymerization of the cyclic lactide or glycolide monomers with water, lactic acid, or glycolic acid provides polymers with the same terminal groups. However, ring-opening of the cyclic monomers with a monofunctional alcohol such as methanol, ethanol, or 1-dodecanol provides a polymer with one hydroxyl group and one ester terminal groups. Ring-opening polymerization of the cyclic monomers with a diol such as 1,6-hexanediol or polyethylene glycol provides a polymer with only hydroxyl terminal groups.

Since the polymer systems of thermoreversible gels dissolve more completely at reduced temperatures, methods of solubilization include adding the required amount of polymer to the amount of water to be used at reduced temperatures. Generally, after wetting the polymer by shaking, the mixture is capped and placed in a cold chamber or in a thermostatic container at about 0-10° C. in order to dissolve the polymer. The mixture is stirred or shaken to bring about a more rapid dissolution of the thermoreversible gel polymer. The active agent and various additives such as buffers, salts, and preservatives are subsequently added and dissolved. In some instances, the active agent and/or other pharmaceutically active agent is suspended if it is insoluble in water. The pH is modulated by the addition of appropriate buffering agents. Round window membrane mucoadhesive characteristics are optionally imparted to a thermoreversible gel by incorporation of round window membrane mucoadhesive carbomers, such as Carbopol® 934P, to the formulation (Majithiya et al., AAPS PharmSciTech (2006), 7(3), p. E1; EP0551626, both of which is incorporated herein by reference for such disclosure).

In one embodiment are *auris*-acceptable pharmaceutical gel formulations which do not require the use of an added viscosity enhancing agent or viscosity modulating agent. Such gel formulations incorporate at least one pharmaceutically acceptable buffer. In one aspect is a gel formulation and a pharmaceutically acceptable buffer. In another embodiment, the pharmaceutically acceptable excipient or carrier is a gelling agent.

In other embodiments, useful *auris*-acceptable pharmaceutical formulations also include one or more pH adjusting agents or buffering agents to provide an endolymph or perilymph suitable pH. Suitable pH adjusting agents or buffers include, but are not limited to acetate, bicarbonate, ammonium chloride, citrate, phosphate, pharmaceutically acceptable salts thereof, and combinations or mixtures thereof. Such pH adjusting agents and buffers are included in an amount required to maintain pH of the formulation from a pH of about 5 to about 9, in one embodiment a pH from about 6.5 to about 7.5, and in yet another embodiment at a pH of about 6.5, 6.6, 6.7, 6.8, 6.9, 7.0, 7.1, 7.2, 7.3, 7.4, 7.5, 7.6, 7.7, 7.8, 7.9, or 8.0. In one embodiment, when one or more buffers are utilized in the formulations of the present disclosure, they are combined, e.g., with a pharmaceutically acceptable vehicle and are present in the final formulation, e.g., in an amount ranging from about 0.1% to about 20%, from about 0.5% to about 10%. In certain embodiments of the present disclosure, the amount of buffer included in the gel formulations are an amount such that the pH of the gel formulation does not interfere with the *Auris media* or *Auris interna*'s natural buffering system, or does not interfere with the natural pH of the endolymph or perilymph, depending on where in the cochlea the otic formulation is targeted. In some embodiments, from about 10 mM to about 200 mM concentration of a buffer is present in the gel formulation. In certain embodiments, from about a 5 mM to about a 200 mM concentration of a buffer is present. In certain embodiments, from about a 20 mM to about a 100 mM concentration of a buffer is present. In one embodiment is a buffer such as acetate or citrate at slightly acidic pH. In one embodiment the buffer is a sodium acetate buffer having a pH of about 4.5 to about 6.5. In one embodiment the buffer is a sodium citrate buffer having a pH of about 5.0 to about 8.0, or about 5.5 to about 7.0.

In an alternative embodiment, the buffer used is tris (hydroxymethyl)aminomethane, bicarbonate, carbonate, or phosphate at slightly basic pH. In one embodiment, the buffer is a sodium bicarbonate buffer having a pH of about 6.5 to about 8.5, or about 7.0 to about 8.0. In another embodiment the buffer is a sodium phosphate dibasic buffer having a pH of about 6.0 to about 9.0.

Also described herein are controlled-release formulations or devices a viscosity enhancing agent or viscosity modulating agent. Suitable viscosity-enhancing agents or viscosity modulating agents include by way of example only, gelling agents and suspending agents. In one embodiment, the enhanced viscosity formulation does not include a buffer. In other embodiments, the enhanced viscosity formulation includes a pharmaceutically acceptable buffer. Sodium chloride or other tonicity agents are optionally used to adjust tonicity, if necessary.

By way of example only, the *auris*-acceptable viscosity agent includes hydroxypropyl methylcellulose, hydroxyethyl cellulose, polyvinylpyrrolidone, carboxymethyl cellulose, polyvinyl alcohol, sodium chondroitin sulfate, sodium hyaluronate. Other viscosity enhancing agents compatible with the targeted *auris* structure include, but are not limited to, acacia (gum arabic), agar, aluminum magnesium silicate, sodium alginate, sodium stearate, bladderwrack, bentonite, carbomer, carrageenan, Carbopol, xanthan, cellulose, microcrystalline cellulose (MCC), *ceratonia*, chitin, carboxymethylated chitosan, chondrus, dextrose, furcellaran, gelatin, Ghatti gum, guar gum, hectorite, lactose, sucrose, maltodextrin, mannitol, sorbitol, honey, maize starch, wheat starch, rice starch, potato starch, gelatin, sterculia gum, xanthum gum, gum tragacanth, ethyl cellulose, ethylhydroxyethyl cellulose, ethylmethyl cellulose, methyl cellulose, hydroxyethyl cellulose, hydroxyethylmethyl cellulose, hydroxypropyl cellulose, poly(hydroxyethyl methacrylate), oxypolygelatin, pectin, polygeline, povidone, propylene carbonate, methyl vinyl ether/maleic anhydride copolymer (PVM/MA), poly(methoxyethyl methacrylate), poly (methoxyethoxyethyl methacrylate), hydroxypropyl cellulose, hydroxypropylmethyl-cellulose (HPMC), sodium carboxymethyl-cellulose (CMC), silicon dioxide, polyvinylpyrrolidone (PVP: povidone), Splenda® (dextrose, maltodextrin and sucralose), or combinations thereof. In specific embodiments, the viscosity-enhancing excipient is a combination of MCC and CMC. In another embodiment, the viscosity-enhancing agent is a combination of carboxymethylated chitosan, or chitin, and alginate. The combination of chitin and alginate with the active agent disclosed herein acts as a controlled-release formulation, restricting the diffusion of the active agent from the formulation. Moreover, the combination of carboxymethylated chitosan and alginate is optionally used to assist in increasing the permeability of the active agent through the round window membrane.

In some embodiments is an enhanced viscosity formulation, comprising from about 0.1 mM and about 100 mM of an active agent, a pharmaceutically acceptable viscosity enhancer or viscosity modulating agent, and water for injection, the concentration of the viscosity enhancer or viscosity modulating agent in the water being sufficient to provide an enhanced viscosity formulation with a final viscosity from about 100 to about 100,000 cP. In certain embodiments, the viscosity of the gel is in the range from about 100 to about 50,000 cP, about 100 cP to about 1,000 cP, about 500 cP to about 1500 cP, about 1000 cP to about 3000 cP, about 2000 cP to about 8,000 cP, about 4,000 cP to about 50,000 cP, about 10,000 cP to about 500,000 cP, about 15,000 cP to about 1,000,000 cP. In certain embodiments, the viscosity of the gel is in the range from about 100 to about 50,000 cP, about 100 cP to about 1,000 cP, about 500 cP to about 1500 cP, about 1000 cP to about 3000 cP, about 2000 cP to about 8,000 cP, about 4,000 cP to about 50,000 cP, about 10,000 cP to about 500,000 cP, about 15,000 cP to about 3,000,000 cP. In other embodiments, when an even more viscous medium is desired, the biocompatible gel comprises at least about 35%, at least about 45%, at least about 55%, at least about 65%, at least about 70%, at least about 75%, or even at least about 80% or so by weight of the active agent. In highly concentrated samples, the biocompatible enhanced viscosity formulation comprises at least about 25%, at least about 35%, at least about 45%, at least about 55%, at least about 65%, at least about 75%, at least about 85%, at least about 90%, at least about 95%, or more by weight of the active agent.

In some embodiments, the viscosity of the gel formulations presented herein are measured by any means described. For example, in some embodiments, an LVDV-II+CP Cone Plate Viscometer and a Cone Spindle CPE-40 is used to calculate the viscosity of the gel formulation described herein. In other embodiments, a Brookfield (spindle and cup) viscometer is used to calculate the viscosity of the gel formulation described herein. In some embodiments, the viscosity ranges referred to herein are measured at room temperature. In other embodiments, the viscosity ranges referred to herein are measured at body temperature (e.g., at the average body temperature of a healthy human).

In one embodiment, the pharmaceutically acceptable enhanced viscosity *auris*-acceptable formulation comprises at least one active agent and at least one gelling agent. Suitable gelling agents for use in preparation of the gel formulation include, but are not limited to, celluloses, cellulose derivatives, cellulose ethers (e.g., carboxymethylcellulose, ethylcellulose, hydroxyethylcellulose, hydroxymethylcellulose, hydroxypropylmethylcellulose, hydroxypropylcellulose, methylcellulose), guar gum, xanthan gum, locust bean gum, alginates (e.g., alginic acid), silicates, starch, tragacanth, carboxyvinyl polymers, carrageenan, paraffin, petrolatum, and any combinations or mixtures thereof. In some other embodiments, hydroxypropylmethylcellulose (Methocel®) is utilized as the gelling agent. In certain embodiments, the viscosity enhancing agents or viscosity modulating agents described herein are also utilized as the gelling agent for the gel formulations presented herein.

In one specific embodiment of the *auris*-acceptable controlled-release formulations described herein, the active agent is provided in a gel matrix, also referred to herein as "*auris*-acceptable gel formulations", "*Auris interna*-acceptable gel formulations", "*Auris media*-acceptable gel formulations", "*Auris externa*-acceptable gel formulations", "*auris* gel formulations", or variations thereof. All the components of the gel formulation must be compatible with the targeted *auris* structure. Further, the gel formulations provide controlled-release of the active agent to the desired site within the targeted *auris* structure; in some embodiments, the gel formulation also has an immediate or rapid release component for delivery of the active agent to the desired target site. In other embodiments, the gel formulation has a sustained release component for delivery of the active agent. In some embodiments, the *auris* gel formulations are biodegradable. In other embodiments, the *auris* gel formulations include a mucoadhesive excipient to allow adhesion to the external mucous layer of the round window membrane. In yet other embodiments, the *auris* gel formulations include a penetration enhancer excipient; in further embodiments, the *auris* gel formulation contains a viscosity enhancing agent sufficient to provide a viscosity of from about 10 to about 1,000,000 centipoise, from about 500 and 1,000,000 centipoise; from about 750 to about 1,000,000 centipoise; from about 1000 to about 1,000,000 centipoise; from about 1000 to about 400,000 centipoise; from about 2000 to about 100,000 centipoise; from about 3000 to about 50,000 centipoise; from about 4000 to about 25,000 centipoise; from about 5000 to about 20,000 centipoise; or from about 6000 to about 15,000 centipoise. In some embodiments, the *auris* gel formulation contains a viscosity enhancing agent sufficient to provide a viscosity of from about 50,0000 to about 1,000,000 centipoise. In some embodiments, the *auris* gel formulation contains a viscosity enhancing agent sufficient to provide a viscosity of from about 50,0000 to about 3,000,000 centipoise.

In some embodiments, the otic pharmaceutical formulations or devices described herein are low viscosity formulations or devices at body temperature. In some embodiments, low viscosity formulations or devices contain from about 1% to about 10% of a viscosity enhancing agent or viscosity modulating agent (e.g., gelling components such as polyoxyethylene-polyoxypropylene copolymers). In some embodiments, low viscosity formulations or devices contain from about 2% to about 10% of a viscosity enhancing agent or viscosity modulating agent (e.g., gelling components such as polyoxyethylene-polyoxypropylene copolymers). In some embodiments, low viscosity formulations or devices contain from about 5% to about 10% of a viscosity enhancing agent or viscosity modulating agent (e.g., gelling components such as polyoxyethylene-polyoxypropylene copolymers). In some embodiments, low viscosity formulations or devices are substantially free of a viscosity enhancing agent or viscosity modulating agent (e.g., gelling components such as polyoxyethylene-polyoxypropylene copolymers). In some embodiments, a low viscosity otic formulation or device described herein provides an apparent viscosity of from about 100 cP to about 10,000 cP. In some embodiments, a low viscosity otic formulation or device described herein provides an apparent viscosity of from about 500 cP to about 10,000 cP. In some embodiments, a low viscosity otic formulation or device described herein provides an apparent viscosity of from about 1000 cP to about 10,000 cP. In some of such embodiments, a low viscosity otic formulation or device is administered in combination with an external otic intervention, e.g., a surgical procedure including but not limited to middle ear surgery, inner ear surgery, typanostomy, cochleostomy, labyrinthotomy, mastoidectomy, stapedectomy, stapedotomy, endolymphatic sacculotomy, or the like. In some of such embodiments, a low viscosity otic formulation or device is administered during an otic intervention. In other such embodiments, a low viscosity otic formulation or device is administered before the otic intervention.

In some embodiments, the otic pharmaceutical formulations or devices described herein are high viscosity formulations or devices at body temperature. In some embodiments, high viscosity formulations or devices contain from about 10% to about 25% of a viscosity enhancing agent or viscosity modulating agent (e.g., gelling components such as polyoxyethylene-polyoxypropylene copolymers). In some embodiments, high viscosity formulations or devices contain from about 14% to about 22% of a viscosity enhancing agent or viscosity modulating agent (e.g., gelling components such as polyoxyethylene-polyoxypropylene copolymers). In some embodiments, high viscosity formulations or devices contain from about 15% to about 21% of a viscosity enhancing agent or viscosity modulating agent (e.g., gelling components such as polyoxyethylene-polyoxypropylene copolymers). In some embodiments, a high viscosity otic formulation or device described herein provides an apparent viscosity of from about 100,000 cP to about 3,000,000 cP. In some embodiments, a high viscosity otic formulation or device described herein provides an apparent viscosity of from about 100,000 cP to about 1,000,000 cP. In some embodiments, a high viscosity otic formulation or device described herein provides an apparent viscosity of from about 150,000 cP to about 500,000 cP. In some embodiments, a high viscosity otic formulation or device described herein provides an apparent viscosity of from about 250,000 cP to about 500,000 cP. In some of such embodiments, a high viscosity formulation or device is a liquid at room temperature and gels at about between room temperature and body temperature (including an individual with a serious fever, e.g., up to about 42° C.). In some embodiments, an otic high viscosity formulation or device is administered as monotherapy for treatment of an otic disease or condition described herein. In some embodiments, an otic high viscosity formulation or device is administered in combination with an external otic intervention, e.g., a surgical procedure including but not limited to middle ear surgery, inner ear surgery, typanostomy, cochleostomy, labyrinthotomy, mastoidectomy, stapedectomy, stapedotomy, endolymphatic sacculotomy, or the like. In some of such embodiments, a high viscosity otic formulation or device is administered after the otic intervention. In other such embodiments, a high viscosity otic formulation or device is administered before the otic intervention.

In other embodiments, the otic pharmaceutical formulations described herein further provide an *auris*-acceptable hydrogel; in yet other embodiments, the otic pharmaceutical formulations provide an *auris*-acceptable microsphere or microparticle; in still other embodiments, the otic pharmaceutical formulations provide an *auris*-acceptable liposome. In some embodiments, the otic pharmaceutical formulations provide an *auris*-acceptable foam; in yet other embodiments, the otic pharmaceutical formulations provide an *auris*-acceptable paint; in still further embodiments, otic pharmaceutical formulations provide an *auris*-acceptable in situ forming spongy material. In some embodiments, the otic pharmaceutical formulations provide an *auris*-acceptable solvent release gel. In some embodiments, the otic pharmaceutical formulations provide an actinic radiation curable gel. Further embodiments include a thermoreversible gel in the otic pharmaceutical formulation, such that upon preparation of the gel at room temperature or below, the formulation is a fluid, but upon application of the gel into or near the *Auris interna* and/or *Auris media* target site, including the tympanic cavity, round window membrane, or the *crista* fenestrae *cochleae*, the otic-pharmaceutical formulation stiffens or hardens into a gel-like substance.

In further or alternative embodiments, the otic gel formulations are capable of being administered on or near the round window membrane via intratympanic injection. In other embodiments, the otic gel formulations are administered on or near the round window or the *crista* fenestrae *cochleae* through entry via a post-auricular incision and surgical manipulation into or near the round window or the *crista* fenestrae *cochleae* area. Alternatively, the otic gel formulation is applied via syringe and needle, wherein the needle is inserted through the tympanic membrane and guided to the area of the round window or *crista* fenestrae *cochleae*. The otic gel formulations are then deposited on or near the round window or *crista* fenestrae *cochleae* for localized treatment of autoimmune otic disorders. In other embodiments, the otic gel formulations are applied via microcathethers implanted into the patient, and in yet further embodiments the formulations are administered via a pump device onto or near the round window membrane. In still further embodiments, the otic gel formulations are applied at or near the round window membrane via a microinjection device. In yet other embodiments, the otic gel formulations are applied in the tympanic cavity. In some embodiments, the otic gel formulations are applied on the tympanic membrane. In still other embodiments, the otic gel formulations are applied onto or in the auditory canal.

Triglyceride Based Otic Formulations and Compositions

Provided herein in one embodiment are otic formulations and compositions comprising triglycerides. Triglycerides are esters derived from glycerol and three fatty acids. In some instances, these fatty acids are saturated fatty acids, unsaturated fatty acids, or a combination thereof. Provided herein in one aspect, is an otic formulation or a composition comprising a therapeutic agent, or pharmaceutically acceptable prodrug or salt thereof; and triglycerides comprising medium chain fatty acids; wherein the triglycerides are present in an amount that is sufficient to stabilize the therapeutic agent for injection into the ear, and wherein the otic pharmaceutical formulation or composition comprises at least about 50% by weight of the triglycerides.

In some instances, these triglycerides are medium chain triglycerides (MCTs). In some embodiments, these triglycerides comprise medium chain fatty acids. In some embodiments, these triglycerides are derived from glycerol and medium-chain fatty acids. In some embodiments, these triglycerides are derived from glycerol and at least two medium-chain fatty acids. In some embodiments, these triglycerides are derived from glycerol, two medium-chain fatty acids, and one long-chain fatty acid. In some embodiments, these triglycerides are derived from glycerol, and three medium-chain fatty acids.

In some embodiments, the triglycerides are derived from glycerol and medium chain fatty acids. In some embodiments, the triglycerides are derived from glycerol and at least two medium-chain fatty acids. In some embodiments, each medium chain fatty acid independently comprises 6 to 12 carbon atoms in the carbon chain. In some embodiments, each medium chain fatty acid independently comprises 8 to 12 carbon atoms in the carbon chain. In some embodiments, each medium chain fatty acid independently comprises 6, 7, 8, 9, 10, 11, or 12 carbon atoms in the carbon chain. In some embodiments, each medium chain fatty acid independently comprises 8 or 10 carbon atoms in the carbon chain. In some embodiments, the medium chain fatty acids are caproic acid (hexanoic acid), enanthic acid (heptanoic acid), caprylic acid (octanoic acid), pelargonic acid (nonanoic acid), capric acid (decanoic acid), undecylenic acid (undec-10-enoic acid), lauric acid (dodecanoic acid), or a combination thereof. In some embodiments, the medium chain fatty acids are caprylic acid (octanoic acid), capric acid (decanoic acid), or a combination thereof.

In some embodiments, the triglycerides comprising medium chain fatty acids are balassee oil, coconut oil, cohune oil, palm kernel oil, tucum oil, or combinations thereof. In some embodiments, triglycerides comprising medium chain fatty acids are coconut oil, cohune oil, palm kernel oil, tucum oil, or any combinations thereof. In some embodiments, the triglycerides comprising medium chain fatty acids are balassee oil. In some embodiments, the triglycerides comprising medium chain fatty acids are coconut oil. In some embodiments, the triglycerides comprising medium chain fatty acids are cohune oil. In some embodiments, the triglycerides comprising medium chain fatty acids are palm kernel oil. In some embodiments, the triglycerides comprising medium chain fatty acids are tucum oil.

In some embodiments, the otic pharmaceutical formulation has triglycerides in an amount that is sufficient to stabilize the therapeutic agent for injection into the ear. In some embodiments, the otic pharmaceutical formulation has triglycerides in an amount that is sufficient to provide sufficient retention time in the ear. In some embodiments, the ear is the outer ear, middle ear, or inner ear. In some embodiments, the otic pharmaceutical formulation has triglycerides in an amount that is sufficient to provide sustained release of the therapeutic agent. In some embodiments, the otic formulation has triglycerides in an amount that is sufficient to allow delivery of the formulation via a narrow-gauge needle.

In some embodiments, the otic pharmaceutical formulation comprises between about 50% to about 99.9% by weight of the triglycerides. In some embodiments, the otic pharmaceutical formulation comprises between about 55% to about 99.9% by weight of the triglycerides. In some embodiments, the otic pharmaceutical formulation comprises between about 60% to about 99.9% by weight of the triglycerides. In some embodiments, the otic pharmaceutical formulation comprises between about 65% to about 99.9% by weight of the triglycerides. In some embodiments, the otic pharmaceutical formulation comprises between about 70% to about 99.9% by weight of the triglycerides. In some embodiments, the otic pharmaceutical formulation comprises between about 75% to about 99.9% by weight of the triglycerides. In some embodiments, the otic pharmaceutical formulation comprises between about 80% to about 99.9% by the weight of the triglycerides. In some embodiments, the otic pharmaceutical formulation comprises between about 85% to about 99.9% by the weight of the triglycerides. In some embodiments, the otic pharmaceutical formulation comprises between about 90% to about 99.9% by the weight of the triglycerides. In some embodiments, the otic pharmaceutical formulation comprises between about 95% to about 99.9% by the weight of the triglycerides.

In some embodiments, the otic pharmaceutical formulation comprises between about 50% to about 99.99% by weight of the triglycerides. In some embodiments, the otic pharmaceutical formulation comprises between about 55% to about 99.99% by weight of the triglycerides. In some embodiments, the otic pharmaceutical formulation comprises between about 60% to about 99.99% by weight of the triglycerides. In some embodiments, the otic pharmaceutical formulation comprises between about 65% to about 99.99% by weight of the triglycerides. In some embodiments, the otic pharmaceutical formulation comprises between about 70% to about 99.99% by weight of the triglycerides. In some embodiments, the otic pharmaceutical formulation comprises between about 75% to about 99.99% by weight of the triglycerides. In some embodiments, the otic pharmaceutical formulation comprises between about 80% to about 99.99% by weight of the triglycerides. In some embodiments, the otic pharmaceutical formulation comprises between about 85% to about 99.99% by weight of the triglycerides. In some embodiments, the otic pharmaceutical formulation comprises between about 90% to about 99.99% by weight of the triglycerides. In some embodiments, the otic pharmaceutical formulation comprises between about 95% to about 99.99% by weight of the triglycerides.

In some embodiments, the otic pharmaceutical formulation comprises between about 50% to about 95% by weight of the triglycerides. In some embodiments, the otic pharmaceutical formulation comprises between about 55% to about 95% by weight of the triglycerides. In some embodiments, the otic pharmaceutical formulation comprises between about 60% to about 95% by weight of the triglycerides. In some embodiments, the otic pharmaceutical formulation comprises between about 65% to about 95% by weight of the triglycerides. In some embodiments, the otic pharmaceutical formulation comprises between about 70% to about 95% by weight of the triglycerides. In some embodiments, the otic pharmaceutical formulation comprises between about 75% to about 95% by weight of the triglycerides. In some embodiments, the otic pharmaceutical formulation comprises between about 80% to about 95% by weight of the triglycerides. In some embodiments, the otic pharmaceutical formulation comprises between about 85% to about 95% by weight of the triglycerides. In some embodiments, the otic pharmaceutical formulation comprises between about 90% to about 95% by weight of the triglycerides.

In some embodiments, the otic pharmaceutical formulation comprises between about 50% to about 55% by weight of the triglycerides. In some embodiments, the otic pharmaceutical formulation comprises between about 55% to about 60% by weight of the triglycerides. In some embodiments, the otic pharmaceutical formulation comprises between about 60% to about 65% by weight of the triglycerides. In some embodiments, the otic pharmaceutical formulation comprises between about 65% to about 70% by weight of the triglycerides. In some embodiments, the otic pharmaceutical formulation comprises between about 70% to about 75% by weight of the triglycerides. In some embodiments, the otic pharmaceutical formulation comprises between about 75% to about 80% by weight of the triglycerides. In some embodiments, the otic pharmaceutical formulation comprises between about 80% to about 85% by weight of the triglycerides. In some embodiments, the otic pharmaceutical formulation comprises between about 85% to about 90% by weight of the triglycerides. In some embodiments, the otic pharmaceutical formulation comprises between about 90% to about 95% by weight of the triglycerides. In some embodiments, the otic pharmaceutical formulation comprises between about 95% to about 99% by weight of the triglycerides. In some embodiments, the otic pharmaceutical formulation comprises between about 95% to about 99.9% by weight of the triglycerides. In some embodiments, the otic pharmaceutical formulation comprises between about 95% to about 99.99% by weight of the triglycerides.

In some embodiments, the otic pharmaceutical formulation comprises between about 50% to about 60% by weight of the triglycerides. In some embodiments, the otic pharmaceutical formulation comprises between about 60% to about 70% by weight of the triglycerides. In some embodiments, the otic pharmaceutical formulation comprises between about 70% to about 80% by weight of the triglycerides. In some embodiments, the otic pharmaceutical formulation comprises between about 80% to about 90% by weight of the triglycerides. In some embodiments, the otic pharmaceutical formulation comprises between about 90% to about 99% by weight of the triglycerides. In some embodiments, the otic pharmaceutical formulation comprises between about 90% to about 99.9% by weight of the triglycerides. In some embodiments, the otic pharmaceutical formulation comprises between about 90% to about 99.99% by weight of the triglycerides.

In some embodiments, the otic pharmaceutical formulation comprises about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% by weight of the triglycerides.

In some embodiments, the otic pharmaceutical formulation comprises about 50% by weight of the triglycerides. In some embodiments, the otic pharmaceutical formulation comprises about 51% by weight of the triglycerides. In some embodiments, the otic pharmaceutical formulation comprises about 52% by weight of the triglycerides. In some embodiments, the otic pharmaceutical formulation comprises about 53% by weight of the triglycerides. In some embodiments, the otic pharmaceutical formulation comprises about 54% by weight of the triglycerides. In some embodiments, the otic pharmaceutical formulation comprises about 55% by weight of the triglycerides. In some embodiments, the otic pharmaceutical formulation comprises about 56% by weight of the triglycerides. In some embodiments, the otic pharmaceutical formulation comprises about 57% by weight of the triglycerides. In some embodiments, the otic pharmaceutical formulation comprises about 58% by weight of the triglycerides. In some embodiments, the otic pharmaceutical formulation comprises about 59% by weight of the triglycerides. In some embodiments, the otic pharmaceutical formulation comprises about 60% by weight of the triglycerides. In some embodiments, the otic pharmaceutical formulation comprises about 61% by weight of the triglycerides. In some embodiments, the otic pharmaceutical formulation comprises about 62% by weight of the triglycerides. In some embodiments, the otic pharmaceutical formulation comprises about 63% by weight of the triglycerides. In some embodiments, the otic pharmaceutical formulation comprises about 64% by weight of the triglycerides. In some embodiments, the otic pharmaceutical formulation comprises about 65% by weight of the triglycerides. In some embodiments, the otic pharmaceutical formulation comprises about 66% by weight of the triglycerides. In some embodiments, the otic pharmaceutical formulation comprises about 67% by weight of the triglycerides. In some embodiments, the otic pharmaceutical formulation comprises about 68% by weight of the triglycerides. In some embodiments, the otic pharmaceutical formulation comprises about 69% by weight of the triglycerides. In some embodiments, the otic pharmaceutical formulation comprises about 70% by weight of the triglycerides. In some embodiments, the otic pharmaceutical formulation comprises about 71% by weight of the triglycerides. In some embodiments, the otic pharmaceutical formulation comprises about 72% by weight of the triglycerides. In some embodiments, the otic pharmaceutical formulation comprises about 73% by weight of the triglycerides. In some embodiments, the otic pharmaceutical formulation comprises about 74% by weight of the triglycerides. In some embodiments, the otic pharmaceutical formulation comprises about 75% by weight of the triglycerides. In some embodiments, the otic pharmaceutical formulation comprises about 76% by weight of the triglycerides. In some embodiments, the otic pharmaceutical formulation comprises about 77% by weight of the triglycerides. In some embodiments, the otic pharmaceutical formulation comprises about 78% by weight of the triglycerides. In some embodiments, the otic pharmaceutical formulation comprises about 79% by weight of the triglycerides. In some embodiments, the otic pharmaceutical formulation comprises about 80% by weight of the triglycerides. In some embodiments, the otic pharmaceutical formulation comprises about 81% by weight of the triglycerides. In some embodiments, the otic pharmaceutical formulation comprises about 82% by weight of the triglycerides. In some embodiments, the otic pharmaceutical formulation comprises about 83% by weight of the triglycerides. In some embodiments, the otic pharmaceutical formulation comprises about 84% by weight of the triglycerides. In some embodiments, the otic pharmaceutical formulation comprises about 85% by weight of the triglycerides. In some embodiments, the otic pharmaceutical formulation comprises about 86% by weight of the triglycerides. In some embodiments, the otic pharmaceutical formulation comprises about 87% by weight of the triglycerides. In some embodiments, the otic pharmaceutical formulation comprises about 88% by weight of the triglycerides. In some embodiments, the otic pharmaceutical formulation comprises about 89% by weight of the triglycerides. In some embodiments, the otic pharmaceutical formulation comprises about 90% by weight of the triglycerides. In some embodiments, the otic pharmaceutical formulation comprises about 91% by weight of the triglycerides. In some embodiments, the otic pharmaceutical formulation comprises about 92% by weight of the triglycerides. In some embodiments, the otic pharmaceutical formulation comprises about 93% by weight of the triglycerides. In some embodiments, the otic pharmaceutical formulation comprises about 94% by weight of the triglycerides. In some embodiments, the otic pharmaceutical formulation comprises about 95% by weight of the triglycerides. In some embodiments, the otic pharmaceutical formulation comprises about 96% by weight of the triglycerides. In some embodiments, the otic pharmaceutical formulation comprises about 97% by weight of the triglycerides. In some embodiments, the otic pharmaceutical formulation comprises about 98% by weight of the triglycerides. In some embodiments, the otic pharmaceutical formulation comprises about 99% by weight of the triglycerides.

In some embodiments, the triglycerides in any one of the otic formulations and compositions described herein are replaced with at least one of the following components in the corresponding amounts of triglyceride in the formulation or composition disclosed herein: mineral oil or any corresponding higher alkanes; Vaseline (petroleum jelly); silicone oil (polydimethylsiloxane) in different molecular weights; beeswax dissolved in any of the oils disclosed herein.

In some embodiments, the otic formulation or composition further comprises at least one viscosity modulating agent. In some embodiments, the at least one viscosity modulating agent is silicon dioxide, povidone, carbomer, poloxamer, or a combination thereof. In some embodiments, the viscosity modulating agent is silicon dioxide. In some embodiments, the viscosity modulating agent is povidone. In some embodiments, the viscosity modulating agent is carbomer. In some embodiments, the viscosity modulating agent is poloxamer. In some embodiments, the viscosity modulating agents are silicon dioxide and povidone. In some embodiments, the viscosity modulating agents are silicon dioxide and carbomer. In some embodiments, the viscosity modulating agents are silicon dioxide and poloxamer. In some embodiments, the poloxamer is P407.

In some embodiments, the otic formulation or composition comprises between about 0.01% to about 40% by weight of the povidone. In some embodiments, the otic formulation or composition comprises between about 0.01% to about 35% by weight of the povidone. In some embodiments, the otic formulation or composition comprises between about 0.01% to about 30% by weight of the povidone. In some embodiments, the otic formulation or composition comprises between about 0.01% to about 25% by weight of the povidone. In some embodiments, the otic formulation or composition comprises between about 0.01% to about 20% by weight of the povidone. In some embodiments, the otic formulation or composition comprises between about 0.01% to about 15% by weight of the povidone. In some embodiments, the otic formulation or composition comprises between about 0.01% to about 10% by weight of the povidone. In some embodiments, the otic formulation or composition comprises about 0.01% to about 7% by weight of the povidone. In some embodiments, the otic formulation or composition comprises between about 0.01% to about 5% by weight of the povidone. In some embodiments, the otic formulation or composition comprises between about 0.01% to about 3% by weight of the povidone. In some embodiments, the otic formulation or composition comprises between about 0.01% to about 2% by weight of the povidone. In some embodiments, the otic formulation or composition comprises about 0.01% to about 1% by weight of the povidone.

In some embodiments, the otic formulation or composition comprises about 0.01% by weight of the povidone. In some embodiments, the otic formulation or composition comprises about 0.02% by weight of the povidone. In some embodiments, the otic formulation or composition comprises about 0.03% by weight of the povidone. In some embodiments, the otic formulation or composition comprises about 0.04% by weight of the povidone. In some embodiments, the otic formulation or composition comprises about 0.05% by weight of the povidone. In some embodiments, the otic formulation or composition comprises about 0.06% by weight of the povidone. In some embodiments, the otic formulation or composition comprises about 0.07% by weight of the povidone. In some embodiments, the otic formulation or composition comprises about 0.08% by weight of the povidone. In some embodiments, the otic formulation or composition comprises about 0.09% by weight of the povidone. In some embodiments, the otic formulation or composition comprises about 0.1% by weight of the povidone. In some embodiments, the otic formulation or composition comprises about 0.2% by weight of the povidone. In some embodiments, the otic formulation or composition comprises about 0.3% by weight of the povidone. In some embodiments, the otic formulation or composition comprises about 0.4% by weight of the povidone. In some embodiments, the otic formulation or composition comprises about 0.5% by weight of the povidone. In some embodiments, the otic formulation or composition comprises about 0.6% by weight of the povidone. In some embodiments, the otic formulation or composition comprises about 0.7% by weight of the povidone. In some embodiments, the otic formulation or composition comprises about 0.8% by weight of the povidone. In some embodiments, the otic formulation or composition comprises about 0.9% by weight of the povidone. In some embodiments, the otic formulation or composition comprises about 1% by weight of the povidone. In some embodiments, the otic formulation or composition comprises about 2% by weight of the povidone. In some embodiments, the otic formulation or composition comprises about 3% by weight of the povidone. In some embodiments, the otic formulation or composition comprises about 4% by weight of the povidone. In some embodiments, the otic formulation or composition comprises about 5% by weight of the povidone. In some embodiments, the otic formulation or composition comprises about 6% by weight of the povidone. In some embodiments, the otic formulation or composition comprises about 7% by weight of the povidone. In some embodiments, the otic formulation or composition comprises about 8% by weight of the povidone. In some embodiments, the otic formulation or composition comprises about 9% by weight of the povidone. In some embodiments, the otic formulation or composition comprises about 10% by weight of the povidone. In some embodiments, the otic formulation or composition comprises about 11% by weight of the povidone. In some embodiments, the otic formulation or composition comprises about 12% by weight of the povidone. In some embodiments, the otic formulation or composition comprises about 13% by weight of the povidone. In some embodiments, the otic formulation or composition comprises about 14% by weight of the povidone. In some embodiments, the otic formulation or composition comprises about 15% by weight of the povidone. In some embodiments, the otic formulation or composition comprises about 16% by weight of the povidone. In some embodiments, the otic formulation or composition comprises about 17% by weight of the povidone. In some embodiments, the otic formulation or composition comprises about 18% by weight of the povidone. In some embodiments, the otic formulation or composition comprises about 19% by weight of the povidone. In some embodiments, the otic formulation or composition comprises about 20% by weight of the povidone. In some embodiments, the otic formulation or composition comprises about 25% by weight of the povidone. In some embodiments, the otic formulation or composition comprises about 30% by weight of the povidone. In some embodiments, the otic formulation or composition comprises about 35% by weight of the povidone. In some embodiments, the otic formulation or composition comprises about 40% by weight of the povidone.

In some embodiments, the otic formulation or composition comprises between about 0.01% to about 40% by weight of the carbomer. In some embodiments, the otic formulation or composition comprises between about 0.01% to about 35% by weight of the carbomer. In some embodiments, the otic formulation or composition comprises between about 0.01% to about 30% by weight of the carbomer. In some embodiments, the otic formulation or composition comprises between about 0.01% to about 25% by weight of the carbomer. In some embodiments, the otic formulation or composition comprises between about 0.01% to about 20% by weight of the carbomer. In some embodiments, the otic formulation or composition comprises between about 0.01% to about 15% by weight of the carbomer. In some embodiments, the otic formulation or composition comprises between about 0.01% to about 10% by weight of the carbomer. In some embodiments, the otic formulation or composition comprises about 0.01% to about 7% by weight of the carbomer. In some embodiments, the otic formulation or composition comprises between about 0.01% to about 5% by weight of the carbomer. In some embodiments, the otic formulation or composition comprises between about 0.01% to about 3% by weight of the carbomer. In some embodiments, the otic formulation or composition comprises between about 0.01% to about 2% by weight of the carbomer. In some embodiments, the otic formulation or composition comprises about 0.01% to about 1% by weight of the carbomer.

In some embodiments, the otic formulation or composition comprises about 0.01% by weight of the carbomer. In some embodiments, the otic formulation or composition comprises about 0.02% by weight of the carbomer. In some embodiments, the otic formulation or composition comprises about 0.03% by weight of the carbomer. In some embodiments, the otic formulation or composition comprises about 0.04% by weight of the carbomer. In some embodiments, the otic formulation or composition comprises about 0.05% by weight of the carbomer. In some embodiments, the otic formulation or composition comprises about 0.06% by weight of the carbomer. In some embodiments, the otic formulation or composition comprises about 0.07% by weight of the carbomer. In some embodiments, the otic formulation or composition comprises about 0.08% by weight of the carbomer. In some embodiments, the otic formulation or composition comprises about 0.09% by weight of the carbomer. In some embodiments, the otic formulation or composition comprises about 0.1% by weight of the carbomer. In some embodiments, the otic formulation or composition comprises about 0.2% by weight of the carbomer. In some embodiments, the otic formulation or composition comprises about 0.3% by weight of the carbomer. In some embodiments, the otic formulation or composition comprises about 0.4% by weight of the carbomer. In some embodiments, the otic formulation or composition comprises about 0.5% by weight of the carbomer. In some embodiments, the otic formulation or composition comprises about 0.6% by weight of the carbomer. In some embodiments, the otic formulation or composition comprises about 0.7% by weight of the carbomer. In some embodiments, the otic formulation or composition comprises about 0.8% by weight of the carbomer. In some embodiments, the otic formulation or composition comprises about 0.9% by weight of the carbomer. In some embodiments, the otic formulation or composition comprises about 1% by weight of the carbomer. In some embodiments, the otic formulation or composition comprises about 2% by weight of the carbomer. In some embodiments, the otic formulation or composition comprises about 3% by weight of the carbomer. In some embodiments, the otic formulation or composition comprises about 4% by weight of the carbomer. In some embodiments, the otic formulation or composition comprises about 5% by weight of the carbomer. In some embodiments, the otic formulation or composition comprises about 6% by weight of the carbomer. In some embodiments, the otic formulation or composition comprises about 7% by weight of the carbomer. In some embodiments, the otic formulation or composition comprises about 8% by weight of the carbomer. In some embodiments, the otic formulation or composition comprises about 9% by weight of the carbomer. In some embodiments, the otic formulation or composition comprises about 10% by weight of the carbomer. In some embodiments, the otic formulation or composition comprises about 11% by weight of the carbomer. In some embodiments, the otic formulation or composition comprises about 12% by weight of the carbomer. In some embodiments, the otic formulation or composition comprises about 13% by weight of the carbomer. In some embodiments, the otic formulation or composition comprises about 14% by weight of the carbomer. In some embodiments, the otic formulation or composition comprises about 15% by weight of the carbomer. In some embodiments, the otic formulation or composition comprises about 16% by weight of the carbomer. In some embodiments, the otic formulation or composition comprises about 17% by weight of the carbomer. In some embodiments, the otic formulation or composition comprises about 18% by weight of the carbomer. In some embodiments, the otic formulation or composition comprises about 19% by weight of the carbomer. In some embodiments, the otic formulation or composition comprises about 20% by weight of the carbomer. In some embodiments, the otic formulation or composition comprises about 25% by weight of the carbomer. In some embodiments, the otic formulation or composition comprises about 30% by weight of the carbomer. In some embodiments, the otic formulation or composition comprises about 35% by weight of the carbomer. In some embodiments, the otic formulation or composition comprises about 40% by weight of the carbomer.

In some embodiments, the otic formulation or composition comprises between about 0.01% to about 40% by weight of the poloxamer. In some embodiments, the otic formulation or composition comprises between about 0.01% to about 35% by weight of the poloxamer. In some embodiments, the otic formulation or composition comprises between about 0.01% to about 30% by weight of the poloxamer. In some embodiments, the otic formulation or composition comprises between about 0.01% to about 25% by weight of the poloxamer. In some embodiments, the otic formulation or composition comprises between about 0.01% to about 20% by weight of the poloxamer. In some embodiments, the otic formulation or composition comprises between about 0.01% to about 15% by weight of the poloxamer. In some embodiments, the otic formulation or composition comprises between about 0.01% to about 10% by weight of the poloxamer. In some embodiments, the otic formulation or composition comprises about 0.01% to about 7% by weight of the poloxamer. In some embodiments, the otic formulation or composition comprises between about 0.01% to about 5% by weight of the poloxamer. In some embodiments, the otic formulation or composition comprises between about 0.01% to about 3% by weight of the poloxamer. In some embodiments, the otic formulation or composition comprises between about 0.01% to about 2% by weight of the poloxamer. In some embodiments, the otic formulation or composition comprises about 0.01% to about 1% by weight of the poloxamer.

In some embodiments, the otic formulation or composition comprises about 0.01% by weight of the poloxamer. In some embodiments, the otic formulation or composition comprises about 0.02% by weight of the poloxamer. In some embodiments, the otic formulation or composition comprises about 0.03% by weight of the poloxamer. In some embodiments, the otic formulation or composition comprises about 0.04% by weight of the poloxamer. In some embodiments, the otic formulation or composition comprises about 0.05% by weight of the poloxamer. In some embodiments, the otic formulation or composition comprises about 0.06% by weight of the poloxamer. In some embodiments, the otic formulation or composition comprises about 0.07% by weight of the poloxamer. In some embodiments, the otic formulation or composition comprises about 0.08% by weight of the poloxamer. In some embodiments, the otic formulation or composition comprises about 0.09% by weight of the poloxamer. In some embodiments, the otic formulation or composition comprises about 0.1% by weight of the poloxamer. In some embodiments, the otic formulation or composition comprises about 0.2% by weight of the poloxamer. In some embodiments, the otic formulation or composition comprises about 0.3% by weight of the poloxamer. In some embodiments, the otic formulation or composition comprises about 0.4% by weight of the poloxamer. In some embodiments, the otic formulation or composition comprises about 0.5% by weight of the poloxamer. In some embodiments, the otic formulation or composition comprises about 0.6% by weight of the poloxamer. In some embodiments, the otic formulation or composition comprises about 0.7% by weight of the poloxamer. In some embodiments, the otic formulation or composition comprises about 0.8% by weight of the poloxamer. In some embodiments, the otic formulation or composition comprises about 0.9% by weight of the poloxamer. In some embodiments, the otic formulation or composition comprises about 1% by weight of the poloxamer. In some embodiments, the otic formulation or composition comprises about 2% by weight of the poloxamer. In some embodiments, the otic formulation or composition comprises about 3% by weight of the poloxamer. In some embodiments, the otic formulation or composition comprises about 4% by weight of the poloxamer. In some embodiments, the otic formulation or composition comprises about 5% by weight of the poloxamer. In some embodiments, the otic formulation or composition comprises about 6% by weight of the poloxamer. In some embodiments, the otic formulation or composition comprises about 7% by weight of the poloxamer. In some embodiments, the otic formulation or composition comprises about 8% by weight of the poloxamer. In some embodiments, the otic formulation or composition comprises about 9% by weight of the poloxamer. In some embodiments, the otic formulation or composition comprises about 10% by weight of the poloxamer. In some embodiments, the otic formulation or composition comprises about 11% by weight of the poloxamer. In some embodiments, the otic formulation or composition comprises about 12% by weight of the poloxamer. In some embodiments, the otic formulation or composition comprises about 13% by weight of the poloxamer. In some embodiments, the otic formulation or composition comprises about 14% by weight of the poloxamer. In some embodiments, the otic formulation or composition comprises about 15% by weight of the poloxamer. In some embodiments, the otic formulation or composition comprises about 16% by weight of the poloxamer. In some embodiments, the otic formulation or composition comprises about 17% by weight of the poloxamer. In some embodiments, the otic formulation or composition comprises about 18% by weight of the poloxamer. In some embodiments, the otic formulation or composition comprises about 19% by weight of the poloxamer. In some embodiments, the otic formulation or composition comprises about 20% by weight of the poloxamer. In some embodiments, the otic formulation or composition comprises about 25% by weight of the poloxamer. In some embodiments, the otic formulation or composition comprises about 30% by weight of the poloxamer. In some embodiments, the otic formulation or composition comprises about 35% by weight of the poloxamer. In some embodiments, the otic formulation or composition comprises about 40% by weight of the poloxamer.

In some embodiments, the otic formulation or composition comprises between about 0.01% to about 20% by weight of the silicon dioxide. In some embodiments, the otic formulation or composition comprises between about 0.01% to about 15% by weight of the silicon dioxide. In some embodiments, the otic formulation or composition comprises between about 0.01% to about 10% by weight of the silicon dioxide. In some embodiments, the otic formulation or composition comprises about 0.010% to about 7% by weight of the silicon dioxide. In some embodiments, the otic formulation or composition comprises between about 0.01% to about 5% by weight of the silicon dioxide. In some embodiments, the otic formulation or composition comprises between about 0.01% to about 3% by weight of the silicon dioxide. In some embodiments, the otic formulation or composition comprises between about 0.01% to about 2% by weight of the silicon dioxide. In some embodiments, the otic formulation or composition comprises about 0.01% to about 1% by weight of the silicon dioxide.

In some embodiments, the otic formulation or composition comprises about 0.01% by weight of the silicon dioxide. In some embodiments, the otic formulation or composition comprises about 0.02% by weight of the silicon dioxide. In some embodiments, the otic formulation or composition comprises about 0.03% by weight of the silicon dioxide. In some embodiments, the otic formulation or composition comprises about 0.04% by weight of the silicon dioxide. In some embodiments, the otic formulation or composition comprises about 0.05% by weight of the silicon dioxide. In some embodiments, the otic formulation or composition comprises about 0.06% by weight of the silicon dioxide. In some embodiments, the otic formulation or composition comprises about 0.07% by weight of the silicon dioxide. In some embodiments, the otic formulation or composition comprises about 0.08% by weight of the silicon dioxide. In some embodiments, the otic formulation or composition comprises about 0.09% by weight of the silicon dioxide. In some embodiments, the otic formulation or composition comprises about 0.1% by weight of the silicon dioxide. In some embodiments, the otic formulation or composition comprises about 0.2% by weight of the silicon dioxide. In some embodiments, the otic formulation or composition comprises about 0.3% by weight of the silicon dioxide. In some embodiments, the otic formulation or composition comprises about 0.4% by weight of the silicon dioxide. In some embodiments, the otic formulation or composition comprises about 0.5% by weight of the silicon dioxide. In some embodiments, the otic formulation or composition comprises about 0.6% by weight of the silicon dioxide. In some embodiments, the otic formulation or composition comprises about 0.7% by weight of the silicon dioxide. In some embodiments, the otic formulation or composition comprises about 0.8% by weight of the silicon dioxide. In some embodiments, the otic formulation or composition comprises about 0.9% by weight of the silicon dioxide. In some embodiments, the otic formulation or composition comprises about 1% by weight of the silicon dioxide. In some embodiments, the otic formulation or composition comprises about 2% by weight of the silicon dioxide. In some embodiments, the otic formulation or composition comprises about 3% by weight of the silicon dioxide. In some embodiments, the otic formulation or composition comprises about 4% by weight of the silicon dioxide. In some embodiments, the otic formulation or composition comprises about 5% by weight of the silicon dioxide. In some embodiments, the otic formulation or composition comprises about 6% by weight of the silicon dioxide. In some embodiments, the otic formulation or composition comprises about 7% by weight of the silicon dioxide. In some embodiments, the otic formulation or composition comprises about 8% by weight of the silicon dioxide. In some embodiments, the otic formulation or composition comprises about 9% by weight of the silicon dioxide. In some embodiments, the otic formulation or composition comprises about 10% by weight of the silicon dioxide. In some embodiments, the otic formulation or composition comprises about 11% by weight of the silicon dioxide. In some embodiments, the otic formulation or composition comprises about 12% by weight of the silicon dioxide. In some embodiments, the otic formulation or composition comprises about 13% by weight of the silicon dioxide. In some embodiments, the otic formulation or composition comprises about 14% by weight of the silicon dioxide. In some embodiments, the otic formulation or composition comprises about 15% by weight of the silicon dioxide. In some embodiments, the otic formulation or composition comprises about 16% by weight of the silicon dioxide. In some embodiments, the otic formulation or composition comprises about 17% by weight of the silicon dioxide. In some embodiments, the otic formulation or composition comprises about 18% by weight of the silicon dioxide. In some embodiments, the otic formulation or composition comprises about 19% by weight of the silicon dioxide. In some embodiments, the otic formulation or composition comprises about 20% by weight of the silicon dioxide.

In some embodiments, the viscosity modulating agent is silicon dioxide. In some embodiments, the viscosity modulating agent is a polymer, such as povidone, carbomer, or poloxamer. In some embodiments, the viscosity modulating agent is a polysaccharide, such as dextran, alginate, or hyaluronic acid. In some embodiments, the viscosity modulating agent is cellulose-based, such as hydroxypropyl cellulose, hydroxypropyl methylcellulose, carboxymethylcellulose, carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), and noncrystalline cellulose. In some embodiments, the viscosity modulating agent is polyvinyl alcohol (PVA). In some embodiments, the viscosity modulating agent is polyethylene glycol (PEG) based.

In some embodiments, the otic formulation or composition comprises between about 0.01% to about 40% by weight of the viscosity modulating agent(s). In some embodiments, the otic formulation or composition comprises between about 0.01% to about 35% by weight of the viscosity modulating agent(s). In some embodiments, the otic formulation or composition comprises between about 0.01% to about 30% by weight of the viscosity modulating agent(s). In some embodiments, the otic formulation or composition comprises between about 0.01% to about 25% by weight of the viscosity modulating agent(s). In some embodiments, the otic formulation or composition comprises between about 0.01% to about 20% by weight of the viscosity modulating agent(s). In some embodiments, the otic formulation or composition comprises between about 0.01% to about 15% by weight of the viscosity modulating agent(s). In some embodiments, the otic formulation or composition comprises between about 0.01% to about 10% by weight of the viscosity modulating agent(s). In some embodiments, the otic formulation or composition comprises about 0.01% to about 7% by weight of the viscosity modulating agent(s). In some embodiments, the otic formulation or composition comprises between about 0.01% to about 5% by weight of the viscosity modulating agent(s). In some embodiments, the otic formulation or composition comprises between about 0.01% to about 3% by weight of the viscosity modulating agent(s). In some embodiments, the otic formulation or composition comprises between about 0.01% to about 2% by weight of the viscosity modulating agent(s). In some embodiments, the otic formulation or composition comprises about 0.01% to about 1% by weight of the viscosity modulating agent(s).

In some embodiments, the otic formulation or composition comprises about 0.01% by weight of the viscosity modulating agent(s). In some embodiments, the otic formulation or composition comprises about 0.02% by weight of the viscosity modulating agent(s). In some embodiments, the otic formulation or composition comprises about 0.03% by weight of the viscosity modulating agent(s). In some embodiments, the otic formulation or composition comprises about 0.04% by weight of the viscosity modulating agent(s). In some embodiments, the otic formulation or composition comprises about 0.05% by weight of the viscosity modulating agent(s). In some embodiments, the otic formulation or composition comprises about 0.06% by weight of the viscosity modulating agent(s). In some embodiments, the otic formulation or composition comprises about 0.07% by weight of the viscosity modulating agent(s). In some embodiments, the otic formulation or composition comprises about 0.08% by weight of the viscosity modulating agent(s). In some embodiments, the otic formulation or composition comprises about 0.09% by weight of the viscosity modulating agent(s). In some embodiments, the otic formulation or composition comprises about 0.1% by weight of the viscosity modulating agent(s). In some embodiments, the otic formulation or composition comprises about 0.2% by weight of the viscosity modulating agent(s). In some embodiments, the otic formulation or composition comprises about 0.3% by weight of the viscosity modulating agent(s). In some embodiments, the otic formulation or composition comprises about 0.4% by weight of the viscosity modulating agent(s). In some embodiments, the otic formulation or composition comprises about 0.5% by weight of the viscosity modulating agent(s). In some embodiments, the otic formulation or composition comprises about 0.6% by weight of the viscosity modulating agent(s). In some embodiments, the otic formulation or composition comprises about 0.7% by weight of the viscosity modulating agent(s). In some embodiments, the otic formulation or composition comprises about 0.8% by weight of the viscosity modulating agent(s). In some embodiments, the otic formulation or composition comprises about 0.9% by weight of the viscosity modulating agent(s). In some embodiments, the otic formulation or composition comprises about 1% by weight of the viscosity modulating agent(s). In some embodiments, the otic formulation or composition comprises about 2% by weight of the viscosity modulating agent(s). In some embodiments, the otic formulation or composition comprises about 3% by weight of the viscosity modulating agent(s). In some embodiments, the otic formulation or composition comprises about 4% by weight of the viscosity modulating agent(s). In some embodiments, the otic formulation or composition comprises about 5% by weight of the viscosity modulating agent(s). In some embodiments, the otic formulation or composition comprises about 6% by weight of the viscosity modulating agent(s). In some embodiments, the otic formulation or composition comprises about 7% by weight of the viscosity modulating agent(s). In some embodiments, the otic formulation or composition comprises about 8% by weight of the viscosity modulating agent(s). In some embodiments, the otic formulation or composition comprises about 9% by weight of the viscosity modulating agent(s). In some embodiments, the otic formulation or composition comprises about 10% by weight of the viscosity modulating agent(s). In some embodiments, the otic formulation or composition comprises about 11% by weight of the viscosity modulating agent(s). In some embodiments, the otic formulation or composition comprises about 12% by weight of the viscosity modulating agent(s). In some embodiments, the otic formulation or composition comprises about 13% by weight of the viscosity modulating agent(s). In some embodiments, the otic formulation or composition comprises about 14% by weight of the viscosity modulating agent(s). In some embodiments, the otic formulation or composition comprises about 15% by weight of the viscosity modulating agent(s). In some embodiments, the otic formulation or composition comprises about 16% by weight of the viscosity modulating agent(s). In some embodiments, the otic formulation or composition comprises about 17% by weight of the viscosity modulating agent(s). In some embodiments, the otic formulation or composition comprises about 18% by weight of the viscosity modulating agent(s). In some embodiments, the otic formulation or composition comprises about 19% by weight of the viscosity modulating agent(s). In some embodiments, the otic formulation or composition comprises about 20% by weight of the viscosity modulating agent(s). In some embodiments, the otic formulation or composition comprises about 25% by weight of the viscosity modulating agent(s). In some embodiments, the otic formulation or composition comprises about 30% by weight of the viscosity modulating agent(s). In some embodiments, the otic formulation or composition comprises about 35% by weight of the viscosity modulating agent(s). In some embodiments, the otic formulation or composition comprises about 40% by weight of the viscosity modulating agent(s).

In some embodiments, the otic formulations and compositions described herein further comprise cholesterol. In some embodiments, the otic formulation or composition comprises between about 0.01% to about 40% by weight of the cholesterol. In some embodiments, the otic formulation or composition comprises between about 0.01% to about 35% by weight of the cholesterol. In some embodiments, the otic formulation or composition comprises between about 0.01% to about 30% by weight of the cholesterol. In some embodiments, the otic formulation or composition comprises between about 0.01% to about 25% by weight of the cholesterol. In some embodiments, the otic formulation or composition comprises between about 0.01% to about 20% by weight of the cholesterol. In some embodiments, the otic formulation or composition comprises between about 0.01% to about 15% by weight of the cholesterol. In some embodiments, the otic formulation or composition comprises between about 0.01% to about 10% by weight of the cholesterol. In some embodiments, the otic formulation or composition comprises about 0.01% to about 7% by weight of the cholesterol. In some embodiments, the otic formulation or composition comprises between about 0.01% to about 5% by weight of the cholesterol. In some embodiments, the otic formulation or composition comprises between about 0.01% to about 3% by weight of the cholesterol. In some embodiments, the otic formulation or composition comprises between about 0.01% to about 2% by weight of the cholesterol. In some embodiments, the otic formulation or composition comprises about 0.01% to about 1% by weight of the cholesterol.

In some embodiments, the otic formulation or composition comprises about 0.01% by weight of the cholesterol. In some embodiments, the otic formulation or composition comprises about 0.02% by weight of the cholesterol. In some embodiments, the otic formulation or composition comprises about 0.03% by weight of the cholesterol. In some embodiments, the otic formulation or composition comprises about 0.04% by weight of the cholesterol. In some embodiments, the otic formulation or composition comprises about 0.05% by weight of the cholesterol. In some embodiments, the otic formulation or composition comprises about 0.06% by weight of the cholesterol. In some embodiments, the otic formulation or composition comprises about 0.07% by weight of the cholesterol. In some embodiments, the otic formulation or composition comprises about 0.08% by weight of the cholesterol. In some embodiments, the otic formulation or composition comprises about 0.09% by weight of the cholesterol. In some embodiments, the otic formulation or composition comprises about 0.10% by weight of the cholesterol. In some embodiments, the otic formulation or composition comprises about 0.2% by weight of the cholesterol. In some embodiments, the otic formulation or composition comprises about 0.3% by weight of the cholesterol. In some embodiments, the otic formulation or composition comprises about 0.4% by weight of the cholesterol. In some embodiments, the otic formulation or composition comprises about 0.5% by weight of the cholesterol. In some embodiments, the otic formulation or composition comprises about 0.6% by weight of the cholesterol. In some embodiments, the otic formulation or composition comprises about 0.7% by weight of the cholesterol. In some embodiments, the otic formulation or composition comprises about 0.8% by weight of the cholesterol. In some embodiments, the otic formulation or composition comprises about 0.9% by weight of the cholesterol. In some embodiments, the otic formulation or composition comprises about 1% by weight of the cholesterol. In some embodiments, the otic formulation or composition comprises about 2% by weight of the cholesterol. In some embodiments, the otic formulation or composition comprises about 3% by weight of the cholesterol. In some embodiments, the otic formulation or composition comprises about 4% by weight of the cholesterol. In some embodiments, the otic formulation or composition comprises about 5% by weight of the cholesterol. In some embodiments, the otic formulation or composition comprises about 6% by weight of the cholesterol. In some embodiments, the otic formulation or composition comprises about 7% by weight of the cholesterol. In some embodiments, the otic formulation or composition comprises about 8% by weight of the cholesterol. In some embodiments, the otic formulation or composition comprises about 9% by weight of the cholesterol. In some embodiments, the otic formulation or composition comprises about 10% by weight of the cholesterol. In some embodiments, the otic formulation or composition comprises about 11% by weight of the cholesterol. In some embodiments, the otic formulation or composition comprises about 12% by weight of the cholesterol. In some embodiments, the otic formulation or composition comprises about 13% by weight of the cholesterol. In some embodiments, the otic formulation or composition comprises about 14% by weight of the cholesterol. In some embodiments, the otic formulation or composition comprises about 15% by weight of the cholesterol. In some embodiments, the otic formulation or composition comprises about 16% by weight of the cholesterol. In some embodiments, the otic formulation or composition comprises about 17% by weight of the cholesterol. In some embodiments, the otic formulation or composition comprises about 18% by weight of the cholesterol. In some embodiments, the otic formulation or composition comprises about 19% by weight of the cholesterol. In some embodiments, the otic formulation or composition comprises about 20% by weight of the cholesterol. In some embodiments, the otic formulation or composition comprises about 25% by weight of the cholesterol. In some embodiments, the otic formulation or composition comprises about 30% by weight of the cholesterol. In some embodiments, the otic formulation or composition comprises about 35% by weight of the cholesterol. In some embodiments, the otic formulation or composition comprises about 40% by weight of the cholesterol.

In some embodiments, the triglycerides are a mixture of long-chain triglycerides and medium-chain triglycerides. In some embodiments, the ratio of long-chain triglycerides to medium-chain triglycerides is from about 0.01:99.99 to about 99.99:0.01. In some embodiments, the ratio of long-chain triglycerides to medium-chain triglycerides is from about 0.1:99.9 to about 99.9:0.1. In some embodiments, the ratio of long-chain triglycerides to medium-chain triglycerides is about 0.1:99.9. In some embodiments, the ratio of long-chain triglycerides to medium-chain triglycerides is about 0.5:99.5. In some embodiments, the ratio of long-chain triglycerides to medium-chain triglycerides is about 1.0:99.0. In some embodiments, the ratio of long-chain triglycerides to medium-chain triglycerides is about 5.0:95.0. In some embodiments, the ratio of long-chain triglycerides to medium-chain triglycerides is about 10.0:80.0. In some embodiments, the ratio of long-chain triglycerides to medium-chain triglycerides is about 15.0:85.0. In some embodiments, the ratio of long-chain triglycerides to medium-chain triglycerides is about 20.0:80.0. In some embodiments, the ratio of long-chain triglycerides to medium-chain triglycerides is about 25.0:75.0. In some embodiments, the ratio of long-chain triglycerides to medium-chain triglycerides is about 30.0:70.0. In some embodiments, the ratio of long-chain triglycerides to medium-chain triglycerides is about 35.0:65.0. In some embodiments, the ratio of long-chain triglycerides to medium-chain triglycerides is about 40.0:60.0. In some embodiments, the ratio of long-chain triglycerides to medium-chain triglycerides is about 45.0:55.0. In some embodiments, the ratio of long-chain triglycerides to medium-chain triglycerides is about 50.0:50.0. In some embodiments, the ratio of long-chain triglycerides to medium-chain triglycerides is about 55.0:45.0. In some embodiments, the ratio of long-chain triglycerides to medium-chain triglycerides is about 60.0:40.0. In some embodiments, the ratio of long-chain triglycerides to medium-chain triglycerides is about 65.0:35.0. In some embodiments, the ratio of long-chain triglycerides to medium-chain triglycerides is about 70.0:30.0. In some embodiments, the ratio of long-chain triglycerides to medium-chain triglycerides is about 75.0:25.0. In some embodiments, the ratio of long-chain triglycerides to medium-chain triglycerides is about 80.0:20.0. In some embodiments, the ratio of long-chain triglycerides to medium-chain triglycerides is about 85.0:15.0. In some embodiments, the ratio of long-chain triglycerides to medium-chain triglycerides is about 90.0:10.0. In some embodiments, the ratio of long-chain triglycerides to medium-chain triglycerides is about 95.0:5.0. In some embodiments, the ratio of long-chain triglycerides to medium-chain triglycerides is about 99.0:1.0. In some embodiments, the ratio of long-chain triglycerides to medium-chain triglycerides is about 99.9:0.1.

Long-chain triglycerides (LCTs) are triglycerides are derived from glycerol and at least two long-chain fatty acids. In some embodiments, the triglycerides are derived from glycerol and three long-chain fatty acids. In some embodiments, the triglycerides are derived from glycerol, two long-chain fatty acids, and one medium-chain fatty acid.

In some embodiments, the long-chain triglycerides are derived from glycerol and at least two long-chain fatty acids. In some embodiments, each long-chain fatty acid independently comprises greater than 12 carbon atoms in the carbon chain. In some embodiments, each long-chain fatty acid independently comprises 13 to 38 carbon atoms in the carbon chain. In some embodiments, the long-chain fatty acid is a saturated long-chain fatty acid, an unsaturated long-chain fatty acid, or a combination thereof. In some embodiments, each long-chain fatty acid independently comprises 13, 14, 15, 16, 17, 18, 19, 20, 21, 22, 23, 24, 25, 26, 27, 28, 29, 30, 31, 32, 33, 34, 35, 36, 37, or 38 carbon atoms in the carbon chain. In some embodiments, each long-chain fatty acid independently comprises 13 to 24 carbon atoms in the carbon chain. In some embodiments, the long-chain fatty acid is a saturated long-chain fatty acid, an unsaturated long-chain fatty acid, or a combination thereof. In some embodiments, each long-chain fatty acid independently comprises 13, 14, 15, 16, 17, 18, 19, 20, 21, 22, 23, or 24 carbon atoms in the carbon chain. In some embodiments, each long-chain fatty acid independently comprises 13 to 22 carbon atoms in the carbon chain. In some embodiments, the long-chain fatty acids are a saturated long-chain fatty acid, an unsaturated long-chain fatty acid, or a combination thereof. In some embodiments, each long-chain fatty acid independently comprises 13, 14, 15, 16, 17, 18, 19, 20, 21, or 22 carbon atoms in the carbon chain.

In some embodiments, each long-chain fatty acid is independently tridecylic acid (tridecanoic acid), myristic acid (tetradecanoic acid), pentadecylic acid (pentadecanoic acid), palmitic acid (hexadecanoic acid), margaric acid (heptadecanoic acid), stearic acid (octadecanoic acid), nonadecylic acid (nonadecanoic acid), arachidic acid (eicosanoic acid), heneicosylic acid (heneicosanoic acid), behenic acid (docosanoic acid), tricosylic acid (tricosanoic acid), lignoceric acid (tetracosanoic acid), pentacosylic acid (pentacosanoic acid), cerotic acid (hexacosanoic acid), heptacosylic acid (heptacosanoic acid), montanic acid (octacosanoic acid), nonacosylic acid (nonacosanoic acid), melissic acid (triacontanoic acid), henatriacontylic acid (henatriacontanoic acid), lacceroic acid (dotriacontanoic acid), psyllic acid (tritriacontanoic acid), geddic acid (tetratriacontanoic acid), ceroplastic acid (pentatriacontanoic acid), hexatriacontylic acid (hexatriacontanoic acid), heptatriacontanoic acid (heptatriacontanoic acid), or octatriacontanoic acid.

In some embodiments, each long-chain fatty acid is independently α-linolenic acid, stearidonic acid, eicosapentaenoic acid, docosahexaenoic acid, linoleic acid, γ-linolenic acid, dihomo-γ-linolenic acid, arachidonic acid, docosatetraenoic acid, palmitoleic acid, vaccenic acid, paullinic acid, oleic acid, elaidic acid, gondoic acid, erucic acid, nervonic acid, or mead acid.

In some embodiments, the otic triglyceride based pharmaceutical formulations have triglycerides in an amount that is sufficient to stabilize the therapeutic agent for injection into the ear. In some embodiments, the injection is into the outer ear. In some embodiments, the injection is into the middle ear. In some embodiments, the injection is intratympanic. In some embodiments, the injection is into the inner ear. In some embodiments, the otic triglyceride based pharmaceutical formulations have triglycerides in an amount that is sufficient to provide sufficient retention time in the ear. In some embodiments, the sufficient retention time in the ear is for the middle ear. In some embodiments, the sufficient retention time in the ear is for the inner ear. In some embodiments, the sufficient retention time in the ear is for the outer ear. In some embodiments, the outer ear is the external auditory canal, the outer surface of the tympanic membrane, or a combination thereof. In some embodiments, the outer ear is the external auditory canal. In some embodiments, the otic triglyceride based pharmaceutical formulations have triglycerides in an amount that is sufficient to provide sustained release of the therapeutic agent. In some embodiments, the sustained release of the therapeutic agent is in the outer ear. In some embodiments, the sustained release of the therapeutic agent is in the middle ear. In some embodiments, the sustained release of the therapeutic agent is in the inner ear.

*Auris*-Acceptable Formulations/Compositions

In some embodiments, the otic formulations or compositions described herein are thickened liquid formulations or compositions. The otic formulations or compositions described herein are suspension formulations or compositions. The otic formulations or compositions described herein are solution formulations or compositions. In some embodiments, the otic formulations or compositions have greater viscosity than an aqueous liquid composition. In some embodiments, the formulation or composition has a viscosity of greater than 1 cP (centipoise). In some embodiments, the formulation or composition has a viscosity of at least about 10 cP, about 20 cP, about 30 cP, about 40 cP, about 50 cP, about 60 cP, about 70 cP, about 80 cP, about 90 cP, about 100 cP, about 200 cP, about 300 cP, about 400 cP, about 500 cP, about 600 cP, about 700 cP, about 800 cP, about 900 cP, about 1,000 cP, about 2,000 cP, about 3,000 cP, about 4,000 cP, about 5,000 cP, about 6,000 cP, about 7,000 cP, about 8,000 cP, about 9,000 cP, about 10,000 cP, about 15,000 cP, or about 20,000 cP. In some embodiments, the formulation or composition has a viscosity of less than about 1,000 cP. In some embodiments, the formulation or composition has a viscosity of less than about 10,000 cP. In some embodiments, the formulation or composition has a viscosity of about 2 cP to about 250,000 cP, about 2 cP to about 100,000 cP, about 2 cP to about 50,000 cP, about 2 cP to about 25,000 cP, about 2 cP to about 10,000 cP, about 2 cP to about 5,000 cP, about 2 cP to about 1,000 cP, about 2 cP to about 500 cP, about 2 cP to about 250 cP, about 2 cP to about 100 cP, about 2 cP to about 90 cP, about 2 cP to about 80 cP, about 2 cP to about 70 cP, about 2 cP to about 60 cP, about 2 cP to about 50 cP, about 2 cP to about 40 cP, about 2 cP to about 30 cP, about 2 cP to about 20 cP, or about 2 cP to about 10 cP. In some embodiments, the liquid formulation or composition has a viscosity of about 2 cP, about 5 cP, about 10 cP, about 20 cP, about 30 cP, about 40 cP, about 50 cP, about 60 cP, about 70 cP, about 80 cP, about 90 cP, about 100 cP, about 200 cP, about 300 cP, about 400 cP, about 500 cP, about 600 cP, about 700 cP, about 800 cP, about 900 cP, about 1,000 cP, about 5,000 cP, about 10,000 cP, about 20,000 cP, about 50,000 cP, about 100,000 cP, or about 250,000 cP.

In some embodiments, the formulation or composition has a viscosity between about 10 cP to about 20,000 cP. In some embodiments, the formulation or composition has a viscosity between about 10 cP to about 10,000 cP. In some embodiments, the formulation or composition has a viscosity between about 10 cP to about 5,000 cP. In some embodiments, the formulation or composition has a viscosity between about 10 cP to about 1,000 cP. In some embodiments, the formulation or composition has a viscosity between about 10 cP to about 500 cP. In some embodiments, the formulation or composition has a viscosity between about 10 cP to about 250 cP. In some embodiments, the formulation or composition has a viscosity between about 10 cP to about 100 cP. In some embodiments, the formulation or composition has a viscosity between about 10 cP to about 50 cP.

In some embodiments, the formulation or composition has a viscosity of about 10 cP. In some embodiments, the formulation or composition has a viscosity of about 20 cP. In some embodiments, the formulation or composition has a viscosity of about 30 cP. In some embodiments, the formulation or composition has a viscosity of about 40 cP. In some embodiments, the formulation or composition has a viscosity of about 50 cP. In some embodiments, the formulation or composition has a viscosity of about 60 cP. In some embodiments, the formulation or composition has a viscosity of about 70 cP. In some embodiments, the formulation or composition has a viscosity of about 80 cP. In some embodiments, the formulation or composition has a viscosity of about 90 cP. In some embodiments, the formulation or composition has a viscosity of about 100 cP. In some embodiments, the formulation or composition has a viscosity of about 150 cP. In some embodiments, the formulation or composition has a viscosity of about 200 cP. In some embodiments, the formulation or composition has a viscosity of about 250 cP. In some embodiments, the formulation or composition has a viscosity of about 300 cP. In some embodiments, the formulation or composition has a viscosity of about 350 cP. In some embodiments, the formulation or composition has a viscosity of about 400 cP. In some embodiments, the formulation or composition has a viscosity of about 450 cP. In some embodiments, the formulation or composition has a viscosity of about 500 cP. In some embodiments, the formulation or composition has a viscosity of about 550 cP. In some embodiments, the formulation or composition has a viscosity of about 600 cP. In some embodiments, the formulation or composition has a viscosity of about 650 cP. In some embodiments, the formulation or composition has a viscosity of about 700 cP. In some embodiments, the formulation or composition has a viscosity of about 750 cP. In some embodiments, the formulation or composition has a viscosity of about 800 cP. In some embodiments, the formulation or composition has a viscosity of about 850 cP. In some embodiments, the formulation or composition has a viscosity of about 900 cP. In some embodiments, the formulation or composition has a viscosity of about 950 cP. In some embodiments, the formulation or composition has a viscosity of about 1,000 cP. In some embodiments, the formulation or composition has a viscosity of about 1,500 cP. In some embodiments, the formulation or composition has a viscosity of about 2,000 cP. In some embodiments, the formulation or composition has a viscosity of about 2,500 cP. In some embodiments, the formulation or composition has a viscosity of about 3,000 cP. In some embodiments, the formulation or composition has a viscosity of about 3,500 cP. In some embodiments, the formulation or composition has a viscosity of about 4,000 cP. In some embodiments, the formulation or composition has a viscosity of about 4,500 cP. In some embodiments, the formulation or composition has a viscosity of about 5,000 cP. In some embodiments, the formulation or composition has a viscosity of about 5,500 cP. In some embodiments, the formulation or composition has a viscosity of about 6,000 cP. In some embodiments, the formulation or composition has a viscosity of about 6,500 cP. In some embodiments, the formulation or composition has a viscosity of about 7,000 cP. In some embodiments, the formulation or composition has a viscosity of about 7,500 cP. In some embodiments, the formulation or composition has a viscosity of about 8,000 cP. In some embodiments, the formulation or composition has a viscosity of about 8,500 cP. In some embodiments, the formulation or composition has a viscosity of about 9,000 cP. In some embodiments, the formulation or composition has a viscosity of about 9,500 cP. In some embodiments, the formulation or composition has a viscosity of about 10,000 cP. In some embodiments, the formulation or composition has a viscosity of about 20,000 cP.

In some embodiments, the otic composition or formulation is free or substantially free of viscosity modulating agent. In some embodiments, the otic formulation or composition contains at least one viscosity modulating agent that provides the otic formulation or composition with a viscosity of at least about 10 cP, about 20 cP, about 30 cP, about 40 cP, about 50 cP, about 60 cP, about 70 cP, about 80 cP, about 90 cP, about 100 cP, about 200 cP, about 300 cP, about 400 cP, about 500 cP, about 600 cP, about 700 cP, about 800 cP, about 900 cP, about 1000 cP, about 2,000 cP, about 3,000 cP, about 4,000 cP, about 5,000 cP, about 6,000 cP, about 7,000 cP, about 8,000 cP, about 9,000 cP, about 10,000 cP, about 15,000 cP, or about 20,000 cP. In some embodiments, the formulation or composition contains at least one viscosity modulating agent that provides the otic formulation or composition with a viscosity of less than about 1,000 cP. In some embodiments, the formulation or composition contains at least one viscosity modulating agent that provides the otic formulation or composition with a viscosity of less than about 10,000 cP. In some embodiments, the otic composition or formulation contains at least one viscosity modulating agent that provides the otic composition or formulation with a viscosity of about 2 cP to about 250,000 cP, about 2 cP to about 100,000 cP, about 2 cP to about 50,000 cP, about 2 cP to about 25,000 cP, about 2 cP to about 10,000 cP, about 2 cP to about 5,000 cP, about 2 cP to about 1,000 cP, about 2 cP to about 500 cP, about 2 cP to about 250 cP, about 2 cP to about 100 cP, about 2 cP to about 90 cP, about 2 cP to about 80 cP, about 2 cP to about 70 cP, about 2 cP to about 60 cP, about 2 cP to about 50 cP, about 2 cP to about 40 cP, about 2 cP to about 30 cP, about 2 cP to about 20 cP, or about 2 cP to about 10 cP. In some embodiments, the otic formulation or composition contains at least one viscosity modulating agent that provides the otic formulation or composition with a viscosity of about 2 cP, about 5 cP, about 10 cP, about 20 cP, about 30 cP, about 40 cP, about 50 cP, about 60 cP, about 70 cP, about 80 cP, about 90 cP, about 100 cP, about 200 cP, about 300 cP, about 400 cP, about 500 cP, about 600 cP, about 700 cP, about 800 cP, about 900 cP, about 1,000 cP, about 5,000 cP, about 10,000 cP, about 20,000 cP, about 50,000 cP, about 100,000 cP, or about 250,000 cP. In some embodiments, the viscosity modulating agent is not a poloxamer. In some embodiments, the viscosity modulating agent is a poloxamer. In some embodiments, the poloxamer is P407. In some embodiments, the viscosity modulating agent is povidone. In some embodiments, the viscosity modulating agent is carbomer. In some embodiments, the viscosity modulating agent is a polymer. In some embodiments, the viscosity modulating agent is silicon dioxide. In some embodiments, the viscosity modulating agent is silicon dioxide, poloxamer, carbomer, povidone, or a combination thereof. In some embodiments, the viscosity modulating agent is a polysaccharide, such as dextran, alginate, or hyaluronic acid. In some embodiments, the viscosity modulating agent is cellulose-based, such as hydroxypropyl cellulose, hydroxypropyl methylcellulose, carboxymethylcellulose, carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), and noncrystalline cellulose. In some embodiments, the viscosity modulating agent is polyvinyl alcohol (PVA). In some embodiments, the viscosity modulating agent is polyethylene glycol (PEG) based. In some embodiments, the viscosity modulating agent is silicon dioxide, poloxamer, carbomer, povidone, polysaccharide, cellulose-based, polyvinyl alcohol, polyethylene glycol, or a combination thereof. In some embodiments, the viscosity modulating agent is an oil. In some embodiments, the viscosity modulating agent is beeswax. In some embodiments, the viscosity modulating agent is Vaseline. In some embodiments, the viscosity modulating agent is petroleum jelly. In some embodiments, the viscosity modulating agent is 12-hydroxystearic acid. In some embodiments, the formulation or composition comprises between about 0.01% to about 80% by weight of the viscosity modulating agent. In some embodiments, the formulation or composition comprises between about 0.010% to about 50% by weight of the viscosity modulating agent. In some embodiments, the formulation or composition comprises between about 0.01% to about 20% by weight of the viscosity modulating agent. In some embodiments, the formulation or composition comprises between about 0.010% to about 15% by weight of the viscosity modulating agent. In some embodiments, the formulation or composition comprises between about 0.01% to about 10% by weight of the viscosity modulating agent. In some embodiments, the formulation or composition comprises between about 0.01% to about 9% by weight of the viscosity modulating agent. In some embodiments, the formulation or composition comprises between about 0.010% to about 8% by weight of the viscosity modulating agent. In some embodiments, the formulation or composition comprises between about 0.01% to about 7% by weight of the viscosity modulating agent. In some embodiments, the formulation or composition comprises between about 0.010% to about 6% by weight of the viscosity modulating agent. In some embodiments, the formulation or composition comprises between about 0.01% to about 5% by weight of the viscosity modulating agent. In some embodiments, the formulation or composition comprises between about 0.010% to about 4% by weight of the viscosity modulating agent. In some embodiments, the formulation or composition comprises between about 0.01% to about 3% by weight of the viscosity modulating agent. In some embodiments, the formulation or composition comprises between about 0.010% to about 2% by weight of the viscosity modulating agent. In some embodiments, the formulation or composition comprises between about 0.01% to about 1% by weight of the viscosity modulating agent. In some embodiments, the formulation or composition comprises between about 0.10% to about 80% by weight of the viscosity modulating agent. In some embodiments, the formulation or composition comprises between about 0.1% to about 50% by weight of the viscosity modulating agent. In some embodiments, the formulation or composition comprises between about 0.10% to about 20% by weight of the viscosity modulating agent. In some embodiments, the formulation or composition comprises between about 0.1% to about 10% by weight of the viscosity modulating agent. In some embodiments, the formulation or composition comprises between about 0.1% to about 5% by weight of the viscosity modulating agent. In some embodiments, the formulation or composition comprises between about 1% to about 80% by weight of the viscosity modulating agent. In some embodiments, the formulation or composition comprises between about 1% to about 50% by weight of the viscosity modulating agent. In some embodiments, the formulation or composition comprises between about 1% to about 20% by weight of the viscosity modulating agent. In some embodiments, the formulation or composition comprises between about 1% to about 10% by weight of the viscosity modulating agent. In some embodiments, the formulation or composition comprises between about 1% to about 5% by weight of the viscosity modulating agent. In some embodiments, the formulation or composition comprises about 0.01%, about 0.05%, about 0.1%, about 0.2%, about 0.3%, about 0.4%, about 0.5%, about 0.6%, about 0.7%, about 0.8%, about 0.9%, about 1.0%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 85%, about 90% by weight of the viscosity modulating agent. In some embodiments, the formulation or composition comprises greater than about 0.01%, greater than about 0.05%, greater than about 0.10%, greater than about 0.2%, greater than about 0.3%, greater than about 0.4%, greater than about 0.5%, greater than about 0.6%, greater than about 0.7%, greater than about 0.8%, greater than about 0.9%, greater than about 1.0%, greater than about 2%, greater than about 3%, greater than about 4%, greater than about 5%, greater than about 6%, greater than about 7%, greater than about 8%, greater than about 9%, greater than about 10%, greater than about 11%, greater than about 12%, greater than about 130%, greater than about 14%, greater than about 15%, greater than about 16%, greater than about 17%, greater than about 18%, greater than about 19%, greater than about 20%, greater than about 25%, greater than about 30%, greater than about 35%, greater than about 40%, greater than about 45%, greater than about 50%, greater than about 55%, greater than about 60%, greater than about 65%, greater than about 70%, greater than about 75%, greater than about 80%, greater than about 85%, greater than about 90% by weight of the viscosity modulating agent. In some embodiments, the formulation or composition comprises less than about 0.01%, less than about 0.05%, less than about 0.1%, less than about 0.2%, less than about 0.3%, less than about 0.4%, less than about 0.5%, less than about 0.6%, less than about 0.7%, less than about 0.8%, less than about 0.9%, less than about 1.0%, less than about 2%, less than about 3%, less than about 4%, less than about 5%, less than about 6%, less than about 7%, less than about 8%, less than about 9%, less than about 10%, less than about 11%, less than about 12%, less than about 13%, less than about 14%, less than about 15%, less than about 16%, less than about 17%, less than about 18%, less than about 19%, less than about 20%, less than about 25%, less than about 30%, less than about 35%, less than about 40%, less than about 45%, less than about 50%, less than about 55%, less than about 60%, less than about 65%, less than about 70%, less than about 75%, less than about 80%, less than about 85%, less than about 90% by weight of the viscosity modulating agent.

In some embodiments, the otic composition or formulation is free or substantially free of water. In some embodiments, the otic composition or formulation comprises less than 10% by weight of water. In some embodiments, the otic composition or formulation comprises less than 9% by weight of water. In some embodiments, the otic composition or formulation comprises less than 8% by weight of water. In some embodiments, the otic composition or formulation comprises less than 7% by weight of water. In some embodiments, the otic composition or formulation comprises less than 6% by weight of water. In some embodiments, the otic composition or formulation comprises less than 5% by weight of water. In some embodiments, the otic composition or formulation comprises less than 4% by weight of water. In some embodiments, the otic composition or formulation comprises less than 3% by weight of water. In some embodiments, the otic composition or formulation comprises less than 2% by weight of water. In some embodiments, the otic composition or formulation comprises less than 1% by weight of water. In some embodiments, the otic composition or formulation comprises less than 0.5% by weight of water. In some embodiments, the otic composition or formulation comprises less than 0.1% by weight of water. In some embodiments, an otic composition or formulation disclosed herein comprises less than about 50 ppm of water. In some embodiments, an otic composition or formulation disclosed herein comprises less than about 25 ppm of water. In some embodiments, an otic composition or formulation disclosed herein comprises less than about 20 ppm of water. In some embodiments, an otic composition or formulation disclosed herein comprises less than about 10 ppm of water. In some embodiments, an otic composition or formulation disclosed herein comprises less than about 5 ppm of water. In some embodiments, an otic composition or formulation disclosed herein comprises less than about 1 ppm of water.

In some embodiments, the otic composition or formulation is free or substantially free of poloxamer. In some embodiments, the otic composition or formulation is free or substantially free of poloxamer 407.

In some embodiments, the otic composition or formulation is free or substantially free of C1-C6 alcohols or C1-C6 glycols. In some embodiments, the otic composition or formulation is free or substantially free of C1-C6 alcohols. In some embodiments, the otic composition or formulation is free or substantially free of C1-C6 glycols. In some embodiments, the otic composition or formulation comprises less than 10% by weight of C1-C6 alcohols or C1-C6 glycols. In some embodiments, the otic composition or formulation comprises less than 9% by weight of C1-C6 alcohols or C1-C6 glycols. In some embodiments, the otic composition or formulation comprises less than 8% by weight of C1-C6 alcohols or C1-C6 glycols. In some embodiments, the otic composition or formulation comprises less than 7% by weight of C1-C6 alcohols or C1-C6 glycols. In some embodiments, the otic composition or formulation comprises less than 6% by weight of C1-C6 alcohols or C1-C6 glycols. In some embodiments, the otic composition or formulation comprises less than 5% by weight of C1-C6 alcohols or C1-C6 glycols. In some embodiments, the otic composition or formulation comprises less than 4% by weight of C1-C6 alcohols or C1-C6 glycols. In some embodiments, the otic composition or formulation comprises less than 3% by weight of C1-C6 alcohols or C1-C6 glycols. In some embodiments, the otic composition or formulation comprises less than 2% by weight of C1-C6 alcohols or C1-C6 glycols. In some embodiments, the otic composition or formulation comprises less than 1% by weight of C1-C6 alcohols or C1-C6 glycols. In some embodiments, the otic composition or formulation comprises less than 0.5% by weight of C1-C6 alcohols or C1-C6 glycols. In some embodiments, the otic composition or formulation comprises less than 0.1% by weight of C1-C6 alcohols or C1-C6 glycols. In some embodiments, an otic composition or formulation disclosed herein comprises less than about 50 ppm of each of C1-C6 alcohols or C1-C6 glycols. In some embodiments, an otic composition or formulation disclosed herein comprises less than about 25 ppm of each of C1-C6 alcohols or C1-C6 glycols. In some embodiments, an otic composition or formulation disclosed herein comprises less than about 20 ppm of each of C1-C6 alcohols or C1-C6 glycols. In some embodiments, an otic composition or formulation disclosed herein comprises less than about 10 ppm of each of C1-C6 alcohols or C1-C6 glycols. In some embodiments, an otic composition or formulation disclosed herein comprises less than about 5 ppm of each of C1-C6 alcohols or C1-C6 glycols. In some embodiments, an otic composition or formulation disclosed herein comprises less than about 1 ppm of each of C1-C6 alcohols or C1-C6 glycols.

In some embodiments, the otic composition or formulation is free or substantially free of C1-C4 alcohols or C1-C4 glycols. In some embodiments, the otic composition or formulation is free or substantially free of C1-C4 alcohols. In some embodiments, the otic composition or formulation is free or substantially free of C1-C4 glycols. In some embodiments, the otic composition or formulation comprises less than 10% by weight of C1-C4 alcohols or C1-C4 glycols. In some embodiments, the otic composition or formulation comprises less than 9% by weight of C1-C4 alcohols or C1-C4 glycols. In some embodiments, the otic composition or formulation comprises less than 8% by weight of C1-C4 alcohols or C1-C4 glycols. In some embodiments, the otic composition or formulation comprises less than 7% by weight of C1-C4 alcohols or C1-C4 glycols. In some embodiments, the otic composition or formulation comprises less than 6% by weight of C1-C4 alcohols or C1-C4 glycols. In some embodiments, the otic composition or formulation comprises less than 5% by weight of C1-C4 alcohols or C1-C4 glycols. In some embodiments, the otic composition or formulation comprises less than 4% by weight of C1-C4 alcohols or C1-C4 glycols. In some embodiments, the otic composition or formulation comprises less than 3% by weight of C1-C4 alcohols or C1-C4 glycols. In some embodiments, the otic composition or formulation comprises less than 2% by weight of C1-C4 alcohols or C1-C4 glycols. In some embodiments, the otic composition or formulation comprises less than 1% by weight of C1-C4 alcohols or C1-C4 glycols. In some embodiments, the otic composition or formulation comprises less than 0.5% by weight of C1-C4 alcohols or C1-C4 glycols. In some embodiments, the otic composition or formulation comprises less than 0.1% by weight of C1-C4 alcohols or C1-C4 glycols. In some embodiments, an otic composition or formulation disclosed herein comprises less than about 50 ppm of each of C1-C4 alcohols or C1-C4 glycols. In some embodiments, an otic composition or formulation disclosed herein comprises less than about 25 ppm of each of C1-C4 alcohols or C1-C4 glycols. In some embodiments, an otic composition or formulation disclosed herein comprises less than about 20 ppm of each of C1-C4 alcohols or C1-C4 glycols. In some embodiments, an otic composition or formulation disclosed herein comprises less than about 10 ppm of each of C1-C4 alcohols or C1-C4 glycols. In some embodiments, an otic composition or formulation disclosed herein comprises less than about 5 ppm of each of C1-C4 alcohols or C1-C4 glycols. In some embodiments, an otic composition or formulation disclosed herein comprises less than about 1 ppm of each of C1-C4 alcohols or C1-C4 glycols.

By way of non-limiting example, the use of the following commonly used solvents should be limited, reduced or eliminated when formulating agents for administration to the ear: alcohols, propylene glycol, and cyclohexane. Thus, in some embodiments, an otic composition or formulation disclosed herein is free or substantially free of alcohols, propylene glycol, and cyclohexane. In some embodiments, an otic composition or formulation disclosed herein comprises less than about 50 ppm of each of alcohols, propylene glycol, and cyclohexane. In some embodiments, an otic composition or formulation disclosed herein comprises less than about 25 ppm of each of alcohols, propylene glycol, and cyclohexane. In some embodiments, an otic composition or formulation disclosed herein comprises less than about 20 ppm of each of alcohols, propylene glycol, and cyclohexane. In some embodiments, an otic composition or formulation disclosed herein comprises less than about 10 ppm of each of alcohols, propylene glycol, and cyclohexane. In some embodiments, an otic composition or formulation disclosed herein comprises less than about 5 ppm of each of alcohols, propylene glycol, and cyclohexane. In some embodiments, an otic composition or formulation disclosed herein comprises less than about 1 ppm of each of alcohols, propylene glycol, and cyclohexane.

In some embodiments, therapeutic agent, or pharmaceutically acceptable prodrug or salt thereof, is multiparticulate. In some embodiments, the therapeutic agent, or pharmaceutically acceptable prodrug or salt thereof, is essentially in the form of micronized particles. In some embodiments, the therapeutic agent, or pharmaceutically acceptable prodrug or salt thereof, is essentially dissolved in the otic pharmaceutical formulation or composition.

Poloxamers

In some embodiments, the otic formulations or compositions described herein further comprise poloxamer. In some embodiments, the otic formulations or compositions described herein are free or substantially free of poloxamer. An example of a poloxamer includes Poloxamer 407 (PF-127) is a nonionic surfactant composed of polyoxyethylene-polyoxypropylene copolymers. Other commonly used poloxamers also include but are not limited to 188 (F-68 grade), 237 (F-87 grade), 338 (F-108 grade).

In some embodiments, the otic formulations or compositions disclosed herein comprise PF-127, 188 (F-68 grade), 237 (F-87 grade), or 338 (F-108 grade). In some embodiments, the otic formulations or compositions disclosed herein comprise poloxamer 407.

In some embodiments, the otic formulations or compositions disclosed herein are free or substantially free of PF-127, 188 (F-68 grade), 237 (F-87 grade), or 338 (F-108 grade). In some embodiments, the otic formulations or compositions disclosed here are free or substantially free of poloxamer 407.

In certain embodiments, the thickening agents (i.e., viscosity enhancing agents or viscosity modulating agents) are also utilized in the otic formulations or compositions presented herein. In some embodiments, the thickening agent is a cellulose based thickening agent. In some instances, the addition of a thickening agent introduces a diffusional barrier and reduces the rate of release of the therapeutic agent. In some embodiments, the thickening agent or viscosity enhancer or viscosity modulating agent is not a poloxamer. In some embodiments, the thickening agent or viscosity enhancer or viscosity modulating agent is not poloxamer 407. In some embodiments, the thickening agent or viscosity enhancer or viscosity modulating agent is a poloxamer. In some embodiments, the thickening agent or viscosity enhancer or viscosity modulating agent is poloxamer 407.

In some embodiments, the otic formulations or compositions disclosed herein also contain preservatives, cosolvents, suspending agents, viscosity enhancing agents, ionic-strength and osmolality adjustors and other excipients in addition to buffering agents. Suitable water soluble preservatives which are employed in the drug delivery vehicle are sodium bisulfite, sodium thiosulfate, potassium thiosulfate, ascorbate, benzalkonium chloride, chlorobutanol, thimerosal, parabens, benzyl alcohol, phenylethanol and others. These agents are present, generally, in amounts of about 0.0010% to about 5% by weight and, preferably, in the amount of about 0.01 to about 2% by weight.

Suitable water-soluble buffering agents are alkali or alkaline earth metal carbonates, phosphates, bicarbonates, citrates, borates, acetates, succinates and the like, such as sodium phosphate, citrate, borate, acetate, bicarbonate, carbonate and tromethamine (TRIS). These agents are present in amounts sufficient to maintain the pH of the system at 7.4±0.2 and preferably, 7.4. As such, the buffering agent is as much as 5% on a weight basis of the total composition in some instances.

In some embodiments, cosolvents are used to enhance drug solubility; however, some drugs are insoluble.

Mucoadhesive Excipients

In some embodiments, mucoadhesive characteristics are also imparted to otic formulations disclosed herein, by incorporation of mucoadhesive carbomers, such as Carbopol 934P, to the composition (Majithiya et al., AAPS PharmSciTech (2006), 7(3), p. E1; EP0551626).

The term 'mucoadhesion' is commonly used for materials that bind to the mucin layer of a biological membrane. To serve as mucoadhesive polymers, the polymers should possess some general physiochemical features such as predominantly anionic hydrophilicity with numerous hydrogen bond forming groups, suitable surface property for wetting mucus/mucosal tissue surfaces and sufficient flexibility to penetrate the mucus network. In some embodiments, mucoadhesive formulations or compositions described herein adhere to the round window and/or the oval window and/or any inner ear structure. In some embodiments, the mucoadhesive agent adheres to the round window membrane. In some embodiments, the mucoadhesive agent is a round window membrane mucoadhesive agent.

Mucoadhesive agents including, but not limited to, at least one soluble polyvinylpyrrolidone polymer (PVP); a water-swellable, fibrous, cross-linked carboxy-functional polymer; a crosslinked poly(acrylic acid) (e.g. Carbopol 947P); a carbomer homopolymer; a carbomer copolymer; a hydrophilic polysaccharide gum, maltodextrin, a cross-linked alginate gum gel, a water-dispersible polycarboxylated vinyl polymer, at least two particulate components selected from the group consisting of titanium dioxide, silicon dioxide, and clay, or a mixture thereof. In some embodiments, the mucoadhesive agent is used in combination with a viscosity increasing excipient or are used alone to increase the interaction of the composition with a mucosal layer. In one non-limiting example, the mucoadhesive agent is maltodextrin and/or an alginate gum. Those of ordinary skill in the art will recognize that the mucoadhesive character imparted to the formulation or composition should be at a level that is sufficient to deliver an effective amount of the composition to, for example, the mucosal membrane of the round window in an amount that coats the mucosal membrane, and thereafter deliver the composition to the affected areas, including by way of example only, the vestibular and/or cochlear structures of the *Auris interna*. Those of ordinary skill in the art are able to determine the mucoadhesive characteristics of the compositions provided herein, and thus determine appropriate ranges. One method for determining sufficient mucoadhesiveness includes monitoring changes in the interaction of the composition with a mucosal layer, including but not limited to measuring changes in residence or retention time of the composition in the absence and presence of the excipient.

Mucoadhesive agents have been described, for example, in U.S. Pat. Nos. 6,638,521, 6,562,363, 6,509,028, 6,348,502, 6,319,513, 6,306,789, 5,814,330, and 4,900,552, each of which is hereby incorporated by reference in its entirety.

In one non-limiting example, the mucoadhesive agent is maltodextrin. Maltodextrin is a carbohydrate produced by the hydrolysis of starch that are derived from corn, potato, wheat or other plant products. Maltodextrin are used either alone or in combination with other mucoadhesive agents to impart mucoadhesive characteristics on the formulations or compositions disclosed herein. In one embodiment, a combination of maltodextrin and a carbopol polymer are used to increase the mucoadhesive characteristics of the formulations or compositions disclosed herein.

In another non-limiting example, a mucoadhesive agent is, for example, at least two particulate components selected from titanium dioxide, silicon dioxide, and clay, wherein the composition is not further diluted with any liquid prior to administration and the level of silicon dioxide, if present, is from about 3% to about 15%, by weight of the composition. Silicon dioxide, if present, are selected from the group consisting of fumed silicon dioxide, precipitated silicon dioxide, coacervated silicon dioxide, gel silicon dioxide, and mixtures thereof. Clay, if present, are kaolin minerals, serpentine minerals, smectites, illite or a mixture thereof. For example, clay is laponite, bentonite, hectorite, saponite, montmorillonites or a mixture thereof.

In one non-limiting example, the mucoadhesive agent is maltodextrin. Maltodextrin is a carbohydrate produced by the hydrolysis of starch that is optionally derived from corn, potato, wheat, or other plant products. Maltodextrin is optionally used either alone or in combination with other mucoadhesive agents to impart mucoadhesive characteristics on the formulations disclosed herein. In one embodiment, a combination of maltodextrin and a carbopol polymer are used to increase the membrane mucoadhesive characteristics of the formulations or devices disclosed herein.

In another embodiment, the membrane mucoadhesive agent is an alkyl-glycoside and/or a saccharide alkyl ester. As used herein, an "alkyl-glycoside" means a compound comprising any hydrophilic saccharide (e.g. sucrose, maltose, or glucose) linked to a hydrophobic alkyl. In some embodiments, the round window membrane mucoadhesive agent is an alkyl-glycoside wherein the alkyl-glycoside comprises a sugar linked to a hydrophobic alkyl (e.g., an alkyl comprising about 6 to about 25 carbon atoms) by an amide linkage, an amine linkage, a carbamate linkage, an ether linkage, a thioether linkage, an ester linkage, a thioester linkage, a glycosidic linkage, a thioglycosidic linkage, and/or a ureide linkage. In some embodiments, the round window membrane mucoadhesive agent is a hexyl-, heptyl-, octyl-, nonyl-, decyl-, undecyl-, dodecyl-, tridecyl-, tetradecyl-, pentadecyl-, hexadecyl-, heptadecyl-, octadecyl α-D-, or octadecyl β-D-maltoside; hexyl-, heptyl-, octyl-, nonyl-, decyl-, undecyl-, dodecyl-, tridecyl-, tetradecyl-, pentadecyl-, hexadecyl-, heptadecyl-, octadecyl α-D-, or octadecyl β-D-glucoside; hexyl-, heptyl-, octyl-, nonyl-, decyl-, undecyl-, dodecyl-, tridecyl-, tetradecyl-, pentadecyl-, hexadecyl-, heptadecyl-, octadecyl α-D-, or octadecyl β-D-sucroside; hexyl-, heptyl-, octyl-, dodecyl-, tridecyl-, or tetradecyl-β-D-thiomaltoside; dodecyl maltoside; heptyl- or octyl-1-thio-α- or β-D-glucopyranoside; alkyl thiosucroses; alkyl maltotriosides; long chain aliphatic carbonic acid amides of sucrose β-amino-alkyl ethers; derivatives of palatinose or isomaltamine linked by an amide linkage to an alkyl chain and derivatives of isomaltamine linked by urea to an alkyl chain; long chain aliphatic carbonic acid ureides of sucrose β-amino-alkyl ethers and long chain aliphatic carbonic acid amides of sucrose β-amino-alkyl ethers, or any combination thereof. In some embodiments, the mucoadhesive agent is an alkyl-glycoside wherein the alkyl glycoside is maltose, sucrose, glucose, or a combination thereof linked by a glycosidic linkage to an alkyl chain of 9-16 carbon atoms (e.g., nonyl-, decyl-, dodecyl- and tetradecyl sucroside; nonyl-, decyl-, dodecyl- and tetradecyl glucoside; and nonyl-, decyl-, dodecyl- and tetradecyl maltoside). In some embodiments, the mucoadhesive agent is an alkyl-glycoside wherein the alkyl glycoside is dodecylmaltoside, tridecylmaltoside, and tetradecylmaltoside.

In some embodiments, the mucoadhesive agent is an alkyl-glycoside wherein the alkyl-glycoside is a disaccharide with at least one glucose. In some embodiments, the *auris*-acceptable penetration enhancer is a surfactant comprising α-D-glucopyranosyl-β-glycopyranoside, n-Dodecyl-4-O-α-D-glucopyranosyl-β-glycopyranoside, and/or n-tetradecyl-4-O-α-D-glucopyranosyl-β-glycopyranoside. In some embodiments, the mucoadhesive agent is an alkyl-glycoside wherein the alkyl-glycoside has a critical micelle concentration (CMC) of less than about 1 mM in pure water or in aqueous solutions. In some embodiments, the mucoadhesive agent is an alkyl-glycoside wherein an oxygen atom within the alkyl-glycoside is substituted with a sulfur atom. In some embodiments, the mucoadhesive agent is an alkyl-glycoside wherein the alkylglycoside is the β anomer. In some embodiments, the mucoadhesive agent is an alkyl-glycoside wherein the alkylglycoside comprises 90%, 91%, 92%, 93%, 94%, 95%, 96%, 97%, 98%, 99%, 99.1%, 99.5%, or 99.9% of the β anomer.

Stabilizers

In one embodiment, stabilizers are selected from, for example, fatty acids, fatty alcohols, alcohols, long chain fatty acid esters, long chain ethers, hydrophilic derivatives of fatty acids, polyvinyl pyrrolidones, polyvinyl ethers, polyvinyl alcohols, hydrocarbons, hydrophobic polymers, moisture-absorbing polymers, and combinations thereof. In some embodiments, amide analogues of stabilizers are also used. In a further embodiment, the chosen stabilizer changes the hydrophobicity of the formulation or composition (e.g., oleic acid, waxes), or improves the mixing of various components in the formulation or composition (e.g., ethanol), controls the moisture level in the formula (e.g., PVP or polyvinyl pyrrolidone), controls the mobility of the phase (substances with melting points higher than room temperature such as long chain fatty acids, alcohols, esters, ethers, amides etc. or mixtures thereof, waxes), and/or improves the compatibility of the formula with encapsulating materials (e.g., oleic acid or wax). In another embodiment some of these stabilizers are used as solvents/co-solvents (e.g., ethanol). In a further embodiment, stabilizers are present in sufficient amount to inhibit the degradation of the active pharmaceutical ingredient. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

In some embodiments, the stabilizer is silicon dioxide. In some embodiments, the silicon dioxide is stabilizer in suspension formulations. In some embodiments, the silicon dioxide is an anticaking agent (i.e. an agent that prevents the formation of lumps). In some embodiments, the silicon dioxide is an anticaking agent (i.e. an agent that prevents the formation of lumps) that stabilizes suspension formulations. In some embodiments, the stabilizer is an anticaking agent.

In some embodiments, the stabilizer is a carbomer. In some embodiments, the carbomer is a complexing agent for positively charged proteins. In some embodiments, the positively charged protein in the complex has reduced solubility and therefore is released slowly from the formulation.

In some embodiments, the stabilizer is a complexing agent. In some embodiments, stabilizer interacts with the therapeutic agent to form a complex. In some embodiments, the stabilizer is a protein complexing agent. In some embodiments, the protein complexing agent is a polymer with a charge that is opposite to charge of the protein therapeutic agent. In some embodiments, the polymer is carbomer or alginate. In some embodiments, the stabilizer forms a complex with the protein therapeutic agent that reduces the solubility of the protein therapeutic agent. In some embodiments, the stabilizer forms a complex with the protein therapeutic agent that provides for the slow release of the protein therapeutic agent. In some embodiments, the stabilizer forms a complex with the protein therapeutic agent that provides for the sustained release of the protein therapeutic agent.

In some embodiments, the stabilizer is a neutral polymer. Examples of a neutral polymer include but are not limited to povidone, poloxamer, and HMPC. In some embodiments, the neutral polymer forms a polymer matrix that encapsulates the therapeutic agent and provides for the slow release of the therapeutic agent. In some embodiments, the neutral polymer forms a polymer matrix that encapsulates the therapeutic agent and provides for the sustained release of the therapeutic agent.

Additional useful *auris*-acceptable formulations or compositions include one or more anti-aggregation additives to enhance stability of otic formulations or compositions by reducing the rate of protein aggregation. The anti-aggregation additive selected depends upon the nature of the conditions to which the therapeutic agents, or otic agents, for example anti-TNF antibodies are exposed. For example, certain formulations or compositions undergoing agitation and thermal stress require a different anti-aggregation additive than a formulation undergoing lyophilization and reconstitution. Useful anti-aggregation additives include, by way of example only, urea, guanidinium chloride, simple amino acids such as glycine or arginine, sugars, polyalcohols, polysorbates, polymers such as polyethylene glycol and dextrans, alkyl saccharides, such as alkyl glycoside, and surfactants.

Other useful formulations or compositions include one or more antioxidants to enhance chemical stability where required. Suitable antioxidants include, by way of example only, ascorbic acid and sodium metabisulfite. In one embodiment, antioxidants are selected from metal chelating agents, thiol containing compounds and other general stabilizing agents.

Still other useful formulations or compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

In some embodiments, the pharmaceutical formulations or compositions described herein are stable with respect to compound degradation over a period of any of at least about 1 day, at least about 2 days, at least about 3 days, at least about 4 days, at least about 5 days, at least about 6 days, at least about 1 week, at least about 2 weeks, at least about 3 weeks, at least about 4 weeks, at least about 5 weeks, at least about 6 weeks, at least about 7 weeks, at least about 8 weeks, at least about 1 month, at least about 2 months, at least about 3 months, at least about 4 months, at least about 5 months, or at least about 6 months. In other embodiments, the formulations or compositions described herein are stable with respect to compound degradation over a period of at least about 1 week. Also described herein are formulations or compositions that are stable with respect to compound degradation over a period of at least about 1 month.

In other embodiments, an additional surfactant (co-surfactant) and/or buffering agent is combined with one or more of the pharmaceutically acceptable vehicles previously described herein so that the surfactant and/or buffering agent maintains the product at an optimal pH for stability. Suitable co-surfactants include, but are not limited to: a) natural and synthetic lipophilic agents, e.g., phospholipids, cholesterol, and cholesterol fatty acid esters and derivatives thereof, b) nonionic surfactants, which include for example, polyoxyethylene fatty alcohol esters, sorbitan fatty acid esters (Spans), polyoxyethylene sorbitan fatty acid esters (e.g., polyoxyethylene (20) sorbitan monooleate (Tween 80), polyoxyethylene (20) sorbitan monostearate (Tween 60), polyoxyethylene (20) sorbitan monolaurate (Tween 20) and other Tweens, sorbitan esters, glycerol esters, e.g., Myrj and glycerol triacetate (triacetin), polyethylene glycols, cetyl alcohol, cetostearyl alcohol, stearyl alcohol, polysorbate 80, poloxamers, poloxamines, polyoxyethylene castor oil derivatives (e.g., Cremophor® RH40, Cremophor A25, Cremophor A20, Cremophor® EL) and other Cremophors, sulfosuccinates, alkyl sulfates (SLS); PEG glyceryl fatty acid esters such as PEG-8 glyceryl caprylate/caprate (Labrasol), PEG-4 glyceryl caprylate/caprate (Labrafac Hydro WL 1219), PEG-32 glyceryl laurate (Gelucire 444/14), PEG-6 glyceryl mono oleate (Labrafil M 1944 CS), PEG-6 glyceryl linoleate (Labrafil M 2125 CS); propylene glycol mono- and di-fatty acid esters, such as propylene glycol laurate, propylene glycol caprylate/caprate; Brij® 700, ascorbyl-6-palmitate, stearylamine, sodium lauryl sulfate, polyoxethyleneglycerol triiricinoleate, and any combinations or mixtures thereof, c) anionic surfactants include, but are not limited to, calcium carboxymethylcellulose, sodium carboxymethylcellulose, sodium sulfosuccinate, dioctyl, sodium alginate, alkyl polyoxyethylene sulfates, sodium lauryl sulfate, triethanolamine stearate, potassium laurate, bile salts, and any combinations or mixtures thereof, and d) cationic surfactants such as quaternary ammonium compounds, benzalkonium chloride, cetyltrimethylammonium bromide, and lauryldimethylbenzyl-ammonium chloride.

In a further embodiment, when one or more co-surfactants are utilized in the formulations or compositions of the present disclosure, they are combined, e.g., with a pharmaceutically acceptable vehicle and is present in the final formulation, e.g., in an amount ranging from about 0.1% to about 20%, from about 0.5% to about 10%. In one embodiment, the surfactant has an HLB value of 0 to 20. In additional embodiments, the surfactant has an HLB value of 0 to 3, of 4 to 6, of 7 to 9, of 8 to 18, of 13 to 15, of 10 to 18.

Preservatives

In some embodiments, the otic formulations or compositions described herein is free of preservatives. In some embodiments, a formulation or composition disclosed herein comprises a preservative. Suitable *auris*-acceptable preservatives for use in a formulation or composition disclosed herein include, but are not limited to benzoic acid, boric acid, p-hydroxybenzoates, benzyl alcohol, lower alkyl alcohols (e.g., ethanol, butanol or the like), quaternary compounds, stabilized chlorine dioxide, mercurials, such as merfen and thimerosal, mixtures of the foregoing and the like. Suitable preservatives for use with a formulation disclosed herein are not ototoxic. In some embodiments, a formulation or composition disclosed herein does not include a preservative that is ototoxic. In some embodiments, a formulation or composition disclosed herein does not include benzalkonium chloride or benzethonium chloride.

In certain embodiments, any otic formulation or composition described herein has an endotoxin level of less than 0.5 EU/kg, less than 0.4 EU/kg or less than 0.3 EU/kg. In certain embodiments, any otic formulation or composition described herein has less than about 60 colony forming units (CFU), has less than about 50 colony forming units, has less than about 40 colony forming units, has less than about 30 colony forming units of microbial agents per gram of formulation or composition. In certain embodiments, any controlled release formulation or composition described herein is substantially free of pyrogens.

In a further embodiment, the preservative is, by way of example only, an antimicrobial agent, within the formulation or composition presented herein. In one embodiment, the formulation or composition includes a preservative such as by way of example only, methyl paraben. In another embodiment, the methyl paraben is at a concentration of about 0.05% to about 1.0%, about 0.1% to about 0.2%. In certain embodiments, the preservative employed in any *auris*-compatible formulation described herein is an antioxidant (e.g., butyl hydroxytoluene (BHT) or the like, as described herein). In certain embodiments, an antioxidant preservative is non-toxic and/or non-irritating to the inner ear environment.

Carriers

Suitable carriers for use in a formulation or composition described herein include, but are not limited to, any pharmaceutically acceptable solvent. For example, suitable solvents include polyalkylene glycols such as, but not limited to, polyethylene glycol (PEG) and any combinations or mixtures thereof. In other embodiments, the base is a combination of a pharmaceutically acceptable surfactant and solvent.

In some embodiments, other excipients include, sodium stearyl fumarate, diethanolamine cetyl sulfate, isostearate, polyethoxylated castor oil, benzalkonium chloride, nonoxyl 10, octoxynol 9, sodium lauryl sulfate, sorbitan esters (sorbitan monolaurate, sorbitan monooleate, sorbitan monopalmitate, sorbitan monostearate, sorbitan sesquioleate, sorbitan trioleate, sorbitan tristearate, sorbitan laurate, sorbitan oleate, sorbitan palmitate, sorbitan stearate, sorbitan dioleate, sorbitan sesqui-isostearate, sorbitan sesquistearate, sorbitan tri-isostearate), lecithins, phospholipids, phosphatidyl cholines (c8-c18), phosphatidylethanolamines (c8-c18), phosphatidylglycerols (c8-c18), pharmaceutical acceptable salts thereof and combinations or mixtures thereof.

In further embodiments, the carrier is polyethylene glycol. Polyethylene glycol is available in many different grades having varying molecular weights. For example, polyethylene glycol is available as PEG 200; PEG 300; PEG 400; PEG 540 (blend); PEG 600; PEG 900; PEG 1000; PEG 1450; PEG 1540; PEG 2000; PEG 3000; PEG 3350; PEG 4000; PEG 4600, and PEG 8000. For purposes of the present disclosure, all grades of polyethylene glycol are contemplated for use in preparation of a formulation described herein. In some embodiments the polyethylene glycol used to prepare a formulation described herein is PEG 300.

In other embodiments, the carrier is a polysorbate. Polysorbates are nonionic surfactants of sorbitan esters. Polysorbates useful in the present disclosure include, but are not limited to polysorbate 20, polysorbate 40, polysorbate 60, polysorbate 80 (Tween 80) and any combinations or mixtures thereof. In further embodiments, polysorbate 80 is utilized as the pharmaceutically acceptable carrier.

In one embodiment, water-soluble glycerin-based *auris*-acceptable enhanced viscosity formulations utilized in the preparation of pharmaceutical delivery vehicles comprise at least one active agent containing at least about 0.10% of the water-soluble glycerin compound or more. In some embodiments, the percentage of active agent is varied between about 1% and about 95%, between about 5% and about 80%, between about 10% and about 60% or more of the weight or volume of the total pharmaceutical formulation. In some embodiments, the amount of the compound(s) in each therapeutically useful formulation is prepared in such a way that a suitable dosage will be obtained in any given unit dose of the compound. Factors such as solubility, bioavailability, biological half-life, route of administration, product shelf life, as well as other pharmacological considerations are contemplated herein.

If desired, the *auris*-acceptable pharmaceutical gels also contain co-solvents, preservatives, cosolvents, ionic strength and osmolality adjustors and other excipients in addition to buffering agents. Suitable *auris*-acceptable water-soluble buffering agents are alkali or alkaline earth metal carbonates, phosphates, bicarbonates, citrates, borates, acetates, succinates and the like, such as sodium phosphate, citrate, borate, acetate, bicarbonate, carbonate, and tromethamine (TRIS). These agents are present in amounts sufficient to maintain the pH of the system at 7.4±0.2 and preferably, 7.4. As such, the buffering agent is as much as 5% on a weight basis of the total formulation.

Cosolvents are used to enhance the active agent solubility, however, some active agents are insoluble. These are often suspended in the polymer vehicle with the aid of suitable suspending or viscosity enhancing agents.

Moreover, some pharmaceutical excipients, diluents or carriers are potentially ototoxic. For example, benzalkonium chloride, a common preservative, is ototoxic and therefore potentially harmful if introduced into the vestibular or cochlear structures. In formulating a controlled-release formulation, it is advised to avoid or combine the appropriate excipients, diluents or carriers to lessen or eliminate potential ototoxic components from the formulation, or to decrease the amount of such excipients, diluents, or carriers. Optionally, a controlled-release formulation includes otoprotective agents, such as antioxidants, alpha lipoic acid, calcium, fosfomycin or iron chelators, to counteract potential ototoxic effects that may arise from the use of specific therapeutic agents or excipients, diluents, or carriers.

In some embodiments, therapeutically acceptable otic formulations are

| Example Formulation | Example Characteristics |
|---|---|
| Chitosan glycerophosphate (CGP) | tunable degradation of matrix in vitro<br>tunable TACE inhibitor release in vitro: e.g., ~50% of drug released after 24 hrs<br>biodegradable<br>compatible with drug delivery to the inner ear<br>suitable for macromolecules and hydrophobic drugs |
| PEG-PLGA-PEG triblock polymers | tunable high stability: e.g., maintains mechanical integrity > 1 month in vitro<br>tunable fast release of hydrophilic drugs: e.g., ~50% of drug released after 24 hrs, and remainder released over ~5 days<br>tunable slow release of hydrophobic drugs: e.g., ~80% released after 8 weeks<br>biodegradable<br>subcutaneous injection of solution: e.g., gel forms within seconds and is intact after 1 month |
| PEO-PPO-PEO triblock copolymers (e.g., Pluronic or Poloxamers) (e.g., F127) | Tunable sol-gel transition temperature: e.g., decreases with increasing F127 concentration |
| Chitosan glycerophosphate with drug-loaded liposomes | CGP formulation tolerates liposomes: e.g., up to 15 μM/ml liposomes.<br>liposomes tunably reduce drug release time (e.g., up to 2 weeks in vitro).<br>increase in liposome diameter optionally reduces drug release kinetics (e.g., liposome size between 100 and 300 nm)<br>release parameters are controlled by changing formulation of liposomes |

The formulations disclosed herein alternatively encompass an otoprotectant agent in addition to at least one of: tiopronin, penicillamine, dimercaprol, captodiame, fursultiamine, famotidine, cysteamine, thiabendazole, succimer, glutathione, mercaptopyruvate, a thiopyrimidine, a thiopurine, a thiouracil, a thiouracil derivative, a thiourea, a thioamide, or a tautomer, prodrug, pharmaceutically acceptable salt, solvate, or hydrate thereof and/or excipients, including but not limited to such agents as antioxidants, alpha lipoic acid, calcium, fosfomycin or iron chelators, to counteract potential ototoxic effects that may arise from the use of specific therapeutic agents or excipients, diluents or carriers.

In some embodiments, the percentage of active pharmaceutical ingredient is varied between about 0.010% and about 20%, between about 0.01% and about 10%, between about 0.01% and about 5% or more of the weight or volume of the total pharmaceutical formulation or composition. In some embodiments, the amount of the compound(s) in each therapeutically useful formulation or composition is prepared in such a way that a suitable dosage will be obtained in any given unit dose of the compound. Factors such as solubility, bioavailability, biological half-life, route of administration, product shelf life, as well as other pharmacological considerations are contemplated herein and the preparation of such pharmaceutical formulations or compositions is presented herein.

Suspending Agents

In one embodiment is an active pharmaceutical ingredient in a pharmaceutically acceptable formulation or composition wherein the formulation or composition comprises at least one suspending agent. In one embodiment is an active pharmaceutical ingredient in a pharmaceutically acceptable gel formulation or composition wherein the formulation or composition comprises at least one suspending agent.

In one embodiment, at least one otoprotectant is included in a pharmaceutically acceptable enhanced viscosity formulation or composition wherein the formulation or composition further comprises at least one suspending agent, wherein the suspending agent assists in imparting controlled release characteristics to the formulation or composition. In some embodiments, suspending agents also serve to increase the viscosity of the *auris*-acceptable therapeutic agent formulations or compositions.

Suspending agents include by example only, compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol has a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like. In some embodiments, useful aqueous suspensions also contain one or more polymers as suspending agents. Useful polymers include water-soluble polymers such as cellulosic polymers, e.g., hydroxypropyl methylcellulose, and water-insoluble polymers such as cross-linked carboxyl-containing polymers. Useful polymers also include hyaluronic acid.

In one embodiment, the present disclosure provides *auris*-acceptable gel formulations comprising a therapeutically effective amount of an active agent in a hydroxyethyl cellulose gel. hydroxyethyl cellulose (HEC) is obtained as a dry powder which is reconstituted in water or an aqueous buffer solution to give the desired viscosity (generally about 200 cps to about 30,000 cps, corresponding to about 0.2% to about 10% HEC). In one embodiment the concentration of HEC is between about 1% and about 15%, about 1% and about 2%, or about 1.5% to about 2%.

In some embodiments, the formulations or compositions include excipients, other medicinal or pharmaceutical agents, carriers, adjuvants, such as preserving, stabilizing, wetting or emulsifying agents, solution promoters, and salts. In some embodiments, the excipients, carriers, adjuvants, are useful in forming a pharmaceutically acceptable formulation or composition. In some embodiments, the formulation or composition comprises a stabilizer. In another embodiment the formulation or composition comprises a solubilizer. In a further embodiment the formulation or composition comprises an antifoaming agent. In yet a further embodiment, the formulation or composition comprises an antioxidant. In yet another embodiment, the formulation or composition comprises a dispersing agent. In one embodiment, the formulation or composition comprises a surfactant. In yet another embodiment, the formulation or composition comprises a wetting agent.

Viscosity Enhancing Agents

In one embodiment is a formulation or composition that is free or substantially free of a viscosity enhancing agent. In one embodiment is a formulation or composition comprising at least one active pharmaceutical ingredient and a viscosity agent. Also described herein are controlled release formulations or compositions that is free or substantially free of a viscosity enhancing agent. Also described herein are controlled release formulations or compositions comprising a therapeutic agent and a viscosity enhancing agent. In some embodiments, suitable viscosity-enhancing agents do not include poloxamers. Suitable viscosity-enhancing agents include by way of example only, thickening agents and suspending agents. In one embodiment, the enhanced viscosity formulation or composition does not include a pharmaceutically acceptable buffer. In other embodiments, the enhanced viscosity formulation or composition includes a pharmaceutically acceptable buffer. Sodium chloride or other tonicity agents are optionally used to adjust tonicity, if necessary.

Described herein are formulations or compositions comprising an active pharmaceutical ingredient and a thickening agent. Suitable thickening agents include by way of example only, suspending agents. In one embodiment, the thickened formulation or composition does not include a pharmaceutically acceptable buffer. In another embodiment, the thickened formulation or composition includes a pharmaceutically acceptable buffer.

By way of example only, the *auris*-acceptable viscosity agents include hydroxypropyl methylcellulose, hydroxyethyl cellulose, polyvinylpyrrolidone (PVP: povidone), carboxymethyl cellulose, polyvinyl alcohol, sodium chondroitin sulfate, sodium hyaluronate. Other viscosity agents that are used in pharmaceutical compositions described herein include, but are not limited to, acacia (gum arabic), agar, aluminum magnesium silicate, sodium alginate, sodium stearate, bladderwrack, bentonite, carbomer, carrageenan, Carbopol, xanthan, cellulose, microcrystalline cellulose (MCC), *ceratonia*, chondrus, dextrose, furcellaran, gelatin, Ghatti gum, guar gum, hectorite, lactose, sucrose, maltodextrin, mannitol, sorbitol, honey, maize starch, wheat starch, rice starch, potato starch, gelatin, *sterculia* gum, xanthum gum, polyethylene glycol (e.g. PEG 200-4500), gum tragacanth, ethyl cellulose, ethylhydroxyethyl cellulose, ethylmethyl cellulose, methyl cellulose, hydroxyethyl cellulose, hydroxyethylmethyl cellulose, hydroxypropyl cellulose, poly(hydroxyethyl methacrylate), oxypolygelatin, pectin, polygeline, povidone, propylene carbonate, methyl vinyl ether/maleic anhydride copolymer (PVM/MA), poly (methoxyethyl methacrylate), poly(methoxyethoxyethyl methacrylate), hydroxypropyl cellulose, hydroxypropylmethyl-cellulose (HPMC), sodium carboxymethyl-cellulose (CMC), silicon dioxide, Splenda® (dextrose, maltodextrin and sucralose) or combinations thereof. In specific embodiments, the viscosity-enhancing excipient is a combination of methylcellulose (MC) and CMC. In another embodiment, the viscosity-enhancing agent is a combination of carboxymethylated chitosan, or chitin, and alginate. The combination of chitin and alginate with the active agents disclosed herein acts as a controlled release formulation, restricting the diffusion of the active agents from the formulation. Moreover, the combination of carboxymethylated chitosan and alginate is optionally used to assist in increasing the permeability of any active agent described herein through the round window membrane.

In further embodiments, the *auris* formulation or composition contains a viscosity enhancing agent or viscosity modulating agent sufficient to provide a viscosity of between about 10 and 1,000,000 centipoise, between about 100 and 1,000,000 centipoise, between about 500 and 1,000,000 centipoise, between about 750 and 1,000,000 centipoise; between about 1000 and 40,000 centipoise; between about 2000 and 35,000 centipoise; between about 3000 and 30,000 centipoise; between about 4000 and 25,000 centipoise; between about 5000 and 20,000 centipoise; or between about 6000 and 15,000 centipoise.

In further embodiments, the *auris* formulation or composition contains a viscosity enhancing agent or viscosity modulating agent sufficient to provide a viscosity of about 2 cP to about 250,000 cP, about 2 cP to about 100,000 cP, about 2 cP to about 50,000 cP, about 2 cP to about 25,000 cP, about 2 cP to about 10,000 cP, about 2 cP to about 5,000 cP, about 2 cP to about 1,000 cP, about 2 cP to about 500 cP, about 2 cP to about 250 cP, about 2 cP to about 100 cP, about 2 cP to about 90 cP, about 2 cP to about 80 cP, about 2 cP to about 70 cP, about 2 cP to about 60 cP, about 2 cP to about 50 cP, about 2 cP to about 40 cP, about 2 cP to about 30 cP, about 2 cP to about 20 cP, or about 2 cP to about 10 cP. In some embodiments, the formulation or composition has a viscosity of about 2 cP, about 5 cP, about 10 cP, about 20 cP, about 30 cP, about 40 cP, about 50 cP, about 60 cP, about 70 cP, about 80 cP, about 90 cP, about 100 cP, about 200 cP, about 300 cP, about 400 cP, about 500 cP, about 600 cP, about 700 cP, about 800 cP, about 900 cP, about 1,000 cP, about 5,000 cP, about 10,000 cP, about 20,000 cP, about 50,000 cP, about 100,000 cP, or about 250,000 cP.

In some embodiments, the viscosity of the otic formulations or compositions presented herein are measured by any means described herein. For example, in some embodiments, an LVDV-II+CP Cone Plate Viscometer and a Cone Spindle CPE-40 is used to calculate the viscosity of the formulation described herein. In other embodiments, a Brookfield (spindle and cup) viscometer is used to calculate the viscosity of the formulation or composition described herein. In some embodiments, the viscosity ranges referred to herein are measured at room temperature. In other embodiments, the viscosity ranges referred to herein are measured at body temperature.

*Auris*-Acceptable Penetration Enhancers

In another embodiment the formulation or composition further comprises one or more penetration enhancers. Penetration into biological membranes is enhanced by the presence of penetration enhancers. Penetration enhancers are chemical entities that facilitate transport of coadministered substances across biological membranes. Penetration enhancers are grouped according to chemical structure. Surfactants, both ionic and non-ionic, such as sodium lauryl sulfate, sodium laurate, polyoxyethylene-20-cetyl ether, laureth-9, sodium dodecylsulfate, dioctyl sodium sulfosuccinate, polyoxyethylene-9-lauryl ether (PLE), Tween 80, nonylphenoxypolyethylene (NP-POE), polysorbates and the like, function as penetration enhancers. Bile salts (such as sodium glycocholate, sodium deoxycholate, sodium taurocholate, sodium taurodihydrofusidate, sodium glycodihydrofusidate and the like), fatty acids and derivatives (such as oleic acid, caprylic acid, mono- and di-glycerides, lauric acids, acylcholines, caprylic acids, acylcarnitines, sodium caprates and the like), chelating agents (such as EDTA, citric acid, salicylates and the like), sulfoxides (such as dimethyl sulfoxide (DMSO), decylmethyl sulfoxide and the like), and alcohols (such as ethanol, isopropanol, propylene glycol, polyethylene glycol, glycerol, propanediol and the like) also function as penetration enhancers. In addition, the peptide-like penetration enhancers described in U.S. Pat. Nos. 7,151,191, 6,221,367 and 5,714,167, herein incorporated by references for such disclosure, are contemplated as an additional embodiment. These penetration enhancers are amino-acid and peptide derivatives and enable drug absorption by passive transcellular diffusion without affecting the integrity of membranes or intercellular tight junctions. In some embodiments, a penetration enhancer is hyaluronic acid.

In some embodiments, the *auris*-acceptable penetration enhancer is a surfactant. In some embodiments, the *auris*-acceptable penetration enhancer is a surfactant comprising an alkyl-glycoside and/or a saccharide alkyl ester. As used herein, an "alkyl-glycoside" means a compound comprising any hydrophilic saccharide (e.g. glucose, fructose, sucrose, maltose, or glucose) linked to a hydrophobic alkyl. In some embodiments, the *auris*-acceptable penetration enhancer is a surfactant comprising an alkyl-glycoside wherein the alkyl-glycoside comprises a sugar linked to a hydrophobic alkyl (e.g., an alkyl comprising about 6 to about 25 carbon atoms) by an amide linkage, an amine linkage, a carbamate linkage, an ether linkage, a thioether linkage, an ester linkage, a thioester linkage, a glycosidic linkage, a thioglycosidic linkage, and/or a ureide linkage. In some embodiments, the *auris*-acceptable penetration enhancer is a surfactant comprising hexyl-, heptyl-, octyl-, nonyl-, decyl-, undecyl-, dodecyl-, tridecyl-, tetradecyl, pentadecyl-, hexadecyl-, heptadecyl-, and octadecyl α- or β-D-maltoside; hexyl-, heptyl-, octyl-, nonyl-, decyl-, undecyl-, dodecyl-, tridecyl-, tetradecyl, pentadecyl-, hexadecyl-, heptadecyl-, and octadecyl α- or β-D-glucoside; hexyl-, heptyl-, octyl-, nonyl-, decyl-, undecyl-, dodecyl-, tridecyl-, tetradecyl, pentadecyl-, hexadecyl-, heptadecyl-, and octadecyl α- or β-D-sucroside; hexyl-, heptyl-, octyl-, dodecyl-, tridecyl-, and tetradecyl-β-D-thiomaltoside; heptyl- or octyl-1-thio-α- or β-D-glucopyranoside; alkyl thiosucroses; alkyl maltotriosides; long chain aliphatic carbonic acid amides of sucrose β-amino-alkyl ethers; derivatives of palatinose or isomaltamine linked by an amide linkage to an alkyl chain and derivatives of isomaltamine linked by urea to an alkyl chain; long chain aliphatic carbonic acid ureides of sucrose β-amino-alkyl ethers and long chain aliphatic carbonic acid amides of sucrose β-amino-alkyl ethers. In some embodiments, the *auris*-acceptable penetration enhancer is a surfactant comprising an alkyl-glycoside wherein the alkyl glycoside is maltose, sucrose, glucose, or a combination thereof linked by a glycosidic linkage to an alkyl chain of 9-16 carbon atoms (e.g., nonyl-, decyl-, dodecyl- and tetradecyl sucroside; nonyl-, decyl-, dodecyl- and tetradecyl glucoside; and nonyl-, decyl-, dodecyl- and tetradecyl maltoside). In some embodiments, the *auris*-acceptable penetration enhancer is a surfactant comprising an alkyl-glycoside wherein the alkyl glycoside is dodecylmaltoside, tridecylmaltoside, and tetradecylmaltoside. In some embodiments, the *auris*-acceptable penetration enhancer is a surfactant comprising an alkyl-glycoside wherein the alkyl glycoside is tetradecyl-β-D-maltoside. In some embodiments, the *auris*-acceptable penetration enhancer is a surfactant comprising an alkyl-glycoside wherein the alkyl-glycoside is a disaccharide with at least one glucose. n some embodiments, the *auris*-acceptable penetration enhancer is a surfactant comprising α-D-glucopyranosyl-β-glycopyranoside, n-Dodecyl-4-O-α-D-glucopyranosyl-β-glycopyranoside, and/or n-tetradecyl-4-O-α-D-glucopyranosyl-β-glycopyranoside. In some embodiments, the *auris*-acceptable penetration enhancer is a surfactant comprising an alkyl-glycoside wherein the alkyl-glycoside has a critical micelle concentration (CMC) of less than about 1 mM in pure water or in aqueous solutions. In some embodiments, the *auris*-acceptable penetration enhancer is a surfactant comprising an alkyl-glycoside wherein an oxygen atom within the alkyl-glycoside is substituted with a sulfur atom. In some embodiments, the *auris*-acceptable penetration enhancer is a surfactant comprising an alkyl-glycoside wherein the alkylglycoside is the β anomer. In some embodiments, the *auris*-acceptable penetration enhancer is a surfactant comprising an alkyl-glycoside wherein the alkylglycoside comprises 90%, 91%, 92%, 93%, 94%, 95%, 96%, 97%, 98%, 99%, 99.1%, 99.5%, or 99.9% of the β anomer.

In certain instances, the penetration enhancing agent is a hyaluronidase. In certain instances, a hyaluronidase is a human or bovine hyaluronidase. In some instances, a hyaluronidase is a human hyaluronidase (e.g., hyaluronidase found in human sperm, PH20 (Halozyme), Hyelenex® (Baxter International, Inc.)). In some instances, a hyaluronidase is a bovine hyaluronidase (e.g., bovine testicular hyaluronidase, Amphadase® (Amphastar Pharmaceuticals), Hydase® (PrimaPharm, Inc). In some instances, a hyaluronidase is an ovine hyaluronidase, Vitrase® (ISTA Pharmaceuticals). In certain instances, a hyaluronidase described herein is a recombinant hyaluronidase. In some instances, a hyaluronidase described herein is a humanized recombinant hyaluronidase. In some instances, a hyaluronidase described herein is a PEGylated hyaluronidase (e.g., PEGPH20 (Halozyme)).

Foams and Paints

In some embodiments, the *auris* therapeutic agents disclosed herein are dispensed as an *auris*-acceptable paint. As used herein, paints (also known as film formers) are solutions comprised of a solvent, a monomer or polymer, an active agent, and optionally one or more pharmaceutically-acceptable excipients. After application to a tissue, the solvent evaporates leaving behind a thin coating comprised of the monomers or polymers, and the active agent. The coating protects active agents and maintains them in an immobilized state at the site of application. This decreases the amount of active agent which are lost and correspondingly increases the amount delivered to the subject. By way of non-limiting example, paints include collodions (e.g. Flexible Collodion, USP), and solutions comprising saccharide siloxane copolymers and a cross-linking agent. Collodions are ethyl ether/ethanol solutions containing pyroxylin (a nitrocellulose). After application, the ethyl ether/ethanol solution evaporates leaving behind a thin film of pyroxylin. In solutions comprising saccharide siloxane copolymers, the saccharide siloxane copolymers form the coating after evaporation of the solvent initiates the cross-linking of the saccharide siloxane copolymers. For additional disclosures regarding paints, see *Remington: The Science and Practice of Pharmacy* which is hereby incorporated in its entirety. The paints contemplated for use herein, are flexible such that they do not interfere with the propagation of pressure waves through the ear. Further, the paints are applied as a liquid (i.e. solution, suspension, or emulsion), a semisolid (i.e. a gel, foam, paste, or jelly) or an aerosol.

In some embodiments, the *auris* therapeutic agents disclosed herein are dispensed as a controlled-release foam. Examples of suitable foamable carriers for use in the compositions disclosed herein include, but are not limited to, alginate and derivatives thereof, carboxymethylcellulose and derivatives thereof, collagen, polysaccharides, including, for example, dextran, dextran derivatives, pectin, starch, modified starches such as starches having additional carboxyl and/or carboxamide groups and/or having hydrophilic side-chains, cellulose and derivatives thereof, agar and derivatives thereof, such as agar stabilized with polyacrylamide, polyethylene oxides, glycol methacrylates, gelatin, gums such as xanthum, guar, karaya, gellan, arabic, tragacanth and locust bean gum, or combinations thereof. Also suitable are the salts of the aforementioned carriers, for example, sodium alginate. The formulation optionally further comprises a foaming agent, which promotes the formation of the foam, including a surfactant or external propellant. Examples of suitable foaming agents include cetrimide, lecithin, soaps, silicones and the like. Commercially available surfactants such as Tween® are also suitable.

In some embodiments, other gel formulations are useful depending upon the particular active agent, other pharmaceutical agent, or excipients/additives used, and as such are considered to fall within the scope of the present disclosure. For example, other commercially-available glycerin-based gels, glycerin-derived compounds, conjugated or cross-linked gels, matrices, hydrogels, and polymers, as well as gelatins and their derivatives, alginates, alginate-based gels, and even various native and synthetic hydrogel and hydrogel-derived compounds are all expected to be useful in the otic formulations described herein. In some embodiments, *auris*-acceptable gels include, but are not limited to, alginate hydrogels SAF®-Gel (ConvaTec, Princeton, N.J.), Duoderm® Hydroactive Gel (ConvaTec), Nu-gel® (Johnson & Johnson Medical, Arlington, Tex.), Carrasyn®(V) Acemannan Hydrogel (Carrington Laboratories, Inc., Irving, Tex.) glycerin gels Elta® Hydrogel (Swiss-American Products, Inc., Dallas, Tex.), and K-Y® Sterile (Johnson & Johnson). In further embodiments, biodegradable biocompatible gels also represent compounds present in *auris*-acceptable formulations disclosed and described herein.

In some formulations developed for administration to a mammal, and for formulations formulated for human administration, the *auris*-acceptable gel comprises substantially all of the weight of the formulation. In other embodiments, the *auris*-acceptable gel comprises as much as about 98% or about 99% of the formulation by weight. This is desirable when a substantially non-fluid or substantially viscous formulation is needed. In a further embodiment, when slightly less viscous, or slightly more fluid *auris*-acceptable pharmaceutical gel formulations are desired, the biocompatible gel portion of the formulation comprises at least about 50% by weight, at least about 60% by weight, at least about 70% by weight, or even at least about 80% or 90% by weight of the compound. All intermediate integers within these ranges are contemplated to fall within the scope of this disclosure, and in some alternative embodiments, even more fluid (and consequently less viscous) *auris*-acceptable gel formulations are formulated, such as for example, those in which the gel or matrix component of the mixture comprises not more than about 50% by weight, not more than about 40% by weight, not more than about 30% by weight, or even those than comprise not more than about 15% or about 20% by weight of the formulation.

*Auris*-Acceptable Actinic Radiation Curable Gel

In other embodiments, the gel is an actinic radiation curable gel, such that following administration to or near the targeted *auris* structure, use of actinic radiation (or light, including UV light, visible light, or infrared light) the desired gel properties are formed. By way of example only, fiber optics are used to provide the actinic radiation so as to form the desired gel properties. In some embodiments, the fiber optics and the gel administration device form a single unit. In other embodiments, the fiber optics and the gel administration device are provided separately.

*Auris*-Acceptable Solvent Release Gel

In some embodiments, the gel is a solvent release gel such that the desired gel properties are formed after administration to or near the targeted *auris* structure, that is, as the solvent in the injected gel formulation diffuses out the gel, a gel having the desired gel properties is formed. For example, a formulation that comprises sucrose acetate isobutyrate, a pharmaceutically acceptable solvent, one or more additives, and the active agent is administered at or near the round window membrane; diffusion of the solvent out of the injected formulation provides a depot having the desired gel properties. For example, use of a water-soluble solvent provides a high viscosity depot when the solvent diffuses rapidly out of the injected formulation. On the other hand, use of a hydrophobic solvent (e.g., benzyl benzoate) provides a less viscous depot. One example of an *auris*-acceptable solvent release gel formulation is the SABER™ Delivery System marketed by DURECT Corporation.

*Auris*-Acceptable Spongy Material

Also contemplated within the scope of the embodiments is the use of a spongy material in the *Auris interna* or *Auris media*. In some embodiments, the spongy material is formed from hyaluronic acid or its derivatives. The spongy material is impregnated with a desired *auris* therapeutic agent and placed within the *Auris media* so as to provide controlled release of the *auris* therapeutic agent within the *Auris media*, or in contact with the round window membrane so as to provide controlled release of the *auris* therapeutic agent into the *Auris interna*. In some embodiments, the spongy material is biodegradable.

Cyclodextrin Formulations/Compositions

In a specific embodiment, the formulation or composition alternatively comprises a cyclodextrin. Cyclodextrins are cyclic oligosaccharides containing 6, 7, or 8 glucopyranose units, referred to as α-cyclodextrin, β-cyclodextrin, or γ-cyclodextrin respectively. Cyclodextrins have been found to be particularly useful in pharmaceutical formulations or compositions. Cyclodextrins have a hydrophilic exterior, which enhances water-soluble, and a hydrophobic interior which forms a cavity. In an aqueous environment, hydrophobic portions of other molecules often enter the hydrophobic cavity of cyclodextrin to form inclusion compounds. Additionally, cyclodextrins are also capable of other types of nonbonding interactions with molecules that are not inside the hydrophobic cavity. Cyclodextrins have three free hydroxyl groups for each glucopyranose unit, or 18 hydroxyl groups on α-cyclodextrin, 21 hydroxyl groups on β-cyclodextrin, and 24 hydroxyl groups on γ-cyclodextrin. One or more of these hydroxyl groups are reacted with any of a number of reagents to form a large variety of cyclodextrin derivatives. Some of the more common derivatives of cyclodextrin are hydroxypropyl ethers, sulfonates, and sulfoalkylethers. Shown below is the structure of β-cyclodextrin and the hydroxypropyl-β-cyclodextrin (HPβCD).

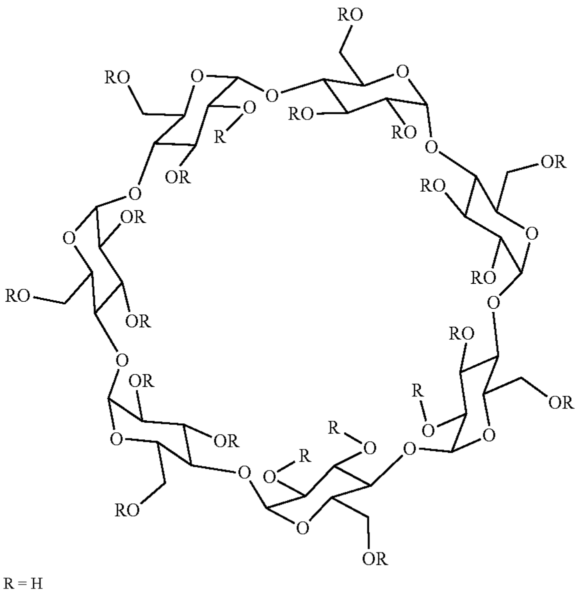

R = H
β-cyclodextrin
R = $CH_2CH(OH)CH_3$
hydroxypropyl β-cyclodextrin

The use of cyclodextrins in pharmaceutical formulations or compositions is well known in the art as cyclodextrins and cyclodextrin derivatives are often used to improve the solubility of a drug. Inclusion compounds are involved in many cases of enhanced solubility; however other interactions between cyclodextrins and insoluble compounds improve solubility. Hydroxypropyl-β-cyclodextrin (HPβCD) is commercially available as a pyrogen free product. It is a nonhygroscopic white powder that readily dissolves in water. HPβCD is thermally stable and does not degrade at neutral pH. Thus, cyclodextrins improve the solubility of a therapeutic agent in a composition or formulation. Accordingly, in some embodiments, cyclodextrins are included to increase the solubility of the therapeutic agents, or *auris*-acceptable otic agents, within the formulations or compositions described herein. In other embodiments, cyclodextrins in addition serve as controlled release excipients within the formulations or compositions described herein.

Preferred cyclodextrin derivatives for use include α-cyclodextrin, β-cyclodextrin, γ-cyclodextrin, hydroxyethyl β-cyclodextrin, hydroxypropyl γ-cyclodextrin, sulfated β-cyclodextrin, sulfated α-cyclodextrin, and sulfobutyl ether β-cyclodextrin.

In some embodiments, the concentration of the cyclodextrin used in the formulations or compositions and methods disclosed herein vary according to the physiochemical properties, pharmacokinetic properties, side effect or adverse events, formulation or composition considerations, or other factors associated with the therapeutic agent, or a salt or prodrug thereof. The properties of other excipients in a formulation or composition are also important in some instances. Thus, the concentration or amount of cyclodextrin used in accordance with the formulations, compositions and methods disclosed herein vary in some embodiments.

In certain embodiments, the composition or formulation further comprise a suitable viscosity agent, such as hydroxypropyl methylcellulose, hydroxyethyl cellulose, polyvinylpyrrolidone, carboxymethyl cellulose, polyvinyl alcohol, sodium chondroitin sulfate, sodium hyaluronate etc. as a dispersant, if necessary. A nonionic surfactant such as polysorbate 80, polysorbate 20, tyloxapol, Cremophor, HCO 40 etc. is optionally used. In certain embodiments, the preparations optionally contain a suitable buffering system, such as phosphate, citrate, borate, tris, etc., and pH regulators such as sodium hydroxide and hydrochloric acid also are optionally used in the formulations of the disclosures. Sodium chloride or other tonicity agents are also used to adjust tonicity, if necessary.

*Auris*-Acceptable Microspheres and Nanospheres

Otic agents and/or other pharmaceutical agents disclosed herein are optionally incorporated within controlled release particles, lipid complexes, liposomes, nanoparticles, microspheres, nanocapsules or other agents which enhance or facilitate the localized delivery of the otic agent. In some embodiments, a single formulation or composition is used, in which at least one active pharmaceutical ingredient is present, while in other embodiments, a pharmaceutical formulation or composition that comprises a mixture of two or more distinct formulations or compositions is used, in which at least one active pharmaceutical ingredient is present. In certain embodiments, the formulations or compositions are cross-linked by one or more agents to alter or improve the properties of the formulation or composition.

Microspheres have been described in the following references, which are incorporated herein by reference: Luzzi, L. A., J. Pharm. Psy. 59:1367 (1970); U.S. Pat. No. 4,530,840; Lewis, D. H., "Controlled Release of Bioactive Agents from Lactides/Glycolide Polymers" in Biodegradable Polymers as Drug Delivery Systems, Chasm, M. and Langer, R., eds., Marcel Decker (1990); U.S. Pat. No. 4,675,189; Beck et al., "Poly(lactic acid) and Poly(lactic acid-co-glycolic acid) Contraceptive Delivery Systems," in Long Acting Steroid Contraception, Mishell, D. R., ed., Raven Press (1983); U.S. Pat. Nos. 4,758,435; 3,773,919; 4,474,572; G. Johns et al. "Broad Applicability of a Continuous Formation Process," Drug Delivery Technology vol. 4 (January/February 2004), each of which is hereby incorporated by reference for such disclosure. Examples of protein therapeutics formulated as microspheres include: U.S. Pat. Nos. 6,458,387; 6,268,053; 6,090,925; 5,981,719; and 5,578,709, and are herein incorporated by reference for such disclosure.

Microspheres usually have a spherical shape, although irregularly-shaped microparticles are possible. The microspheres vary in size, ranging from submicron to 1000 micron diameters. Preferably, submicron to 250 micron diameter microspheres, are desirable, allowing administration by injection with a standard gauge needle. The microspheres are thus prepared by any method which produces microspheres in a size range acceptable for use in an injectable formulation or composition. Injections are accomplished with standard gauge needles used for administering liquid formulation or compositions.

Suitable examples of polymeric matrix materials include poly(glycolic acid), poly-d,l-lactic acid, poly-1-lactic acid, copolymers of the foregoing, poly(aliphatic carboxylic acids), copolyoxalates, polycaprolactone, polydioxonene, poly(orthocarbonates), poly(acetals), poly(lactic acid-caprolactone), polyorthoesters, poly(glycolic acid-caprolactone), polydioxonene, polyanhydrides, polyphosphazines, and natural polymers including albumin, casein, and some waxes, such as, glycerol mono- and distearate, and the like. Various commercially available poly (lactide-co-glycolide) materials (PLGA) are used in the method disclosed herein. For example, poly (d,l-lactic-co-glycolic acid) is commercially available from Boehringer-Ingelheim as RESOMER RG 503 H. This product has a mole percent composition of 50% lactide and 50% glycolide. These copolymers are available in a wide range of molecular weights and ratios of lactic acid to glycolic acid. A preferred polymer for use is poly(d,l-lactide-co-glycolide). It is preferred that the molar ratio of lactide to glycolide in such a copolymer be in the range of from about 95:5 to about 50:50. In other embodiments, PLGA copolymers with polyethylene glycol (PEG) are suitable polymeric matrices for the formulations disclosed herein. For example, PEG-PLGA-PEG block polymers are biodegradable matrices that provide high mechanical stability of the resulting formulation. Mechanical stabilities of formulations using PEG-PLGA-PEG block polymers have been maintained for more than one month in vitro. In some embodiments, PEG-PLGA-PEG block polymers are used to control the release rate of the active agents with different physical properties. Particularly, in some embodiments, hydrophilic active agents are released more quickly, e.g., approximately 50% of drug release after 24 hours, the remainder released over approximately 5 days, whereas hydrophobic agents are released more slowly, e.g., approximately 80% after 8 weeks.

The molecular weight of the polymeric matrix material is of some importance. The molecular weight should be high enough so that it forms satisfactory polymer coatings, i.e., the polymer should be a good film former. Usually, a satisfactory molecular weight is in the range of 5,000 to 500,000 daltons. The molecular weight of a polymer is also important from the point of view that molecular weight influences the biodegradation rate of the polymer. For a diffusional mechanism of drug release, the polymer should remain intact until all of the drug is released from the microparticles and then degrade. The drug is also released from the microparticles as the polymeric excipient bioerodes. By an appropriate selection of polymeric materials, a microsphere formulation is made such that the resulting microspheres exhibit both diffusional release and biodegradation release properties. This is useful in affording multiphasic release patterns.

A variety of methods are known by which compounds are encapsulated in microspheres. In these methods, the active pharmaceutical ingredient is generally dispersed or emulsified, using stirrers, agitators, or other dynamic mixing techniques, in a solvent containing a wall-forming material. Solvent is then removed from the microspheres, and thereafter the microsphere product is obtained.

In one embodiment, controlled release formulations or compositions are made through the incorporation of the otic agents and/or other pharmaceutical agents into ethylene-vinyl acetate copolymer matrices. (See U.S. Pat. No. 6,083,534, incorporated herein for such disclosure). In another embodiment, otic agents are incorporated into poly (lactic-glycolic acid) or poly-L-lactic acid microspheres. In yet another embodiment, the otic agents are encapsulated into alginate microspheres. (See U.S. Pat. No. 6,036,978, incorporated herein for such disclosure). Biocompatible methacrylate-based polymers to encapsulate the otic agents or compositions are optionally used in the formulations and methods disclosed herein. A wide range of methacrylate-based polymer systems are commercially available, such as the EUDRAGIT polymers marketed by Evonik. One useful aspect of methacrylate polymers is that the properties of the formulation are varied by incorporating various co-polymers. For example, poly(acrylic acid-co-methylmethacrylate) microparticles exhibit enhanced mucoadhesion properties as the carboxylic acid groups in the poly(acrylic acid) form hydrogen bonds with mucin (Park et al, Pharm. Res. (1987) 4(6):457-464). Variation of the ratio between acrylic acid and methylmethacrylate monomers serves to modulate the properties of the co-polymer. Methacrylate-based microparticles have also been used in protein therapeutic formulations (Naha et al, Journal of Microencapsulation 4 Feb. 2008 (online publication)). In one embodiment, the enhanced viscosity *auris*-acceptable formulations described herein comprise otic agent microspheres wherein the microspheres are formed from a methacrylate polymer or copolymer. In an additional embodiment, the enhanced viscosity formulation described herein comprises otic agent microspheres wherein the microspheres are mucoadhesive. Other controlled release systems, including incorporation or deposit of polymeric materials or matrices onto solid or hollow spheres containing otic agents, are also explicitly contemplated within the embodiments disclosed herein. The types of controlled release systems available without significantly losing activity of the otic agent are determined using the teachings, examples, and principles disclosed herein An example of a conventional microencapsulation process for pharmaceutical preparations is shown in U.S. Pat. No. 3,737,337, incorporated herein by reference. The substances to be encapsulated or embedded are dissolved or dispersed in the organic solution of the polymer (phase A), using conventional mixers, including (in the preparation of dispersion) vibrators and high-speed stirrers, etc. The dispersion of phase (A), containing the core material in solution or in suspension, is carried out in the aqueous phase (B), again using conventional mixers, such as high-speed mixers, vibration mixers, or even spray nozzles, in which case the particle size of the microspheres will be determined not only by the concentration of phase (A), but also by the emulsate or microsphere size. With conventional techniques for the microencapsulation of active pharmaceutical ingredients, the microspheres form when the solvent containing an active agent and a polymer is emulsified or dispersed in an immiscible solution by stirring, agitating, vibrating, or some other dynamic mixing technique, often for a relatively long period of time.

Conventional methods for the construction of microspheres are also described in U.S. Pat. Nos. 4,389,330, and 4,530,840, incorporated herein by reference. The desired agent is dissolved or dispersed in an appropriate solvent. To the agent-containing medium is added the polymeric matrix material in an amount relative to the active ingredient which gives a product of the desired loading of active agent. Optionally, all of the ingredients of the microsphere product are blended in the solvent medium together. Suitable solvents for the agent and the polymeric matrix material include organic solvents such as acetone, halogenated hydrocarbons such as chloroform, methylene chloride and the like, aromatic hydrocarbon compounds, halogenated aromatic hydrocarbon compounds, cyclic ethers, alcohols, ethyl acetate, and the like.

In some embodiments, the controlled-release *auris*-acceptable microspheres are combined in a controlled-release *auris*-acceptable increased-viscosity formulation or composition.

A suitable controlled-release *auris*-acceptable microsphere example for use with the *auris*-acceptable therapeutic agents disclosed herein includes CHRONIJECT™, a PLGA-based controlled release injectable drug delivery system. Chroniject microspheres are useful for both hydrophobic and hydrophilic *auris* therapeutic agents, with achieved durations of release ranging from as short as 1 week to as long as 1 year. Release profiles for the microspheres are achieved by modifying polymer and/or process conditions, with initial release or burst of the *auris* therapeutic agent also available. The manufacturing process is adaptable to aseptic conditions, allowing direct therapeutic use of the manufactured product. Chroniject manufacturing processes are described in U.S. Pat. Nos. 5,945,126; 6,270,802 and 6,3361,798, each of which is hereby incorporated by reference for such disclosure.

In some embodiments, the mixture of ingredients in the solvent is emulsified in a continuous-phase processing medium; the continuous-phase medium being such that a dispersion of microdroplets containing the indicated ingredients is formed in the continuous-phase medium. Naturally, the continuous-phase processing medium and the organic solvent must be immiscible, and most commonly is water although nonaqueous media such as xylene and toluene and synthetic oils and natural oils are used. Usually, a surfactant is added to the continuous-phase processing medium to prevent the microparticles from agglomerating and to control the size of the solvent microdroplets in the emulsion. A preferred surfactant-dispersing medium combination is a 1 to 10 wt. % poly vinyl alcohol in water mixture. The dispersion is formed by mechanical agitation of the mixed materials. An emulsion is also formed by adding small drops of the active agent-wall forming material solution to the continuous phase processing medium. The temperature during the formation of the emulsion is not especially critical but, in some cases, influences the size and quality of the microspheres and the solubility of the drug in the continuous phase. It is desirable to have as little of the agent in the continuous phase as possible. Moreover, depending on the solvent and continuous-phase processing medium employed, the temperature must not be too low, or the solvent and processing medium will solidify, or the processing medium will become too viscous for practical purposes, or too high that the processing medium will evaporate, or that the liquid processing medium will not be maintained. Moreover, the temperature of the medium cannot be so high that the stability of the particular agent being incorporated in the microspheres is adversely affected. Accordingly, the dispersion process is conducted at any temperature which maintains stable operating conditions, which preferred temperature being about 30° C. to 60° C., depending upon the drug and excipient selected.

In some embodiments, the dispersion which is formed is a stable emulsion and from this dispersion the organic solvent immiscible fluid is optionally partially removed in the first step of the solvent removal process. The solvent is easily removed by common techniques such as heating, the application of a reduced pressure or a combination of both. The temperature employed to evaporate solvent from the microdroplets is not critical but should not be that high that it degrades the agent employed in the preparation of a given microparticle, nor should it be so high as to evaporate solvent at such a rapid rate to cause defects in the wall forming material. Generally, from 5 to 75%, of the solvent is removed in the first solvent removal step.

In some embodiments, after the first stage, the dispersed microparticles in the solvent immiscible fluid medium are isolated from the fluid medium by any convenient means of separation. Thus, for example, the fluid is decanted from the microsphere or the microsphere suspension is filtered. Still other, various combinations of separation techniques are used if desired.

In some embodiments, following the isolation of the microspheres from the continuous-phase processing medium, the remainder of the solvent in the microspheres is removed by extraction. In this step, the microspheres are suspended in the same continuous-phase processing medium used in step one, with or without surfactant, or in another liquid. The extraction medium removes the solvent from the microspheres and yet does not dissolve the microspheres. During the extraction, the extraction medium with dissolved solvent is optionally removed and replaced with fresh extraction medium. This is best done on a continual basis. Obviously, the rate of extraction medium replenishment of a given process is a variable which is easily determined at the time the process is performed and, therefore, no precise limits for the rate must be predetermined. After the majority of the solvent has been removed from the microspheres, the microspheres are dried by exposure to air or by other conventional drying techniques such as vacuum drying, drying over a desiccant, or the like. This process is very efficient in encapsulating the agent since core loadings of up to 80 wt. %, preferably up to 60 wt. % are obtained.

In some embodiments, controlled release microspheres containing an active pharmaceutical agent are prepared through the use of static mixers. Static or motionless mixers consist of a conduit or tube in which is received a number of static mixing agents. Static mixers provide homogeneous mixing in a relatively short length of conduit, and in a relatively short period of time. With static mixers, the fluid moves through the mixer, rather than some part of the mixer, such as a blade, moving through the fluid.

In some embodiments, a static mixer is used to create an emulsion. When using a static mixer to form an emulsion, several factors determine emulsion particle size, including the density and viscosity of the various solutions or phases to be mixed, volume ratio of the phases, interfacial tension between the phases, static mixer parameters (conduit diameter; length of mixing element; number of mixing elements), and linear velocity through the static mixer. Temperature is a variable because it affects density, viscosity, and interfacial tension. The controlling variables are linear velocity, sheer rate, and pressure drop per unit length of static mixer.

In order to create microspheres containing an active pharmaceutical agent, an organic phase and an aqueous phase are combined in some embodiments. The organic and aqueous phases are largely or substantially immiscible, with the aqueous phase constituting the continuous phase of the emulsion. The organic phase includes an active pharmaceutical agent as well as a wall-forming polymer or polymeric matrix material. In some embodiments, the organic phase is prepared by dissolving an active pharmaceutical agent in an organic or other suitable solvent, or by forming a dispersion or an emulsion containing the active agent. The organic phase and the aqueous phase are pumped so that the two phases flow simultaneously through a static mixer, thereby forming an emulsion which comprises microspheres containing the active pharmaceutical agent encapsulated in the polymeric matrix material. The organic and aqueous phases are pumped through the static mixer into a large volume of quench liquid to extract or remove the organic solvent. Organic solvent is removed from the microspheres while they are washing or being stirred in the quench liquid. After the microspheres are washed in a quench liquid, they are isolated, as through a sieve, and dried.

In some embodiments, the process whereby microspheres are prepared using a static mixer is optionally carried out for a variety of techniques used to encapsulate active agents. In some embodiments, the process is not limited to the solvent extraction technique discussed above and is used with other encapsulation techniques. For example, the process is used with a phase separation encapsulation technique in some instances. To do so, an organic phase is prepared that comprises an active pharmaceutical agent suspended or dispersed in a polymer solution. The non-solvent second phase is free from solvents for the polymer and active agent. A preferred non-solvent second phase is silicone oil. The organic phase and the non-solvent phase are pumped through a static mixer into a non-solvent quench liquid, such as heptane. The semi-solid particles are quenched for complete hardening and washing. The process of microencapsulation also includes spray drying, solvent evaporation, a combination of evaporation and extraction, and melt extrusion.

In another embodiment, the microencapsulation process involves the use of a static mixer with a single solvent. This process is described in detail in U.S. application Ser. No. 08/338,805, herein incorporated by reference. An alternative process involves the use of a static mixer with co-solvents. In this process for preparing biodegradable microspheres comprising a biodegradable polymeric binder and an active pharmaceutical agent, a blend of at least two substantially non-toxic solvents, free of halogenated hydrocarbons, is used to dissolve both the agent and the polymer. The solvent blend containing the dissolved agent and polymer is dispersed in an aqueous solution to form droplets. The resulting emulsion is then added to an aqueous extraction medium preferably containing at least one of the solvents of the blend, whereby the rate of extraction of each solvent is controlled, whereupon the biodegradable microspheres containing the pharmaceutically active agent are formed. The process has the advantage that less extraction medium is required because the solubility of one solvent in water is substantially independent of the other and solvent selection is increased, especially with solvents that are particularly difficult to extract.

Nanoparticles are material structures of about 100 nm or less in size. One use of nanoparticles in pharmaceutical formulations is the formation of suspensions as the interaction of the particle surface with solvent is strong enough to overcome differences in density. Nanoparticle suspensions are sterilized as the nanoparticles are small enough to be subjected to sterilizing filtration (U.S. Pat. No. 6,139,870). Nanoparticles comprise at least one hydrophobic, water-insoluble and water-indispersible polymer or copolymer emulsified in a solution or aqueous dispersion of surfactants, phospholipids or fatty acids. The active pharmaceutical ingredient is introduced with the polymer or the copolymer into the nanoparticles.

Lipid nanocapsules act as controlled release structures, as well for penetrating the round window membrane and reaching *Auris interna* targets, is also contemplated herein. See Zou et al. *J. Biomed. Materials Res*., online pub. (Apr. 24, 2008). Lipid nanocapsules are formed by emulsifying 1.028 g capric and caprylic acid triglycerides (LABRAFAC WL 1349; avg. mw 512), 0.075 g soybean lecithin (LIPOID S75-3; 69% phosphatidylcholine and other phospholipids), 0.846 g surfactant (SOLUTOL HS15), mixture of polyethylene glycol 660 hydroxystearate and free polyethylene glycol 660; 0.089 g NaCl and 2.962 g water. The mixture is stirred at room temperature to obtain an oil emulsion in water. After progressive heating at a rate of 4° C./min under magnetic stirring, a short interval of transparency should occur close to 70° C., and the inverted phase (water droplets in oil) obtained at 85° C. Three cycles of cooling and heating is then applied between 85° C. and 60° C. at the rate of 4° C./min, and a fast dilution in cold water at a temperature close to 0° C. to produce a suspension of nanocapsules. To encapsulate *Auris interna* active agents, the agents are added just prior to the dilution with cold water.

In some instances, agents are inserted into the lipid nanocapsules by incubation for 90 minutes with an aqueous micellar solution of the *Auris interna* active agent. The suspension is then vortexed every 15 minutes, and then quenched in an ice bath for 1 minute.

Suitable surfactants are, by way of example, cholic acid or taurocholic acid salts. Taurocholic acid, the conjugate formed from cholic acid and taurine, is a fully metabolizable sulfonic acid surfactant. An analog of taurocholic acid, tauroursodeoxycholic acid (TUDCA), is a naturally occurring bile acid and is a conjugate of taurine and ursodeoxycholic acid (UDCA). Other naturally occurring anionic (e.g., galactocerebroside sulfate), neutral (e.g., lactosylceramide) or zwitterionic surfactants (e.g., sphingomyelin, phosphatidyl choline, palmitoyl carnitine) are used to prepare nanoparticles in some instances.

The phospholipids are chosen, by way of example, from natural, synthetic or semisynthetic phospholipids; lecithins (phosphatidylcholine) such as, for example, purified egg or soya lecithins (lecithin E100, lecithin E80 and phospholipons, for example phospholipon 90), phosphatidylethanolamine, phosphatidylserine, phosphatidylinositol, phosphatidylglycerol, dipalmitoylphosphatidylcholine, dipalmitoylglycerophosphatidylcholine, dimyristoylphosphatidylcholine, distearoylphosphatidylcholine and phosphatidic acid or mixtures thereof are used more particularly.

The fatty acids are chosen from, by way of example, from lauric acid, mysristic acid, palmitic acid, stearic acid, isostearic acid, arachidic acid, behenic acid, oleic acid, myristoleic acid, palmitoleic acid, linoleic acid, alpha-linoleic acid, arachidonic acid, eicosapentaenoic acid, erucic acid, docosahexaenoic acid, and the like.

Suitable surfactants are preferably selected from known organic and inorganic pharmaceutical excipients. Such excipients include various polymers, low molecular weight oligomers, natural products, and surfactants. Preferred surface modifiers include nonionic and ionic surfactants. Two or more surface modifiers are used in combination for some embodiments.

Representative examples of surfactants include cetyl pyridinium chloride, gelatin, casein, lecithin (phosphatides), dextran, glycerol, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters; polyethylene glycols, dodecyl trimethyl ammonium bromide, polyoxyethylenestearates, colloidal silicon dioxide, phosphates, sodium dodecylsulfate, carboxymethylcellulose calcium, hydroxypropyl cellulose (HPC, HPC-SL, and HPC-L), hydroxypropyl methylcellulose (HPMC), carboxymethylcellulose sodium, methylcellulose, hydroxyethylcellulose, hydroxypropylcellulose, hydroxypropylmethyl-cellulose phthalate, noncrystalline cellulose, magnesium aluminum silicate, triethanolamine, polyvinyl alcohol (PVA), polyvinylpyrrolidone (PVP), 4-(1,1,3,3-tetaamethylbutyl)-phenol polymer with ethylene oxide and formaldehyde (also known as tyloxapol, superione, and triton), poloxamers, poloxamines, a charged phospholipid such as dimyristoyl phosphatidyl glycerol, dioctylsulfosuccinate (DOSS); Tetronic 1508, dialkylesters of sodium sulfosuccinic acid, Duponol P, Tritons X-200, Crodestas F-110, p-isononylphenoxypoly-(glycidol), Crodestas SL-40® (Croda, Inc.); and SA9OHCO, which is $C_{18}H_{37}CH_2$ (CON ($CH_3$)—$CH_2$ $(CHOH)_4$ $(CH_2OH)_2$ (Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucarmide; n-octyl-β-D-glucopyranoside; octyl β-D-thioglucopyranoside; and the like.

Most of these surfactants are known pharmaceutical excipients and are described in detail in the Handbook of Pharmaceutical Excipients, published jointly by the American Pharmaceutical Association and The Pharmaceutical Society of Great Britain (The Pharmaceutical Press, 1986), specifically incorporated by reference.

The hydrophobic, water-insoluble and water-indispersible polymer or copolymer are chosen from biocompatible and biodegradable polymers, for example lactic or glycolic acid polymers and copolymers thereof, or polylactic/polyethylene (or polypropylene) oxide copolymers, preferably with molecular weights of between 1000 and 200000, polyhydroxybutyric acid polymers, polylactones of fatty acids containing at least 12 carbon atoms, or polyanhydrides.

In one embodiment, the nanoparticles are suitable for use with hydrophobic active principles. In some embodiments, the active principles are chosen from the major classes of medicaments for use in human or veterinary medicine. In some embodiments, the active principles are chosen from principles for use in the cosmetics or agrifood industry or sports medicine or from diagnostic agents. By way of example, active principles which are of interest in the pharmaceutical industry are chosen, in a non-limiting manner, from antirheumatic, non-steroidal anti-inflammatory (e.g., NSAIDs), analgesic, antitussive and psychotropic agents, steroids, barbiturates, antimicrobial, antiallergenic, antiasthmatic, antispasmodic, antisecretory and cardiovascular agents, cerebral vasodilators, cerebral and hepatic protective agents, therapeutic agents of the gastrointestinal tract, anticancer or antiviral agents, vitamins, contraceptives, vaccines, etc.

The nanoparticles are obtained by the technique of evaporation of solvent, from an aqueous dispersion or solution of phospholipids and of an oleic acid salt into which is added an immiscible organic phase comprising the active principle and the hydrophobic, water-insoluble and water-indispersible polymer or copolymer. The mixture is pre-emulsified and then subjected to homogenization and evaporation of the organic solvent to obtain an aqueous suspension of very small-sized nanoparticles.

A variety of methods are employed to fabricate nanoparticles. These methods include vaporization methods, such as free jet expansion, laser vaporization, spark erosion, electro explosion, and chemical vapor deposition; physical methods involving mechanical attrition (e.g., “pearlmilling” technology, Elan Nanosystems), super critical $CO_2$ and interfacial deposition following solvent displacement. In one embodiment, the solvent displacement method is used. The size of nanoparticles produced by this method is sensitive to the concentration of polymer in the organic solvent; the rate of mixing; and to the surfactant employed in the process. Continuous flow mixers provide the necessary turbulence to ensure small particle size. One type of continuous flow mixing device that is used to prepare nanoparticles has been described (Hansen et al. J Phys Chem 92, 2189-96, 1988). In other embodiments, ultrasonic devices, flow through homogenizers or supercritical $CO_2$ devices are used to prepare nanoparticles.

If suitable nanoparticle homogeneity is not obtained on direct synthesis, then size-exclusion chromatography is used to produce highly uniform drug-containing particles that are freed of other components involved in their fabrication. Size-exclusion chromatography (SEC) techniques, such as gel-filtration chromatography, is used to separate particle-bound drug from free drug or to select a suitable size range of drug-containing nanoparticles. Various SEC media, such as Superdex 200, Superose 6, and Sephacryl 1000 are commercially available and are readily employed by persons of skill in the art for the size-based fractionation of mixture. Additionally, nanoparticles are purified by centrifugation, membrane filtration and by use of other molecular sieving devices, crosslinked gels/materials and membranes.

In some embodiments, liposomes or lipid particles are also employed to encapsulate the otic agent formulations or compositions. Phospholipids that are gently dispersed in an aqueous medium form multilayer vesicle with areas of entrapped aqueous media separating the lipid layers. Sonication, or turbulent agitation, of these multilayer vesicles results in the formation of single layer vesicles, commonly referred to as liposomes, with sizes of about 10-1000 nm. These liposomes have many advantages as drug carriers. They are biologically inert, biodegradable, non-toxic and non-antigenic. Liposomes are formed in various sizes and with varying compositions and surface properties. Additionally, they are able to entrap a wide variety of small molecule drugs and release the drug at the site of liposome collapse.

Suitable phospholipids for use in the present compositions are, for example, phosphatidyl cholines, ethanolamines and serines, sphingomyelins, cardiolipins, plasmalogens, phosphatictic acids and cerebrosides, in particular those which are soluble together with piroxicam in non-toxic, pharmaceutically acceptable organic solvents. Preferred phospholipids are, for example, phosphatidyl choline, phosphatidyl ethanolamine, phosphatidyl serine, phosphatidyl inositol, lysophosphatidyl choline, phosphatidyl glycerol and the like, and mixtures thereof especially lecithin, e.g. soya lecithin. The amount of phospholipid used in the present formulation ranges from about 10 to about 30%, preferably from about 15 to about 25% and in particular is about 20%.

Lipophilic additives are employed advantageously to modify selectively the characteristics of the liposomes. Examples of such additives include, for example, stearylamine, phosphatictic acid, tocopherol, cholesterol, cholesterol hemisuccinate and lanolin extracts. The amount of lipophilic additive used ranges from 0.5 to 8%, preferably from 1.5 to 4% and in particular is about 2%. Generally, the ratio of the amount of lipophilic additive to the amount of phospholipid ranges from about 1:8 to about 1:12 and in particular is about 1:10. Said phospholipid, lipophilic additive and the active ingredient piroxicam are employed in conjunction with a non-toxic, pharmaceutically acceptable organic solvent system which dissolves said ingredients. The solvent system not only must dissolve the active pharmaceutical ingredient completely, but it also has to allow the formulation of stable single bilayered liposomes. The solvent system comprises dimethylisosorbide and tetraglycol (glycofurol, tetrahydrofurfuryl alcohol polyethylene glycol ether) in an amount of about 8 to about 30%. In said solvent system, the ratio of the amount of dimethylisosorbide to the amount of tetraglycol ranges from about 2:1 to about 1:3, in particular from about 1:1 to about 1:2.5 and preferably is about 1:2. The amount of tetraglycol in the final composition thus varies from 5 to 20%, in particular from 5 to 15% and preferably is approximately 10%. The amount of dimethylisosorbide in the final composition thus ranges from 3 to 10%, in particular from 3 to 7% and preferably is approximately 5%.

The term "organic component" as used hereinafter refers to mixtures comprising said phospholipid, lipophilic additives and organic solvents.

The active pharmaceutical ingredient is dissolved in the organic component. It is advantageous to use micronized forms of the active ingredient to facilitate its dissolution. The amount of active ingredient in the final formulation ranges from 0.1 to 5.0%. In addition, other ingredients such as antioxidants are added to the organic component. Examples include tocopherol, butylated hydroxyanisole, butylated hydroxytoluene, ascorbyl palmitate, ascorbyl oleate, and the like.

In some embodiments, the aqueous component of the present formulation comprises mainly water and optionally contains various additives such as electrolytes, buffer systems, preservatives and the like. Suitable electrolytes include metal salts, in particular alkali metal and earth alkaline metal salts such as, for example, calcium chlorides, sodium chloride, potassium chloride, preferably sodium chloride. In some instances, the concentration of the electrolytes varies over a wide range and depends on the nature and the concentration of each of the ingredients in the final formulation and should be sufficient to stabilize the liposomal membranes. In the present composition the amount of sodium chloride ranges from 0.05 to 0.2%. Buffer systems comprise mixtures of appropriate amounts of an acid such as phosphoric, succinic, or preferably citric acid, and a base, in particular sodium hydroxide. Said buffer systems should maintain the pH of the formulation within the range of 3 to 9, alternatively within the range or 6 to 8 or between the range of 5 to 7. Preservatives which are employed in the present composition to prevent degradation by microorganisms comprise benzoic acid, methylparaben and propylparaben in some embodiments.

Liposomal formulations are optionally prepared by (a) heating the phospholipid and the organic solvent system to about 60-80° C. in a vessel, dissolving the active ingredient, then adding any additional formulating agents, and stirring the mixture until complete dissolution is obtained; (b) heating the aqueous solution to 90-95° C. in a second vessel and dissolving the preservatives therein, allowing the mixture to cool and then adding the remainder of the auxiliary formulating agents and the remainder of the water, and stirring the mixture until complete dissolution is obtained; thus preparing the aqueous component; (c) transferring the organic phase directly into the aqueous component, while homogenizing the combination with a high performance mixing apparatus, in particular a high-shear mixer; and (d) adding a thickener to the resulting mixture while further homogenizing. Preferably, the aqueous component is placed in a suitable vessel which is equipped with a homogenizer and homogenization is effected by creating great turbulence during the injection of the organic component. Any mixing means or homogenizer which exerts high shear forces on the mixture is employed. Generally, a mixer capable of speeds from about 1,500 to 20,000 rpm, in particular from about 3,000 to about 6,000 rpm are employed. Suitable thickening agents for use in process step (d) are for example, xanthan gum, hydroxypropyl cellulose, hydroxypropyl methylcellulose or mixtures thereof, cellulose derivatives being preferred. The amount of thickening agent depends on the nature and the concentration of the other ingredients and in general ranges from about 0.5 to 1.5%, and in particular is approximately 1.5%. In order to prevent degradation of the materials used during the preparation of the liposomal formulation, it is advantageous to purge all solutions with an inert gas such as nitrogen or argon, and to conduct all steps under an inert atmosphere. Liposomes prepared by the above described method usually contain most of the active ingredient bound in the lipid bilayer and separation of the liposomes from unencapsulated material is not required.

*Auris*-Acceptable Lipid Formulations/Compositions

In some embodiments, the drug delivery formulation or composition is a lipid-based formulation or composition. In some embodiments, the lipid-based drug delivery formulation or composition is a lipid emulsion (e.g., microemulsions and oil-in-water emulsions), a lipid vesicle (e.g., liposomes, micelles and transfersomes) or a combination thereof. In some embodiments, the lipid-based drug delivery formulation or composition is a lipid vesicle wherein the lipid vesicle is a liposome. In some embodiments, the lipid-based drug delivery formulation or composition is a phospholipid-based formulation or composition. In some embodiments, the lipid-based drug delivery formulation or composition is a phospholipid-based formulation or composition wherein the natural or synthetic phospholipid is phosphatidylethanolamine, phosphatidylserine, phosphatidylinositol, phosphatidylglycerol, phosphatidic acid, lysophospholipids, egg or soybean phospholipid, or a combination thereof. The phospholipid is optionally salted or desalted, hydrogenated or partially hydrogenated, natural, synthetic, or semisynthetic. In some embodiments, the lipid-based drug delivery formulation is a phospholipid-based formulation (e.g., hydrogenated or nonhydrogenated phospholipids, lecithins, phosphatidyl cholines (C8-C18), phosphatidylethanolamines (C8-C18), phosphatidylglycerols (C8C18)) wherein the phospholipid is phospholipon 90H (1,2-dia-cyl-SN-glycero-3-phosphatidyl choline), egg phospholipids P123, Lipoid E80; Phospholipon 80H®, 80G®, 90H® and 100H®, or combinations thereof.

In some embodiments, the lipid-based drug delivery formulation or composition comprises a water-soluble preservative (i.e., a component that prevents microbes from substantially growing and multiplying). In some embodiments, the lipid-based drug delivery formulation or composition comprises a water-soluble preservative wherein the preservative is a benzethonium salt (e.g., benzethonium chloride), benzoic acid, and/or a benzylkonium salt (e.g., benzylkonium chloride). As used herein, water soluble means that the component has a solubility in water from about 100 μg/mL (0.01%) to about 0.01 mg/mL (0.1%).

In some embodiments, the lipid-based drug delivery formulation or composition comprises a lipid soluble antioxidant. In some embodiments, the lipid-based drug delivery formulation or composition comprises vitamin E.

In some embodiments, the lipid-based drug delivery formulation or composition comprises less than about 2% w/w, less than about 1.5%, less than about 1.0%, less than about 0.5%, or less than about 0.25% of a viscosity enhancing agent.

In some embodiments, the lipid-based drug delivery formulation or composition has a viscosity of at least about 10,000 centipoise, at least about 20,000 centipoise, at least about 30,000 centipoise, at least about 40,000 centipoise, at least about 50,000 centipoise, at least about 60,000 centipoise, or at least about 70,000 centipoise, all at 58° C., without the presence of any methyl-cellulose or other viscosity enhancing agents. In some embodiments, the lipid-based drug delivery formulation or composition comprises oleyl alcohol to enhance the transmembrane penetration.

In some embodiments, the lipid-based drug delivery formulation or composition comprises a penetration enhancer (e.g., a low molecular weight alcohol (e.g., ethanol, oleyl alcohol), alkyl methanol sulphoxides, N-methyl-2-pyrrolidone, fatty amines (e.g., oleylamine), fatty acids (e.g., oleic acid, palmitoleic acid, linoleic acid, myristate acid), gluconic acid (the hexonic acid derived from glucose by oxidation of the aldehyde group at C-1 to a carboxyl group) and its derivatives, such as gluconolactone (especially, glucono-D-lactone, a chelating agent produced by the oxidation of glucose), azone and propylene glycol, singly or in combination). In some embodiments, the lipid-based drug delivery formulation or composition comprises a penetration enhancer wherein the penetration enhancer is propylene glycol, either alone or in up to a 1:1 ratio with another enhancer, such as oleic acid or ethanol. In some embodiments, the lipid-based drug delivery formulation or composition comprises a penetration enhancer wherein the penetration enhancer is gluconolactone (e.g., glucono-D-lactone), either alone or in up to a 1:1 ratio with another enhancer, such as propylene glycol.

In some embodiments, the lipid-based drug delivery formulation or composition comprises about 25% v/v or less of any one or more chemical penetration enhancer(s), most preferably from about 2% to 15% v/v, although the exact formulation or composition will vary depending on the presence and amounts of excipients, preservatives, water, pH modulators, and the like included therein.

In some embodiments, prepared liposomes loaded with the active agents herein are gently mixed with viscosity, mucosal adhesives or absorption penetration enhancers. For example, the active agents loaded into liposomes are mixed with a chitosan-glycerophosphate composition. The liposome size is optionally increased or decreased to modulate the release kinetics of the controlled release particles. In additional aspects, release kinetics is altered by changing the lipid composition of the liposomes as described above.

The formulations or compositions described herein are administered in any suitable form. By way of non-limiting examples, the formulations are administered as otic drops, as intratympanic injections, as foams or as otic paints. The formulations or compositions are administered via cannula and/or injection, via a drop dispenser, as a spray in the ear canal, or as a paint via a cotton tipped stick.

Controlled Release Kinetics

The goal of every drug delivery technique is to deliver the proper amount of drug to the site of action at the right time to obtain a therapeutic benefit. In general, controlled release drug formulations impart control over the release of drug with respect to site of release and time of release within the body. As discussed herein, controlled release refers to any release other than solely immediate release. In some instances, controlled release is delayed release, extended release, sustained release and/or pulsatile release (e.g., a combination of extended release and immediate release) or a combination thereof. Many advantages are offered by controlled release. First, controlled release of a pharmaceutical agent allows less frequent dosing and thus minimizes repeated treatment. Second, controlled release treatment results in more efficient drug utilization and less of the compound remains as a residue. Third, controlled release offers the possibility of localized drug delivery by placement of a delivery device or formulation at the site of disease. Still further, controlled release offers the opportunity to administer and release two or more different drugs, each having a unique release profile, or to release the same drug at different rates or for different durations, by means of a single dosage unit.

In a specific embodiment the formulations or compositions described herein provide a therapeutically effective amount of at least one active pharmaceutical ingredient at the site of disease with no systemic exposure. In an additional embodiment the formulations or compositions described herein provide a therapeutically effective amount of at least one active pharmaceutical ingredient at the site of disease with no detectable systemic exposure.

In certain embodiments, the formulations or compositions comprise an excipient that increases the release rate of the therapeutic agent. In certain embodiments, the formulations or compositions comprise an excipient that decreases the release rate of the therapeutic agent.

The formulation or composition is designed to provide drug delivery over a desired period of time, including periods up to several weeks. As such, the patient will not need repeated administration of the drug, or at the least, fewer and less frequent administration of the drug.

Drugs delivered to the *Auris interna* have commonly been administered systemically via oral, intravenous or intramuscular routes. However, systemic administration for pathologies local to the *Auris interna* increases the likelihood of systemic toxicities and side effects and creates a non-productive distribution of drug in which high levels drug are found in the serum and correspondingly lower levels are found at the *Auris interna*.

In one embodiment, the formulations or compositions disclosed herein additionally provides an immediate release of the therapeutic agent, or otic agent, from the formulation or composition, or within 1 minute, or within 5 minutes, or within 10 minutes, or within 15 minutes, or within 30 minutes, or within 60 minutes, or within 90 minutes. In other embodiments, a therapeutically effective amount of at least one therapeutic agent, or otic agent, is released from the formulation or composition immediately, or within 1 minute, or within 5 minutes, or within 10 minutes, or within 15 minutes, or within 30 minutes, or within 60 minutes, or within 90 minutes. Additional embodiments of the formulation or composition also include an agent that enhances the viscosity of the formulations included herein.

An immediate or rapid release option includes use of different viscosity-enhancing polymers, multi-component formulations or compositions and nanospheres (or sub-micron spheres). In addition, the microspheres are optionally coated with an immediate-release component and a controlled-release component.

In certain embodiments the formulation or composition provides immediate release of at least one active pharmaceutical ingredient. Additional embodiments of the formulation or composition also include a thickener that thickens the formulations or compositions included herein. In other embodiments the formulation or composition comprises a liposomal formulation or composition providing immediate release of at least one active pharmaceutical ingredient. In certain other embodiments the formulation or composition comprises a cyclodextrin-containing formulation or composition providing immediate release of at least one active pharmaceutical ingredient. In additional embodiments the formulation or composition comprises a microsphere formulation or composition providing immediate release of at least one active pharmaceutical ingredient. In additional embodiments the formulation or composition comprises a nanoparticle formulation or composition providing immediate release of at least one active pharmaceutical ingredient.

In other or further embodiments, the formulation or composition provides a controlled release formulation or composition of at least one therapeutic agent, or otic agent. In certain embodiments, diffusion of at least one otic agent from the formulation or composition occurs for a time period exceeding 5 minutes, or 15 minutes, or 30 minutes, or 1 hour, or 4 hours, or 6 hours, or 12 hours, or 18 hours, or 1 day, or 2 days, or 3 days, or 4 days, or 5 days, or 6 days, or 7 days, or 10 days, or 12 days, or 14 days, or 18 days, or 21 days, or 25 days, or 30 days, or 45 days, or 2 months, or 3 months, or 4 months, or 5 months, or 6 months, or 9 months, or 1 year. In other embodiments, a therapeutically effective amount of at least one otic agent is released from the formulation or composition for a time period exceeding 5 minutes, or 15 minutes, or 30 minutes, or 1 hour, or 4 hours, or 6 hours, or 12 hours, or 18 hours, or 1 day, or 2 days, or 3 days, or 4 days, or 5 days, or 6 days, or 7 days, or 10 days, or 12 days, or 14 days, or 18 days, or 21 days, or 25 days, or 30 days, or 45 days, or 2 months, or 3 months, or 4 months, or 5 months, or 6 months, or 9 months, or 1 year.

In other embodiments, the formulation or composition provides both an immediate release and an extended release formulation or composition of a therapeutic agent, or an otic agent. In yet other embodiments, the formulation or composition contains a 0.25:1 ratio, or a 0.5:1 ratio, or a 1:1 ratio, or a 1:2 ratio, or a 1:3, or a 1:4 ratio, or a 1:5 ratio, or a 1:7 ratio, or a 1:10 ratio, or a 1:15 ratio, or a 1:20 ratio of immediate release and extended release formulations or compositions. In a further embodiment the formulation or composition provides an immediate release of a first otic agent and an extended release of a second otic agent or another therapeutic agent. In yet other embodiments, the formulation or composition provides an immediate release and extended release formulation or composition of at least one otic agent, and at least one therapeutic agent. In some embodiments, the formulation or composition provides a 0.25:1 ratio, or a 0.5:1 ratio, or a 1:1 ratio, or a 1:2 ratio, or a 1:3, or a 1:4 ratio, or a 1:5 ratio, or a 1:7 ratio, or a 1:10 ratio, or a 1:15 ratio, or a 1:20 ratio of immediate release and extended release formulations or compositions of a first otic agent and second therapeutic agent, respectively.

In a specific embodiment the formulation or composition provides a therapeutically effective amount of at least one otic agent at the site of disease with essentially no systemic exposure. In an additional embodiment the formulation or composition provides a therapeutically effective amount of at least one otic agent at the site of disease with essentially no detectable systemic exposure. In other embodiments, the formulation or composition provides a therapeutically effective amount of at least one otic therapeutic agent at the site of disease with little or no detectable systemic exposure.

In some instances, upon administration (e.g., intratympanic injection) of a conventional otic formulation or composition (e.g., DSP in a buffer), the concentration of a drug in the perilymph of an individual will rise sharply ($C_{max}$ at about 1-2 hours) and then taper off to below $C_{min}$. In some instances, administration of an otic formulation or composition described herein lowers the ratio of $C_{max}$ to $C_{min}$ and provides a larger Area Under the Curve (AUC) with a prolonged PK profile based on the $C_{min}$. In certain instances, controlled release formulations or compositions described herein delay the time to $C_{max}$. In certain instances, the controlled steady release of a drug prolongs the time the concentration of the drug will stay above the minimum therapeutic concentration (i.e., $C_{min}$). In some instances, controlled release of an otic agent provided by the formulations or compositions described herein allows for release of an otic agent at concentrations greater than $C_{min}$ for a period of at least 1 day, 3 days, 4 days, 5 days, 6 days, 7 days, 10 days, 14 days, 3 weeks, 1 month, or 6 months. In some embodiments, *auris* formulations or compositions described herein prolong the residence time of a drug in the inner ear. In certain instances, once drug exposure (e.g., concentration in the perilymph) of a drug reaches steady state, the concentration of the drug in the perilymph stays at or about the therapeutic dose for an extended period of time (e.g., one day, 2 days, 3 days, 4 days, 5 days, 6 days, 1 week, 2 weeks, 1 month, or 6 months). In some embodiments, otic formulations or compositions described herein increase the bioavailability and/or steady state levels of a drug in *auris* structures (e.g., in inner ear and/or the endolymph and/or the perilymph).

In some instances, upon administration of a controlled release *auris* formulation or composition described herein (e.g., a formulation comprising a therapeutic agent), drug concentrations relative to the binding constants of one or more otic receptors are relevant in determining a biologically meaningful PK profile or the minimum concentration of an active agent required for a therapeutic effect. In some instances, upon administration of a controlled release *auris* formulation or composition described herein, drug concentrations relative to the binding constants of two receptors, such as, by way of example only, mineralcorticoid receptor (MR) and glucocorticoid receptor (GR), are relevant in determining the $C_{min}$ or the biologically most meaningful PK profile. In some instances, for example, a drug saturates a first receptor (e.g. GR) first, then saturates a second receptor (e.g., MR), and there is therapeutic benefit even when the first receptor is saturated, and the second receptor is not yet saturated. In some instances, the drug concentration for saturation the second receptor is about the same as the $C_{min}$. In some of such instances, for example, a next dose is administered when drug concentration drops below saturation levels of the second receptor and/or the $C_{min}$.

The combination of immediate release, delayed release and/or extended release otic compositions or formulations are combined with other pharmaceutical agents, as well as the excipients, diluents, stabilizers, tonicity agents and other components disclosed herein. As such, depending upon the otic agent used, the thickness or viscosity desired, or the mode of delivery chosen, alternative aspects of the embodiments disclosed herein are combined with the immediate release, delayed release and/or extended release embodiments accordingly.

In certain embodiments, the pharmacokinetics of the otic formulations or compositions described herein are determined by injecting the formulation on or near the round window membrane of a test animal (including by way of example, a guinea pig, a chinchilla, or a rat). At a determined period of time (e.g., 6 hours, 12 hours, 1 day, 2 days, 3 days, 4 days, 5 days, 6 days, 7 days, and 14 days for testing the pharmacokinetics of a formulation or composition over a 1 or 2 week period), the test animal is euthanized and the inner ear removed and tested for the presence of the otic agent. As needed, the level of otic agent is measured in other organs. In addition, the systemic level of the otic agent is measured by withdrawing a blood sample from the test animal. In order to determine whether the formulation or composition impedes hearing, the hearing of the test animal is optionally tested.

Alternatively, an inner ear is provided (as removed from a test animal) and the migration of the otic agent is measured. As yet another alternative, an in vitro model of a round window membrane is provided and the migration of the otic agent is measured.

Retention Time

In some embodiments, the formulation or composition has a retention time in the ear of about 5 minutes, about 15 minutes, about 30 minutes, about 1 hour, about 4 hours, about 6 hours, about 12 hours, about 18 hours, about 1 day, about 2 days, about 3 days, about 4 days, about 5 days, about 6 days, about 7 days, about 10 days, about 12 days, about 14 days, about 18 days, about 21 days, about 25 days, about 30 days, about 45 days, about 2 months, about 3 months, about 4 months, about 5 months, about 6 months, about 9 months or about 1 year. In some embodiments, the formulation or composition has a retention time in the ear of at least 5 minutes, at least 15 minutes, at least 30 minutes, at least 1 hour, at least 4 hours, at least 6 hours, at least 12 hours, at least 18 hours, at least 1 day, at least 2 days, at least 3 days, at least 4 days, at least 5 days, at least 6 days, at least 7 days, at least 10 days, at least 12 days, at least 14 days, at least 18 days, at least 21 days, at least 25 days, at least 30 days, at least 45 days, at least 2 months, at least 3 months, at least 4 months, at least 5 months, at least 6 months, at least 9 months or at least 1 year.

In some embodiments, the ear is the outer ear, middle ear, or inner ear. In some embodiments, the ear is the middle ear. In some embodiments, the ear is the inner ear. In some embodiments, the ear is the outer ear. In some embodiments, the outer ear is the external auditory canal, the outer surface of the tympanic membrane, or a combination thereof.

Modes of Administration

The compounds (e.g., otoprotectants) disclosed herein can be administered by any acceptable route, such oral, intraadiposal, intraarterial, intraarticular, intracranial, intradermal, intralesional, intramuscular, intranasal, intraocularal, intrapericardial, intraperitoneal, intrapleural, intraprostatical, intrarectal, intrathecal, intratracheal, intratumoral, intraumbilical, intravaginal, intravenous, intravesicullar, intravitreal, liposomal, local, mucosal, parenteral, rectal, subconjunctival, subcutaneous, sublingual, topical, transbuccal, transdermal, vaginal, in cremes, in lipid compositions, via a catheter, via a lavage, via continuous infusion, via infusion, via inhalation, via injection, via local delivery, via localized perfusion, bathing target cells directly, or any combination thereof.

In one embodiment, the pharmaceutical compositions are provided in a dosage form for oral administration, which comprise a compound provided herein, and one or more pharmaceutically acceptable excipients or carriers. The pharmaceutical compositions provided herein that are formulated for oral administration may be in tablet, capsule, powder, or liquid form. A tablet may comprise a solid carrier or an adjuvant. Liquid pharmaceutical compositions generally comprise a liquid carrier such as water, petroleum, animal or vegetable oils, mineral oil, or synthetic oil. Physiological saline solution, dextrose or other saccharide solution, or glycols such as ethylene glycol, propylene glycol, or polyethylene glycol may be included. A capsule may comprise a solid carrier such as gelatin.

In another embodiment, the pharmaceutical compositions are provided in a dosage form for parenteral administration, which comprise a compound provided herein, and one or more pharmaceutically acceptable excipients or carriers. Where pharmaceutical compositions may be formulated for intravenous, cutaneous or subcutaneous injection, the active ingredient will be in the form of a parenterally acceptable aqueous solution, which is pyrogen-free and has a suitable pH, isotonicity, and stability. Those of relevant skill in the art are well able to prepare suitable solutions using, for example, isotonic vehicles, such as Sodium Chloride injection, Ringer's injection, or Lactated Ringer's injection. Preservatives, stabilisers, buffers, antioxidants, and/or other additives may be included as required.

In yet another embodiment, the pharmaceutical compositions are provided in a dosage form for topical administration, which comprise a compound provided herein, and one or more pharmaceutically acceptable excipients or carriers.

The pharmaceutical compositions can also be formulated as modified release dosage forms, including delayed-, extended-, prolonged-, sustained-, pulsatile-, controlled-, accelerated-, fast-, targeted-, and programmed-release, and gastric retention dosage forms. These dosage forms can be prepared according to conventional methods and techniques known to those skilled in the art (see, *Remington: The Science and Practice of Pharmacy*, supra; *Modified-Release Drug Delivery Technology,* 2nd Edition, Rathbone et al., Eds., Marcel Dekker, Inc.: New York, NY, 2008).

The pharmaceutical compositions provided herein can be provided in a unit-dosage form or multiple-dosage form. A unit-dosage form, as used herein, refers to physically discrete a unit suitable for administration to a human and animal subject, and packaged individually as is known in the art. Each unit-dose contains a predetermined quantity of an active ingredient(s) sufficient to produce the desired therapeutic effect, in association with the required pharmaceutical carriers or excipients. Examples of a unit-dosage form include an ampoule, syringe, and individually packaged tablet and capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

The pharmaceutical compositions provided herein can be administered at once, or multiple times at intervals of time.

It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

A. Oral Administration

The pharmaceutical compositions provided herein for oral administration can be provided in solid, semisolid, or liquid dosage forms for oral administration. As used herein, oral administration also includes buccal, lingual, and sublingual administration. Suitable oral dosage forms include, but are not limited to, tablets, fastmelts, chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In addition to the active ingredient(s), the pharmaceutical compositions can contain one or more pharmaceutically acceptable carriers or excipients, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, PA); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The amount of a binder or filler in the pharmaceutical compositions provided herein varies upon the type of formulation, and is readily discernible to those of ordinary skill in the art. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. The amount of a diluent in the pharmaceutical compositions provided herein varies upon the type of formulation, and is readily discernible to those of ordinary skill in the art.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The amount of a disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, MD) and CAB-O-SIL® (Cabot Co. of Boston, MA); and mixtures thereof. The pharmaceutical compositions provided herein may contain about 0.1 to about 5% by weight of a lubricant.

Suitable glidants include, but are not limited to, colloidal silicon dioxide, CAB-O-SIL® (Cabot Co. of Boston, MA), and asbestos-free talc. Suitable coloring agents include, but are not limited to, any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Suitable flavoring agents include, but are not limited to, natural flavors extracted from plants, such as fruits, and synthetic blends of compounds which produce a pleasant taste sensation, such as peppermint and methyl salicylate. Suitable sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suitable suspending and dispersing agents include, but are not limited to, sodium carboxymethylcellulose, pectin, tragacanth, Veegum, acacia, sodium carbomethylcellulose, hydroxypropyl methylcellulose, and polyvinylpyrrolidone. Suitable preservatives include, but are not limited to, glycerin, methyl and propylparaben, benzoic add, sodium benzoate and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric and tartaric acid. Suitable sources of carbon dioxide include, but are not limited to, sodium bicarbonate and sodium carbonate.

Many carriers and excipients may serve several functions, even within the same formulation.

The pharmaceutical compositions provided herein for oral administration can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms can be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein for oral administration can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein for oral administration can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient (s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations can further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration can be also provided in the forms of liposomes, micelles, microspheres, or nanosystems. Micellar dosage forms can be prepared as described in U.S. Pat. No. 6,350,458.

The pharmaceutical compositions provided herein for oral administration can be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein for oral administration can be formulated as immediate or modified release dosage forms, including delayed-, sustained, pulsed-, controlled, targeted-, and programmed-release forms.

B. Parenteral Administration

The pharmaceutical compositions provided herein can be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical compositions provided herein for parenteral administration can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Suitable non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Suitable water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl β-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents are those described herein, including polyoxyethylene sorbitan monolaurate, polyoxyethylene sorbitan monooleate 80, and triethanolamine oleate. Suitable sequestering or chelating agents include but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, KS).

When the pharmaceutical compositions provided herein are formulated for multiple dosage administration, the multiple dosage parenteral formulations must contain an antimicrobial agent at bacteriostatic or fungistatic concentrations. All parenteral formulations must be sterile, as known and practiced in the art.

In one embodiment, the pharmaceutical compositions for parenteral administration are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein for parenteral administration can be formulated as immediate or modified release dosage forms, including delayed-, sustained, pulsed-, controlled, targeted-, and programmed-release forms.

The pharmaceutical compositions provided herein for parenteral administration can be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include, but are not limited to, polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include but are not limited to, polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

C. Topical Administration

The pharmaceutical compositions provided herein can be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

The pharmaceutical compositions provided herein can be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, and dermal patches. The topical formulation of the pharmaceutical compositions provided herein can also comprise liposomes, micelles, microspheres, nanosystems, and mixtures thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical compositions can also be administered topically by electroporation, iontophoresis, phonophoresis, sonophoresis, or microneedle or needle-free injection, such as POWDERJECT™ (Chiron Corp., Emeryville, CA), and BIOJECT™ (Bioject Medical Technologies Inc., Tualatin, OR).

The pharmaceutical compositions provided herein can be provided in the forms of ointments, creams, and gels. Suitable ointment vehicles include oleaginous or hydrocarbon vehicles, including lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, *Remington: The Science and Practice of Pharmacy*, supra). These vehicles are emollient but generally require addition of antioxidants and preservatives.

Suitable cream base can be oil-in-water or water-in-oil. Suitable cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include, but are not limited to, crosslinked acrylic acid polymers, such as carbomers, carboxypolyalkylenes, and CARBOPOL®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions provided herein can be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in *Remington: The Science and Practice of Pharmacy*, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (*theobroma* oil), glycerin-gelatin, carbowax (polyoxyethylene glycol), spermaceti, paraffin, white and yellow wax, and appropriate mixtures of mono-, di- and triglycerides of fatty acids, and hydrogels, such as polyvinyl alcohol, hydroxyethyl methacrylate, and polyacrylic acid. Combinations of the various vehicles can also be used. Rectal and vaginal suppositories may be prepared by compressing or molding. The typical weight of a rectal and vaginal suppository is about 2 to about 3 g.

The pharmaceutical compositions provided herein for topical administration can be formulated to be immediate release or modified release, including delayed-, sustained-, pulsed-, controlled-, targeted, and programmed release.

D. Modified Release

The pharmaceutical compositions provided herein can be formulated as a modified release dosage form. As used herein, the term "modified release" refers to a dosage form in which the rate or place of release of the active ingredient (s) is different from that of an immediate dosage form when administered by the same route. Modified release dosage forms include, but are not limited to, delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix-controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphorism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500.

In some embodiments, the *auris* formulations or compositions described herein are administered into the ear canal, or in the vestibule of the ear. Access to, for example, the vestibular and cochlear apparatus occurs through the *Auris media* including the round window membrane, the oval window/stapes footplate, the annular ligament and through the otic capsule/temporal bone. In some embodiments, otic administration of the formulations or compositions described herein avoids toxicity associated with systemic administration (e.g., hepatotoxicity, cardiotoxicity, gastrointestinal side effects, and renal toxicity) of the active agents. In some instances, localized administration in the ear allows an active agent to reach a target organ (e.g., inner ear) in the absence of systemic accumulation of the active agent. In some instances, local administration to the ear provides a higher therapeutic index for an active agent that otherwise have dose-limiting systemic toxicity.

Provided herein are modes of treatment for otic formulations or compositions that ameliorate or lessen otic disorders described herein. Drugs delivered to the inner ear have been administered systemically via oral, intravenous or intramuscular routes.

Provided herein are methods comprising the administration of said *auris* formulations or compositions on or near the round window membrane via intratympanic injection. In some embodiments, a composition disclosed herein is administered on or near the round window or the *crista* fenestrae *cochleae* through entry via a post-auricular incision and surgical manipulation into or near the round window or the *crista* fenestrae *cochleae* area. Alternatively, a formulation or composition disclosed herein is applied via syringe and needle, wherein the needle is inserted through the tympanic membrane and guided to the area of the round window or *crista* fenestrae *cochleae*. In some embodiments, a formulation or composition disclosed herein is then deposited on or near the round window or *crista* fenestrae *cochleae* for localized treatment. In other embodiments, a formulation or composition disclosed herein is applied via microcathethers implanted into the patient, and in yet further embodiments a composition disclosed herein is administered via a pump device onto or near the round window membrane. In still further embodiments, a formulation or composition disclosed herein is applied at or near the round window membrane via a microinjection device. In yet other embodiments, a formulation or composition disclosed herein is applied in the tympanic cavity. In some embodiments, a formulation or composition disclosed herein is applied on the tympanic membrane. In still other embodiments, a formulation or composition disclosed herein is applied onto or in the auditory canal. The formulations or compositions described herein, and modes of administration thereof, are also applicable to methods of direct instillation or perfusion of the inner ear compartments. Thus, the formulations or compositions described herein are useful in surgical procedures including, by way of non-limiting examples, cochleostomy, labyrinthotomy, mastoidectomy, stapedectomy, endolymphatic sacculotomy or the like.

Intratympanic Injections

In some embodiments, a surgical microscope is used to visualize the tympanic membrane. In some embodiments, the tympanic membrane is anesthetized by any suitable method (e.g., use of phenol, lidocaine, and xylocaine). In some embodiments, the anterior-superior and posterior-inferior quadrants of the tympanic membrane are anesthetized.

In some embodiments, a puncture is made in the tympanic membrane to vent any gases behind the tympanic membrane. In some embodiments, a puncture is made in the anterior-superior quadrant of the tympanic membrane to vent any gases behind the tympanic membrane. In some embodiments, the puncture is made with a needle (e.g., a 25-gauge needle). In some embodiments, the puncture is made with a laser (e.g., a $CO_2$ laser). In one embodiment the delivery system is a syringe and needle apparatus that is capable of piercing the tympanic membrane and directly accessing the round window membrane or *crista* fenestrae *cochleae* of the *Auris interna*.

In one embodiment, the needle is a hypodermic needle used for instant delivery of the formulation. The hypodermic needle is a single use needle or a disposable needle. In some embodiments, a syringe is used for delivery of the pharmaceutically acceptable otic agent-containing compositions as disclosed herein wherein the syringe has a press-fit (Luer) or twist-on (Luer-lock) fitting. In one embodiment, the syringe is a hypodermic syringe. In another embodiment, the syringe is made of plastic or glass. In yet another embodiment, the hypodermic syringe is a single use syringe. In a further embodiment, the glass syringe is capable of being sterilized. In yet a further embodiment, the sterilization occurs through an autoclave. In another embodiment, the syringe comprises a cylindrical syringe body wherein the formulation is stored before use. In other embodiments, the syringe comprises a cylindrical syringe body wherein the pharmaceutically acceptable otic formulations or compositions as disclosed herein is stored before use which conveniently allows for mixing with a suitable pharmaceutically acceptable buffer. In other embodiments, the syringe contains other excipients, stabilizers, suspending agents, diluents, or a combination thereof to stabilize or otherwise stably store the otic agent or other pharmaceutical compounds contained therein.

In some embodiments, the syringe comprises a cylindrical syringe body wherein the body is compartmentalized in that each compartment is able to store at least one component of the *auris*-acceptable otic formulation. In a further embodiment, the syringe having a compartmentalized body allows for mixing of the components prior to injection into the *Auris media* or *Auris interna*. In other embodiments, the delivery system comprises multiple syringes, each syringe of the multiple syringes contains at least one component of the formulation such that each component is pre-mixed prior to injection or is mixed subsequent to injection. In a further embodiment, the syringes disclosed herein comprise at least one reservoir wherein the at least one reservoir comprises an otic agent, or a pharmaceutically acceptable buffer, or a viscosity enhancing agent, or a combination thereof. Commercially available injection devices are optionally employed in their simplest form as ready-to-use plastic syringes with a syringe barrel, needle assembly with a needle, plunger with a plunger rod, and holding flange, to perform an intratympanic injection.

In some embodiments, a needle is used to deliver the formulations or compositions described herein. In some embodiments, a needle punctures the posterior-inferior quadrant of the tympanic membrane. In some embodiments, the needle is a standard gauge needle. In some embodiments, the needle is a narrow-gauge needle. In some embodiments, the needle is wider than an 18-gauge needle. In another embodiment, the needle gauge is from about 18 gauge to about 30 gauge. In some embodiments, the needle gauge is from about 20 gauge to about 30 gauge. In some embodiments, the needle gauge is from about 25 gauge to about 30 gauge. In some embodiments, the needle gauge is about 18 gauge, about 19 gauge, about 20 gauge, about 21 gauge, about 22 gauge, about 23 gauge, about 24 gauge, about 25 gauge, about 26 gauge, about 27 gauge, about 28 gauge, about 29 gauge, or about 30 gauge. In a further embodiment, the needle is a 25-gauge needle. Depending upon the thickness or viscosity of a formulation or composition disclosed herein, the gauge level of the syringe or hypodermic needle is varied accordingly. In some embodiments, the formulations or compositions described herein are liquids and are administered via narrow gauge needles or cannulas (e.g., 22-gauge needle, 25 gauge needle, or cannula), minimizing damage to the tympanic membrane upon administration. The formulations or compositions described herein are administered with minimal discomfort to a patient.

In some embodiments, an otoendoscope (e.g., about 1.7 mm in diameter) is used to visualize the round window membrane. In some embodiments, any obstructions to the round window membrane (e.g., a false round window membrane, a fat plug, fibrous tissue) are removed.

In some embodiments, a formulation or composition disclosed herein is injected onto the round window membrane. In some embodiments, 0.1 to 0.5 cc of a formulation or composition disclosed herein is injected onto the round window membrane.

In some embodiments, the tympanic membrane puncture is left to heal spontaneously. In some embodiments, a paper patch myringoplasty is performed by a trained physician. In some embodiments, a tympanoplasty is performed by a trained physician. In some embodiments, an individual is advised to avoid water. In some embodiments, a cotton ball soaked in petroleum-jelly is utilized as a barrier to water and other environmental agents.

Other Delivery Routes

In some embodiments, a formulation or composition disclosed herein is administered locally to the outer ear, such as the external auditory canal, the outer surface of the tympanic membrane, or a combination thereof. In some embodiments, the formulations or compositions described herein are not administered through the tympanic membrane.

In some embodiments, a formulation or composition disclosed herein is administered to the inner ear. In some embodiments, a formulation or composition disclosed herein is administered to the inner ear via an incision in the stapes footplate. In some embodiments, a formulation or composition disclosed herein is administered to the cochlea via a cochleostomy. In some embodiments, a formulation or composition disclosed herein is administered to the vestibular apparatus (e.g., semicircular canals or vestibule).

In some embodiments, a formulation or composition disclosed herein is applied via syringe and needle. In other embodiments, a formulation or composition disclosed herein is applied via microcatheters implanted into the patient. In some embodiments, a formulation or composition disclosed herein is administered via a pump device. In still further embodiments, a formulation or composition disclosed herein is applied via a microinjection device. In some embodiments, a formulation or composition disclosed herein is administered via a prosthesis, a cochlear implant, a constant infusion pump, or a wick.

In some embodiments, the delivery device is an apparatus designed for administration of therapeutic agents to the middle and/or inner ear. By way of example only: GYRUS Medical GmbH offers micro-otoscopes for visualization of and drug delivery to the round window niche; Arenberg has described a medical treatment device to deliver fluids to inner ear structures in U.S. Pat. Nos. 5,421,818; 5,474,529; and 5,476,446, each of which is incorporated by reference herein for such disclosure. U.S. patent application Ser. No. 08/874,208, which is incorporated herein by reference for such disclosure, describes a surgical method for implanting a fluid transfer conduit to deliver therapeutic agents to the inner ear. U.S. Patent Application Publication 2007/0167918, which is incorporated herein by reference for such disclosure, further describes a combined otic aspirator and medication dispenser for intratympanic fluid sampling and medicament application.

Dosage

In some embodiments, *auris* formulations or compositions described herein are controlled release formulations and are administered at reduced dosing frequency compared to the current standard of care. In certain instances, when an *auris* formulation or composition is administered via intratympanic injection, a reduced frequency of administration alleviates discomfort caused by multiple intratympanic injections in individuals undergoing treatment for a middle and/or inner ear disease, disorder or condition. In certain instances, a reduced frequency of administration of intratympanic injections reduces the risk of permanent damage (e.g., perforation) to the ear drum. In some embodiments, formulations or compositions described herein provide a constant, sustained, extended, delayed or pulsatile rate of release of an active agent into the inner ear environment and thus avoid any variability in drug exposure in treatment of otic disorders.

The formulations or compositions containing the compound(s) described herein are administered for prophylactic and/or therapeutic treatments. In therapeutic applications, the formulations or compositions are administered to a patient already suffering from a disease, condition or disorder, in an amount sufficient to cure or at least partially arrest the symptoms of the disease, disorder or condition. Amounts effective for this use will depend on the severity and course of the disease, disorder or condition, previous therapy, the patient's health status and response to the drugs, and the judgment of the treating physician.

The amount of a given agent that will correspond to such an amount will vary depending upon factors such as the particular compound, disease condition and its severity, but is nevertheless routinely determined in a manner known in the art according to the particular circumstances surrounding the case, including, e.g., the specific agent being administered, the route of administration, the condition being treated, and the subject or host being treated. In general, however, doses employed for adult human treatment will typically be in the range of 0.02-50 mg per administration, preferably 1-15 mg per administration. In some embodiments, the desired dose is conveniently presented in a single dose or as divided doses administered simultaneously (or over a short period of time) or at appropriate intervals.

Frequency of Administration

In the case wherein the patient's condition does not improve, upon the doctor's discretion the administration of the compounds is administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the compounds are administered continuously; alternatively, the dose of drug being administered are temporarily reduced or temporarily suspended for a certain length of time (i.e., a "drug holiday"). The length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. The dose reduction during a drug holiday are from 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, the dosage or the frequency of administration, or both, is reduced, as a function of the symptoms, to a level at which the improved disease, disorder or condition is retained. Patients, however, require intermittent treatment on a long-term basis upon any recurrence of symptoms in some embodiments.

In some embodiments, the initial administration is of a particular formulation and the subsequent administration is of a different formulation or active pharmaceutical ingredient.

Otic Surgery and Implants

In some embodiments, the pharmaceutical formulations or compositions described herein are used in combination with (e.g., implantation, short-term use, long-term use, or removal of) implants (e.g., cochlear implants). As used herein, implants include *auris*-interna or *auris*-media medical devices, examples of which include cochlear implants, hearing-sparing devices, hearing-improvement devices, short electrodes, micro-prostheses or piston-like prostheses; needles; stem cell transplants; drug delivery devices; any cell-based therapeutic; or the like. In some instances, the implants are used in conjunction with a patient experiencing hearing loss.

In some instances, an implant is an immune cell or a stem cell transplant in the ear. In some instances, an implant is a small electronic device that has an external portion placed behind the ear, and a second portion that is surgically placed under the skin that helps provide a sense of sound to a person who is profoundly deaf or severely hard-of-hearing. By way of example, such cochlear medical device implants bypass damaged portions of the ear and directly stimulate the auditory nerve. In some instances, cochlear implants are used in single sided deafness. In some instances, cochlear implants are used for deafness in both ears.

In some embodiments, administration of a formulation or composition or device described herein in combination with an otic intervention (e.g., an intratympanic injection, a stapedectomy, a medical device implant, or a cell-based transplant) delays or prevents collateral damage to *auris* structures, (e.g., irritation, cell damage, cell death, osteoneogenesis, and/or further neuronal degeneration) caused by the external otic intervention (e.g., installation of an external device and/or cells in the ear). In some embodiments, administration of a formulation or device described herein in combination with an implant allows for a more effective restoration of hearing loss compared to an implant alone.

In some embodiments, administration of formulation or composition or device described herein reduces damage to cochlear structures caused by underlying conditions (e.g., bacterial meningitis, autoimmune ear disease (AIED)) allowing for successful cochlear device implantation. In some embodiments, administration of a formulation or composition or device described herein, in conjunction with otic surgery, medical device implantation, and/or cell transplantation, reduces or prevents cell damage and/or death (e.g., *auris* sensory hair cell death and/or damage) associated with otic surgery, medical device implantation, and/or cell transplantation.

In some embodiments, administration of a formulation or composition or device described herein in conjunction with a cochlear implant or stem cell transplant has atrophic effect (e.g., promotes healthy growth of cells and/or healing of tissue in the area of an implant or transplant). In some embodiments, atrophic effect is desirable during otic surgery or during intratympanic injection procedures. In some embodiments, atrophic effect is desirable after installation of a medical device or after a cell transplant. In some of such embodiments, the formulations or compositions or devices described herein are administered via direct cochlear injection, through a cochleostomy or via deposition on the round window.

In some embodiments, administration of the formulations or compositions described herein reduces inflammation and/or infections associated with otic surgery, implantation of a medical device or a cell transplant. In some instances, perfusion of a surgical area with a formulation described herein reduces or eliminates post-surgical and/or post-implantation complications (e.g., inflammation, hair cell damage, neuronal degeneration, osteoneogenesis, or the like). In some instances, perfusion of a surgical area with a formulation or composition described herein reduces post-surgery or post-implantation recuperation time. In some embodiments, a medical device is coated with a formulation or composition described herein prior to implantation in the ear.

In one aspect, the formulations or compositions described herein, and modes of administration thereof, are applicable to methods of direct perfusion of the inner ear compartments. Thus, the formulations or compositions described herein are useful in combination with otic interventions. In some embodiments, an otic intervention is an implantation procedure (e.g., implantation of a hearing device in the cochlea). In some embodiments, an otic intervention is a surgical procedure including, by way of non-limiting examples, cochleostomy, labyrinthotomy, mastoidectomy, stapedectomy, stapedotomy, endolymphatic sacculotomy, tympanostomy, or the like. In some embodiments, the inner ear compartments are perfused with a formulation or composition described herein prior to otic intervention, during otic intervention, or after otic intervention, or a combination thereof.

In some embodiments, when perfusion is carried out in combination with otic intervention, the formulations or compositions are immediate release compositions. In some of such embodiments, the immediate release formulations described herein are substantially free of extended release components.

Kits and Other Articles of Manufacture

The disclosure also provides kits for preventing, treating or ameliorating the symptoms of a diseases or disorder in a mammal described herein. Such kits generally will comprise one or more of the pharmaceutically acceptable compositions as disclosed herein, and instructions for using the kit. The disclosure also contemplates the use of one or more of the formulations or compositions, in the manufacture of medicaments for treating, abating, reducing, or ameliorating the symptoms of a disease, dysfunction, or disorder in a mammal, such as a human that has, is suspected of having, or at risk for developing an *Auris interna* disorder.

In some embodiments, a kit disclosed herein comprises a needle that penetrates a tympanic membrane and/or a round window. In some embodiments, a kit disclosed herein further comprises a hydrogel with a penetration enhancer (e.g., an alkylglycoside and/or a saccharide alkyl ester).

In some embodiments, kits include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. In other embodiments, the containers are formed from a variety of materials such as glass or plastic.

The articles of manufacture provided herein contain packaging materials. Packaging materials for use in packaging pharmaceutical products presented herein. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations or compositions of the compounds and formulations or compositions provided herein are contemplated as are a variety of treatments for any disease, disorder, or condition that would benefit by extended release administration of a therapeutic agent to the *Auris interna*.

In some embodiments, a kit will typically include one or more additional containers, each with one or more of various materials (such as reagents, optionally in concentrated form, and/or devices) desirable from a commercial and user standpoint for use of a formulation or composition described herein. Non-limiting examples of such materials include, but not limited to, buffers, diluents, filters, needles, syringes; carrier, package, container, vial, and/or tube labels listing contents and/or instructions for use, and package inserts with instructions for use. A set of instructions will also typically be included.

In a further embodiment, a label is on or associated with the container. In yet a further embodiment, a label is on a container when letters, numbers or other characters forming the label are attached, molded or etched into the container itself, a label is associated with a container when it is present within a receptacle or carrier that also holds the container, e.g., as a package insert. In other embodiments a label is used to indicate that the contents are to be used for a specific therapeutic application. In yet another embodiment, a label also indicates directions for use of the contents, such as in the methods described herein.

In certain embodiments, the pharmaceutical formulations or compositions are presented in a pack or dispenser device which contains one or more unit dosage forms containing a compound provided herein. In another embodiment, the pack for example contains metal or plastic foil, such as a blister pack. In a further embodiment, the pack or dispenser device is accompanied by instructions for administration. In yet a further embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. In another embodiment, such notice, for example, is the labeling approved by the U.S. Food and Drug Administration for prescription drugs, or the approved product insert. In yet another embodiment, compositions containing a compound provided herein formulated in a compatible pharmaceutical carrier are also prepared, placed in an appropriate container, and labeled for treatment of an indicated condition.

In some embodiments, a pharmaceutical composition of the present disclosure may be an aqueous formulation. In some embodiments, a pharmaceutical composition of the present disclosure may be a buffered aqueous formulation. In some embodiments, a pharmaceutical composition of the present disclosure may not be configured to provide sustained release of a therapeutic agent therein.

Additional Embodiments

Embodiments include embodiment P1 to P67 following.

Embodiment P1. A method of treating and/or preventing drug-induced ototoxicity, comprising administering to a subject in need thereof a pharmaceutical composition, comprising:

(i) an otoprotectant;

(ii) and at least one pharmaceutically acceptable excipient or carrier, wherein the otoprotectant comprises at least one of a thiopyrimidine, a thiopurine, a thiopurine derivative, a thiouracil, a thiouracil derivative, a thiourea, a thioamide, or a sulfur-containing compound selected from tiopronin, penicillamine, dimercaprol, captodiame, fursultiamine, famotidine, cysteamine, thiabendazole, succimer, glutathione, or mercaptopyruvate.

Embodiment P2. The method of embodiment P1, wherein the otoprotectant comprises at least one of a thiopyrimidine, a thiopurine, a thiouracil, a thiouracil derivative, a thiourea, a thioamide, or a tautomer, prodrug, pharmaceutically acceptable salt, solvate, or hydrate thereof.

Embodiment P3. A method of treating and/or preventing drug-induced ototoxicity, comprising administering to a subject in need thereof a pharmaceutical composition, comprising:

(i) an otoprotectant;

(ii) and at least one pharmaceutically acceptable excipient or carrier, wherein the otoprotectant comprises a thiopurine or thiopurine derivative of structural Formula (I):

(I)

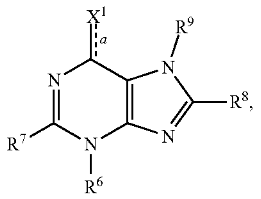

or a tautomer, prodrug, pharmaceutically acceptable salt, solvate, or hydrate thereof, wherein:

$X^1$ is S or $SR^{10}$;

$\overset{a}{- - -}$ is a single bond or double bond, wherein if $\overset{a}{- - -}$ is a single bond, then $X^1$ is $SR^{10}$, and if $\overset{a}{- - -}$ is a double bond, then $X^1$ is S; and $R^6$, $R^7$, $R^8$, $R^9$, and $R^{10}$ are each independently hydrogen, substituted or unsubstituted alkyl, substituted or unsubstituted alkenyl, substituted or unsubstituted alkynyl, substituted or unsubstituted alkylthio, substituted or unsubstituted amine, hydroxyl, imine, amide, cyano, isocyano, carbonyl, carboxyl, carboxamide, substituted or unsubstituted amine alkylsulfonyl, substituted or unsubstituted amine arylsulfonyl, ketone, aldehyde, ester, heteroalkyl, nitrile, amidine, acetal, ketal, substituted or unsubstituted cycloalkyl, substituted or unsubstituted heterocycloalkyl, substituted or unsubstituted aryl, substituted or unsubstituted heteroaryl, aziridine, carbamate, imide, urea, or thiourea.

Embodiment P4. The method of embodiment P3, wherein $R^7$ is $—NH_2$.

Embodiment P5. The method of embodiment P3 or P4, wherein $\overset{a}{- - -}$ is a double bond and $X^1$ is S.

Embodiment P6. The method of any one of embodiments P3-P5, wherein $R^8$ is hydrogen.

Embodiment P7. The method of any one of embodiments P3-P6, wherein $R^9$ is hydrogen, substituted or unsubstituted cycloalkyl, or substituted or unsubstituted heterocycloalkyl.

Embodiment P8. The method of any one of embodiments P1-P7, wherein the thiopurine or thiopurine derivative is:

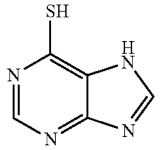

,

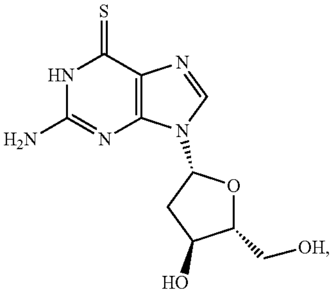

-continued

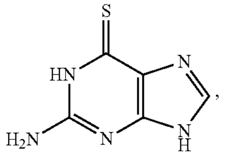

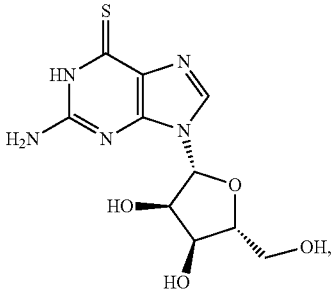

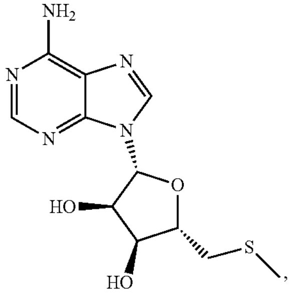

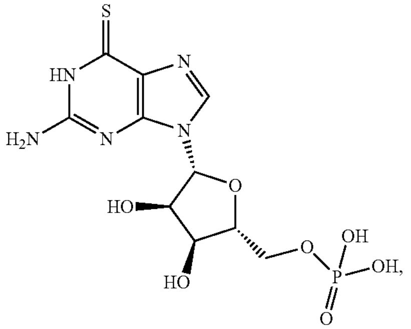

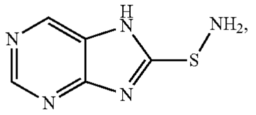

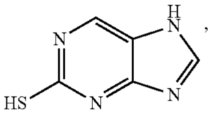

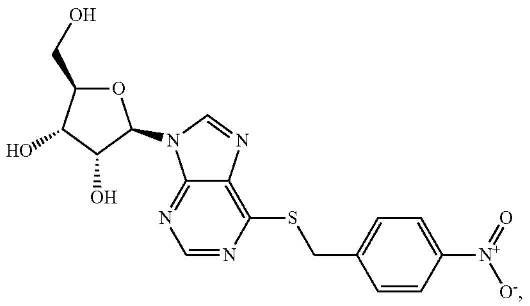

-continued

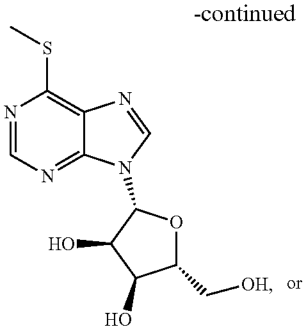

or

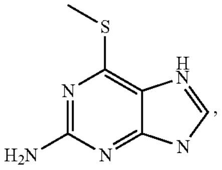

or a tautomer, prodrug, pharmaceutically acceptable salt, solvate, or hydrate thereof.

Embodiment P9. A method of treating and/or preventing drug-induced ototoxicity, comprising administering to a subject in need thereof a pharmaceutical composition, comprising:

(i) an otoprotectant;

(ii) and at least one pharmaceutically acceptable excipient or carrier, wherein the otoprotectant comprises a thiourea of structural Formula (II-A) or (II-B):

(II-A)

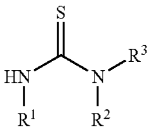

or (II-B)

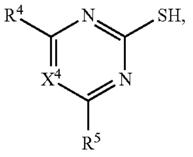

or a tautomer, prodrug, pharmaceutically acceptable salt, solvate, or hydrate thereof, wherein:

$X^4$ is a bond, —O—, —S—, or —C—$R^{21}$; and $R^1$, $R^2$, $R^3$ are each independently hydrogen, substituted or unsubstituted alkyl, substituted or unsubstituted alkenyl, substituted or unsubstituted alkynyl, substituted or unsubstituted alkylthio, substituted or unsubstituted amine, hydroxyl, imine, amide, cyano, isocyano, carbonyl, carboxyl, carboxamide, substituted or unsubstituted amine alkylsulfonyl, substituted or unsubstituted amine arylsulfonyl, ketone, aldehyde, ester, heteroalkyl, nitrile, amidine, acetal, ketal, substituted or unsubstituted cycloalkyl, substituted or unsubstituted heterocycloalkyl, substituted or unsubstituted aryl, substituted or unsubstituted heteroaryl, aziridine, carbamate, imide, urea, or thiourea, or $R^1$ and $R^2$; or $R^2$ and $R^3$ taken together form a substituted or unsubstituted aryl, substituted or unsubstituted heteroaryl, substituted or unsubstituted cycloalkyl, or substituted or unsubstituted heterocycloalkyl having 4 to 8 members;

$R^4$, $R^5$, and $R^{21}$ are each independently hydrogen, substituted or unsubstituted alkyl, substituted or unsubstituted alkenyl, substituted or unsubstituted alkynyl, substituted or unsubstituted alkylthio, imine, substituted or unsubstituted amine, amide, cyano, isocyano, carbonyl, carboxyl, carboxamide, substituted or unsubstituted alkylsulfonyl, substituted or unsubstituted arylsulfonyl, ketone, aldehyde, ester, heteroalkyl, nitrile, amidine, acetal, ketal, substituted or unsubstituted cycloalkyl, substituted or unsubstituted heterocycloalkyl, substituted or unsubstituted aryl, substituted or unsubstituted heteroaryl, aziridine, carbamate, imide, urea, or thiourea, or $R^4$ and $R^{21}$ joined together form a substituted or unsubstituted aryl, substituted or unsubstituted heteroaryl, substituted or unsubstituted cycloalkyl, or substituted or unsubstituted heterocycloalkyl ring having 4 to 8 members.

Embodiment P10. The method of embodiment P9, wherein the thiourea has structural Formula (II-A), or a tautomer, prodrug, pharmaceutically acceptable salt, solvate, or hydrate thereof.

Embodiment P11. The method of embodiment P9 or P10, wherein $R^1$ and $R^2$ are each independently hydrogen, substituted or unsubstituted alkyl or substituted or unsubstituted aryl.

Embodiment P12. The method of any one of embodiments P9-P11, wherein $R^3$ is hydrogen.

Embodiment P13. The method of embodiment P9, wherein the thiourea has structural Formula (II-B), or a tautomer, prodrug, pharmaceutically acceptable salt, solvate, or hydrate thereof.

Embodiment P14. The method of embodiment P9 or P13, wherein $X^4$ is —C—$R^{21}$ and $R^{21}$ is hydrogen.

Embodiment P15. The method of any one of embodiments P9 or P13-P14, wherein $R^4$ is —$NH_2$ or hydrogen and $R^5$ is hydrogen.

Embodiment P16. The method of any one of embodiments P1-2, P9, or P13-P15, wherein the thiourea is:

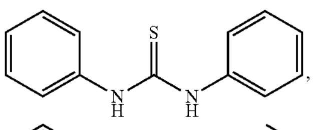,

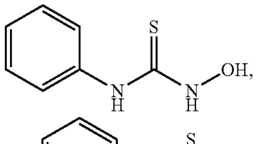

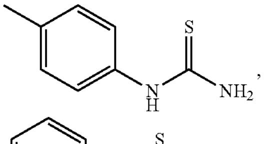,

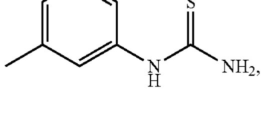

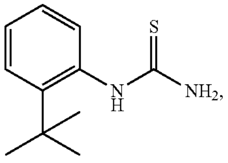

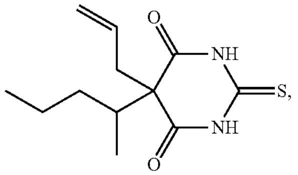

-continued

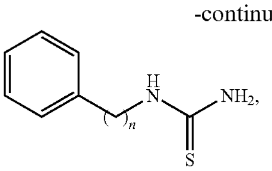

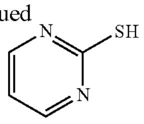,

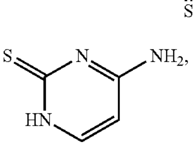 or

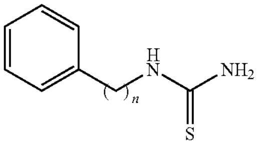, or a tautomer, prodrug, pharmaceutically acceptable salt, solvate, or hydrate thereof, wherein n is an integer from 0 to 6.

Embodiment P17. The method of embodiment P16, wherein the thiourea is:

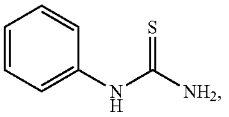

or a tautomer, prodrug, pharmaceutically acceptable salt, solvate, or hydrate thereof.

Embodiment P18. A method of treating and/or preventing drug-induced ototoxicity, comprising administering to a subject in need thereof a pharmaceutical composition, comprising:

(i) an otoprotectant;

(ii) and at least one pharmaceutically acceptable excipient or carrier, wherein the otoprotectant comprises a thiouracil or thiouracil derivative of structural Formula (III):

(III)

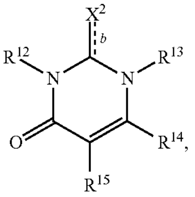

or a tautomer, prodrug, pharmaceutically acceptable salt, solvate, or hydrate thereof, wherein:

$X^2$ is S or SRD;

$\overset{b}{\text{- - -}}$ is a single bond or double bond, wherein if $\overset{b}{\text{- - -}}$ is a single bond, then $X^2$ is $SR^{11}$, and if $\overset{b}{\text{- - -}}$ is a double bond, then $X^2$ is S; and $R^{11}$, $R^{12}$, $R^{13}$, $R^{14}$, and $R^{15}$ are each independently hydrogen, substituted or unsubstituted alkyl, substituted or unsubstituted alkenyl, substituted or unsubstituted alkynyl, substituted or unsubstituted alkylthio, imine, substituted or unsubstituted amine, hydroxyl, amide, cyano, isocyano, carbonyl, carboxyl, carboxamide, substituted or unsubstituted alkylsulfonyl, substituted or unsubstituted arylsulfonyl, ketone, aldehyde, substituted or unsubstituted ester, heteroalkyl, nitrile, amidine, acetal, ketal, substituted or unsubstituted cycloalkyl, substituted or unsubstituted heterocycloalkyl, substituted or unsubstituted aryl, substituted or unsubstituted heteroaryl, aziridine, carbamate, imide, urea, or thiourea.

Embodiment P19. The method of embodiment P18, wherein $\underline{-b-}$ is a double bond and $X^2$ is S.

Embodiment P20. The method of any one of embodiments P1-P2 or P18-P19, wherein the thiouracil is:

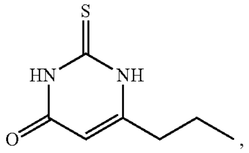
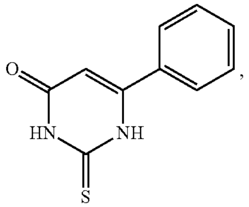
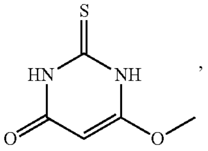
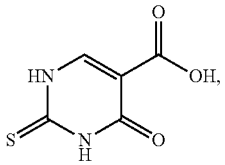
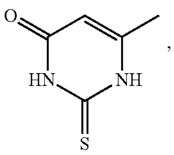
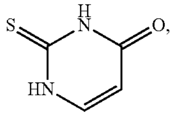
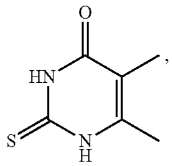
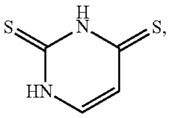
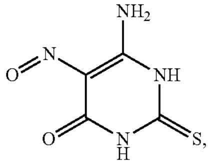
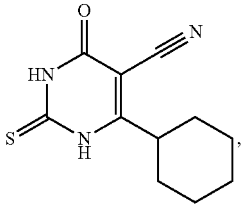
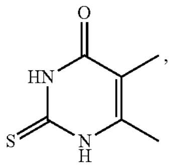
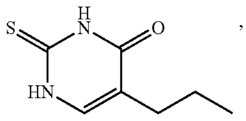
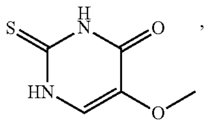
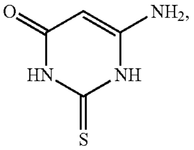
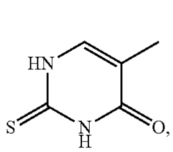
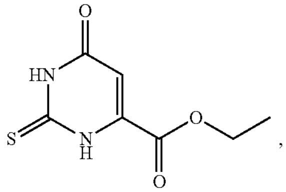

-continued

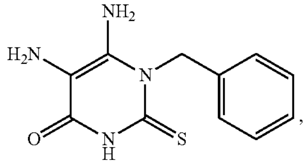
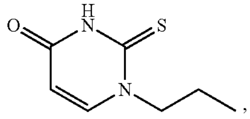
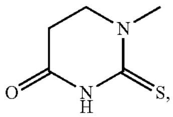
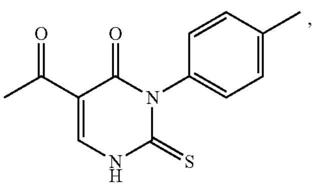
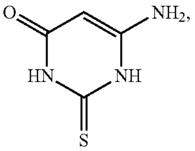
or
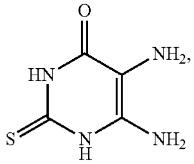

or a tautomer, prodrug, pharmaceutically acceptable salt, solvate, or hydrate thereof.

Embodiment P21. The method of any one of embodiments P1-P2 or P18-P19, wherein the thiouracil derivative is:

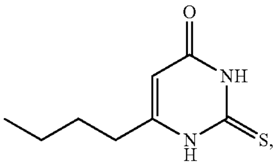
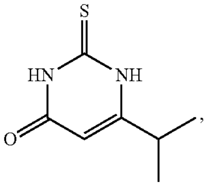
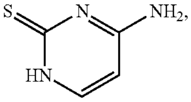
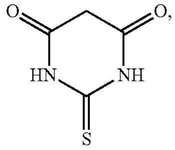
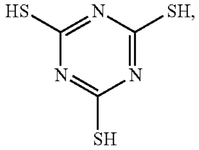
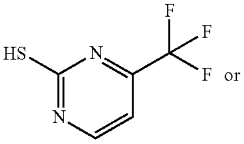
or
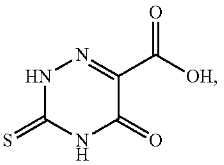

or a tautomer, prodrug, pharmaceutically acceptable salt, solvate, or hydrate thereof.

Embodiment P22. The method of embodiment P1 or P2, wherein the thioamide is:

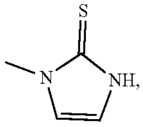,
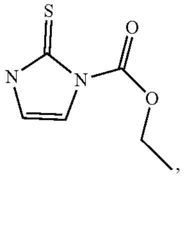,
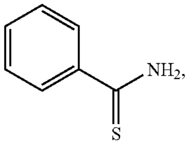,
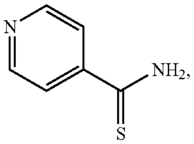,
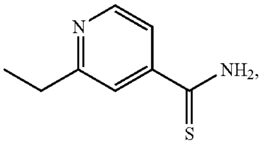,
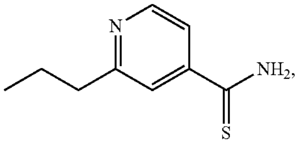,
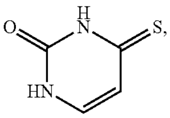, or
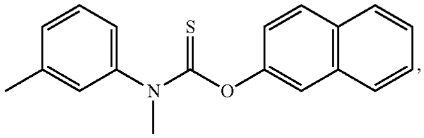, or a tautomer, prodrug pharmaceutically acceptable salt, solvate, or hydrate thereof.

Embodiment P23. A method of treating and/or preventing drug-induced ototoxicity, comprising administering to a subject in need thereof a pharmaceutical composition, comprising:

(i) an otoprotectant;

(ii) and at least one pharmaceutically acceptable excipient or carrier, wherein the otoprotectant comprises a thiopyrimidine of structural Formula (IV):

(IV)

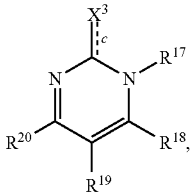, or a tautomer, prodrug, pharmaceutically acceptable salt, solvate, or hydrate thereof, wherein:

$X^3$ is S or $SR^{16}$;

$\overset{c}{---}$ is a single bond or double bond, wherein if $\overset{c}{---}$ is a single bond, then $X^3$ is $SR^{16}$, and if $\overset{c}{---}$ is a double bond, then $X^3$ is S; and $R^{16}$, $R^{17}$, $R^{18}$, $R^{19}$, and $R^{20}$ are each independently hydrogen, substituted or unsubstituted alkyl, substituted or unsubstituted alkenyl, substituted or unsubstituted alkynyl, substituted or unsubstituted alkylthio, imine, substituted or unsubstituted amine, hydroxyl, amide, cyano, isocyano, carbonyl, carboxyl, carboxamide, substituted or unsubstituted alkylsulfonyl, substituted or unsubstituted arylsulfonyl, ketone, aldehyde, substituted or unsubstituted ester, heteroalkyl, nitrile, amidine, acetal, ketal, substituted or unsubstituted cycloalkyl, substituted or unsubstituted heterocycloalkyl, substituted or unsubstituted aryl, substituted or unsubstituted heteroaryl, aziridine, carbamate, imide, urea, or thiourea.

Embodiment P24. The method of embodiment P23, wherein $R^{20}$ is $—NH_2$.

Embodiment P25. The method of embodiment P23 or P24, wherein $\overset{c}{---}$ is a double bond and $X^3$ is S.

Embodiment P26. The method of any one of embodiments P23-P25, wherein $R^{16}$, $R^{17}$, $R^{18}$, $R^{19}$, and $R^{20}$ are each independently hydrogen, $—NH_2$, hydroxyl, or substituted or unsubstituted heterocycloalkyl.

Embodiment P27. The method of any one of embodiments P1-P2 or P23-P26, wherein the thiopyrimidine is:

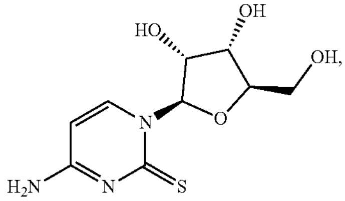,
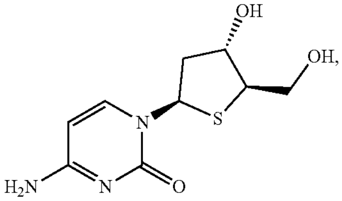,
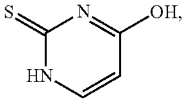,
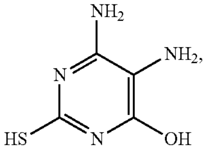,
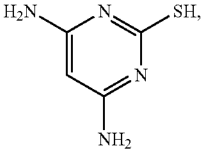, or
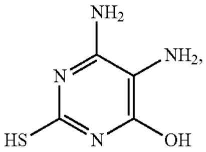, or a tautomer, prodrug pharmaceutically acceptable salt, solvate, or hydrate thereof.

Embodiment P28. The method of embodiment P1, wherein the otoprotectant comprises 6-phenyl-2-thiouracil, 6-propyl-2-thiouracil, 6-thio-2-deoxyguanosine, 6-thioguanine, 6-mercaptopurine, 6-thioguanosine, or 6-methoxymethyl-2-thiouracil, or 5-carboxy-2-thiouracil, or a combination thereof.

Embodiment P29. The method of any one of embodiments P1-P28, wherein the composition provides sustained release of the otoprotectant for a period of at least one (1) day after a single administration.

Embodiment P30. The method of any one of embodiments P1-P29, wherein the composition provides sustained release of the otoprotectant for a period of at least five (5) days after a single administration.

Embodiment P31. The method of any one of embodiments P1-P30, wherein the drug-induced ototoxicity comprises hearing loss.

Embodiment P32. The method of any one of embodiments P1-P31, wherein the drug-induced ototoxicity is chemotherapy-induced ototoxicity.

Embodiment P33. The method of embodiment P32, wherein the chemotherapy-induced ototoxicity is caused by a platinum-based chemotherapeutic agent, a bis-platinate, vincristine, an aminoglycoside antibiotic, a macrolide antibiotic, a diuretic, or a salicylate, or a combination thereof.

Embodiment P34. The method of embodiment 33, wherein the platinum based chemotherapeutic agent is cisplatin, carboplatin, or oxiplatin.

Embodiment P35. The method of any one of embodiments P33-P34, wherein the chemotherapeutic agent is first-line treatment, primary treatment, or adjuvant treatment.

Embodiment P36. The method of any one of embodiments P33-P35, further comprising surgery, radiation therapy, bone marrow transplantion, or a combination thereof.

Embodiment P37. The method of any one of embodiments P1-P36, wherein the composition comprises a gel or a viscous preparation.

Embodiment P38. The method of embodiment P37, wherein the gel is a thermoreversible gel.

Embodiment P39. The method of embodiment P37 or P38, wherein the gel comprises a copolymer of polyoxyethylene and polyoxypropylene.

Embodiment P40. The method of embodiment P39, wherein the composition comprises from about 14 wt % to about 18 wt % of the copolymer of polyoxytheylene and polyoxypropylene.

Embodiment P41. The method of any one of embodiments P37-P40, wherein the gel has a gelation viscosity of from about 15,000 cP to about 3,000,000 cP.

Embodiment P42. The method of any one of embodiments P37-P41, wherein the composition further comprises at least one viscosity modulating agent.

Embodiment P43. The method of embodiment P42, wherein the at least one viscosity modulating agent is silicon dioxide, povidone, carbomer, poloxamer, or a combination thereof.

Embodiment P44. The method of any one of embodiments P37-P43, wherein the composition has a gelation temperature of from about 19° C. to about 42° C.

Embodiment P45. The method of any one of embodiments P1-P44, wherein the composition has an osmolarity from about 100 mOsm/L to about 1000 mOsm/L.

Embodiment P46. The method of any one of embodiments P1-P45, wherein the composition has a pH of from about 7.0 to about 8.0.

Embodiment P47. The method of any one of embodiments P1-P46, wherein the composition comprises triglycerides comprising medium chain fatty acids.

Embodiment P48. The method of embodiment P47, wherein the medium chain fatty acids are saturated medium chain fatty acids, unsaturated medium chain fatty acids, or any combinations thereof.

Embodiment P49. The method of embodiment P47 or P48, wherein the composition comprises at least about 50% by weight of the triglycerides.

Embodiment P50. The method of any one of embodiments P1-P49, wherein the otoprotectant is multiparticulate.

Embodiment P51. The method of any one of embodiments P1-P50, wherein the otoprotectant is essentially in the form of micronized particles.

Embodiment P52. The method of any one of embodiments P1-P51, wherein the otoprotectant is essentially dissolved in the composition.

Embodiment P53. The method of any one of embodiments P1-P52, wherein the composition further comprises an antioxidant, a mucoadhesive, a penetration enhancer, a preservative, a thickening agent, a viscosity modulator agent, a chelator, an antimicrobial agent, a dye, cholesterol, an excipient that increases the release rate of the otoprotectant, or an excipient that increases the release rate of the otoprotectant, or any combination thereof.

Embodiment P54. The method of any one of embodiments P1-P53, wherein the otoprotectant is not:

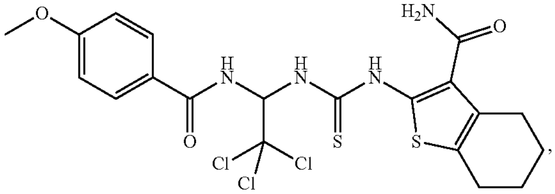

,

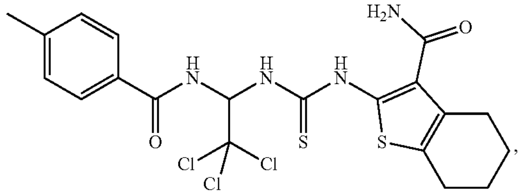

, or

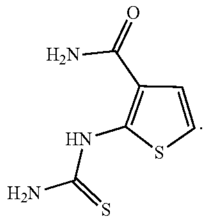

.

Embodiment P55. The method of any one of embodiments P1-P53, wherein the otoprotectant is not a compound of Formula (V):

(V)

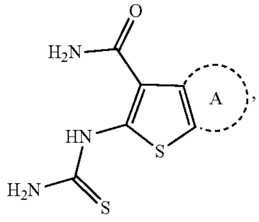

, wherein A is a 5-7 membered aryl, heteroaryl, or heterocycloalkyl optionally containing one more heteroatoms N, O, or S.

Embodiment P56. The method of any one of embodiments P1-P55, wherein the pharmaceutical composition and the ototoxic drug are administered simultaneously, approximately simultaneously, or sequentially, in any order.

Embodiment P57. The method of any one of embodiments P1-P56, wherein the pharmaceutical composition and the ototoxic drug are administered sequentially.

Embodiment P58. The method of embodiment P57, wherein the pharmaceutical composition is administered before the ototoxic drug.

Embodiment P59. The method of embodiment P57, wherein the pharmaceutical composition is administered after the ototoxic drug.

Embodiment P60. The method of embodiment P59, wherein the pharmaceutical composition is administered at least one day after the ototoxic drug.

Embodiment P61. The method of embodiment P59 or P60, wherein the pharmaceutical composition is administered at least seven days after the ototoxic drug.

Embodiment P62. The method of any one of embodiments P1-P61, wherein the pharmaceutical composition is administered by enteral route or by parenteral route.

Embodiment P63. The method of any one of embodiments P1-P62, wherein the otoprotectant is formulated for oral administration, injection, topical administration, sublingual administration, buccal administration, transdermal administration, or transmucosal administration.

Embodiment P64. The method of any one of embodiments P1-P63, wherein the composition is formulated for administration by injection.

Embodiment P65. The method of embodiment P64, wherein the injection is a depot injection.

Embodiment P66. The method of any one of embodiments P1-P65, wherein the otoprotectant is formulated for intratympanic administration.

Further embodiments include embodiment 1 to 40 following.

Embodiment 1. A method of treating and/or preventing drug-induced ototoxicity, comprising administering to a subject in need thereof a pharmaceutical composition, comprising:

(i) an otoprotectant; and (ii) at least one pharmaceutically acceptable excipient or carrier, wherein the otoprotectant comprises at least one of: a thiopyrimidine, a thiopurine, a thiouracil, a thiouracil derivative, a thiourea, a thioamide, or a tautomer, prodrug, pharmaceutically acceptable salt, solvate, or hydrate thereof, and wherein the otoprotectant has a rate constant (k) of at least about 0.07 when reacting with cisplatin.

Embodiment 2. A method of treating and/or preventing drug-induced ototoxicity, comprising administering to a subject in need thereof a pharmaceutical composition, comprising:

(i) an otoprotectant; and (ii) at least one pharmaceutically acceptable excipient or carrier, a thiouracil or a thiouracil derivative of structural Formula (III):

(III)

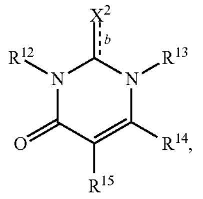

or a tautomer, prodrug, pharmaceutically acceptable salt, solvate, or hydrate thereof, wherein:

$X^2$ is S or $SR^{11}$;

$\underline{\,b\,}$ is a single bond or double bond, wherein if $\underline{\,b\,}$ is a single bond, then $X^2$ is $SR^{11}$, and if $\underline{\,b\,}$ is a double bond, then $X^2$ is S; and $R^{11}$, $R^{12}$, $R^{13}$, $R^{14}$, and $R^{15}$ are each independently hydrogen, substituted or unsubstituted alkyl, substituted or unsubstituted alkenyl, substituted or unsubstituted alkynyl, substituted or unsubstituted alkylthio, imine, substituted or unsubstituted amine, hydroxyl, amide, cyano, isocyano, carbonyl, carboxyl, carboxamide, substituted or unsubstituted alkylsulfonyl, substituted or unsubstituted arylsulfonyl, ketone, aldehyde, substituted or unsubstituted ester, heteroalkyl, nitrile, amidine, acetal, ketal, substituted or unsubstituted cycloalkyl, substituted or unsubstituted heterocycloalkyl, substituted or unsubstituted aryl, substituted or unsubstituted heteroaryl, aziridine, carbamate, imide, urea, or thiourea.

Embodiment 3. The method of embodiment 1 or 2, wherein $\underline{\,b\,}$ is a double bond and $X^2$ is S.

Embodiment 4. The method of any one of embodiments 1-3, wherein $R^{12}$ is hydrogen, substituted or unsubstituted alkyl, or substituted or unsubstituted aryl.

Embodiment 5. The method of any one of embodiments 1-4, wherein $R^{13}$ is hydrogen.

Embodiment 6. The method of any one of embodiments 1-5, wherein $R^{14}$ is hydrogen, substituted or unsubstituted alkyl, substituted or unsubstituted aryl, or a carboxyl.

Embodiment 7. The method of any one of embodiments 1-6, wherein $R^{15}$ is hydrogen or a $C_1$-$C_6$ ketone.

Embodiment 8. The method of any one of embodiments 1-7, wherein the thiouracil is:

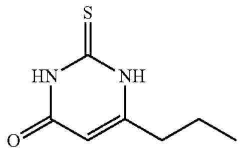,
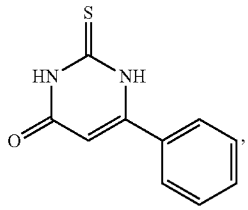 [SMILES: O=c1cc(-c2ccccc2)[nH]c(=S)[nH]1],
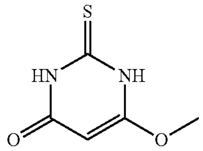,
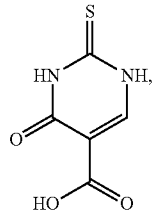,
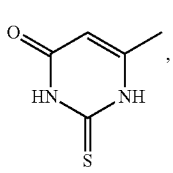,
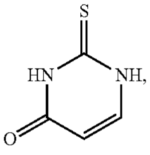,
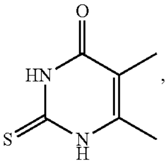,
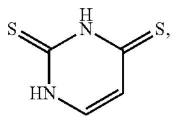,
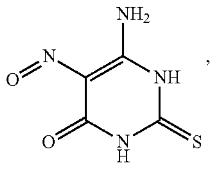, -continued

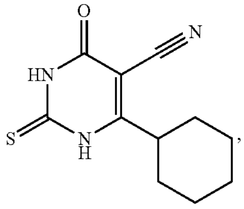, 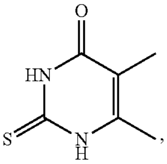,

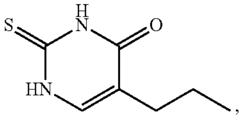, 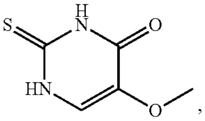,

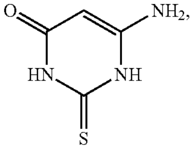 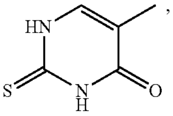,

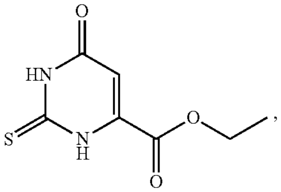,

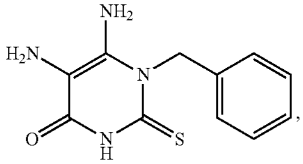,

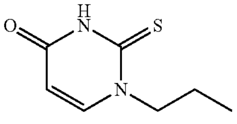, 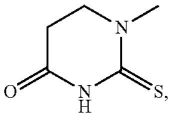

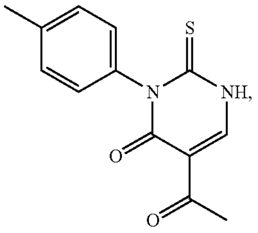

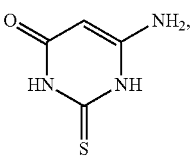 or 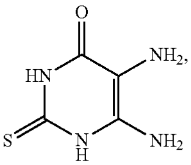

or a tautomer, prodrug, pharmaceutically acceptable salt, solvate, or hydrate thereof.

Embodiment 9. The method of any one of embodiments 1-8, wherein the thiouracil is:

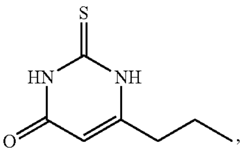

or a tautomer, prodrug, pharmaceutically acceptable salt, solvate, or hydrate thereof.

Embodiment 10. The method of any one of embodiments 1-8, wherein the thiouracil is:

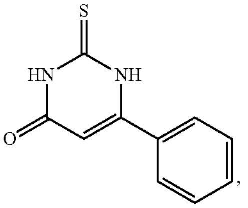

or a tautomer, prodrug, pharmaceutically acceptable salt, solvate, or hydrate thereof.

Embodiment 11. The method of any one of embodiments 1-8, wherein the thiouracil is:

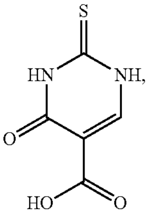 [SMILES: O=C(O)c1c[nH]c(=S)[nH]c1=O]

or a tautomer, prodrug, pharmaceutically acceptable salt, solvate, or hydrate thereof.

Embodiment 12. The method of any one of embodiments 1-8, wherein the thiouracil is:

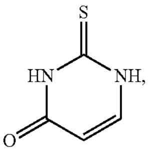

or a tautomer, prodrug, pharmaceutically acceptable salt, solvate, or hydrate thereof.

Embodiment 13. The method of any one of embodiments 1-8, wherein the thiouracil is:

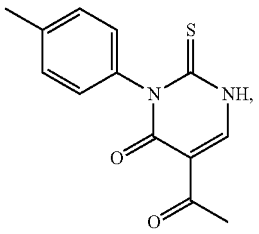 [SMILES: CC(=O)c1c[nH]c(=S)n(-c2ccc(C)cc2)c1=O]

or a tautomer, prodrug, pharmaceutically acceptable salt, solvate, or hydrate thereof.

Embodiment 14. The method of embodiments 1 or 2, wherein the thiouracil derivative is:

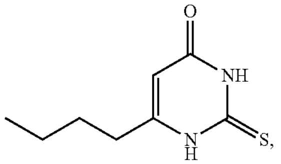

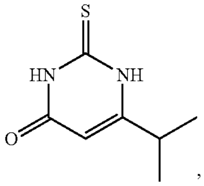

,

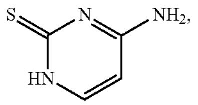

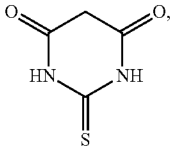

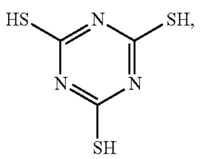

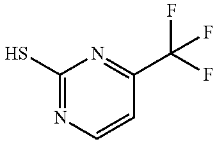

or

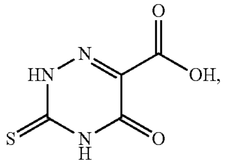

or a tautomer, prodrug, pharmaceutically acceptable salt, solvate, or hydrate thereof.

Embodiment 15. The method of any one of embodiments 1-14, wherein the composition provides sustained release of the otoprotectant for a period of at least one (1) day after a single administration.

Embodiment 16. The method of any one of embodiments 1-15, wherein the composition provides sustained release of the otoprotectant for a period of at least five (5) days after a single administration.

Embodiment 17. The method of any one of embodiments 1-16, wherein the drug-induced ototoxicity comprises hearing loss.

Embodiment 18. The method of any one of embodiments 1-17, wherein the drug-induced ototoxicity is chemotherapy-induced ototoxicity.

Embodiment 19. The method of any one of embodiments 1-18, wherein the composition comprises a gel or a viscous preparation.

Embodiment 20. The method of embodiment 19, wherein the gel is a thermoreversible gel.

Embodiment 21. The method of embodiment 19 or 20, wherein the gel comprises a copolymer of polyoxyethylene and polyoxypropylene.

Embodiment 22. The method of embodiment 21, wherein the composition comprises from about 14 wt % to about 18 wt % of the copolymer of polyoxytheylene and polyoxypropylene.

Embodiment 23. The method of any one of embodiments 19-22, wherein the gel has a gelation viscosity of from about 15,000 cP to about 3,000,000 cP.

Embodiment 24. The method of any one of embodiments 1-23, wherein the composition further comprises at least one viscosity modulating agent.

Embodiment 25. The method of embodiment 24, wherein the at least one viscosity modulating agent is silicon dioxide, povidone, carbomer, poloxamer, or a combination thereof.

Embodiment 26. The method of any one of embodiments 20-25, wherein the composition has a gelation temperature of from about 19° C. to about 42° C.

Embodiment 27. The method of any one of embodiments 1-26, wherein the composition has an osmolarity from about 100 mOsm/L to about 1000 mOsm/L.

Embodiment 28. The method of any one of embodiments 1-27, wherein the composition comprises triglycerides comprising medium chain fatty acids.

Embodiment 29. The method of embodiment 28, wherein the medium chain fatty acids are saturated medium chain fatty acids, unsaturated medium chain fatty acids, or any combinations thereof.

Embodiment 30. The method of embodiment 28 or 29, wherein the composition comprises at least about 50% by weight of the triglycerides.

Embodiment 31. The method of any one of embodiments 1-30, wherein the otoprotectant is multiparticulate.

Embodiment 32. The method of any one of embodiments 1-31, wherein the otoprotectant is essentially in the form of micronized particles.

Embodiment 33. The method of any one of embodiments 1-32, wherein the otoprotectant is essentially dissolved in the composition.

Embodiment 34. The method of any one of embodiments 1-33, wherein the composition further comprises an antioxidant, a mucoadhesive, a penetration enhancer, a preservative, a thickening agent, a viscosity modulator agent, a chelator, an antimicrobial agent, a dye, cholesterol, an excipient that increases the release rate of the otoprotectant, or an excipient that increases the release rate of the otoprotectant, or any combination thereof.

Embodiment 35. The method of any one of embodiments 1-34, wherein the otoprotectant is not:

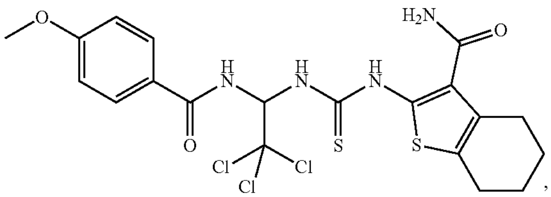

,

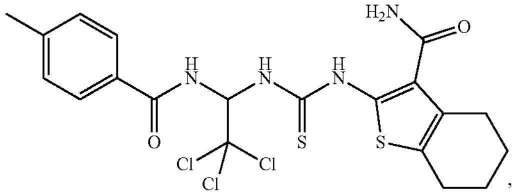

, or

-continued

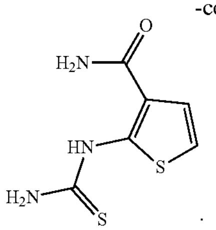

Embodiment 36. The method of any one of embodiments 1-35, wherein the otoprotectant is not a compound of Formula (V):

(V)

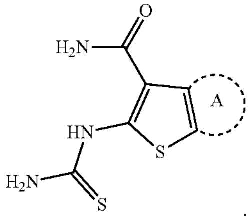

wherein A is a 5-7 membered aryl, heteroaryl, or heterocycloalkyl optionally containing one more heteroatoms N, O, or S.

Embodiment 37. The method of any one of embodiments 1-36, wherein the pharmaceutical composition and the ototoxic drug are administered simultaneously, approximately simultaneously, or sequentially, in any order.

Embodiment 38. The method of embodiment 37, wherein the pharmaceutical composition is administered at least one day after the ototoxic drug.

Embodiment 39. The method of embodiment 39 or 38, wherein the pharmaceutical composition is administered at least seven days after the ototoxic drug.

Embodiment 40. The method of any one of embodiments 1-39, wherein the otoprotectant is formulated for intratympanic administration.

The disclosure will be further understood by the following non-limiting examples.

EXAMPLES

| Compound | Structure |
|---|---|
| OMY-141 | 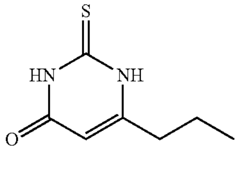 |
| OMY-150 | 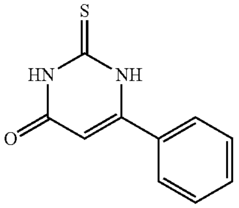 [SMILES: O=c1cc(-c2ccccc2)[nH]c(=S)[nH]1] |

-continued

| Compound | Structure |
|---|---|
| 5-carboxy-2-thiouracil | 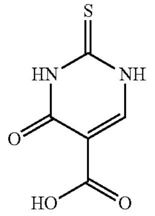 |
| 2-thiouracil | 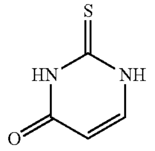 |
| 5-acetyl-3-(p-tolyl)-2-thiouracil | 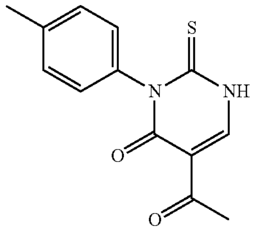 [SMILES: CC(=O)c1c[nH]c(=S)n(-c2ccc(C)cc2)c1=O] |
| sodium thiosulfate (STS) | 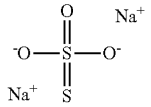 |

Example A1—Preparation of a Thermoreversible Gel Formulation with a Thiopurine

TABLE A

| Thermoreversible Gel Thiopurine Otic Formulation | |
|---|---|
| Ingredient | Concentration in 1000 mL aqueous solution |
| Thiopurine | 0.001-10 (wt %) |
| Polyoxyethylene-polypropylene triblock copolymer (e.g. Poloxamer 407) | 14-21 (wt %) |
| Tromethane | 50 mM |
| NaCl | 0.45% (wt %) |
| pH adjusting agent (e.g., HCl) | q.s. for pH = 5.5-8.0 |
| Sterile water | q.s. to 100 mL |

An exemplary batch of gel formulation containing, for example, 1.5% of a thiopurine described herein will be prepared by dissolving Poloxamer 407 (BASF Corp.) in 50 mM Tris buffer and 77 mM NaCl solution with a pH between 5.5-8.0. The appropriate amount of the thiopurine will be added and the formulation will be mixed until a homogenous suspension is produced. The mixture will be maintained below room temperature until use.

Example A2—Preparation of a Thermoreversible Gel Formulations

An exemplary batch of gel formulation as described in Example A1 containing, for example, 1.5% of tiopronin, penicillamine, dimercaprol, captodiame, fursultiamine, famotidine, cysteamine, thiabendazole, succimer, glutathione, mercaptopyruvate, a thiopyrimidine, a thiopurine, a thiouracil, a thiouracil derivative, a thiourea, a thioamide, or a tautomer, prodrug, pharmaceutically acceptable salt, solvate, or hydrate thereof will be prepared by dissolving Poloxamer 407 (BASF Corp.) in 50 mM Tris buffer and 77 mM NaCl solution with a pH between 5.5-8.0. The appropriate amount of tiopronin, penicillamine, dimercaprol, captodiame, fursultiamine, famotidine, cysteamine, thiabendazole, succimer, glutathione, mercaptopyruvate, a thiopyrimidine, a thiopurine, a thiouracil, a thiouracil derivative, a thiourea, a thioamide, or a tautomer, prodrug, pharmaceutically acceptable salt, solvate, or hydrate thereof is added and the formulation is mixed until a homogenous suspension is produced. The mixture will be maintained below room temperature until use.

Example A3—In Vitro Comparison of Gelation Temperature

The effect of Poloxamer 188 and any one of the therapeutic agents described herein, such as any one of tiopronin, penicillamine, dimercaprol, captodiame, fursultiamine, famotidine, cysteamine, thiabendazole, succimer, glutathione, mercaptopyruvate, a thiopyrimidine, a thiopurine, a thiouracil, a thiouracil derivative, a thiourea, a thioamide, or a tautomer, prodrug, pharmaceutically acceptable salt, solvate, or hydrate thereof on the gelation temperature and viscosity of Poloxamer 407 formulations will be evaluated with the purpose of manipulating the gelation temperature.

A 25% Poloxamer 407 stock solution in PBS buffer and Poloxamer 188NF from BASF will be used. An appropriate amount of the therapeutic agent is added to the solutions described in Table B to provide a 2% formulation of the therapeutic agent.

A PBS buffer (pH 7.3) will be prepared by dissolving 805.5 mg of sodium chloride (Fisher Scientific), 606 mg of sodium phosphate dibasic anhydrous (Fisher Scientific), 247 mg of sodium phosphate monobasic anhydrous (Fisher Scientific), then QS to 200 g with sterile filtered DI water.

TABLE B

Preparation of Samples Containing Poloxamer 407/Poloxamer 188

| Sample | 25% P407 Stock Solution (g) | Poloxamer 188 (mg) | PBS Buffer (g) |
|---|---|---|---|
| 16% P407/10% P188 | 3.207 | 501 | 1.3036 |
| 17% P407/10% P188 | 3.4089 | 500 | 1.1056 |
| 18% P407/10% P188 | 3.6156 | 502 | 0.9072 |
| 19% P407/10% P188 | 3.8183 | 500 | 0.7050 |
| 20% P407/10% P188 | 4.008 | 501 | 0.5032 |
| 20% P407/5% P188 | 4.01 | 256 | 0.770 |

Gelation temperature of the above formulations will be measured using procedures described herein.

An equation will be fitted to the data obtained and will be utilized to estimate the gelation temperature of F127/F68 mixtures (for 17-20% F127 and 0-10% F68).

$$T_{gel}=-1.8(\%\ F127)+1.3(\%\ F68)+53.$$

An equation will be fitted to the data obtained and can be utilized to estimate the Mean Dissolution Time (hr) based on the gelation temperature of F127/F68 mixtures (for 17-25% F127 and 0-10% F68), using results obtained in examples above:

$$MDT=-0.2(T_{gel})+8.$$

Example A4—Preparation of Medium Chain Triglyceride Formulations Comprising Thiopurines Formulations 1, 2, and 3 are prepared with the appropriate amounts of a thiopurine, such as any one of the thiopurines described herein, and medium chain triglycerides (CRODAMOL, GTCC-LQ-(MV), PhEur) as shown in the below table (Table C).

The formulations will be prepared by adding the target weight percentage of any one of the thiopurines described herein to the appropriate amount of medium chain triglyceride for a total volume of about 100 mL. The formulations will be mixed until complete dissolution. The formulations will then be sterilized by passing the formulations through 0.22 μm sterilizing grade filters under aseptic conditions. The sterilized solutions are then filled into vials or pre-filled syringes, which were then used to test the formulations. If the thiopurines are not soluble at the target concentrations, the thiopurines will be sterilized by either dry heat or gamma irradiation before being added to the sterile-filtered MCT. Mix thoroughly and if needed, homogenize to achieve the target particle size under aseptical conditions. The sterilized suspensions are then filled into vials, which were then used to test the formulations.

TABLE C

| Component | Formulation 1 | Formulation 2 | Formulation 3 |
|---|---|---|---|
| Thiopurine | 0.01 wt % | 0.15 wt % | 0.5 wt % |
| CRODAMOL, GTCC-LQ-(MV), PhEur | QS to 100 mL | QS to 100 mL | QS to 100 mL |

Example A5—Additional Preparation of Medium Chain Triglyceride Formulations Comprising Thiopurines Formulations 4, 5, and 6 will be prepared with the appropriate amounts of a thiopurine, such as any one of the thiopurines described herein, and medium chain triglyceride (CRODAMOL, GTCC-LQ-(MV), PhEur) as shown in the below table (Table D).

The formulations will be prepared by adding the target weight percentage of the thiopurine to the appropriate amount of medium chain triglyceride. The formulations will be mixed until complete dissolution. The formulations will be then sterilized by passing the formulations through 0.22 μm sterilizing grade filters under aseptic conditions. The sterilized solutions will then be filled into vials or pre-filled syringes, which then will be used to test the formulations. If the thiopurines are not soluble at the target concentrations, the thiopurines will be sterilized by either dry heat or gamma irradiation before being added to the sterile-filtered MCT. Mix thoroughly and if needed, homogenize to achieve the target particle size under aseptical conditions. The sterilized suspensions will then be filled into vials, which were then used to test the formulations.

TABLE D

| Component | Formulation 4 | Formulation 5 | Formulation 6 |
|---|---|---|---|
| Thiopurine | 1 wt % | 5 wt % | 10 wt % |
| CRODAMOL, GTCC-LQ-(MV), PhEur | QS to 100 mL | QS to 100 mL | QS to 100 mL |

Example A6—Medium Chain Triglyceride Formulations

Medium chain triglyceride formulations comprising tiopronin, penicillamine, dimercaprol, captodiame, fursultiamine, famotidine, cysteamine, thiabendazole, succimer, glutathione, mercaptopyruvate, a thiopyrimidine, a thiopurine, a thiouracil, a thiouracil derivative, a thiourea, a thioamide, or a tautomer, prodrug, pharmaceutically acceptable salt, solvate, or hydrate thereof will be prepared as described in Examples A5 and A6 with the exception that the thiopurine is replaced with tiopronin, penicillamine, dimercaprol, captodiame, fursultiamine, famotidine, cysteamine, thiabendazole, succimer, glutathione, mercaptopyruvate, a thiopyrimidine, a thiopurine, a thiouracil, a thiouracil derivative, a thiourea, a thioamide, or a tautomer, prodrug, pharmaceutically acceptable salt, solvate, or hydrate thereof.

Example A7—Preparation of Medium Chain Triglyceride Formulations with Thiopurines Medium chain triglyceride formulations will be prepared with the appropriate amount of a thiopurine, medium chain triglyceride, and viscosity modulating agents as shown in the below tables (Tables E-H). In some embodiments, the formulations will further comprise cholesterol as shown in the below tables (Tables I-L). Also, in some instances, the medium chain triglyceride as shown in below tables will be replaced with a mixture of mixture of long-chain triglyceride and medium-chain triglycerides (0.1:99.9 to 99.9:0.1).

Thiopurine Solution in MCT

The formulation will be prepared by dissolving the appropriate amount of a thiopurine and one or more than one of the viscosity modulating agents, such as PVP, carbomer, and P407, in water for injection and sterile filtering the solution. The sterilized solution will be lyophilized to form the dry cake. The appropriate amount of the dry cake is aseptically added to the appropriate amount of sterile filtered medium chain triglyceride. The formulation will be mixed until a uniform suspension is achieved. If needed, the suspension will be homogenized to reduce the particle size to below 10 microns (D50). Then the appropriate amount of sterilized silicon dioxide will be added to the suspension, if needed. The final formulation is mixed until a uniform suspension is achieved and then is filled into vials.

Thiopurine Suspension in MCT and $SiO_2$

The formulation will be prepared by adding the target weight percentage of a thiopurine that has been micronized and gamma irradiated to the appropriate amount of medium chain triglyceride that has been sterilized via filtration. The formulation will be mixed until a uniform suspension is formed. The appropriate amount of $SiO_2$ will then be added and will be mixed until uniform. The resulting uniform suspension will then be filled into vials.

Thiopurine Nano-Suspension in MCT and $SiO_2$

The formulation is prepared by adding the target weight percentage of a thiopurine that has been micronized and gamma irradiated to the appropriate amount of medium chain triglyceride that has been sterilized via filtration. The formulation is mixed until a uniform suspension is formed. Ball milling equipment will then be used to reduce the particle size to below 0.2 μm. The appropriate amount of $SiO_2$ will then be added and is mixed until uniform. The resulting uniform suspension will then be filled into vials.

TABLE E

| Component | Amount (wt %) |
|---|---|
| Thiopurine | 0.0001%-10% |
| Medium Chain Triglyceride | QS to 100 mL |

TABLE F

| Component | Amount (wt %) |
|---|---|
| Thiopurine | 0.0001%-10% |
| Medium Chain Triglyceride | QS to 100 mL |
| $SiO_2$ | 0.01%-10% |

TABLE G

| Component | Amount (wt %) |
|---|---|
| Thiopurine | 0.0001%-10% |
| Medium Chain Triglyceride | QS to 100 mL |
| PVP, P407, or carbomer | 0.01-20% |

TABLE H

| Component | Amount (wt %) |
|---|---|
| Thiopurine | 0.0001%-10% |
| Medium Chain Triglyceride | QS to 100 mL |
| $SiO_2$ | 0.01%-10% |
| PVP, P407, or carbomer | 0.01%-20% |

TABLE I

| Component | Amount (wt %) |
|---|---|
| Thiopurine | 0.0001%-10% |
| Cholesterol | 0.01%-20% |
| Medium Chain Triglyceride | QS to 100 mL |

TABLE J

| Component | Amount (wt %) |
|---|---|
| Thiopurine | 0.0001%-10% |
| Medium Chain Triglyceride | QS to 100 mL |
| $SiO_2$ | 0.01%-10% |
| Cholesterol | 0.01%-20% |

TABLE K

| Component | Amount (wt %) |
|---|---|
| Thiopurine | 0.0001%-10% |
| Medium Chain Triglyceride | QS to 100 mL |
| PVP, P407, or carbomer | 0.01-20% |
| Cholesterol | 0.01%-20% |

TABLE L

| Component | Amount (wt %) |
|---|---|
| Thiopurine | 0.0001%-10% |
| Medium Chain Triglyceride | QS to 100 mL |
| $SiO_2$ | 0.01%-10% |
| PVP, P407, or carbomer | 0.01%-20% |
| Cholesterol | 0.01%-20% |

Example A9—Preparation of Other Medium Chain Triglyceride Formulations

Medium chain triglyceride formulation comprising transplatin as the therapeutic agent are prepared as described in Example A8 with the exception that the thiopurine is replaced with tiopronin, penicillamine, dimercaprol, captodiame, fursultiamine, famotidine, cysteamine, thiabendazole, succimer, glutathione, mercaptopyruvate, a thiopyrimidine, a thiopurine, a thiouracil, a thiouracil derivative, a thiourea, a thioamide, or a tautomer, prodrug, pharmaceutically acceptable salt, solvate, or hydrate thereof.

Example A10—Cochlear Explant Model to Evaluate Otoprotective Efficacy Against Aminoglycoside or Cisplatin Damage Ex Vivo Exposure of neonatal rat cochlear explants to various doses of cisplatin or aminoglycosides, including but not limited to gentamicin, neomycin, kanamycin amikacin, anisomycin and tobramycin, ranging from 5-200 μM for periods of 12 to 48 hours will induce varying degrees of cochlear hair cell death as well as spiral ganglion neuron (SGN) damage. Similarly, stria vascularis explants or dissociated cells of the stria vascularis from neonatal or adult *cochleae* are established in culture and are used to evaluate the otoprotective effects of various compounds against strial damage from ototoxic agents. To evaluate the ability of any one of the therapeutic agents described herein to protect SGNs or the stria vascularis, or block hair cell death or restore hair cells following cisplatin or aminoglycoside insult, the following ex vivo models are used.

For hair cell and spiral ganglion assessment, postnatal Sprague-Dawley rats (P2-P4) of both sexes are anesthetized with isoflurane and decapitated. Temporal bones are removed and transferred to a cell culture dish with ice-cold $Ca^{2+}/Mg^{2+}$-containing phosphate-buffered saline (PBS; Invitrogen) or cold HBSS medium enriched with glucose. Under microscopic visualization, the cochlear capsules are carefully removed from the temporal bone using forceps and transferred to a new cell culture dish containing ice-cold PBS. The *cochleae* are then dissected from the cochlear capsule using fine forceps. The stria vascularis is removed from the cochlear tissue and discarded. Dissected cochlear epithelia are transferred to permeable membrane inserts (Millicell organotypic culture plate inserts, Millipore) which are placed into 1 mL of culture media (Dulbecco's modified Eagle's medium (high glucose, Glutamax, 25 mM HEPES) with 10% fetal bovine serum, 1% N2 supplement and 10 units/ml penicillin) in a 6-well plate. Up to 4 *cochleae* are placed onto each membrane. Explants are placed in a humidified chamber with 5% $CO_2$ at 37° C. for a minimum of 18 hours prior to treatment. Cultures are then pre-treated with test compounds and returned to the incubator for a period of 10 minutes to 48 hours. Cultures are then co-incubated with various doses of the test compounds and either cisplatin or an aminoglycoside at varying doses for 12 to 96 hours.

Following the incubation period, cochlear samples are fixed in 4% paraformaldehyde for a minimum of 30 minutes after treatment then permeabilized in 0.5% Triton in PBS (PBST) for 1 hour, followed by overnight incubation at 4° C. in primary antibodies in 10% goat or donkey serum (Sigma). Samples are then rinsed in PBST 2 times for 10 minutes each then incubated in alexa-488 conjugated secondary antibodies for 2 hours at room temperature or overnight at 4° C. in 10% goat or donkey serum (Sigma). Samples are then rinsed 2 times in PBS then incubated in DAPI (1:3000) in PBS for 5 minutes prior to mounting on slides. To evaluate the otoprotective efficacy of the compounds, cochlear samples are immunostained using combination of antibodies generated against markers specific for hair cells (Myosin V1, Myosin VIIA, Parvalbumin, etc.), SGNs (TUJ1, Neurofilament, etc.), f-actin, cell death, cell stress, etc. as well as a nuclear stain to identify cell nuclei.

Immunostained samples are mounted on glass slides and imaged with an LSM880 laser scanning confocal microscope (Zeiss) or an Operetta high-content imager (Perkin Elmer). The entire explant is imaged for all antibody and nuclear labeling in a 3-dimensional X-Y-Z plane in which the Z-plane consists of a stack imaged at intervals of 0.5-5 μm. The total length of the organ of *Corti* in each explant is then determined and is divided into 4 equal length regions. Basal, middle and apical hair cells or SGNS are counted at the regions approximately 25%, 50% or 75% of the total cochlear length from the base, respectively. Hair cell survival is determined by counting the number of inner and outer hair cells at these three different regions (base, middle and apex) in each cochlear explant and determining the number of missing/dead hair cells per cochlear region. Hair cell counts are obtained by placing a 200 μm length scale bar parallel to the rows of hair cells at each region and manually counting the total number of outer hair cells (OHCs) and inner hair cells (IHCs) within the 200 μm. Similarly, to evaluate the health and survival of SGNs, the density of SGN fibers or soma is also determined per region by manual counting for same region selected for counting hair cells. Nuclear staining is analyzed to confirm the presence or absence of cell nuclei and to evaluate nuclear health. Image analysis and quantification is performed using Zeiss Zen Blue software, or Perkin Elmer Columbus software.

For strial explants, the stria vascularis is isolated from the cochlear tissue and transferred to a clean dish with cell culture media. For dissociated strial cultures, the stria vascularis is pulled off the lateral wall and collected separately. Strial cells are then dissociated using a pipette post-trypsinization and seeded onto Poly-d-lysine or collagen-coated 96-well plates. Cells are grown for 48-72 hours to achieve 80-90% confluency before treatment. Strial cultures are then exposed to cisplatin for 22-24 hours. Following treatment, cells are exposed to the Caspase-Glo 3/7 (Promega) reagent for 30 minutes then fluorescence is read on a plate reader. In addition to the cell culture media described above, strial explants can also be maintained in the following media: MEM with Earle's salts, 15 mM HEPES buffer, 2 mM L-glutamine, 10 mg/L MEM non-essential amino acids, 2.5 mg/L fungizone, 100 units/ml penicillin, 100 mg/L streptomycin, 400 μg/L hydrocortisone, 5 mg/L transferrin, 2 nM triiodothyronine, 5 mg/L insulin, 100 μM cholera toxin, 10 μg/L epidermal growth factor, and 10% fetal bovine serum.

Example A11—Otoprotective Profiles of Compounds in Ex Vivo Models of Cisplatin-Induced Hearing Loss The effects of active agents disclosed herein on cisplatin-induced hearing loss were assessed in ex vivo models.

Methods

Animals

Neonatal (P2-P4) Sprague-Dawley rats were used for the experiments described here. Animals were euthanized following anesthesia using isoflurane. Rat *cochleae* were then dissected in cold HBSS medium enriched with glucose.

Preparation of Cochlear Explants

After dissecting the organ of *Corti*, cochlear explants were established in DMEM containing 10% FBS, antibiotics and N2 supplement and allowed to acclimate overnight at 37° C. (5% $CO_2$). For pretreatment and treatment, media was replaced with DMEM containing 2% FBS. Cultures were then maintained for another 72 hours.

Pre-Treatment Treatment

For pretreatment, compounds under screening were added at various doses for 1.5 hours. After pre-treatment, both the test compound and cisplatin were added in media (at the concentrations mentioned below).

Fixation and Immunostaining

Following completion of the incubation, cultures were fixed using 4% PFA for 25 minutes at room temperature or at 4° C. overnight. Explants were then washed in PBS and immunostained using Chicken Neurofilament (marker for SGNs), Mouse Myosin VIIa (Hair cell marker), Phalloidin (actin marker) and DAPI (nuclear staining).

Imaging

All the images for quantification were acquired using a Zeiss LSM880 confocal microscope. Samples for quantification were imaged at 20× and hair cells within a 200 μm region within the mid and basal turns were quantified. SGN fibers innervating the HCs within the selected region were also quantified.

Dissociated Strial Cultures

Following cochlear dissection, Reissner's membrane and the lateral wall were separated and the stria vascularis was then removed from the lateral wall. Strial cells were then dissociated, seeded onto Poly-d-lysine coated 96 well plates and grown to achieve 80-90% confluency before treatment. Compounds under screening were added for 1.5 hours as pretreatment and then as co-treatment with 20 μM cisplatin for 22 hours. After incubation, cells were lysed using the Promega caspase 3/7 Glo kit and the intensity of caspase 3/7 were read using Perkin-Elmer Enspire plate reader.

Compounds

Compounds tested included 6-phenyl-2-thiouracil, 6-propyl-2-thiouracil, 6-thio-2-deoxyguanosine, 6-thioguanine, 6-mercaptopurine, 6-thioguanosine, 6-methoxymethyl-2-thiouracil and 5-carboxy-2-thiouracil.

Example A12—Pharmacokinetic Study of Active Compounds after Intratympanic Administration OMY-141 in P407: 16 and 50 mg/mL in P407—16 mg/g or 50 mg/g of OMY-141 in 0.6% Tris, 0.45% NaCl, 16% Poloxamer 407, pH 7-8.

OMY-150 in P407: 16 and 50 mg/mL in P407—16 mg/g or 50 mg/g of OMY-150 in 0.6% Tris, 0.45% NaCl, 16% Poloxamer 407, pH 7-8.

Pharmacokinetics

Female rats (Charles River) weighing 200-300 g of approximately 12-16 weeks of age served as subjects (N=4 per group). Prior to any procedures, animals were anesthetized using a combination of xylazine (10 mg/kg), ketamine (50 mg/kg), and acepromazine (1 mg/kg) for up to an hour via the intraperitoneal route. If needed, an intraoperative booster was administered intraperitoneal representing a one-tenth of the original dose.

Intratympanic injection—Each animal was positioned so that the head was tilted at an angle to favor injection towards the round window niche. Briefly, under visualization with an operating microscope, 20 μL of the formulation was injected using a 25G (Gauge) 11/2 needle through the tympanic membrane into the superior posterior quadrant. Formulations were delivered using a perfusion pump at the rate of 2 μL/sec. Contact with the round window membrane was maintained for 30 minutes by placing the animal in a recumbent position. During the procedure and until recovery, animals were placed on a temperature controlled (40° C.) heating pad until consciousness was regained at which time they were returned to the vivarium.

Perilymph sampling procedure—The skin behind the ear of anesthetized rats was shaved and disinfected with povidone-iodine. An incision was then made behind the ear, and muscles were carefully retracted from over the bulla. A hole was drilled through the bulla using a dental burr so that the middle ear was exposed and accessed. The cochlea and the round window membrane were visualized under a stereo surgical microscope. The basal turn of bulla was cleaned by using small cotton ball. A unique microhole was hand drilled through the bony shell of the cochlea (cochlear capsule) adjacent to the round window. Perilymph (about 2 μL) was then collected using a microcapillary inserted into the cochlear *scala tympani*. Perilymph samples were added to a vial containing 18 μL of acetonitrile/water, stored at −80° C. until analysis.

Cochlear epithelium sampling procedure—Under a dissection scope, the bulla was opened, and the cochlea was exposed by removing all surrounding muscles, blood vessels and bone tissues. Holding the bulla, the cochlear wall bony structure was removed working from the base to the apex of the cochlea, exposing the organ of *Corti*. The exposed cochlear epithelium was gently dabbed with cotton swab to remove excess of liquid from tissue, carefully transferred to labelled tube. Each 2-mL plastic tube that contained acid washed 2.8 mm stainless steel beads was pre-weighed. The tubes were reweighed after adding cochlea epithelium and weights were recorded. All cochlea epithelium samples were placed in dry ice immediately after collection and stored at −80° C. prior to analysis.

Plasma sampling procedure—Blood samples were collected by cardiac puncture into labeled micro-tubes, containing lithium heparin as anticoagulant. Plasma were immediately harvested from the blood by centrifugation and collection for supernatants. All plasma samples were stored at −80° C. prior to analysis.

OMY-141 Analytical Method

Samples were extracted by protein precipitation, then vortexed and centrifuged. The supernatant was collected and diluted with two folds of water. A high-performance liquid chromatography system (Agilent 1200 series) with Waters Cortecs C18 Plus column (50*4.6 mm, 2.7 μm) were used. The flow rate was set at 0.700 mL/min. A gradient method with an analytical run time of 5 minutes was used. Mobile phase A consisted of 0.01% ammonium formate, 0.03% formic acid in water. Mobile phase B consisted of 0.01% ammonium formate, 0.03% formic acid in acetonitrile: methanol (70:30, v/v). The gradient began with 30% B, stepped to 70% B at 2.75 minutes and held for 1 minute and then stepped back to 30% B to re-equilibrate the column.

Ionizations and detection of analyte and internal standard were performed on a triple quadruple mass spectrometer, API 5500 Q-Trap equipped with Turbo IonSpray@, from SCIEX (Toronto, Canada). Electro spray ionization (ESI) mass spectra was operated in the positive ion mode. Carbutamide was used as the internal standard (IS).

Quantification was done using MRM mode to monitor protonated precursor product ion transition of m/z 171.05 x/y 112.10 amu, and m/z 272.15 x/y 155.70 amu for OMY-141 and carbutamide, respectively. Peak areas of OMY-141 were determined using Analyst™1.6 (Applied Biosystems). The calibration curves were obtained by fitting the peak area ratios of OMY-141/internal standard (IS) and the standard concentrations to a suitable equation. Sample OMY-141 concentrations were then interpolated using the equations derived from the calibration curves.

OMY-150 Analytical Method

Samples were extracted by protein precipitation, then vortexed and centrifuged. The supernatant was collected and diluted with two folds of water. A high-performance liquid chromatography system (Agilent 1200 series) with Waters Cortecs C18 Plus column (50*4.6 mm, 2.7 μm) were used. The flow rate was set at 0.500 mL/min. A gradient method with an analytical run time of 4.6 minutes was used. Mobile phase A consisted of 0.01% formic acid in water:acetonitrile (95:5, v/v). Mobile phase B consisted of 0.01% formic acid in acetonitrile: water (95:5, v/v). The gradient began with 50% B, stepped to 95% B at 2.75 minutes and held for 1 minute and then stepped back to 50% B to re-equilibrate the column.

Ionizations and detection of analyte and internal standard were performed on a triple quadruple mass spectrometer, API 5500 Q-Trap equipped with Turbo IonSpray@, from SCIEX (Toronto, Canada). Electro spray ionization (ESI) mass spectra was operated in the positive ion mode. Carbutamide was used as the internal standard (IS).

Quantification was done using MRM mode to monitor protonated precursor product ion transition of m/z 205.03 x/y 103.00 amu, and m/z 272.15 x/y 155.70 amu for OMY-150 and carbutamide, respectively. Peak areas of OMY-150 were determined using Analyst™1.6 (Applied Biosystems). The calibration curves were obtained by fitting the peak area ratios of OMY-150/internal standard (IS) and the standard concentrations to a suitable equation. Sample OMY-150 concentrations were then interpolated using the equations derived from the calibration curves.

Cisplatin Analytical Method

Total platinum level in samples were analyzed by a qualified inductively coupled plasma mass spectrometric detection (ICP-MS) developed in QPS (Netherlands Lab). Ruthenium were used as internal standard. A flow injection analysis (FIA) method was used to using HPLC pump to introduce samples and internal standard into the systems but without HPLC column. The ICP-quadrupole-MS of Perkin Elmer Sciex Elan 6100 ICP-MS System equipped with a peristaltic pump, nebulizer, spray chamber, and quartz torch were used in platinum analyses.

Sample transport from the autosampler to the nebulizer was performed using a peristaltic pump. The instrument was cooled by using argon gas of 99.999% purity. Data were acquired and processed using the Analyst 1.6. The instrument settings of the ICP-MS had the following operating parameters: ICP radio frequency (RF) power, 1500 W; RF matching, 1.80 V; sampling depth, 8.0 mm; carrier gas, 0.90 L/min; makeup gas, 0.21 L/min; nebulizer pump, 0.10 rps; He gas, 4.5 mL/min; extract 1, 0.0 V; extract 2, −120.0 V; cell entrance, −30 V; cell exit, −30 V; QP bias, −16.0 V; Octp bias, −20.0 V.

The mass to charge ratio is determined by the detector. Platinum and ruthenium were monitoring at m/z of 195.084 and 187.95, respectively. Electronic signals were compared to the standardized curve generated from ultra-high purity platinum samples and solvents. Accounting for dilutions, comparison of the sample signal to the standardized curve will allow for the determination of the original total platinum concentration.

Example A13—Cisplatin Reaction Kinetics Study Cisplatin Reaction Kinetics Study A cisplatin reaction study was used for characterization of improved method to evaluate compounds binding to cisplatin.

Cisplatin reaction kinetics experiments (FIGS. 6-9), kinetic experiments based on 1 mM Cisplatin+1 mM active agent were performed. The results were analyzed by European Pharmacopoeia (Ph. Eur.) Cisplatin Compendial Method. kinetics experiments monitor change in cisplatin main peak over time and also monitor change in the mono-aqua complex form over time. The Kinetic Equations used for the cisplatin reaction kinetic study are as follows:

(1) Rate constant (k)
(2) Reaction rate 0, 1, 2 order (relates concentration to rate)
(3) Integrated rate law at a defined temperature (relates concentration to time)
(4) Half-life can be determined All samples dissolved in 0.9% NaCl. Reaction Temperature=20° C. Reactions are monitored up to 36 hours. The reaction kinetics profiles of various compounds are useful for evaluating active agents in terms of their ability to inactive cisplatin, especially in combination with the PK study results of the compounds.

Example A14—PK Study Measuring Cisplatin Levels in Cochlear after IP Administration Analysis of cisplatin levels after intraper injection was carrier as above for intratympanic injection as in Example A13 except for the following:

Intraperitoneal injection—The lower right quadrant of the abdomen was shaved and disinfected with alcohol and then povidone iodine. Animals were placed in a supine position and the hind legs were lifted at a 40-degree angle in order to move the abdominal organs towards the diaphragm. A 1" 23G needle or larger was inserted into the abdominal cavity, directed towards the animal's head, at a 15-20-degree angle and inserted approximately 5 mm. Aspiration was attempted to ensure that an abdominal viscus has not been penetrated, and cisplatin was slowly injected for a duration of 30 minutes, with an infusion rate of 8 ml/hr using a pump. After removal of the syringe from the peritoneal cavity, triple antibiotic was placed on the injection site to help prevent infection. During the procedure and until recovery, animals were placed on a temperature controlled (40° C.) heating pad until consciousness was regained at which time they were returned to the vivarium.

Results

Figure 1B:
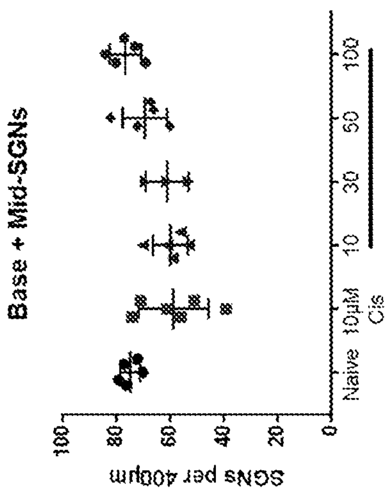

FIG. 1 show quantified graphs for outer hair cells (OHCs) (FIG. 1A) and spiral ganglion neurons (SGNs) (FIG. 1B), combined from base and mid region, showing complete protection of hair cells and spiral ganglion neurons against cisplatin in a cochlear explant model with 1.5 hour pretreatment followed by co-treatment of a thiopyrimidine compound (6-Phenyl-2-thiouracil) at different concentrations with 10 μM cisplatin.

Figure 2B:
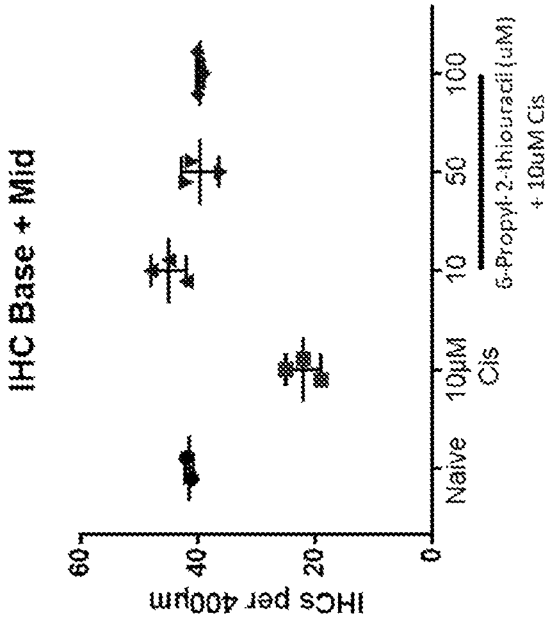
FIGS. 2A-2B show quantified graphs for outer hair cells (OHCs) (FIG. 2A) and inner hair cells (IHCs) (FIG. 2B), combined from base and mid region, showing complete protection of hair cells against cisplatin in a cochlear explant model with 1.5 hour pretreatment followed by co-treatment of a thiopyrimidine compound (6-Propyl-2-thiouracil) at different concentrations with 10 μM cisplatin.
Figure 2A:
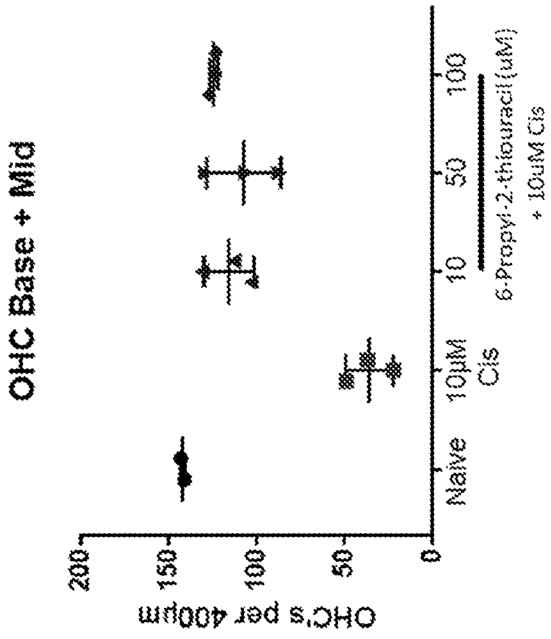

FIG. 2 show quantified graphs for outer hair cells (OHCs) (FIG. 2A) and inner hair cells (IHCs) (FIG. 1B), combined from base and mid region, showing complete protection of hair cells against cisplatin in a cochlear explant model with 1.5 hour pretreatment followed by co-treatment of a thiopyrimidine compound (6-propyl-2-thiouracil) at different concentrations with 10 μM cisplatin.

Figure 3B:
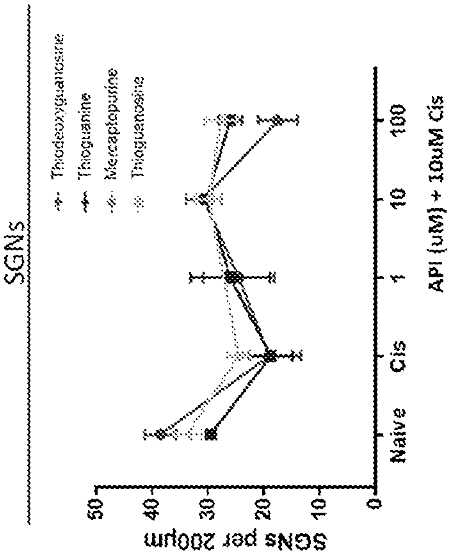
FIGS. 3A-3B show quantified graphs for outer hair cells (OHCs) (FIG. 3A) and spiral ganglion neurons (SGNs) (FIG. 3B) showing complete protection of hair cells and near complete protection of spiral ganglion neurons against 1 μM cisplatin in a cochlear explant model with 1.5 hour pretreatment followed by co-treatment of thiopurine compounds 6-thio-2-deoxyguanosine (triangle), 6-thioguanine (diamond), 6-mercaptopurine (circle) and 6-thioguanosine (square) at different concentrations with cisplatin.
Figure 3A:
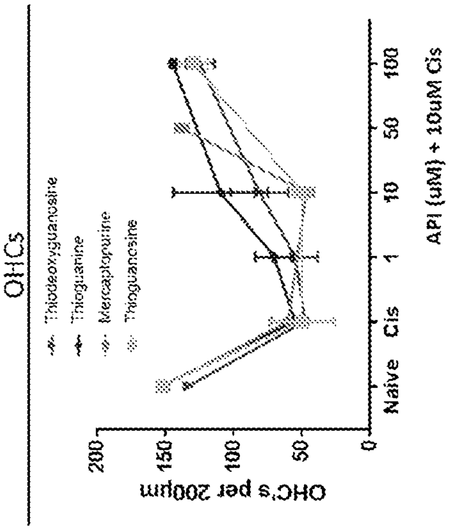

FIG. 3 show quantified graphs for outer hair cells (OHCs) (FIG. 3A) and spiral ganglion neurons (SGNs) (FIG. 3B) showing complete protection of hair cells and near complete protection of spiral ganglion neurons against 10 μM cisplatin in a cochlear explant model with 1.5 hour pretreatment followed by co-treatment of thiopurine compounds 6-thio-2-deoxyguanosine (triangle), 6-thioguanine (diamond), 6-mercaptopurine (circle) and 6-thioguanosine (square) at different concentrations with cisplatin.

Figure 4:
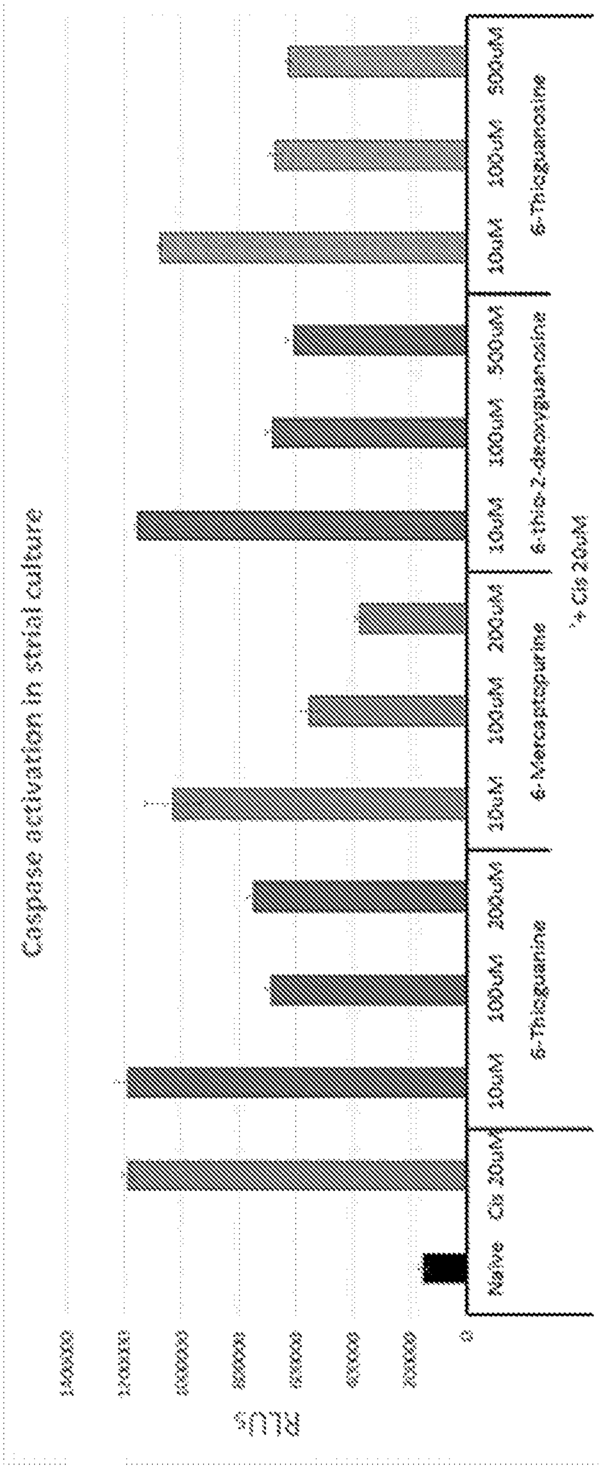
FIG. 4 shows caspase activation in stria vascularis cells with 1.5 hour pretreatment of thiopurines followed by co-treatment with 20 μM cisplatin.
Figure 5:
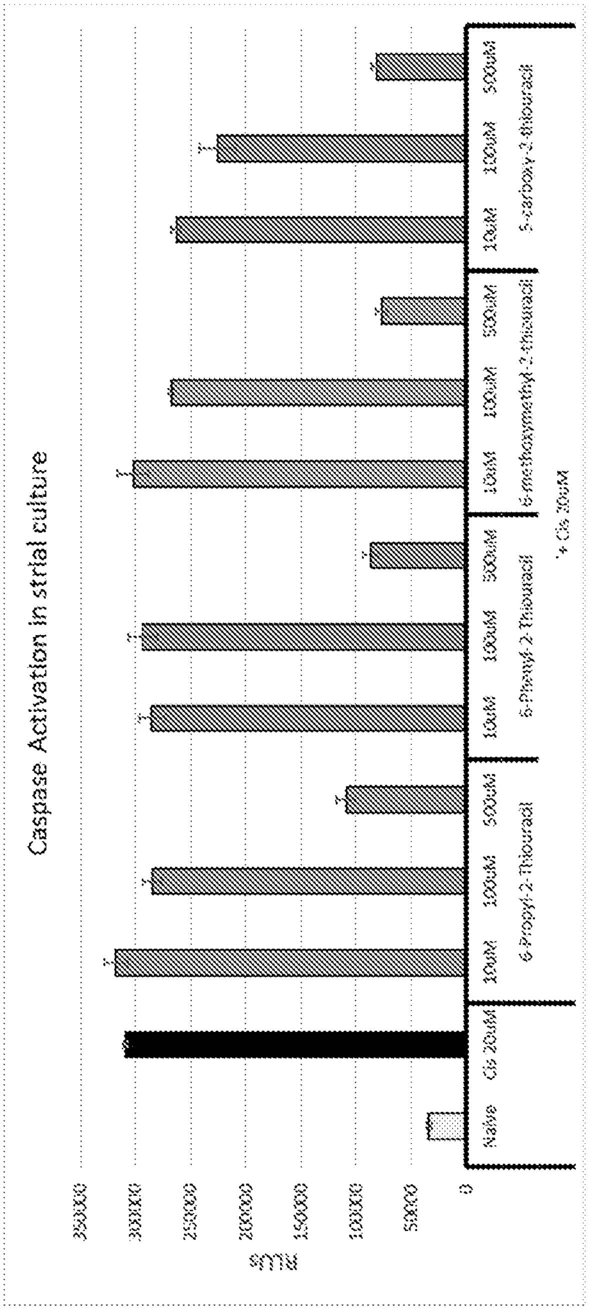
FIG. 5 shows caspase activation in stria vascularis cells with 1.5 hour pretreatment of thiopyrimidines followed by co-treatment with 20 μM cisplatin.
Figure 6:
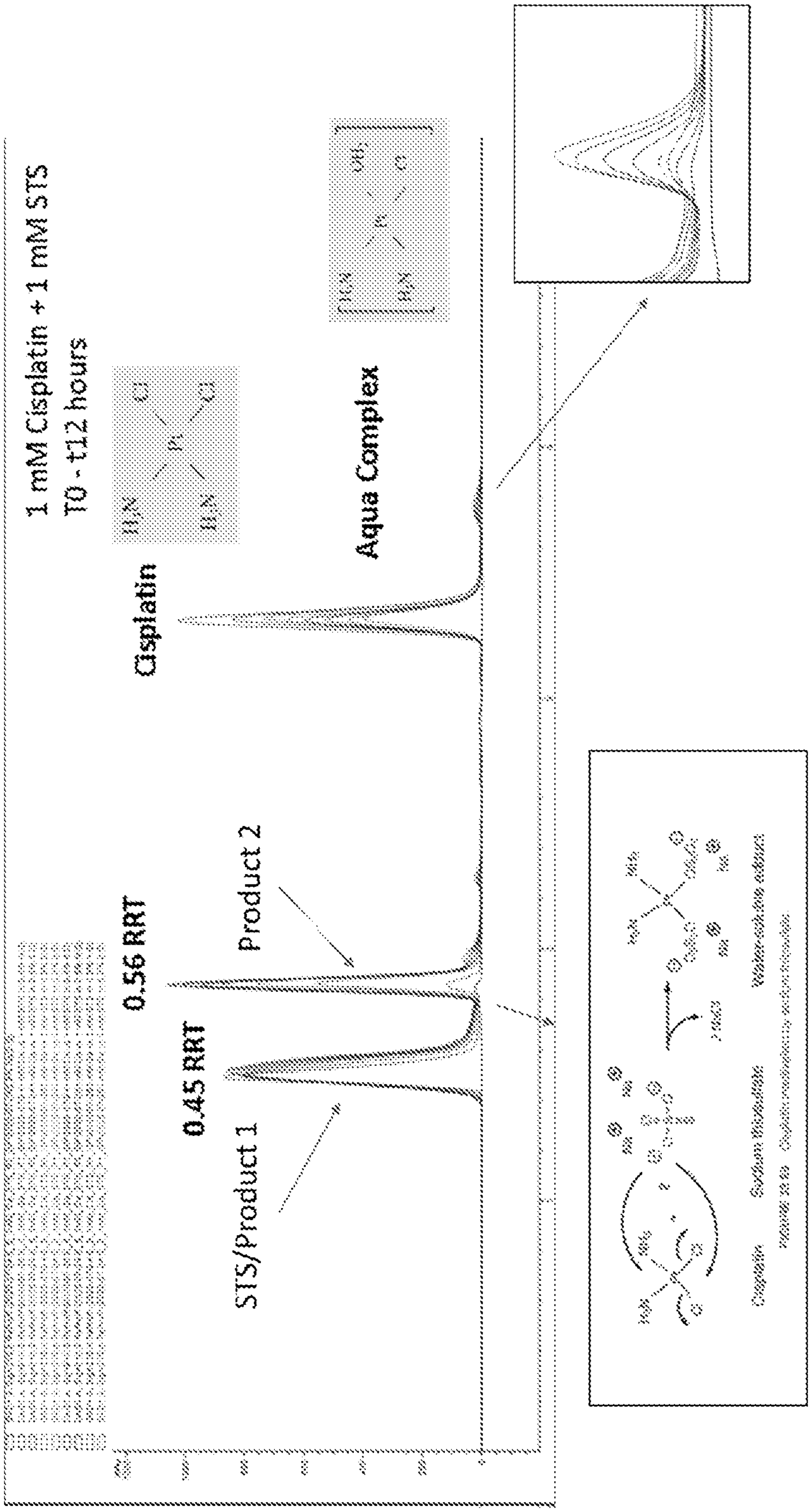
FIG. 6 shows a cisplatin reaction study.
Figure 7:
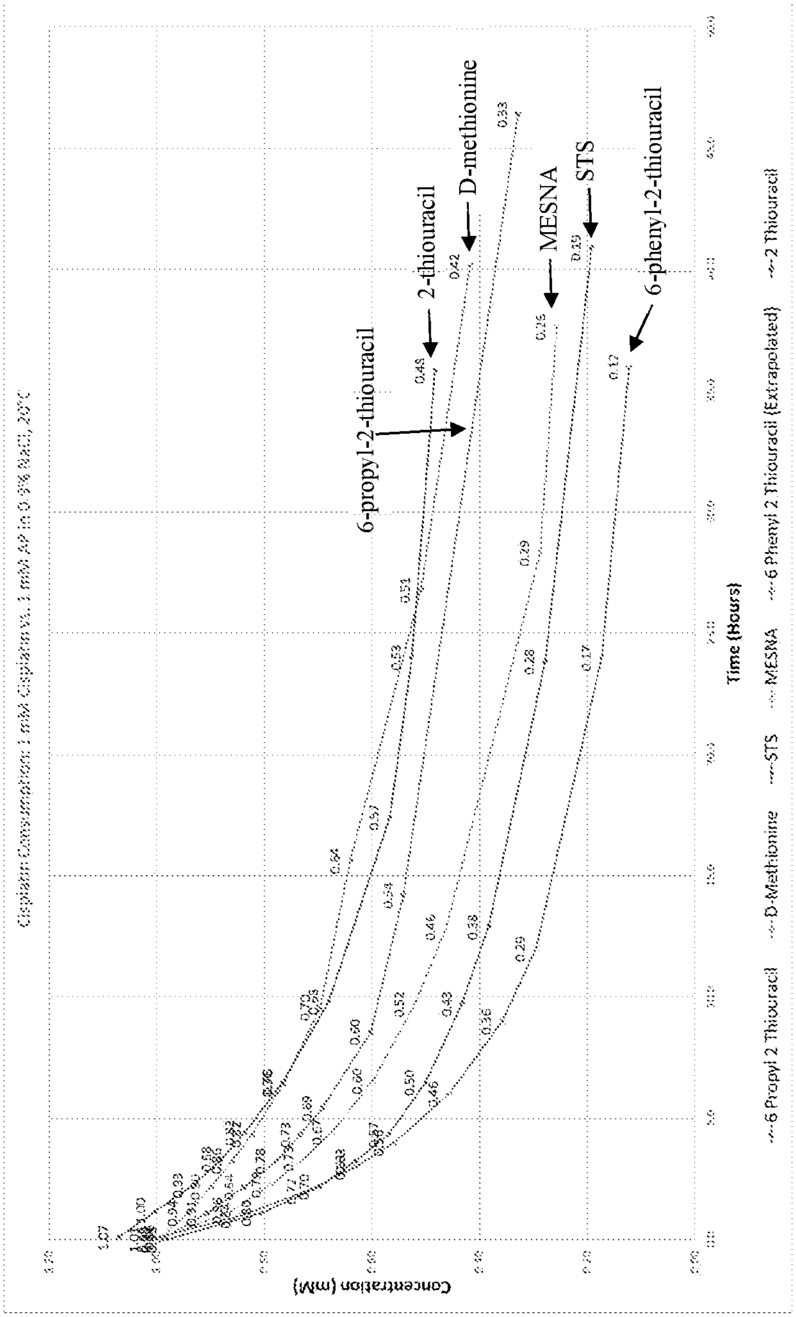
FIG. 7 shows a cisplatin reaction study.
Figure 9:
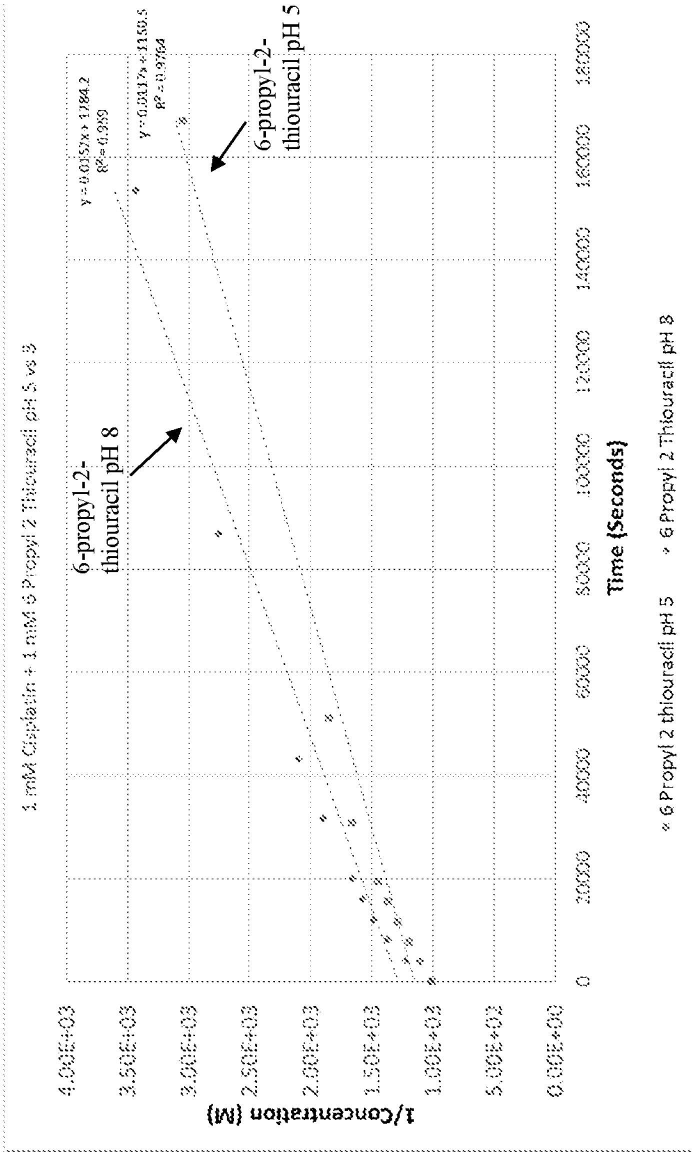
FIG. 9 shows 6-propyl-2-thiouracil at pH 5 versus pH 8.

FIGS. 4-5 shows that thiopurines (FIG. 4) and thiopyrimidines (FIG. 5) at higher doses result in reduced caspase 3/7 activation in stria vascularis cells with 1.5 hour pretreatment followed by co-treatment with 20 μM cisplatin, indicating protection of the strial cells.

Inner Ear and Plasma PK of Thiouracils after IT Injection:

The OMY-141 PK Study Design is as follows: Single IT injection in rats with 4 animals per time point. Time points are: 30 minutes, 1 hr, day 1 and day 3. Samples are: perilymph, cochlear epithelium and plasma. Treatment groups are:

OMY 141 at 50 mg/mL in MCT. Bio-analytical method: LC/MS/MS. Lower limits of quantification (LLOQ):

a. Plasma (1 ng/mL)

b. Perilymph (4 ng/mL)

c. Cochlear epithelium (6 ng/mL)

Figures 10A, 10B, 10C:
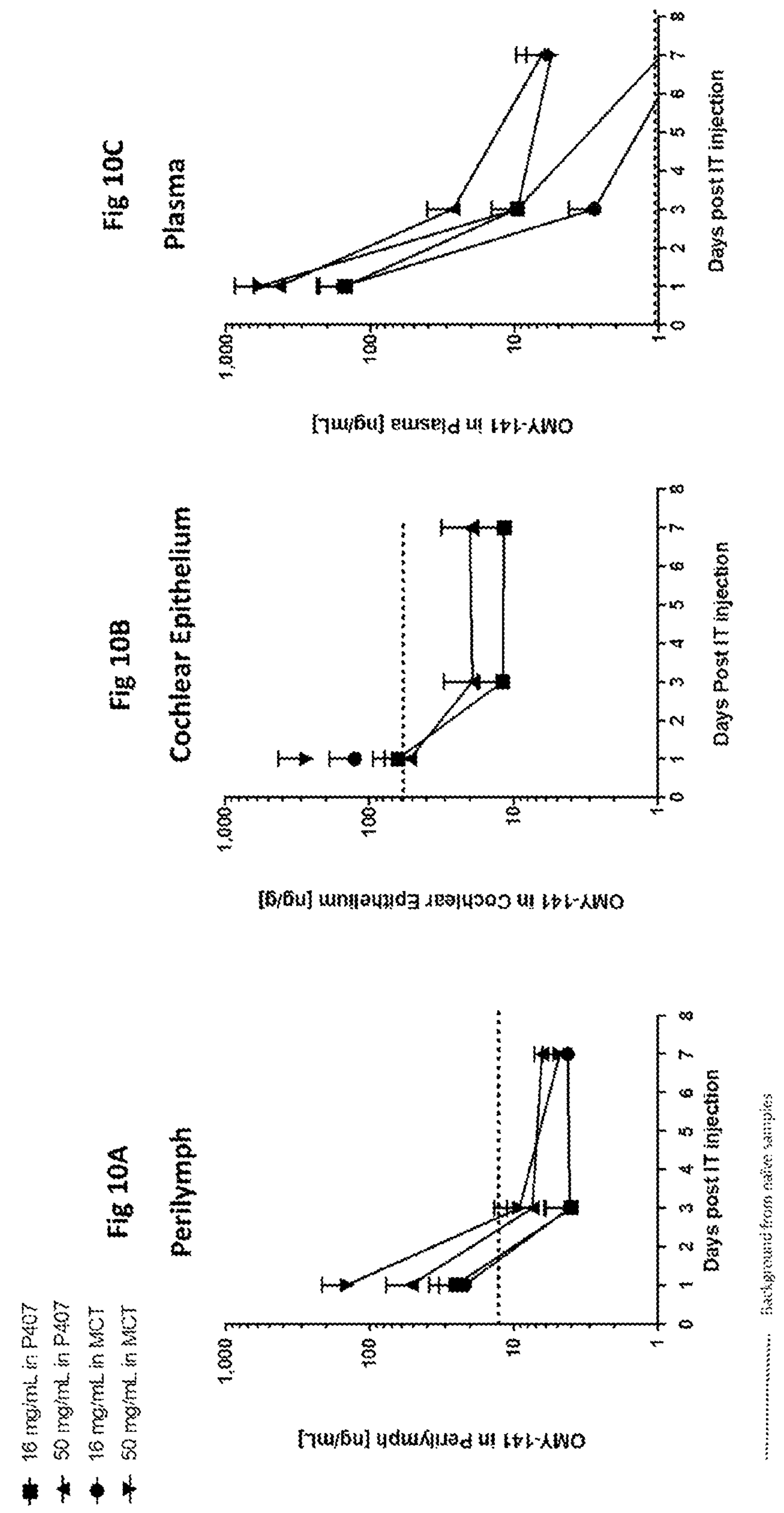
FIGS. 10A-10C show the OMY-141 pharmacokinetic results for A: the perilymph; B: cochlear epithelium; and C: plasma.

OMY-141 (6-propyl-2-thiouracil) shows good perilymph and cochlear epithelium exposure after IT injection in both MCT and poloxamer formulations, as illustrated in FIGS. 10A-10B. OMY-141 also shows some plasma exposure, as illustrated in FIG. 10C.

Figures 11A, 11B, 11C:
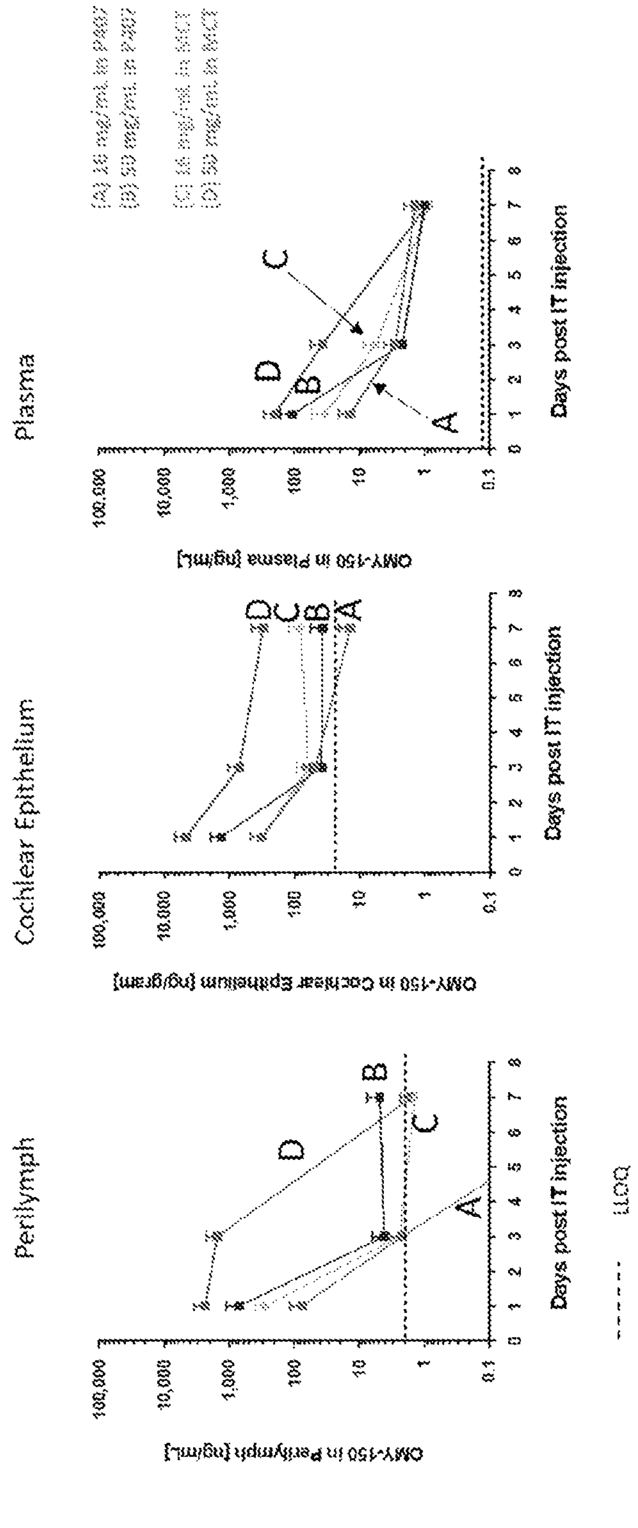
FIGS. 11A-11C show the OMY-150 pharmacokinetic results for A: the perilymph; B: cochlear epithelium; and C: plasma at various concentrations.
Figure 12A:
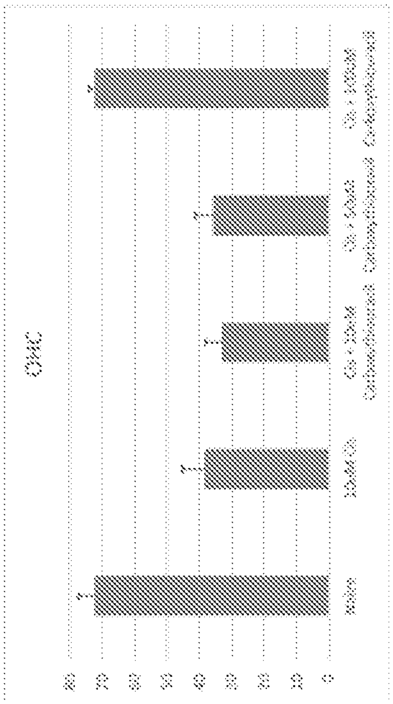
FIGS. 12A-12E show the ex vivo efficacy of 5-carboxy-2-thiouracil. A: OHC; B: IHC; C: SGN-base, mild combined; D: OHC-based and mid; and E: phenylthiouracil SGNs per 20 μM.
Figure 12B:
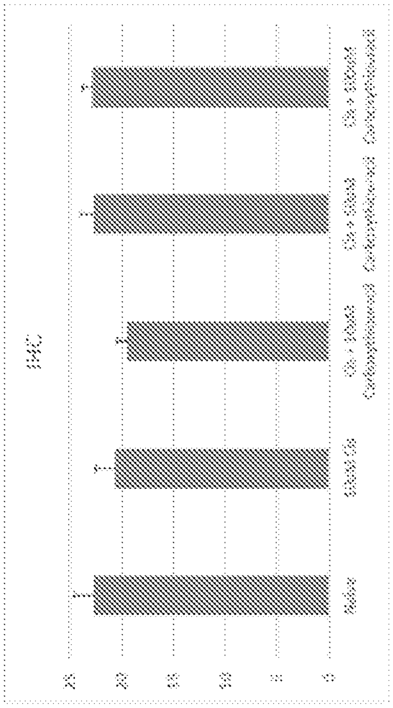
Figure 12C:
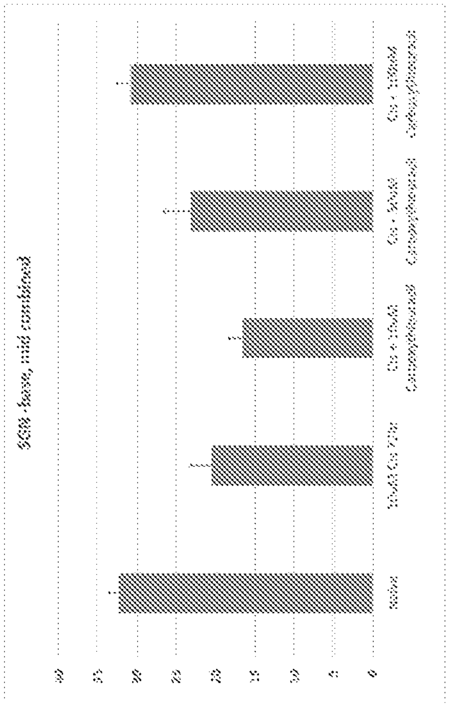
Figure 12D:
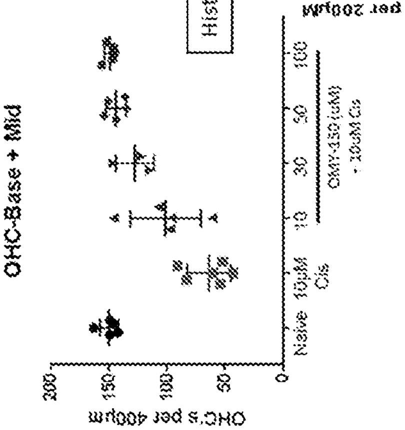
Figure 12E:
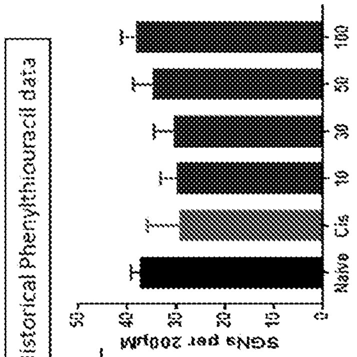
Figure 14:
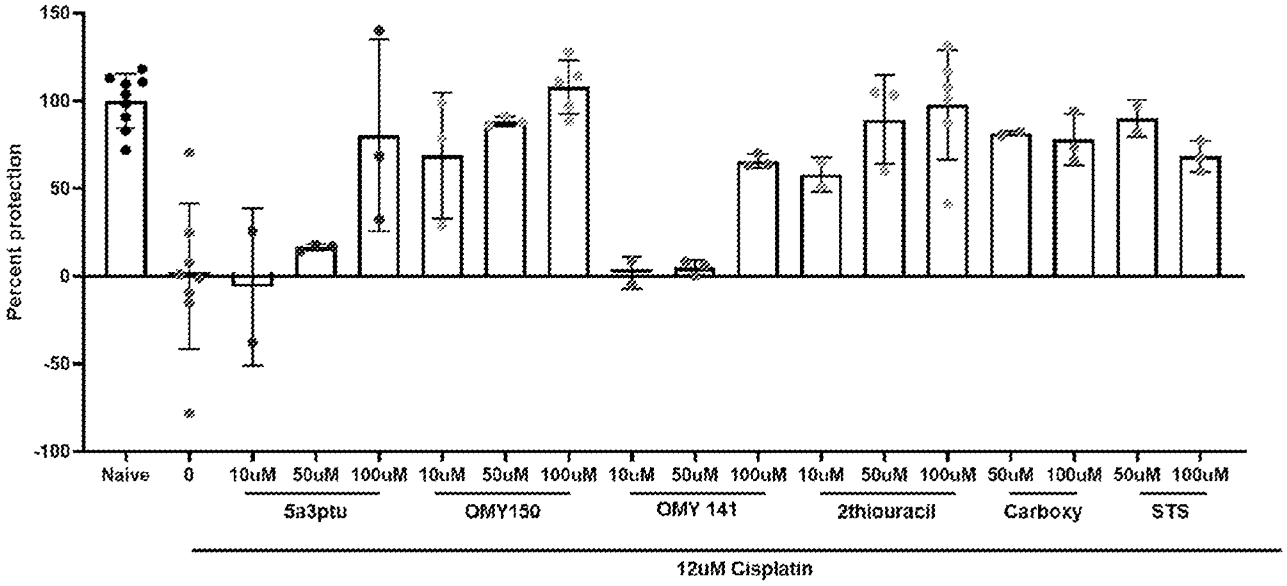
FIG. 14 shows thiouracil comparison of potency in hair cells for various compounds of the present disclosure.
Figure 15:
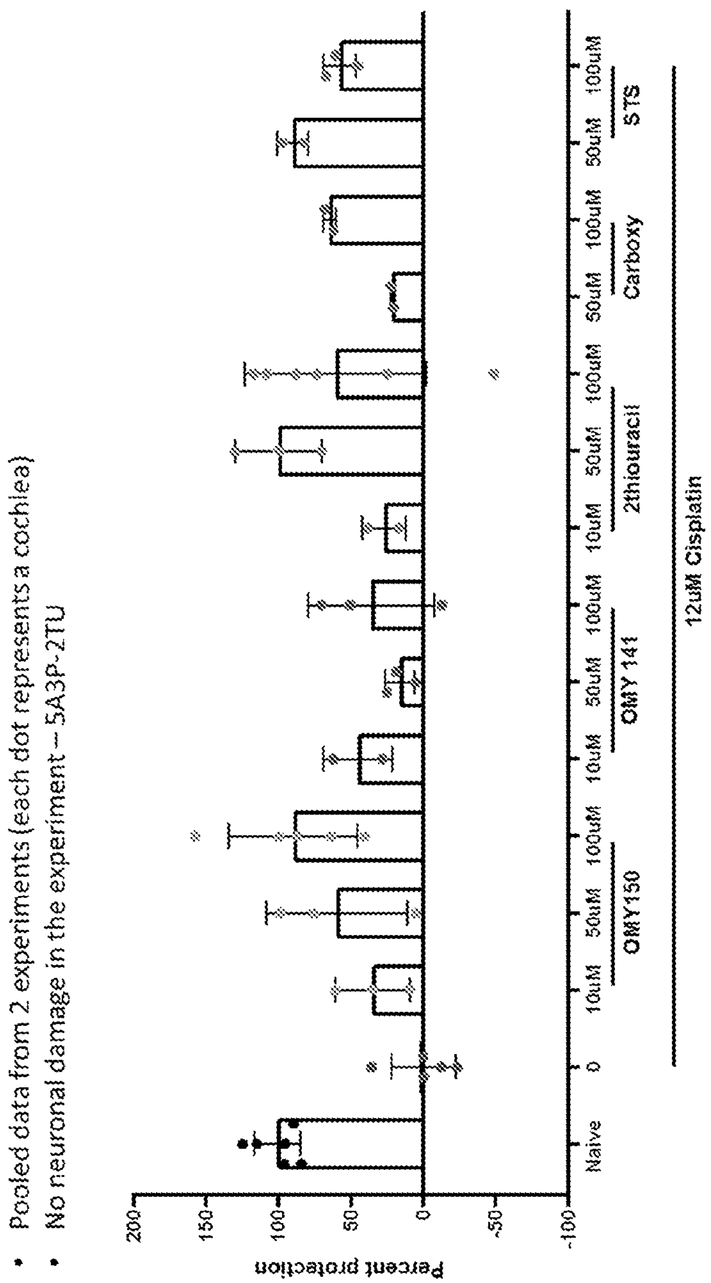
FIG. 15 shows thiouracil comparison of potency-SGNs for various compounds of the present disclosure.
Figure 16A:
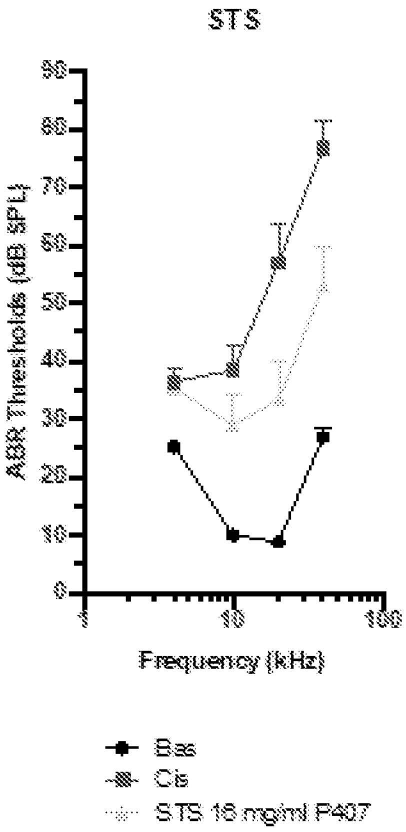
FIGS. 16A-16B show OMY150 in 3-day acute CIHL model (OTO600-RSP026)-ABR thresholds. A: STS; and B: OMY-150 P407.
Figure 16B:
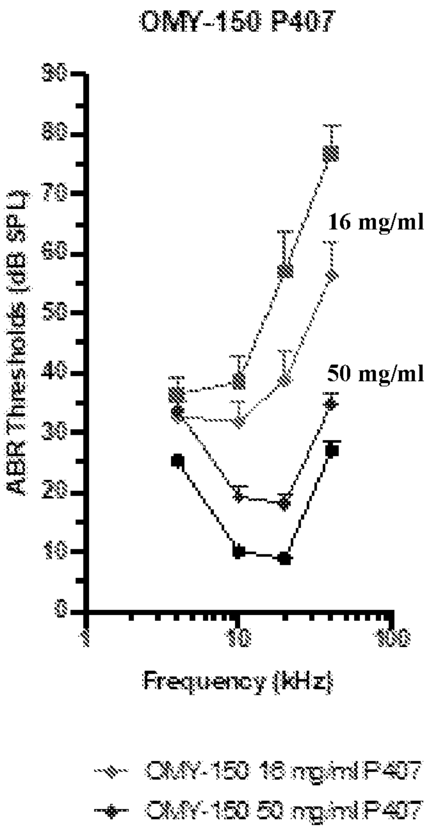
Figure 17A:
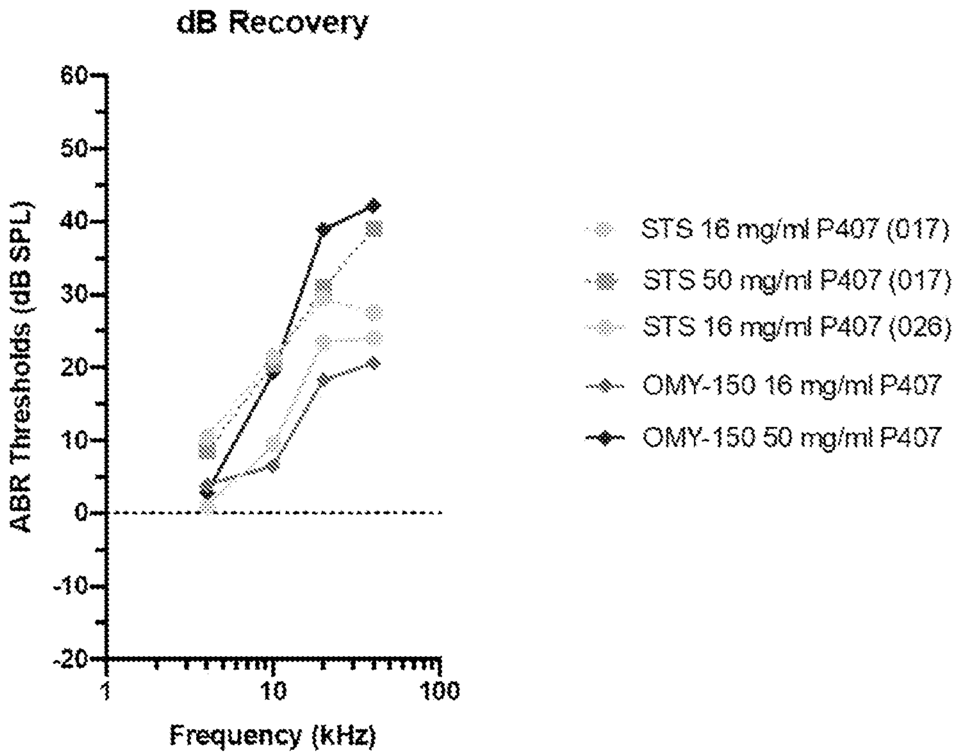
FIGS. 17A-17B show OMY-150 in 3-day acute CIHL model (OTO600-RSP026). A: dB recovery; and B: ABR threshold for various concentrations of OMY-150.
Figure 17B:
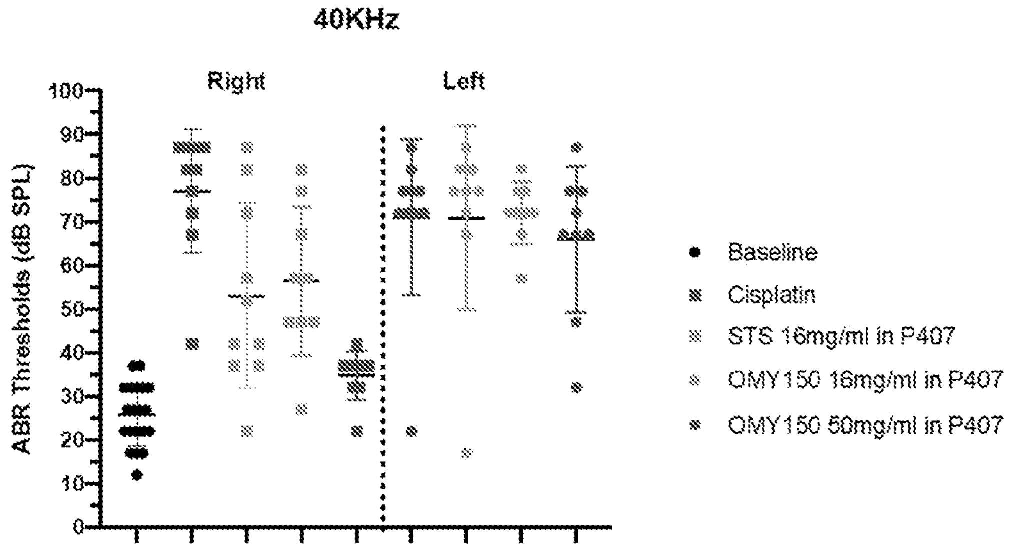
Figure 18B:
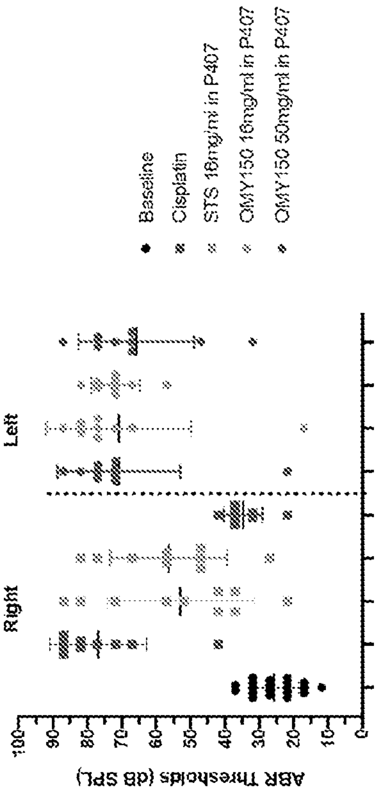
FIGS. 18A-18B show comparative experimental data for compounds of the present disclosure.
Figure 18A:
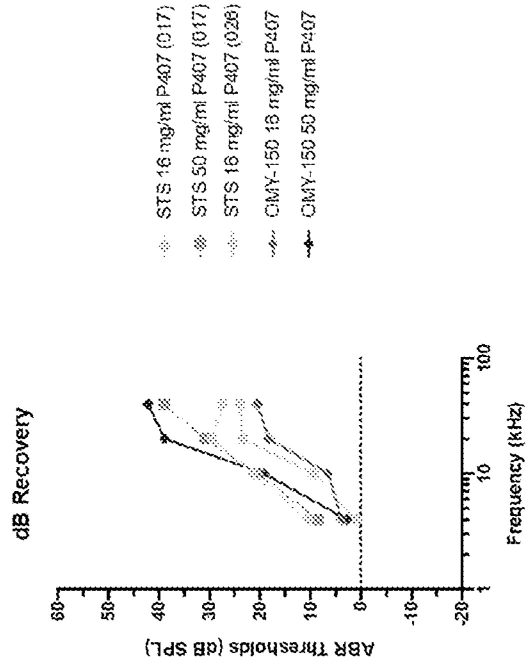
Figures 19A, 19B, 19C:
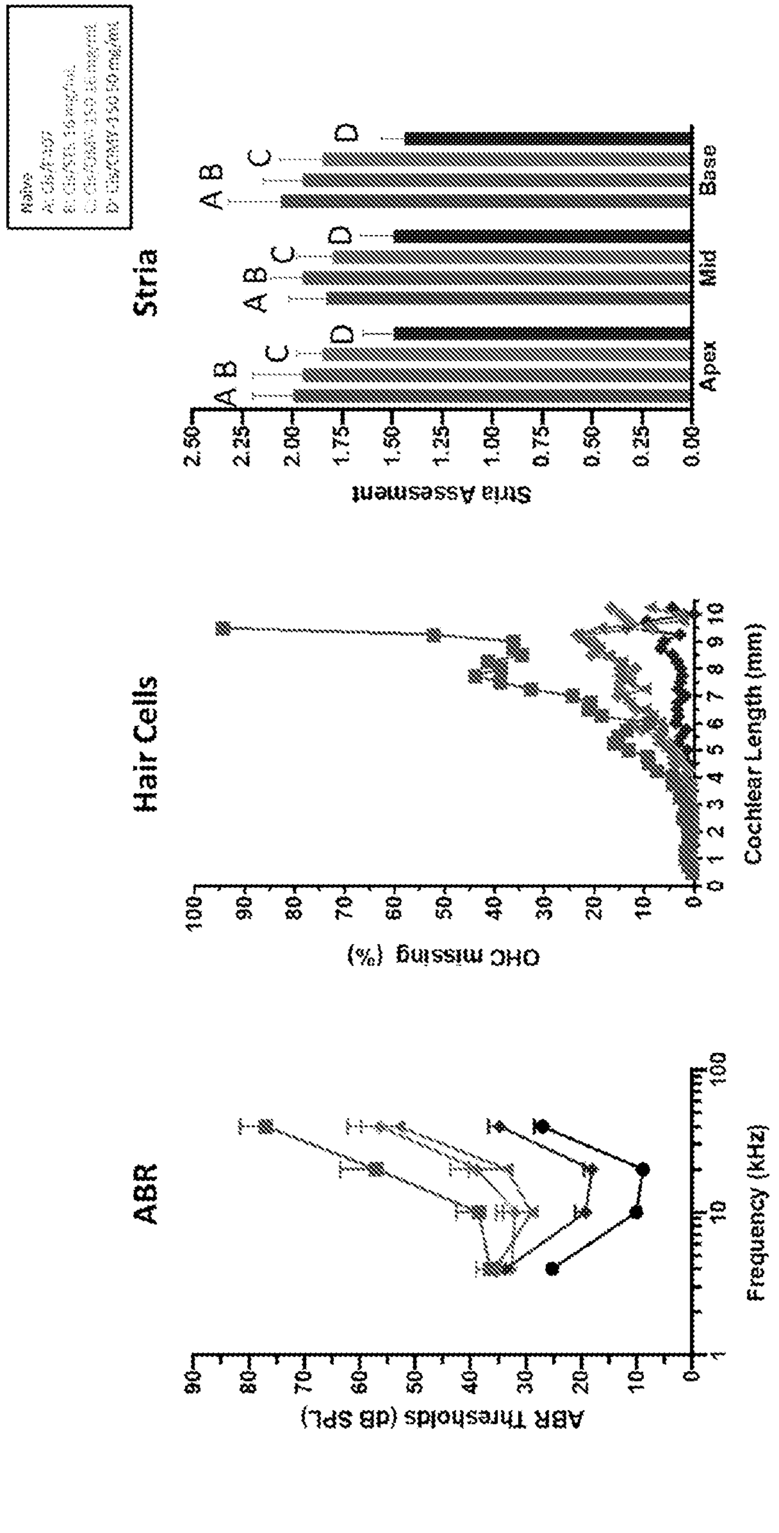
FIGS. 19A-19C show thiouracil efficacy over STS. A: ABR; B: hair cells; and C: stria.
Figure 21A:
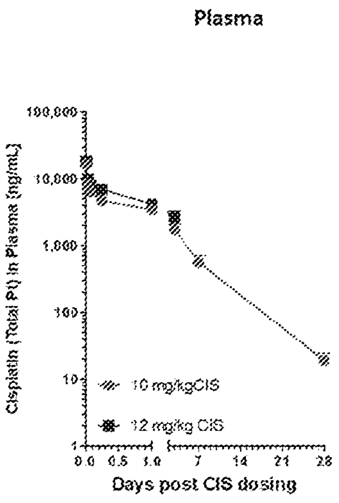
FIGS. 21A-21C show the cisplatin IP injection pharmacokinetic results for A: the plasma; B: perilymph; and C: cochlear epithelium.
Figure 21B:
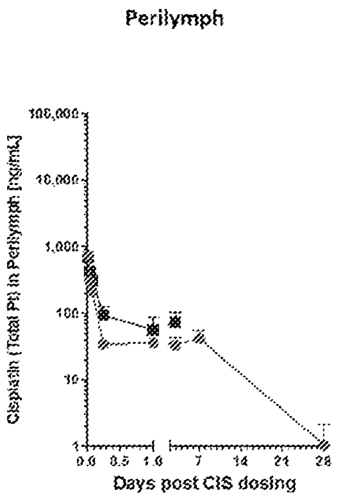
Figure 21C:
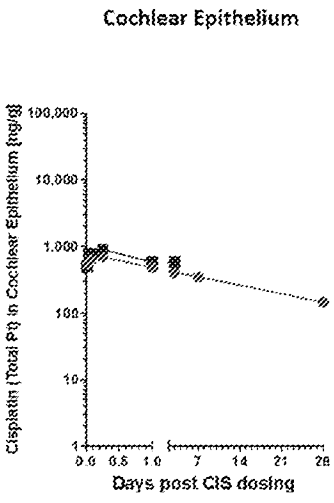

OMY-150 (6-phenyl-2-thiouracil) shows good perilymph and cochlear epithelium exposure after IT injection in and poloxamer formulation, as illustrated in FIGS. 11A-11B. OMY-150 shows significantly lower (e.g. up to 10 times or more) plasma exposure than OMY-141, as illustrated in FIG. 11C. OMY-150 also shows lower plasma exposure than sodium thiosulfate (STS).

Table M shows inner ear exposure for P407 formulations.

TABLE M

| Compounds | Structure | Log P (calculated) | Aqueous Solubility (predicted |
|---|---|---|---|
| OMY-141 | 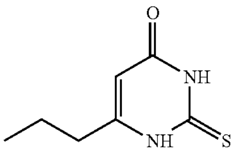 | 1.37 +/− 0.37 | Soluble 1.46 mg/mL |
| OMY-150 | 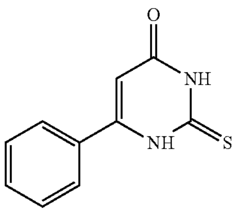 [SMILES: O=c1cc(-c2ccccc2)[nH]c(=S)[nH]1] | 1.92 +/− 0.75 | Moderately Soluble 0.57 mg/mL |

Efficacy in Ex-Vivo Cochlear Explants and Strial Cells 5-carboxy-2-thiouracil shows good protection for on OHC, SGN and strial cell protection; the pooled data for OMY-141, OMY-151, 2-thiouracil, 5-carboxy-2-thiouracil on HC and SGN protection; the lower potency of 5-acetyl-3-(p-tolyl)-2-thiouracil (5a3PTU) on HC protection; and potency comparison of thiouracils. Compare different TU molecules head to head to identify their relative potencies. Comparison of OMY-150 with 2-TU (base structure) and test a complicated 2TU structure.

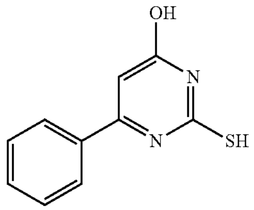

6-Phenyl-2-thiouracil (OMY150)

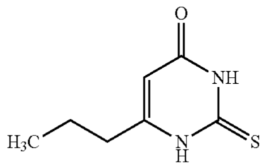

6-Propyl-2-thiouracil (OMY141)

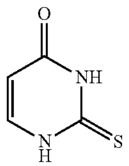

2-thiouracil

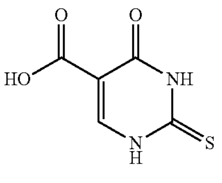

5-carboxy-2-thiouracil

-continued

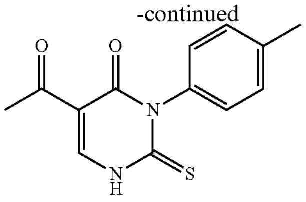

5-ACETYL-3-(P-TOLYL)-2-THIOURACIL

Comparison with Sodium Thiosulfate (STS):

(STS)

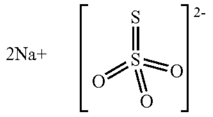

Sodium thiosulfate

OMY150 in 3-Day Acute CIHL Animal Model

Study Design includes: CIS 12 mg/kg (IP)/N=10 in-life duration 3 days at ABR (4, 10, 20, 40 kHz). Formulation was delivered IT unilaterally (right ear) 30 min prior CIS. There was gross visual necropsy observation performed at termination.

Tissue Collected for CCG Evaluation

A: Cis IP/Vehicle P407

B: Cis IP/STS 16 mg/ml in P407

C: Cis IP/OMY-150 16 mg/ml in P407

D: Cis IP/OMY-150 50 mg/ml in P407

Consistent effect on ABR thresholds with newest cisplatin batch. STS (16 mg/ml in P407) imparts less protection than in previous studies (different batch of STS).

OMY150 in P407 at 16 mg/ml in P407 shows strong protection and at 50 mg/ml in P407 shows almost complete recovery PK Study Measuring Cisplatin Levels in Cochlear after IP Administration Rat Cisplatin IP PK Study Dose Article: Cisplatin injection (1 mg/mL cisplatin sterile aqueous solution) from BluePoint Laboratories. Doses and Route of Administration: 10 mg/kg cisplatin IP; and 12 mg/kg cisplatin IP.

Protocol: 3 animals per group at time points. Group A: 30 min, 1 hr, 2 hr, 6 hr, 1 day, 3 day, 7 day, 28 day. Group B: 30 min, 1 hr, 2 hr, 6 hr, 1 day, 3 day. Bioanalysis: Plasma, Perilymph, Cochlear epithelium, CSF. Bioanalytical Method: Total Platinum by ICP-MS.

Pharmacokinetics—Summary

Following intraperitoneal (IP) administration, cisplatin levels peak in perilymph within 30 min, and in cochlear tissues at 6 hours.

Cmax concentrations in perilymph and cochlear tissues are comparable, reaching 700-750 ng/mL (2.3-2.5 μM) when dosed at 10 mg/kg and 700-900 ng/mL (2.3-3.0 μM) when dosed at 12 mg/kg.

Ratio of plasma/inner ear levels are 20-25 fold (Cmax) and 7-65 fold (AUC).

Platinum can still be detected in plasma and cochlear tissues one month post-administration.

Cisplatin Kinetics Analytical Method

Reaction kinetics between Cisplatin and the compound of interest (nucleophile) were monitored by high performance liquid chromatography. Isocratic separation was achieved using a Waters Spherisorb C8 column (4×250 mm, 5 μm, 80 Å). The flow rate was set to 1.00 mL/min. The mobile phase consisted of 5 mM Sodium Octanesulfonate+5 mM Tetrabutyl Ammonium Hydrogen Sulfate+20 mM Potassium Dihydrogen Phosphate adjusted to pH 5.9. Detection was performed at a wavelength of 210 nm.

Reactions were conducted at equimolar concentrations in buffered aqueous media and held at 37° C. Rate constants (k) were determined by monitoring the disappearance of Cisplatin as a function of time.

TABLE N

Kinetics of 50 μM cisplatin + 50 μM of compound (API) in PBS, pH 7.4, 37° C. (pH of Cisplatin Stock in 0.9% NaCl: 4.7).

| | Reaction | Kinetics | |
|---|---|---|---|
| Neutralizing agent | pH | k ($M^{-1}s^{-1}$) | Half-Life at 50 μM (hrs.) |
| STS | 7.4 | 0.52 | 10.7 |
| OMY-0150 | 7.4 | 0.50 | 11.2 |
| OMY-0141 | 7.5 | 10.27 | 20.4 |
| 2-Thiouracil | 7.4 | 0.15 | 37.1 |
| D-Methionine | 7.4 | 0.07 | 79.1 |
| MESNA | 7.5 | 0.05 | 110.7 |

The rate constant (k): STS/OMY-150>OMY-141>2-Thiouracil>D-Methionine>MESNA. Phosphate Buffered Saline, pH 7.4 as a diluent eliminates solution pH fluctuations.

TABLE O

Summary of studies

| Class | Compound | Cisplatin Binding % bound (in 30 min) at 1:10 ratio | Ex-vivo Efficacy Conc. for complete protection of hair cells (uM) | In vivo PK in Cochlear Epithelium (24 h after dosing) |
|---|---|---|---|---|
| Thiols | Sodium thiosulfate | 50% | 100 | ~1100 ng/gm CE |
| | D-methionine | 40% | 10,000 | ~200 ng/gm CE |
| Thiopurines | 6-mercaptopurine | 60% | 50-100 | |
| | 6-thioguanine | 80% | 50-100 | |
| | 6-thioguanosine | | 50-100 | |

TABLE O-continued

Summary of studies

| Class | Compound | Cisplatin Binding % bound (in 30 min) at 1:10 ratio | Ex-vivo Efficacy Conc. for complete protection of hair cells (uM) | In vivo PK in Cochlear Epithelium (24 h after dosing) |
|---|---|---|---|---|
| | 6-thio-2'-deoxy guanosine | 50% | 100 | |
| | 5-Deoxy-5-methylthioadenosine | | No protection | |
| Thiouracils | 2-thiouracil | | 50-100 | |
| | 6-phenyl-2-thiouracil | 97% | 50 | ~1000 ng/gm CE |
| | 6-Propyl-2-thiouracil | 95% | 50-100 | ~300 ng/gm CE |
| | 6-methoxy-2-thiouracil | | 50-100 | |
| | 5-carboxy-2-thiouracil | 95% | 50-100 | |
| | 5-acetyl-3-(p-tolyl)-thiouracil | | 500 | |

While preferred embodiments of the present disclosure have been shown and described herein, such embodiments are provided by way of example only. Various alternatives to the embodiments described herein are optionally employed. It is intended that the following claims define the scope of the disclosure and that methods and structures within the scope of these claims and their equivalents be covered thereby.

What is claimed is:

1. A method of treating and/or preventing drug-induced ototoxicity, comprising administering to a subject in need thereof a pharmaceutical composition, comprising:

a. an otoprotectant that is:

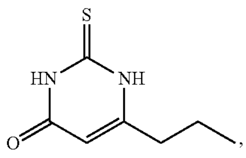

,

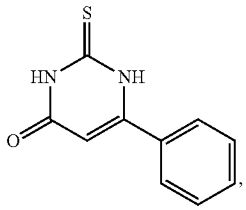

, or

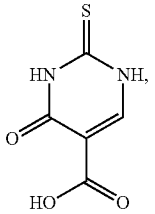

, or a tautomer, pharmaceutically acceptable salt, or a tautomer of a pharmaceutically acceptable salt thereof; and b. at least one pharmaceutically acceptable excipient or carrier.

2. The method of claim 1, wherein the composition provides sustained release of the otoprotectant for a period of at least one day after a single administration.

3. The method of claim 1, wherein the drug-induced ototoxicity is chemotherapy-induced ototoxicity, comprises hearing loss, or both.

4. The method of claim 1, wherein the composition comprises a gel or a viscous preparation.

5. The method of claim 4, wherein the gel is a thermoreversible gel.

6. The method of claim 4, wherein the gel comprises about 14 wt % to about 18 wt % of a copolymer of polyoxyethylene and polyoxypropylene.

7. The method of claim 4, wherein the gel has a gelation viscosity of about 15,000 cP to about 3,000,000 cP.

8. The method of claim 1, wherein the pharmaceutical composition and the ototoxic drug are administered simultaneously, approximately simultaneously, or sequentially, in any order.

9. The method of claim 8, wherein the pharmaceutical composition is administered before the ototoxic drug.

10. The method of claim 1, wherein the otoprotectant is formulated for intratympanic administration.

* * * * *